(12) United States Patent
He

(10) Patent No.: US 10,072,045 B1
(45) Date of Patent: Sep. 11, 2018

(54) ANTIBACTERIAL LIPOPEPTIDES AND METHODS FOR THEIR PREPARATION AND USE

(71) Applicant: Ramapo Pharmaceuticals, Inc., Monmouth Junction, NJ (US)

(72) Inventor: Haiyin He, Mahwah, NJ (US)

(73) Assignee: RAMAPO PHARMACEUTICALS, INC., Monmouth Junction, NJ (US)

( * ) Notice: Subject to any disclaimer, the term of this patent is extended or adjusted under 35 U.S.C. 154(b) by 0 days.

(21) Appl. No.: 15/889,497

(22) Filed: Feb. 6, 2018

Related U.S. Application Data

(60) Provisional application No. 62/524,856, filed on Jun. 26, 2017.

(51) Int. Cl.
*A61K 38/00* (2006.01)
*C07K 7/64* (2006.01)
*A61P 31/04* (2006.01)

(52) U.S. Cl.
CPC ............... *C07K 7/64* (2013.01); *A61P 31/04* (2018.01); *A61K 38/00* (2013.01)

(58) Field of Classification Search
None
See application file for complete search history.

(56) References Cited

U.S. PATENT DOCUMENTS

| | | | |
|---|---|---|---|
| 4,537,717 A * | 8/1985 | Abbott | C07K 7/08 530/317 |
| 6,767,718 B2 | 7/2004 | Leese et al. | |
| 6,911,525 B2 | 6/2005 | Hill et al. | |
| 7,262,268 B2 | 8/2007 | Morytko et al. | |
| 8,507,647 B2 | 8/2013 | Metcalf, III et al. | |

FOREIGN PATENT DOCUMENTS

EP 2261237 A2 12/2010

* cited by examiner

*Primary Examiner* — Jeanette M Lieb
(74) *Attorney, Agent, or Firm* — Leason Ellis LLP

(57) ABSTRACT

Novel antibacterial lipopeptides, pharmaceutical compositions, and methods for their preparation and use are described.

8 Claims, No Drawings

ANTIBACTERIAL LIPOPEPTIDES AND METHODS FOR THEIR PREPARATION AND USE

CROSS-REFERENCE TO RELATED APPLICATIONS

This application claims the benefit of priority under 35 U.S.C. Section 119(e) of U.S. Application Ser. No. 62/524,856, filed on Jun. 26, 2017, which is hereby incorporated by reference in its entirety.

FIELD

The present disclosure is directed to novel antibacterial lipopeptides that exhibit antibiotic activity against a spectrum of microorganisms including those resistant to vancomycin, penicillin and methicillin, pharmaceutical compositions, and methods for their preparation and use.

BACKGROUND

The emerging bacterial resistance to antibiotics is a major problem for public health. See, Ginzburg, E.; Namias, N.; Brown, M.; Ball, S.; Hameed, S. M.; Cohn, S. M. *Int. J. Antimicrob. Agents,* 2000, 16 (Suppl.), S39-S42; Chopra, I. J.; Hodgson, B. M.; Poste, G. *Antimicrob. Agents Chemother.,* 1997, 41, 497-503. Increasing rate of infections caused by drug-resistant Gram positive and Gram negative bacteria demands accelerated research and development of new antibiotics. As an example, Daptomycin which is a thirteen-amino acid cyclic lipopeptide antibiotic (Huber et al., U.S. Pat. No. 4,885,243) is used in the treatment of systemic and life-threatening infections caused by Gram-positive organisms. See, Kline, M., Mason, E., Jr., Kaplan S., Lamberth, L., and Johnson, G., Comparative in-vitro activity of LY146032 and eight other antibiotics against Gram-positive bacteria isolated from children, *Journal of Antimicrobial Chemotherapy,* 1987, 20, 203-207; Steenbergen, J.; J. Alder, J.; Thorne, G. and Tally, F.; Daptomycin: a lipopeptide antibiotic for the treatment of serious Gram-positive infections, *Journal of Antimicrobial Chemotherapy,* 2005, 55, 283-288. It is particularly used in adults in the United States for skin and skin structure infections caused by Gram-positive bacteria *Staphylococcus aureus,* left-sided *S. aureus* endocarditis, osteomyelitis, prosthetic infections, and *enterococcus* infections. See, Fowler, G.; Boucher, H.; Corey, G.; Daptomycin versus standard therapy for bacteremia and endocarditis caused by *Staphylococcus aureus, N Engl J Med.* 2006, 355 (7), 653-65; Davis, S.; McKinnon, P.; Hall, L.; *Pharmacotherapy.* 2007, 27 (12), 1611-1618; Steenbergen, J.; J. Alder, J.; Thorne, G. and Tally, F.; Daptomycin: a lipopeptide antibiotic for the treatment of serious Gram-positive infections, *Journal of Antimicrobial Chemotherapy,* 2005, 55, 283-288. Daptomycin is a natural product isolated from the broths of *Streptomyces roseosporus.* See, Debono, M.; Abbott, B. J.; Molloy, M; & et al.; Enzymatic and chemical modifications of lipopeptide antibiotic A21978C: the synthesis and evaluation of daptomycin (LY146032). *J Antibiotics,* 1988, 41, 1093-1105; Miao V.; Coëffet-Legal F.; Brian P.; Daptomycin biosynthesis in *Streptomyces roseosporus*: cloning and analysis of the gene cluster and revision of peptide stereochemistry, *Microbiology (Reading, Engl.),* 2005, 151 (Pt 5), 1507-23. Studies demonstrate that this compound disrupts multiple aspects of bacterial cell membrane function and therefore is effective in treating infections caused by multiple drug-resistant bacteria. See, Pogliano J; Pogliano, N; Silverman, J.; Daptomycin-Mediated Reorganization of Membrane Architecture Causes Mislocalization of Essential Cell Division Proteins, *Journal of Bacteriology,* 2012, 194 (17), 4494-4504; Baltz R.; Daptomycin: mechanisms of action and resistance, and biosynthetic engineering, *Current Opinion in Chemical Biology,* 2009, 13 (2), 144-151. However, the in vitro activity of daptomycin against Eterococci, including vancomycin-resistent Eterococci (VRE) is moderate and therefore its use in treatment of infections caused by VRE, without combining with other antibiotics, is limited. See, Moise; P A; Sakoulas G; McKinnell J A; Lamp K C; DePestel D D; Yoon M J; Reyes K; Zervos M J; Clinical Outcomes of Daptomycin for Vancomycin-resistant *Enterococcus* Bacteremia, *Clin. Ther.,* 2015 Jul. 1, 37(7), 1443-1453. In recent years, daptomycin-resistance in Enterococci, particularly in vancomycin-resistant *E. faecium* and *E. farcalis,* has been increasingly reported in the United States, Europe, and Asia. See, Cleveland, K.; Gelfand, M.; Daptomycin-Nonsusceptible Enterococcal Infections, *Infect Dis Clin Pract,* 2013, 21, 79-84.

There is an urgent need for new antibiotic agents that are efficacious against microorganisms including those resistant to vancomycin, penicillin and methicillin.

SUMMARY

Novel antibacterial lipopeptides have been discovered that exhibit antibiotic activity against a spectrum of organisms including those resistant to vancomycin, penicillin and methicillin, as well as non-toxic pharmaceutically acceptable salts and prodrugs of these antibacterial lipopeptides, pharmaceutical compositions, and methods of using them alone or in combination with other agents for the treatment of bacterial infections in mammals, i.e., humans and animals. New intermediates have been utilized in syntheses of these novel antibacterial lipopeptides.

Novel compounds represented by Formulas I, II and III have antibacterial activity and can be used in pharmaceutical compositions and for methods of treating bacterial infections in mammals.

In certain embodiments, a compound comprises Formula I as follows:

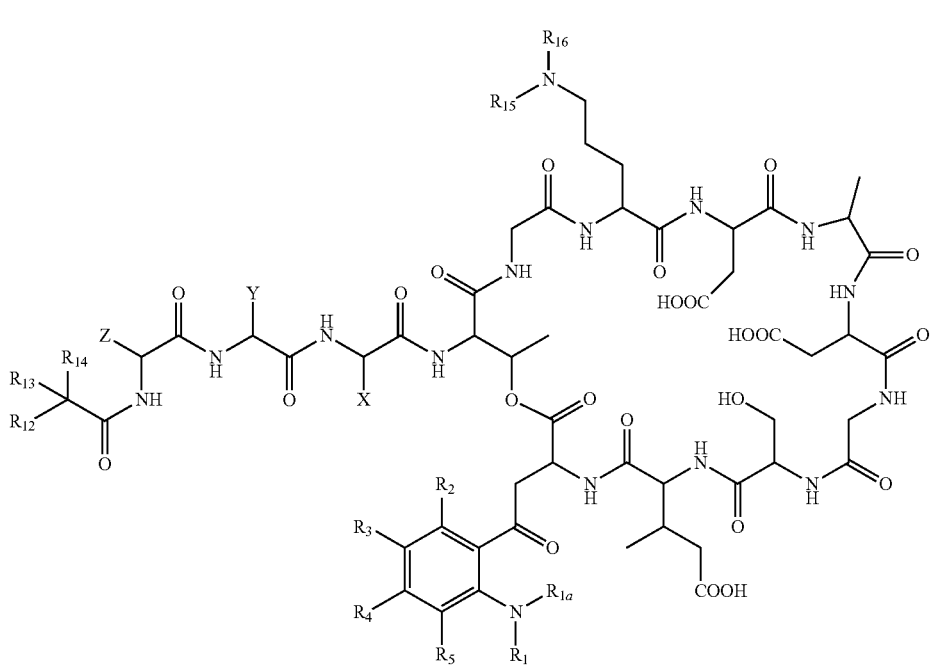

Formula I wherein:

X and Y are independently selected from hydrogen, alkyl, alkenyl, cycloalkyl, cycloalkenyl, alkynyl, aryl, or heteroaryl group. Examples of X and Y include, without limitation, the following groups:

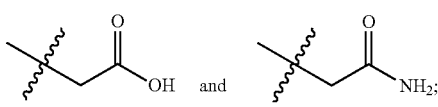 [SMILES: *CC(=O)O ; *CC(N)=O]

Z is selected from hydrogen, alkyl, cycloalkyl, alkenyl, cycloalkenyl, alkynyl, aryl, heteroaryl group. Examples include, without limitation, the following indolylmethyl moiety

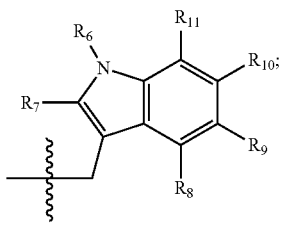

$R_1$, $R_{1a}$, and $R_6$ are each independently selected from hydrogen, alkyl, alkenyl, alkynyl, cycloalkyl, cycloalkenyl, aryl, heteroaryl, acyl, OH, OR, NHR, or $NR_2$ group; wherein R is a $C_1$-$C_6$ alkyl, $C_2$-$C_6$ alkenyl, $C_2$-$C_6$ alkynyl, cycloalkyl, cycloalkenyl, aryl, or heteroaryl group;

$R_2$, $R_3$, $R_4$, $R_5$, $R_7$, $R_8$, $R_9$, $R_{10}$, and $R_{11}$ are each independently selected from hydrogen, halogen, alkyl, alkenyl, alkynyl, cycloalkyl, cycloalkenyl, aryl, heteroaryl, cyano, isocyano, thiocyano, isothiocyano, phosphate, phosphoryl, sulfate, sulfinyl, sulfonyl, formyl, acyl, amino, acylamino, acyloxy, thiocarbonyl, imino, carboalkoxy, carboxy, carboxyamido, hydroxyl, nitro, thio, alkoxy, aryloxy, OC=$OR_a$, OC=$OOR_a$, OC=$ONHR_a$, OC=$ON(R_a)_2$, $NHR_a$, or $N(R_a)_2$ group; wherein $R_a$ is selected from a $C_1$-$C_6$ alkyl, $C_2$-$C_6$ alkenyl, $C_2$-$C_6$ alkynyl, cycloalkyl, cycloalkenyl, aryl or heteroaryl group;

$R_{12}$, $R_{13}$, $R_{14}$ are each independently selected from hydrogen, $C_1$-$C_{25}$ alkyl, $C_2$-$C_{25}$ alkenyl, $C_2$-$C_{25}$ alkynyl, aryl, heteroaryl, cycloalkyl, cycloalkenyl, or a group containing branched or unbranched polyethylene —(OCH$_2$CH$_2$)$_n$—, or polypropylene —(OCH$_2$CH$_2$CH$_2$)$_m$— group, wherein each n and m is an integer between 1 and 10;

$R_{15}$ and $R_{16}$ are each selected from H or —(P'Q'), whereas P' is an alkyl, alkenyl, cycloalkyl, or cycloalkenyl moiety, and Q' is a primary, secondary, tertiary or quaternary amino group;

provided that at least one of $R_1$, $R_{1a}$, $R_2$, $R_3$, $R_4$, and $R_5$ is not H;

and further provided that when Z is the following indolylmethyl group

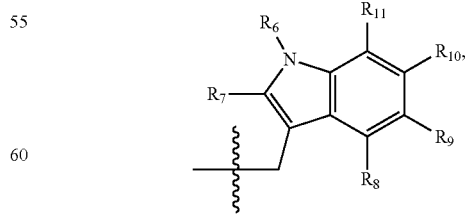

at least one of $R_6$, $R_7$, $R_8$, $R_9$, $R_{10}$, and $R_{11}$ is not H;

and pharmaceutically acceptable salts and prodrugs thereof.

In one embodiment, a compound having Formula I as described above, may have Z as the following indolylmethyl group

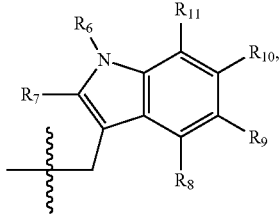

and $R_2$, $R_3$, $R_4$, $R_5$, $R_7$, $R_8$, $R_9$, $R_{10}$, and $R_{11}$ are each independently selected from hydrogen, halogen, alkyl, alkenyl, alkynyl, cycloalkyl, cycloalkenyl, aryl, heteroaryl, cyano, isocyano, thiocyano, isothiocyano, phosphate, phosphoryl, sulfate, sulfinyl, sulfonyl, formyl, acyl, amino, acylamino, acyloxy, thiocarbonyl, imino, carboalkoxy, carboxy, carboxyamido, hydroxyl, nitro, thio, alkoxy, aryloxy, OC=$OR_a$, OC=$OOR_a$, OC=$ONHR_a$, OC=$ON(R_a)_2$, $NHR_a$, or $N(R_a)_2$ group; wherein $R_a$ is selected from a $C_1$-$C_6$ alkyl, $C_2$-$C_6$ alkenyl, $C_2$-$C_6$ alkynyl, cycloalkyl, cycloalkenyl, aryl or heteroaryl group;

provided that at least one of $R_1$, $R_{1a}$, $R_2$, $R_3$, $R_4$, and $R_5$ is not H;

and further provided that at least one of $R_6$, $R_7$, $R_8$, $R_9$, $R_{10}$, and $R_{11}$ is not H;

and pharmaceutically acceptable salts thereof.

In certain embodiments, a compound comprises Formula II as follows:

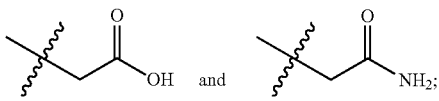 [SMILES: *CC(=O)O ; *CC(N)=O]

$R_1$ and $R_{1a}$ are each independently selected from hydrogen, alkyl, alkenyl, alkynyl, cycloalkyl, cycloalkenyl, aryl, heteroaryl, acyl, OH, OR, NHR, or $NR_2$ group; wherein R is a $C_1$-$C_6$ alkyl, $C_2$-$C_6$ alkenyl, $C_2$-$C_6$ alkynyl, cycloalkyl, cycloalkenyl, aryl, or heteroaryl group;

$R_2$, $R_3$, $R_4$, $R_5$ are each independently selected from hydrogen, halogen, alkyl, alkenyl, alkynyl, cycloalkyl, cycloalkenyl, aryl, heteroaryl, cyano, isocyano, thiocyano, isothiocyano, phosphate, phosphoryl, sulfate, sulfinyl, sulfonyl, formyl, acyl, amino, acylamino, acyloxy, thiocarbonyl, imino, carboalkoxy, carboxy, carboxyamido, hydroxyl, nitro, thio, alkoxy, aryloxy, OC=$OR_a$, OC=$OOR_a$, OC=$ONHR_a$, OC=$ON(R_a)_2$, $NHR_a$, or $N(R_a)_2$ group; wherein $R_a$ is selected from a $C_1$-$C_6$ alkyl, $C_2$-$C_6$ alkenyl, $C_2$-$C_6$ alkynyl, cycloalkyl, cycloalkenyl, aryl or heteroaryl group; $R_{12}$, $R_{13}$, $R_{14}$ are each independently selected from hydrogen, $C_1$-$C_{25}$ alkyl, $C_2$-$C_{25}$ alkenyl, $C_2$-$C_{25}$ alkynyl, aryl, heteroaryl, cycloalkyl, cycloalkenyl, or a group containing branched or unbranched polyethylene —$(OCH_2CH_2)_n$—, or polypropylene —$(OCH_2CH_2CH_2)_m$— group, wherein each n and m is an integer between 1 and 10;

$R_{15}$ and $R_{16}$ are each selected from H or —(P'Q'), whereas P' is an alkyl, alkenyl, cycloalkyl, or cycloalkenyl moiety, and Q' is a primary, secondary, tertiary, or quaternary amino group;

Formula II

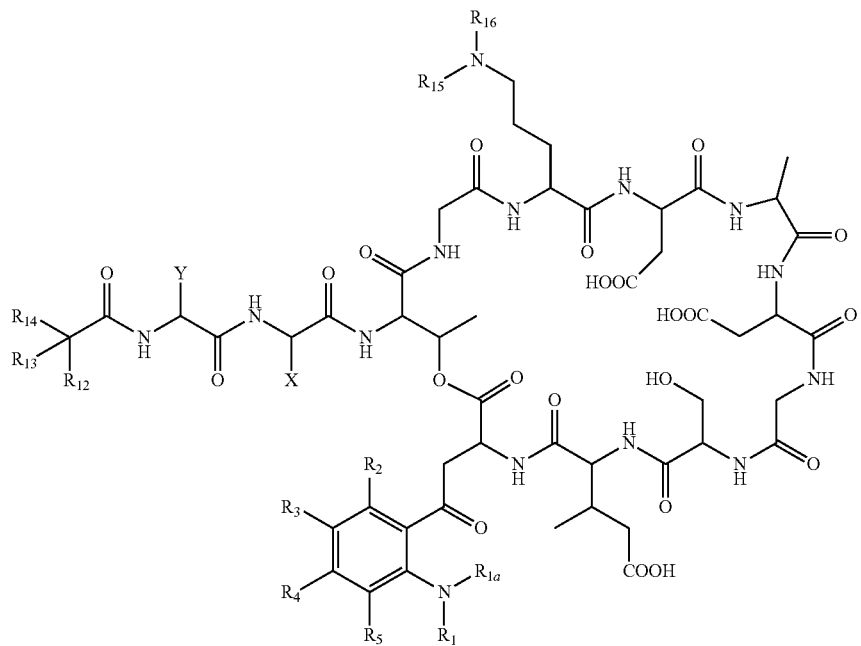

wherein:

X and Y are independently selected from hydrogen, alkyl, cycloalkyl, alkenyl, cycloalkenyl, alkynyl, aryl, or heteroaryl group. Examples of X and Y include, without limitation, the following groups:

provided that at least one of $R_1$ and $R_{1a}$ is not H;

and pharmaceutically acceptable salts and prodrugs thereof.

In certain embodiments, a compound comprises Formula III as follows:

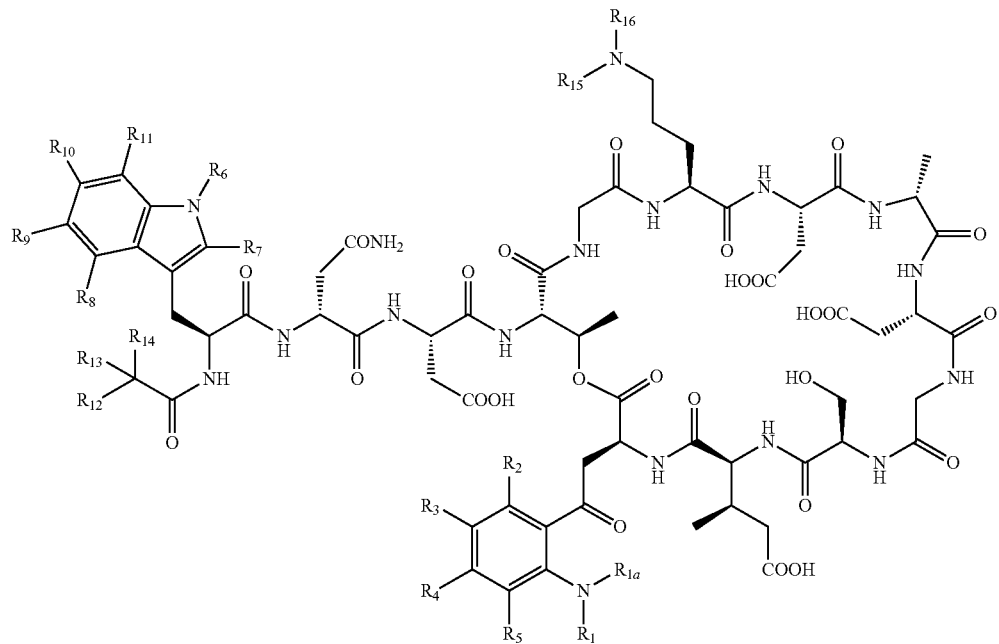

Formula III wherein:

$R_1$, $R_{1a}$, and $R_6$ are each independently selected from hydrogen, alkyl, alkenyl, alkynyl, cycloalkyl, cycloalkenyl, aryl, heteroaryl, acyl, OH, OR, NHR, or $NR_2$ group; wherein R is a $C_1$-$C_6$ alkyl, $C_2$-$C_6$ alkenyl, $C_2$-$C_6$ alkynyl, cycloalkyl, cycloalkenyl, aryl, or heteroaryl group; $R_2$, $R_3$, $R_4$, $R_5$, $R_7$, $R_8$, $R_9$, $R_{10}$, and $R_{11}$ are each independently selected from hydrogen, halogen, alkyl, alkenyl, alkynyl, cycloalkyl, cycloalkenyl, aryl, heteroaryl, cyano, isocyano, thiocyano, isothiocyano, phosphate, phosphoryl, sulfate, sulfinyl, sulfonyl, formyl, acyl, amino, acylamino, acyloxy, thiocarbonyl, imino, carboalkoxy, carboxy, carboxyamido, hydroxyl, nitro, thio, alkoxy, aryloxy, OC=$OR_a$, OC=$OOR_a$, OC=$ONHR_a$, OC=$ON(R_a)_2$, $NHR_a$, or $N(R_a)_2$ group; wherein $R_a$ is selected from a $C_1$-$C_6$ alkyl, $C_2$-$C_6$ alkenyl, $C_2$-$C_6$ alkynyl, cycloalkyl, cycloalkenyl, aryl or heteroaryl group;

$R_{12}$, $R_{13}$, $R_{14}$ are each independently selected from hydrogen, substituted, unsubstituted, branched, unbranched $C_1$-$C_{25}$ alkyl, $C_2$-$C_{25}$ alkenyl, $C_2$-$C_{25}$ alkynyl, aryl, heteroaryl, cyclic alkyl, cyclic alkenyl, cyclic alkynyl, or a group containing branched or unbranched polyethylene —$(OCH_2CH_2)_n$—, or polypropylene —$(OCH_2CH_2CH_2)_m$— group, wherein each n and m is an integer between 1 and 10;

$R_{15}$ and $R_{16}$ are each selected from H or —(P'Q'), whereas P' is an alkyl, alkenyl, cycloalkyl, or cycloalkenyl moiety, and Q' is a primary, secondary, tertiary, or quaternary amino group;

provided that at least one of $R_1$, $R_{1a}$, $R_2$, $R_3$, $R_4$, and $R_5$ is not H;

and further provided that at least one of $R_6$, $R_7$, $R_8$, $R_9$, $R_{10}$, and $R_{11}$ is not H;

and pharmaceutically acceptable salts and prodrugs thereof.

Exemplary compounds having antibacterial activity are provided and are designated RP002, RP003, RP004, RP005, RP006, RP007, RP008, RP009, RP010, RP011, RP012, RP013, RP014, RP015, RP016, RP017, RP018, RP019, RP020, RP021 and RP022, which have the formulas provided below. These compounds can be used in pharmaceutical compositions and for methods of treating bacterial infections in mammals.

In certain embodiments, a compound having antibacterial activity is selected from the group consisting of compounds designated RP002, RP003, RP004, RP005, RP006, RP007, RP008, RP009, RP010, RP011, RP012, RP013, RP014, RP015, RP016, RP017, RP018, RP019, RP020, RP021 and RP022, and having the following formulas:

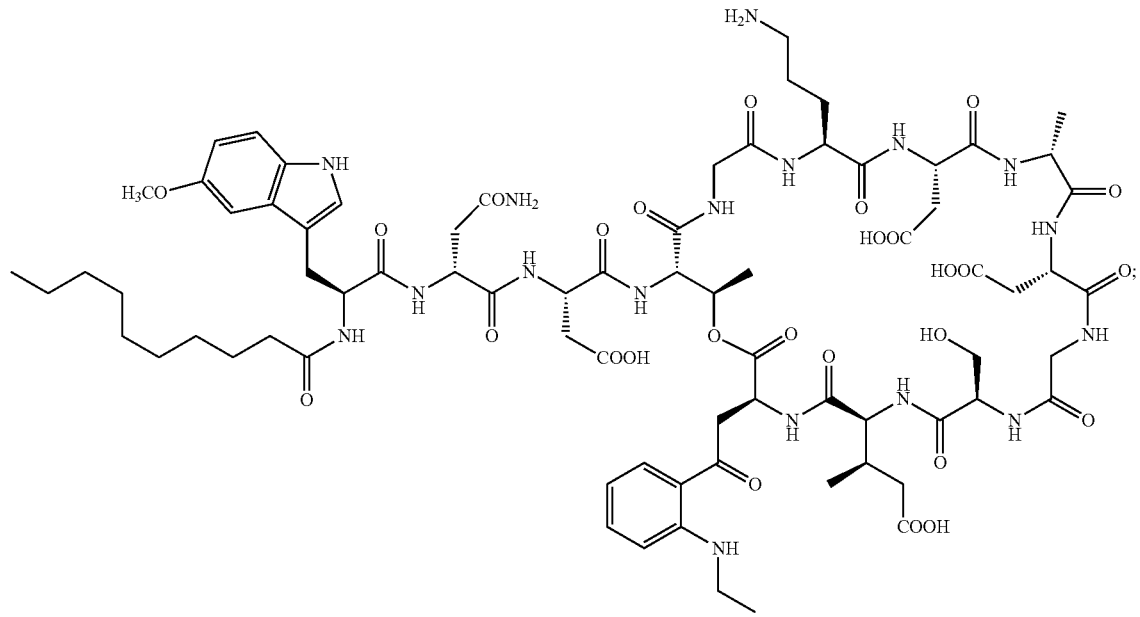
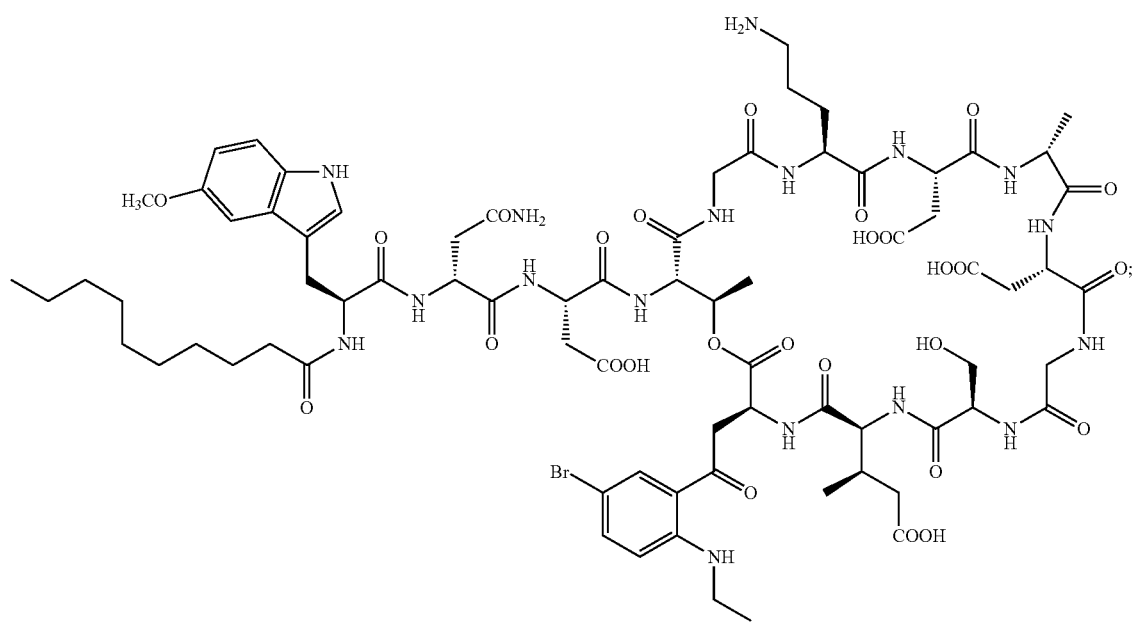

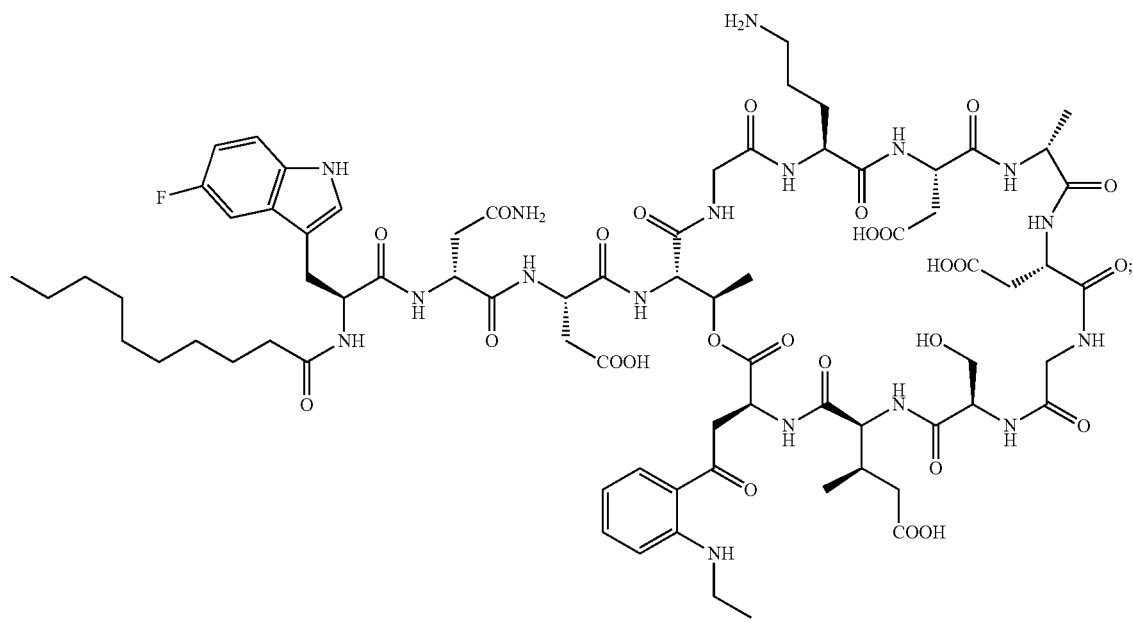
RP004
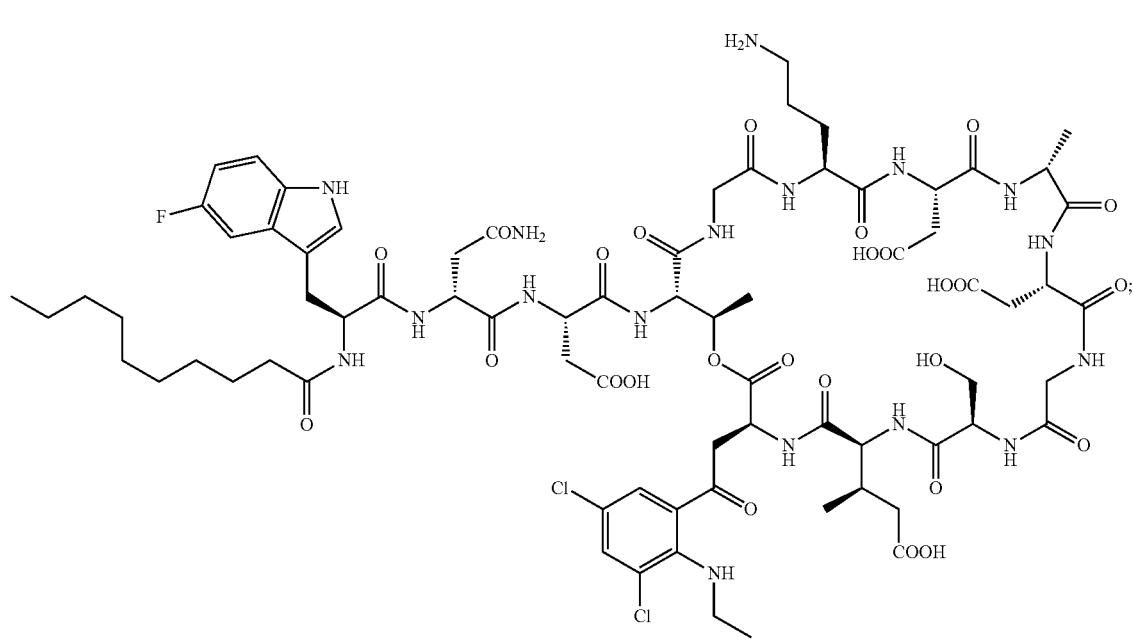
RP005

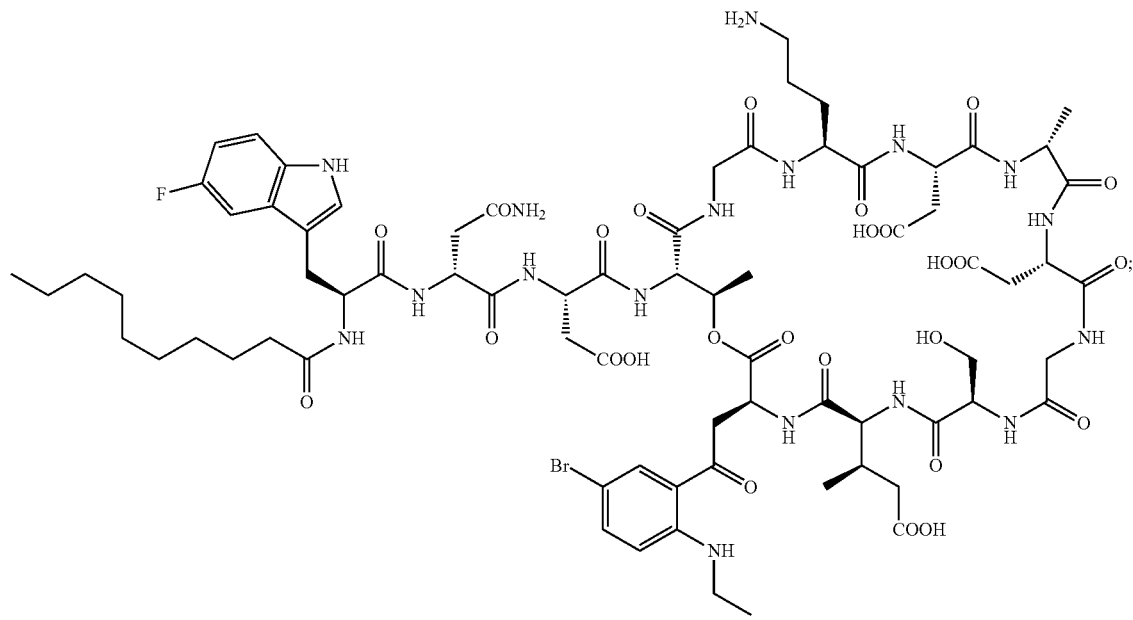
RP006
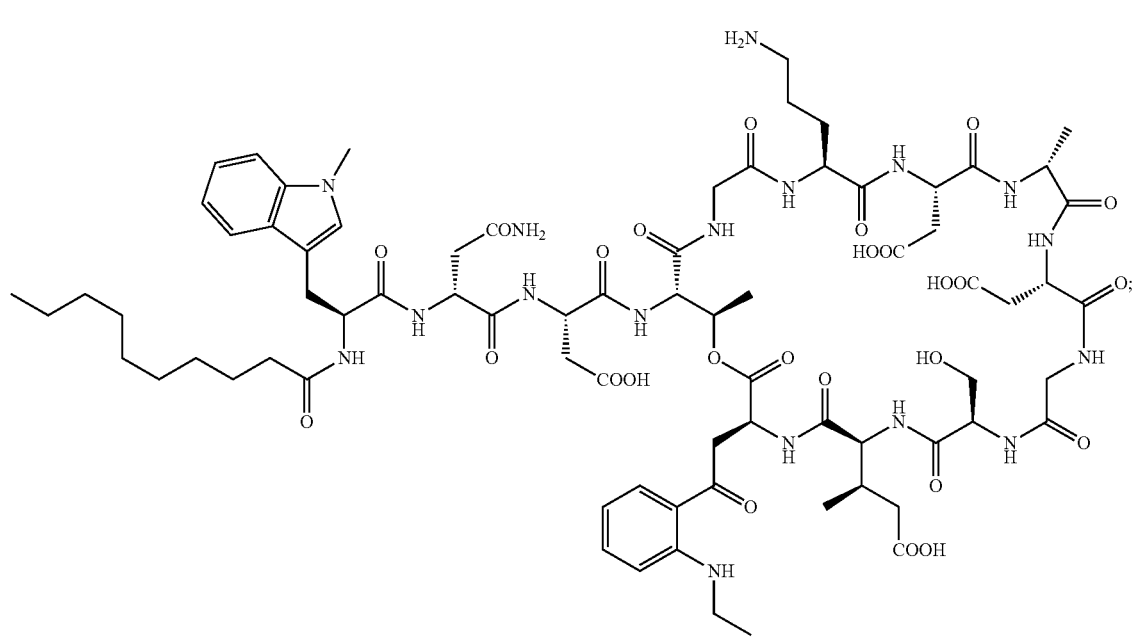
RP007

-continued
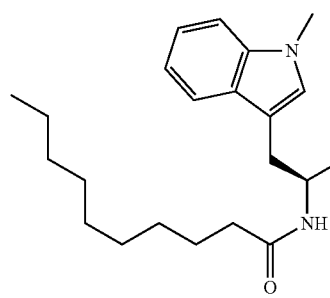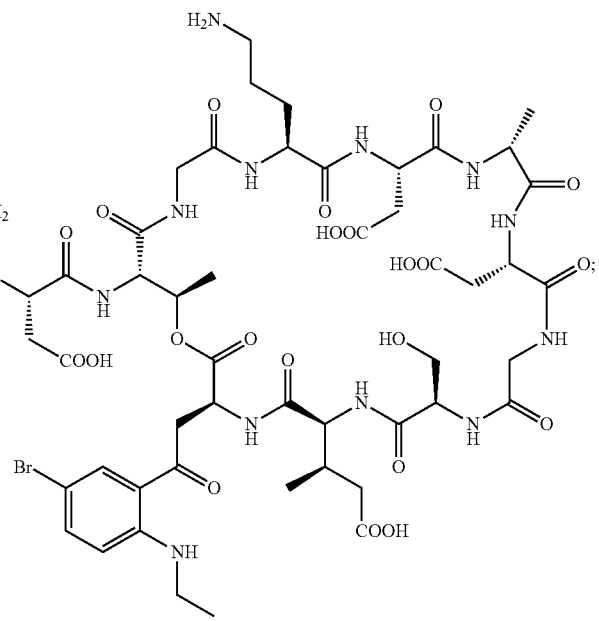
RP008
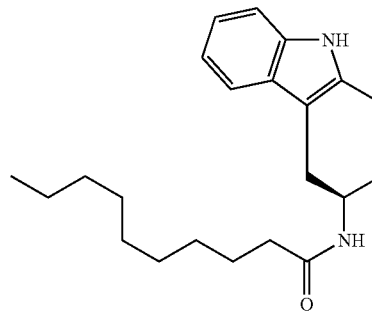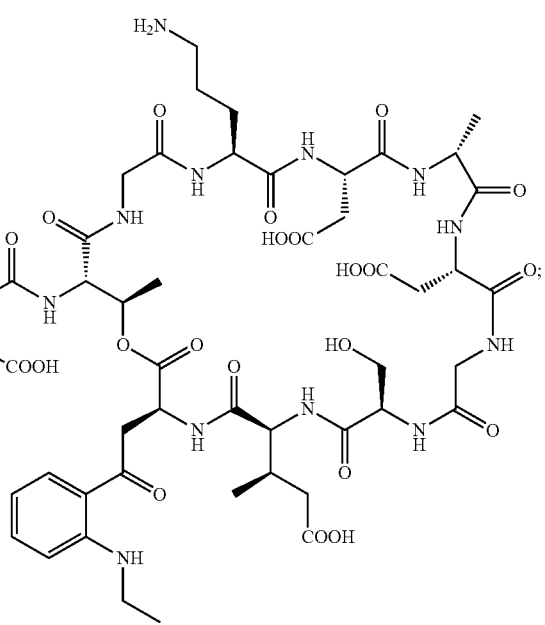
RP009

-continued
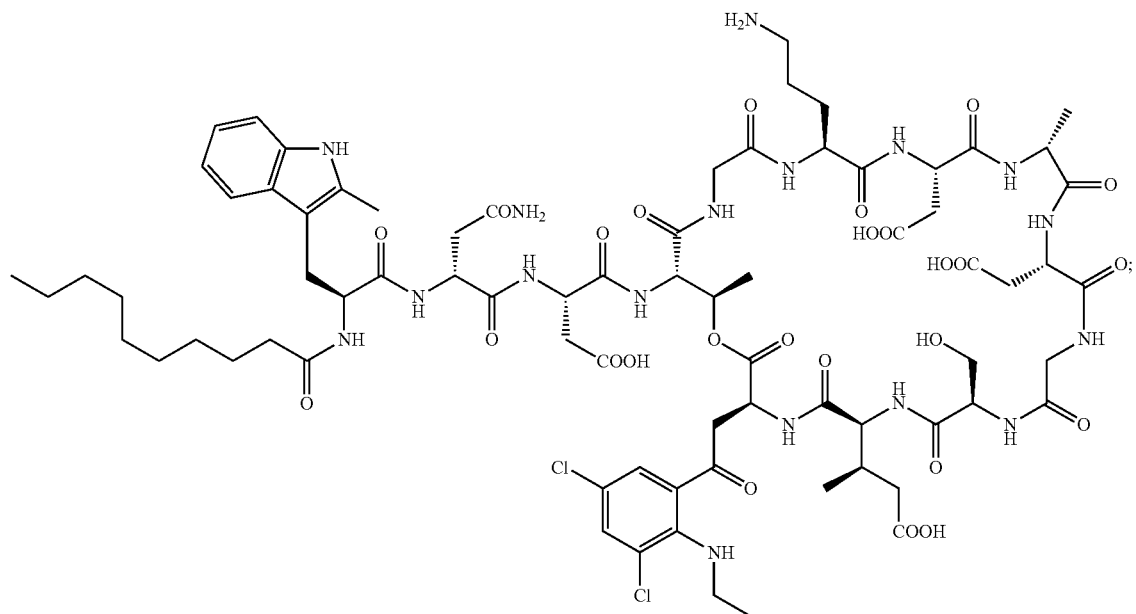
RP010
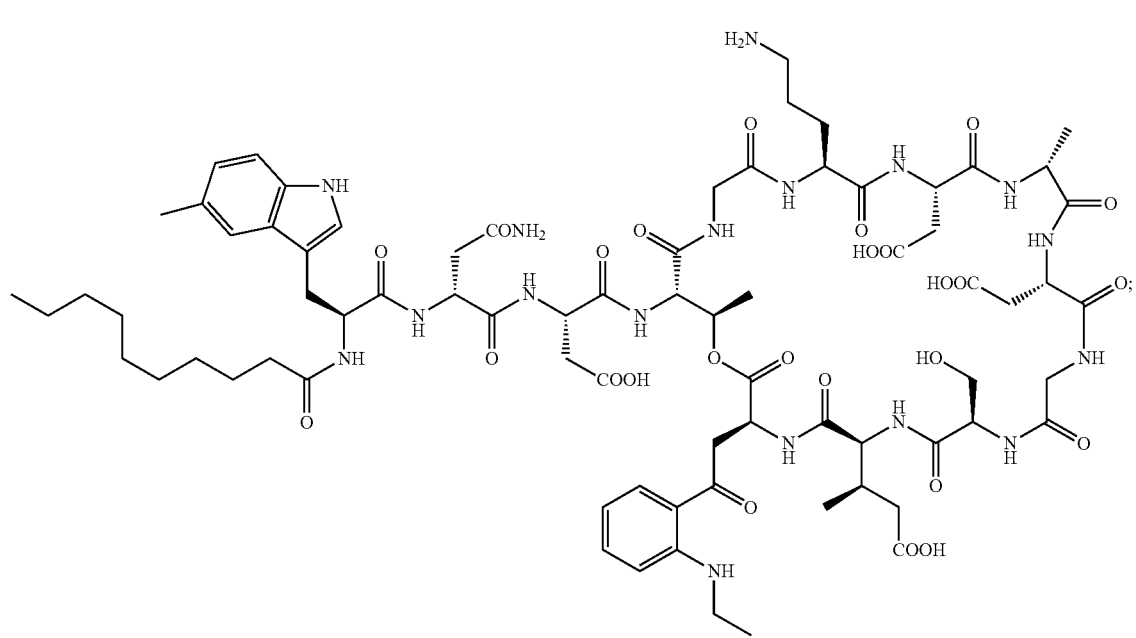
RP011

-continued
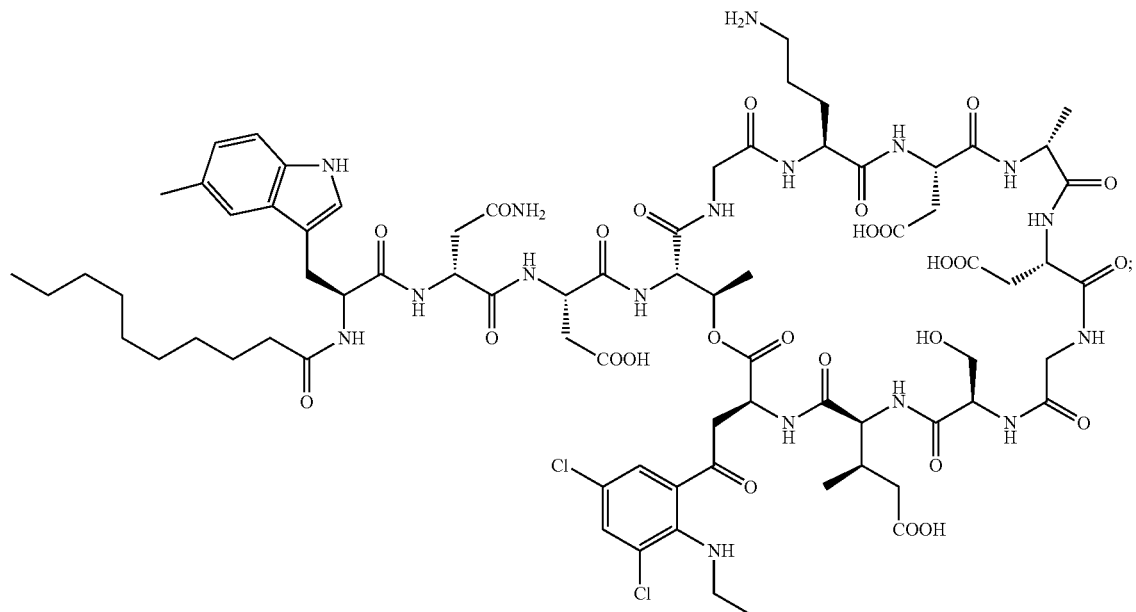
RP012
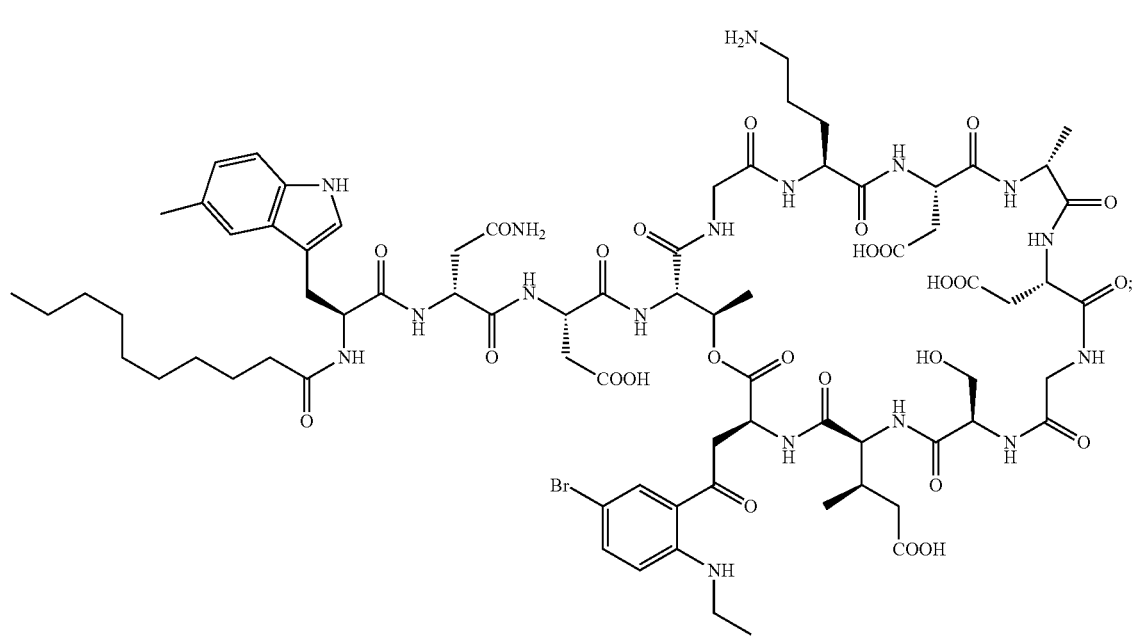
RP013

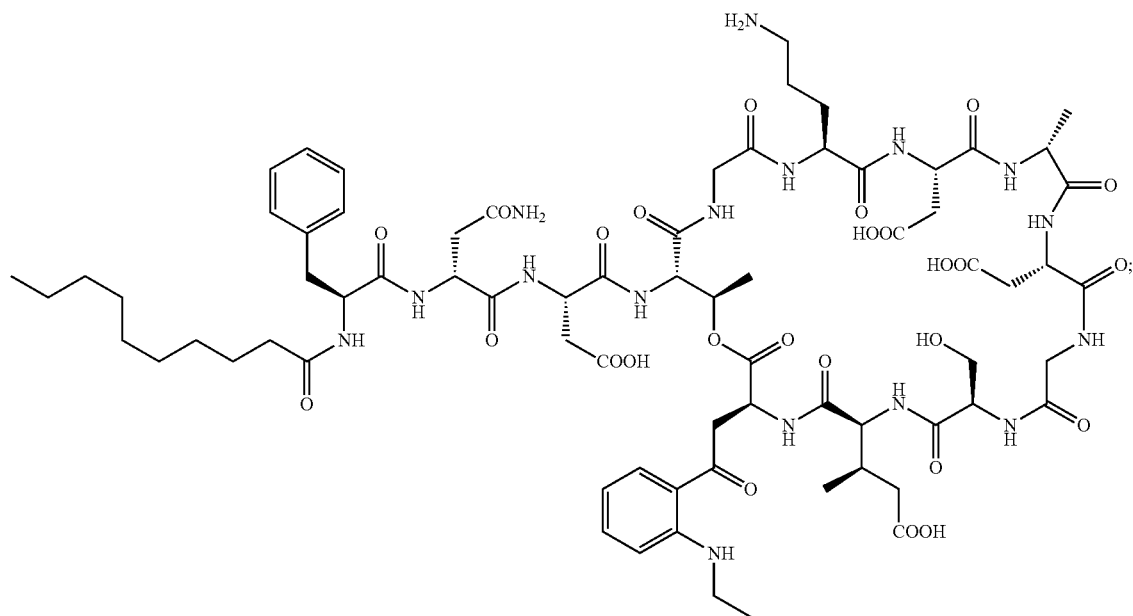
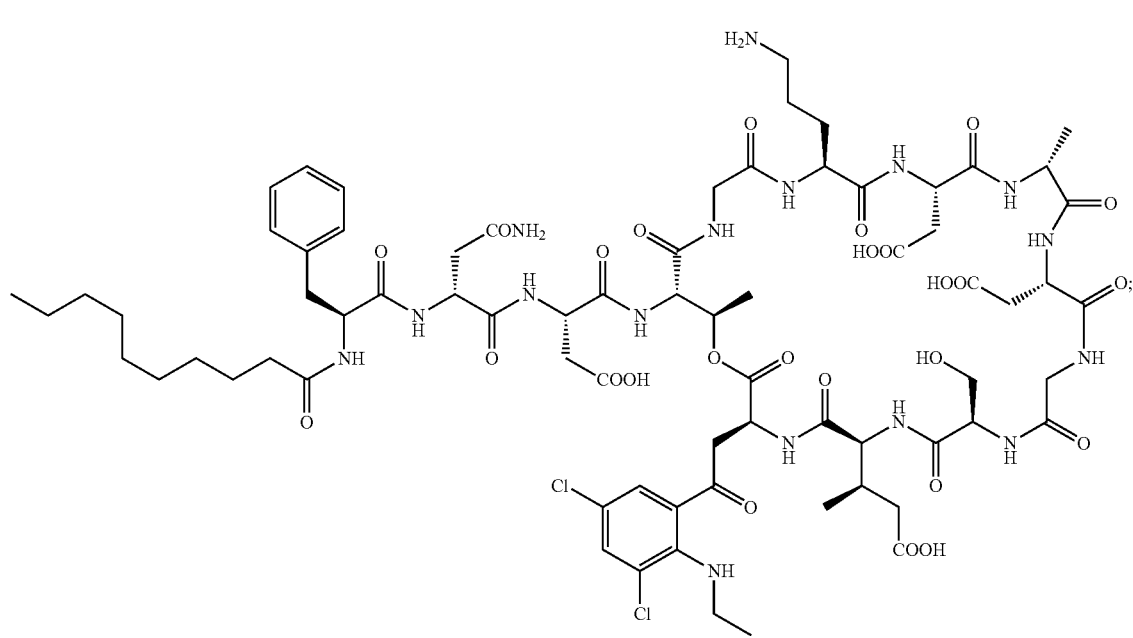

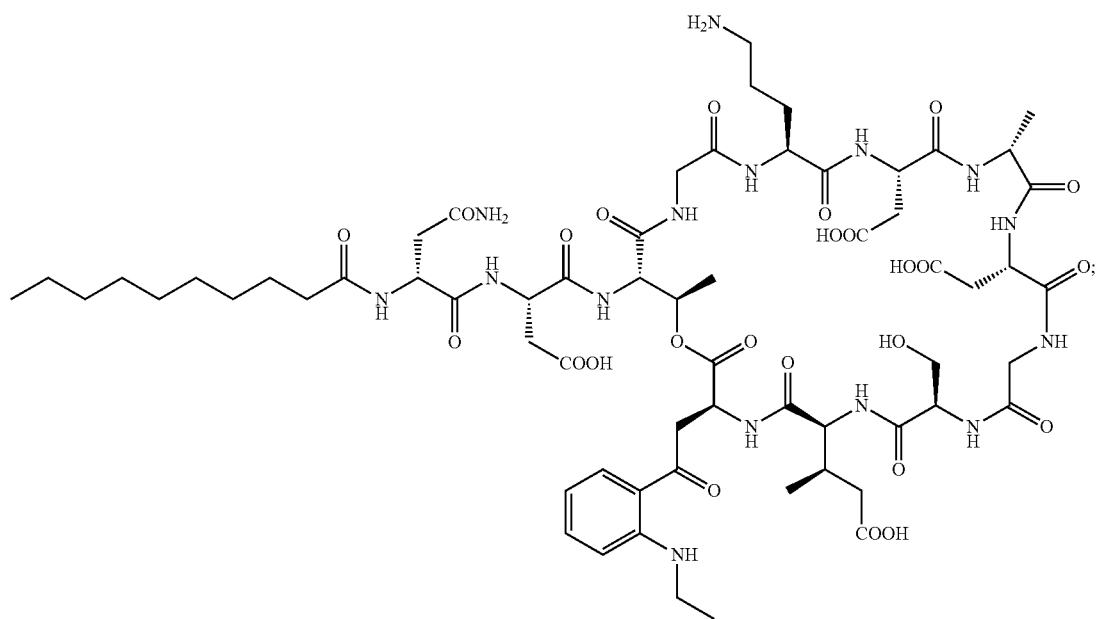
RP016
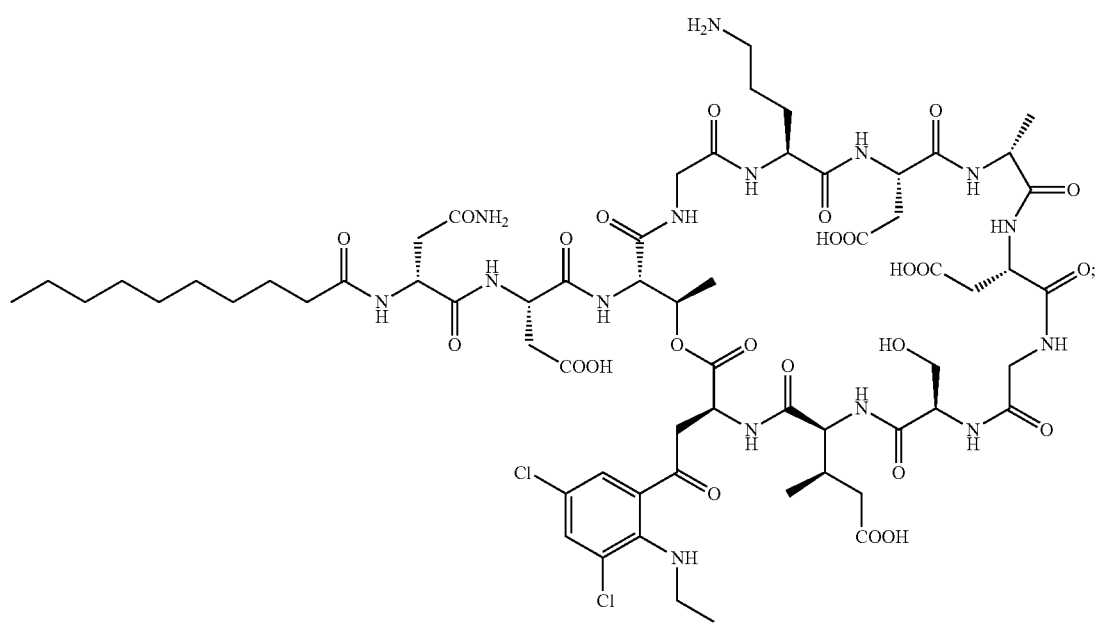
RP017

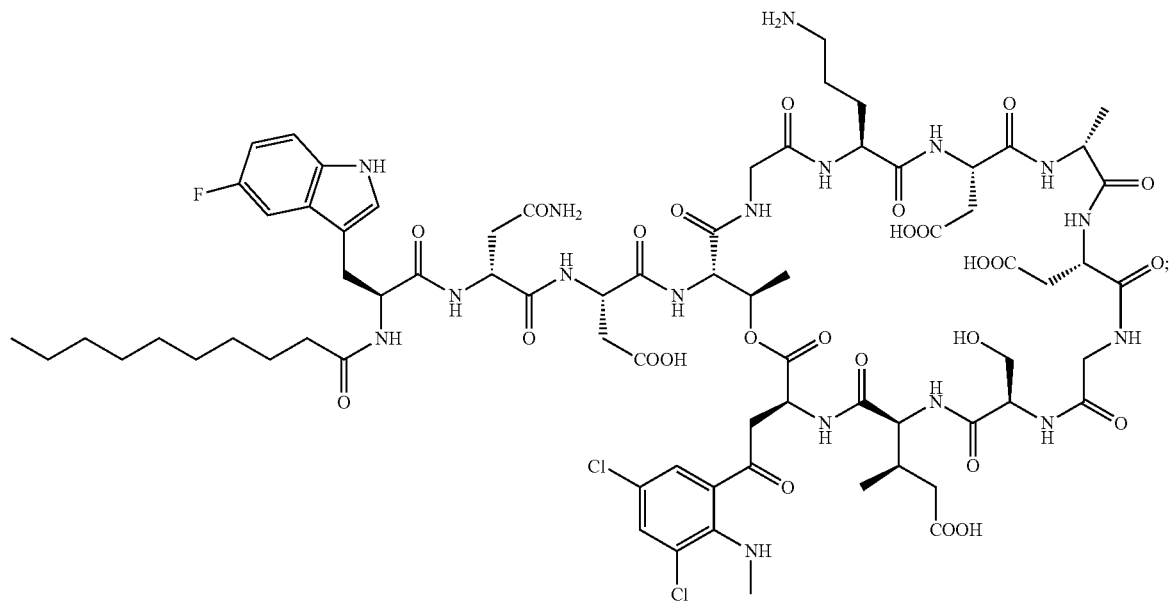
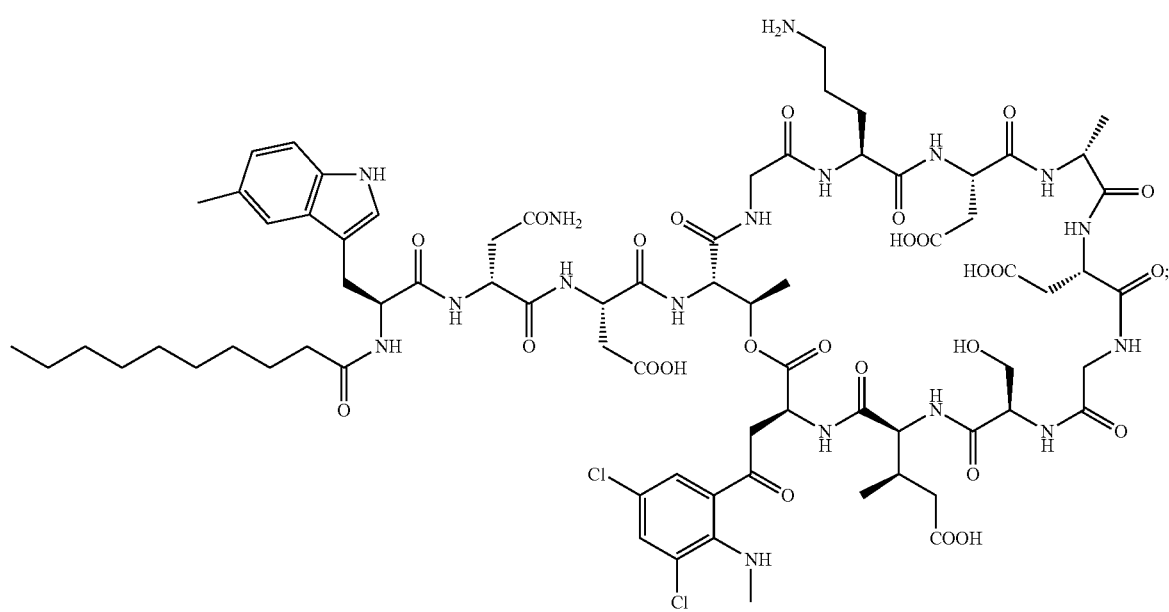

-continued
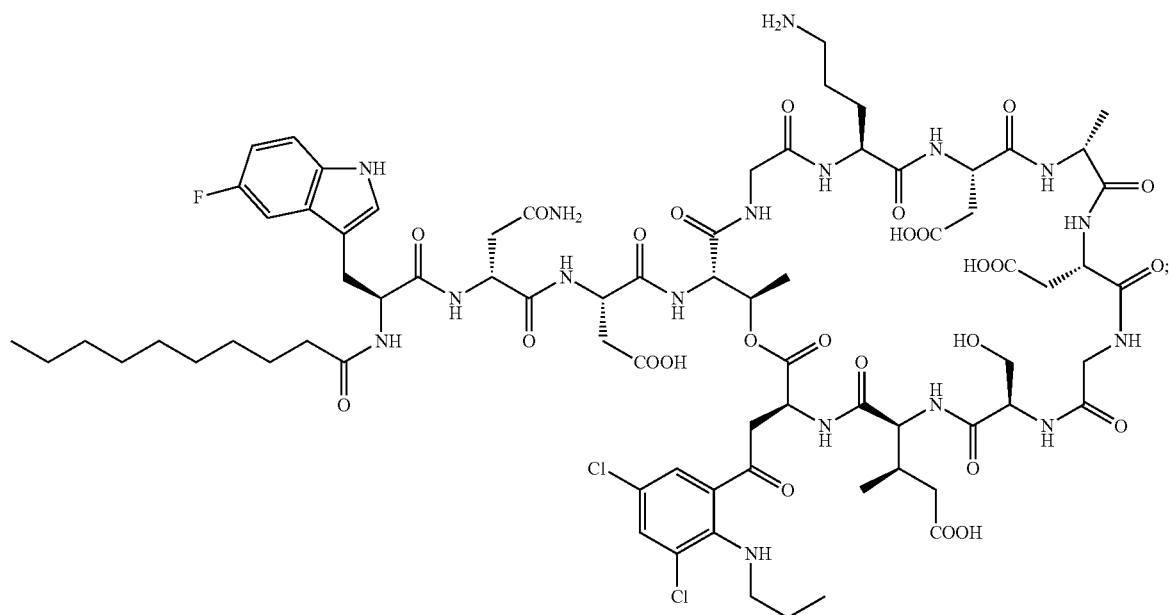
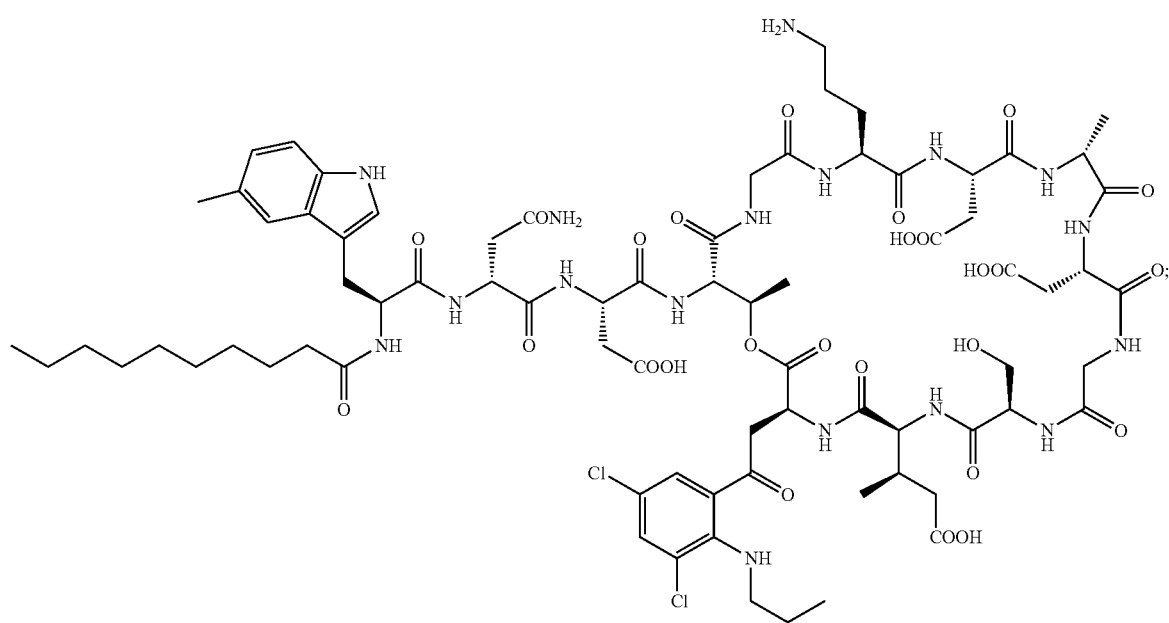

RP022

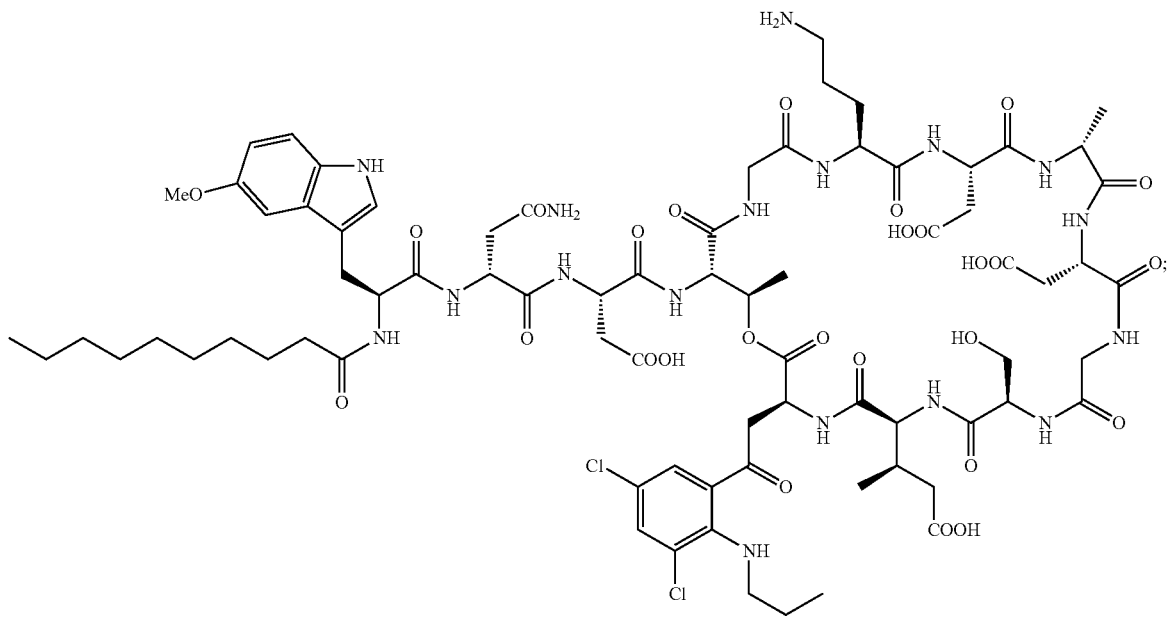

and pharmaceutically acceptable salts thereof.

In certain embodiments, pharmaceutical compositions are provided, which comprise compounds of Formula I, II or III or their pharmaceutically acceptable salts and prodrugs, and a pharmaceutically acceptable carrier.

In certain embodiments, pharmaceutical compositions are provided, which comprise a compound having antibacterial activity selected from the group consisting of compounds designated RP002, RP003, RP004, RP005, RP006, RP007, RP008, RP009, RP010, RP011, RP012, RP013, RP014, RP015, RP016, RP017, RP018, RP019, RP020, RP021 and RP022, having the formulas provided above or their pharmaceutically acceptable salts, and a pharmaceutically acceptable carrier.

In certain embodiments, methods of treating a mammal affected by bacterial infections are provided, which comprise administering an effective amount of the compound of Formula I, II or III, or its pharmaceutically acceptable salt or prodrug, to a mammal.

In one embodiment, the amount of the compound may be from 0.1 to 50 mg/kg per day.

In one embodiment, the compound may be administered in a single dose or multiple doses per day.

In certain embodiments, methods of treating a mammal affected by bacterial infections are provided, which comprise administering an effective amount of a compound having antibacterial activity selected from the group consisting of compounds designated RP002, RP003, RP004, RP005, RP006, RP007, RP008, RP009, RP010, RP011, RP012, RP013, RP014, RP015, RP016, RP017, RP018, RP019, RP020, RP021, and RP022, having the formulas provided above, or their pharmaceutically acceptable salts or prodrugs, to a mammal.

In one embodiment, the amount of the compound may be from 0.1 to 50 mg/kg per day.

In one embodiment, the compound may be administered in a single dose or multiple doses per day.

Definitions

The term "acyl" is defined as a carbonyl radical attached to an alkyl, alkenyl, alkynyl, cycloalkyl, heterocycyl, aryl or heteroaryl group, examples including, without limitation, such radicals as acetyl and benzoyl.

The term "heterocyclyl" as used herein represents a saturated 3 to 8 membered ring containing 1 to 3 heteroatoms selected from nitrogen, oxygen and sulfur. Representative examples are indolyl, pyrrolidyl, piperidyl, piperazinyl, morpholinyl, thiomorpholinyl, aziridinyl, tetrahydrofuranyl and the like.

One or more hydrogen atoms may also be replaced by a substituent group selected from acyl, amino, acylamino, acyloxy, oxo, thiocarbonyl, imino, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl.

The term "aryl" as used herein the term aryl as a group or part of a group, e.g., aralkyl, aroyl, means an aromatic moiety having 6, 10 or 14 carbon atoms, preferably 6 to 10 carbon atoms, which can be optionally substituted with 1 to 3 substituents independently selected from halogen, nitro, cyano, alkenyl, hydroxyl, alkyl, haloalkyl, alkoxy, benzyloxy, amino, alkylamino, dialkylamino, carboxyl, alkoxycarbonyl, methylenedioxy and phenyl. In particular, aryl is phenyl or naphthyl optionally substituted with 1 to 3 substituents.

The term "amino" denotes a nitrogen radical containing two substituents independently selected from the group consisting of hydrido, alkyl, cycloalkyl, carboalkoxy, heterocyclyl, aryl, heteroaryl and sulfonyl. Subsets of the term amino are (1) the term "unsubstituted amino" which denotes an NH.sub.2 radical, (2) the term "mono substituted amino" which is defined as a nitrogen radical containing a hydrido group and a substituent group selected from alkyl, cycloalkyl, heterocyclyl, aryl, or heteroaryl, and (3) the term "disubstituted amino" which is defined as a nitrogen radical containing two substituent groups independently selected from, alkyl, cycloalkyl, heterocyclyl, aryl, and heteroaryl. Preferred mono substituted amino radicals are "lower mono substituted amino" radicals, whereby the substituent group is a lower alkyl group. Preferred disubstituted amino radicals are "lower disubstituted amino" radicals, whereby the substituent groups are lower alkyl.

The term "acyloxy" denotes an oxygen radical adjacent to an acyl group.

The term "acylamino" denotes a nitrogen radical adjacent to an acyl group.

The term "carboalkoxy" is defined as a carbonyl radical adjacent to an alkoxy or aryloxy group.

The term "carboxyamido" denotes a carbonyl radical adjacent to an amino group.

The term "halo" or "halogen" is defined as a bromo, chloro, fluoro or iodo radical.

The term "thio" denotes a radical containing a substituent group independently selected from hydrido, alkyl, cycloalkyl, heterocyclyl, aryl and heteroaryl, attached to a divalent sulfur atom, such as, methylthio and phenylthio.

The term "alkyl" is defined as a linear or branched, saturated radical having one to about twenty carbon atoms unless otherwise specified. Preferred alkyl radicals are "lower alkyl" radicals having one to about five carbon atoms. One or more hydrogen atoms can also be replaced by a substitutent group selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, indolyl, heteroaryl, alkoxy, aryloxy, sulfinyl, sulfonyl, oxo, guanidino, formyl and an amino acid side chain. Examples of alkyl groups include, without limitation, methyl, tertbutyl, isopropyl, and methoxymethyl. Subsets of the term alkyl are (1) "unsubstituted alkyl" which is defined as an alkyl group that bears no substituent groups (2) "substituted alkyl" which denotes an alkyl radical in which (a) one or more hydrogen atoms is replaced by a substituent group selected from acyl, acyloxy, carboalkoxy, carboxy, carboxyamido, cyano, nitro, thio, alkyl, alkenyl, alkynyl, cycloalkyl, heterocyclyl, aryl, indolyl, heteroaryl, alkoxy, aryloxy, sulfinyl, sulfonyl, N-sulfonylcarboxyamido, N-acylaminosulfonyl or (b) two or more hydrogen atoms are each replaced by a substituent group independently selected from hydroxyl, carboxy, $C_1$-$C_3$ alkoxy, amino, acylamino, oxo or guanidino; and (3) the term "selected substituted alkyl" which denotes an alkyl radical in which (a) one proton is replaced by a group selected from hydroxyl, $C_1$-$C_3$ alkoxy, unsubstituted amino, acylamino, or acylamino phenyl or (b) one to three protons is replaced by a halo substituent.

The term "alkenyl" is defined as linear or branched radicals having two to about twenty carbon atoms, preferably three to about ten carbon atoms, and containing at least one carboncarbon double bond. One or more hydrogen atoms can also be replaced by a substituent group selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, formyl, oxo and guanidino. The double bond portion(s) of the unsaturated hydrocarbon chain may be either in the cis or trans configuration. Examples of alkenyl groups include, without limitation, ethylenyl or phenyl ethylenyl.

The term "alkynyl" denotes linear or branched radicals having from two to about ten carbon atoms, and containing at least one carbon-carbon triple bond. One or more hydrogen atoms can also be replaced by a substituent group selected from acyl, amino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, formyl, oxo and guanidino. An example of alkynyl group includes, without limitation, propynyl.

The term "aryl" or "aryl ring" denotes aromatic radicals in a single or fused carbocyclic ring system, having from five to fourteen ring members. In a preferred embodiment, the ring system has from six to ten ring members. One or more hydrogen atoms may also be replaced by a substituent group selected from acyl, amino, acylamino, acyloxy, azido, alkylthio, carboalkoxy, carboxy, carboxyamido, cyano, halogen, hydroxyl, nitro, thio, alkyl, alkenyl, alkynyl, cycloalkyl, heterocyclyl, aryl, heteroaryl, alkoxy, aryloxy, sulfinyl, sulfonyl and formyl. Examples of aryl groups include, without limitation, phenyl, naphthyl, biphenyl, terphenyl. Subsets of the term aryl are (1) the term "phenyl", and (2) the term "substituted phenyl" which is defined as a phenyl radical in which one or more protons are replaced by a substituent group selected from acyl, amino, acyloxy, azido, alkylthio, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, N-sulfonylcarboxyamido, and N-acylaminosulfonyl, and (3) the term "acylamino phenyl" denotes a phenyl radical in which one hydrogen atom is replaced by an acylamino group. One or more additional hydrogen atoms can also be replaced by a substituent group selected from acyl, amino, acylamino, acyloxy, azido, alkylthio, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, N-sulfonylcarboxyamido, and N-acylaminosulfonyl.

"Heteroaryl" or "heteroaryl ring" denotes an aromatic radical which contain one to four hetero atoms or hetero groups selected from O, N, S in a single or fused heterocyclic ring system, having from five to fifteen ring members. In a preferred embodiment, the heteroaryl ring system has from six to ten ring members, One or more hydrogen atoms may also be replaced by a substituent group selected from acyl, amino, acylamino, acyloxy, carboalkoxy, carboxy, carboxyamido, cyano, halo, hydroxyl, nitro, thio, thiocarbonyl, alkyl, alkenyl, alkynyl, cycloalkyl, heterocyclyl, aryl, heteroaryl, alkoxy, aryloxy, sulfinyl, sulfonyl, and formyl. Examples of heteroaryl groups include, without limitation, pyridinyl, thiazolyl, thiadiazoyl, isoquinolinyl, pyrazolyl, oxazolyl, oxadiazoyl, triazolyl, pyrrolyl, and indolylmethyl groups. Subsets of the term heteroaryl are (1) the term "pyridinyl" and (2) the term "substituted pyridinyl" which is defined as a pyridinyl radical in which one or more protons is replaced by a substituent group selected from acyl, amino, acyloxy, carboalkoxy, carboxy, carboxyamido, cyano, halogen, hydroxyl, nitro, thio, alkyl, alkenyl, alkynyl, cycloalkyl, heterocyclyl, aryl, heteroaryl, alkoxy, aryloxy, sulfinyl, sulfonyl, N-sulfonylcarboxyamido, and N-acylaminosulfonyl and (3) the term "acylamino pyridinyl" which denotes a pyridinyl radical in which one hydrogen atom is replaced by an acylamino group, additionally, one or more additional hydrogen atoms can also be replaced by a substituent group selected from acyl, amino, acylamino, acyloxy, carboalkoxy, carboxy, carboxyamido, cyano, halogen, hydroxyl, nitro, thio, thiocarbonyl, alkyl, alkenyl, alkynyl, cycloalkyl, heterocyclyl, aryl, heteroaryl, alkoxy, aryloxy, sulfinyl, sulfonyl, N-sulfonylcarboxyamido, and N-acylaminosulfonyl.

The term "cycloalkyl" or "cycloalkyl ring" is defined as a saturated or partially unsaturated carbocyclic ring in a single or fused carbocyclic ring system having from three to twelve ring members. In a preferred embodiment, a cycloalkyl is a ring system having three to eight ring members. One or more hydrogen atoms may also be replaced by a substituent group selected from acyl, amino, acylamino, acyloxy, carboalkoxy, carboxy, carboxyamido, cyano, halogen, hydroxyl, nitro, thio, alkyl, alkenyl, alkynyl, cycloalkyl, heterocyclyl, aryl, heteroaryl, alkoxy, aryloxy, sulfinyl, sulfonyl and formyl. Examples of a cycloalkyl group include, without limitation, cyclopropyl, cyclobutyl, cyclohexyl, and cycloheptyl.

The term "cycloalkenyl" is defined as an unsaturated or partially unsaturated carbocyclic ring in a single or fused carbocyclic ring system having from three to twelve ring members. In a preferred embodiment, a cycloalkenyl is a ring system having three to eight ring members and containing at least one carboncarbon double bond. One or more hydrogen atoms may also be replaced by a substituent group selected from acyl, amino, acylamino, acyloxy, carboalkoxy, carboxy, carboxyamido, cyano, halogen, hydroxyl, nitro, thio, alkyl, alkenyl, alkynyl, cycloalkyl, heterocyclyl, aryl, heteroaryl, alkoxy, aryloxy, sulfinyl, sulfonyl and formyl. Examples of a cycloalkyl group include, without limitation, cyclopentenyl, cyclohexenyl, and cycloheptenyl.

The term "heterocyclyl," "heterocyclic" or "heterocyclyl ring" is defined as a saturated or partially unsaturated ring containing one to four hetero atoms or hetero groups selected from O, N, NH, in a single or fused heterocyclic ring system having from three to twelve ring members. In a preferred embodiment, a heterocyclyl is a ring system having three to seven ring members One or more hydrogen atoms may also be replaced by a substituent group selected from acyl, amino, acylamino, acyloxy, oxo, thiocarbonyl, imino, carboalkoxy, carboxy, carboxyamido, cyano, halogen, hydroxyl, nitro, thio, alkyl, alkenyl, alkynyl, cycloalkyl, heterocyclyl, aryl, heteroaryl, alkoxy, aryloxy, sulfinyl, sulfonyl and formyl Examples of a heterocyclyl group include, without limitation, morpholinyl, piperidinyl, and pyrrolidinyl.

The term "alkoxy" denotes oxy-containing radicals substituted with an alkyl, cycloalkyl or heterocyclyl group. Examples include, without limitation, methoxy, tert-butoxy, benzyloxy and cyclohexyloxy.

The term "aryloxy" denotes oxy containing radicals substituted with an aryl or heteroaryl group. Examples include, without limitation, phenoxy.

The term "amino acid side chain" denotes any side chain (R group) from a naturally-occurring or a non-naturally occurring amino acid.

The term "sulfinyl" is defined as a tetravalent sulfur radical substituted with an oxo substituent and a second substituent selected from the group consisting of alkyl, cycloalkyl, heterocyclyl, aryl, or heteroaryl group.

The term "sulfonyl" is defined as a hexavalent sulfur radical substituted with two oxo substituents and a third substituent selected from alkyl, cycloalkyl, heterocyclyl aryl, or heteroaryl.

The term "carbamate amino protecting group" is defined as a recognized amino protecting group that when bound to an amino group forms a carbamate. Examples of carbamate amino protecting groups can be found in "Protective Groups in Organic Synthesis" by Theodora W. Greene, John Wiley and Sons, New York, 1981. Examples of carbamate amino protecting groups include benzyloxycarbonyl, tert-butoxycarbonyl, tert-amyloxycarbonyl, isobornyloxycarbonyl, adamantyloxycarbonyl, chlorobenzyloxycarbonyl, nitrobenzyloxycarbonyl or the like.

The term "pharmaceutically acceptable salt" refers to any salt(s) of a compound provided herein which retains its biological properties and which is not toxic or otherwise undesirable for pharmaceutical use. Such salts may be derived from a variety of organic and inorganic counter-ions well known in the art.

The term "prodrug" refers to a derivative of an active ingredient, compound or drug that, after administration to a subject, is converted biochemically or chemically into the active ingredient, compound or pharmaceutically active drug.

The terms "compound", "agent" and "drug" are interchangeable.

The phrases "pharmaceutically acceptable" or "pharmacologically acceptable" refer to molecular entities and compositions that do not produce an adverse, toxic, allergic, inflammatory, or other untoward reaction when administered to an animal, or human. As used herein, "pharmaceutically acceptable carrier" includes any and all solvents, dispersion media, coatings, antibacterial and antifungal agents, isotonic and absorption delaying agents, and the like that are pharmaceutically acceptable as the term is used herein and preferably inert. The use of such media and agents for pharmaceutical active substances is well known in the art. Except insofar as any conventional media or agent is incompatible with the active ingredients, its use in therapeutic compositions is contemplated.

The term "an effective amount" refers to the amount of an agent, composition or drug that is sufficient to effect beneficial or desired results.

The term "prophylactically effective amount" refers to an amount of an agent, composition or drug effective, at dosages and for periods of time necessary, to achieve the desired prophylactic result.

In certain embodiments, since a prophylactic dose is used in subjects prior to or at an earlier stage of a disorder, the prophylactically effective amount is less than the therapeutically effective amount. In certain embodiments, the prophylactically effective amount is similar to, identical to, or more than, a therapeutically effective amount.

The term "therapeutically effective amount" refers to an amount of of an agent, composition or drug sufficient to treat a specified disorder or disease or alternatively to obtain a pharmacological response treating a disorder or disease. Methods of determining the most effective means and dosage of administration can vary with the composition used for therapy, the purpose of the therapy, the target cell being treated, and the subject being treated. Treatment dosages generally may be titrated to optimize safety and efficacy. Single or multiple administrations can be carried out with the dose level and pattern being selected by the treating physician. When the compounds described herein are co-administered with another agent or therapy, the effective amount may be less than when the agent is used alone. Suitable dosage formulations and methods of administering the agents can be readily determined by those of skill in the art. For example, a compound described herein may be administered in an amount from 0.1 to 50 mg/kg per day. A therapeutically effective amount may vary depending on the compound, the disorder and its severity and the age, weight, physical condition and responsiveness of the subject to be treated.

The term "treating" or "treatment" of a state, disorder or condition includes: (1) preventing or delaying the appearance of clinical symptoms of the state, disorder, or condition developing in a person who may be afflicted with or predisposed to the state, disorder or condition but does not yet experience or display clinical symptoms of the state, disorder or condition; or (2) inhibiting the state, disorder or condition, i.e., arresting, reducing or delaying the development of the disease or a relapse thereof (in case of maintenance treatment) or at least one clinical symptom, sign, or test, thereof; or (3) relieving the disease, i.e., causing regression of the state, disorder or condition or at least one of its clinical or sub-clinical symptoms or signs.

The term "synergistic effect" refers to the interaction between two or more components or chemicals when the combined effect is larger than the sum of the effects of the individual components.

The term "treating" or "treatment" of a disorder refers, in one embodiment, to ameliorating the symptoms from the disorder that exists in a subject. In another embodiment, "treating" or "treatment" includes ameliorating at least one physical parameter, which may be indiscernible by the subject.

The benefit to a subject to be treated is either statistically significant or at least perceptible to the patient or to the physician.

The term "about" refers to ±0.5 for a numerical value.

DETAILED DESCRIPTION

In the following detailed description, numerous specific details are set forth to provide a thorough understanding of claimed subject matter. However, it will be understood by those skilled in the art that claimed subject matter may be practiced without these specific details. In other instances, methods, apparatuses, or systems that would be known by one of ordinary skill have not been described in detail so as not to obscure claimed subject matter. It is to be understood that particular features, structures, or characteristics described may be combined in various ways in one or more implementations.

The present disclosure is directed to novel antibacterial lipopeptides that exhibit antibiotic activity against a spectrum of organisms including those resistant to vancomycin, penicillin and methicillin, pharmaceutical compositions, and methods for their preparation and use.

Earlier work on the semisynthesis of daptomycin has been reported in the literature. In the past, a large number of natural and unnatural acyl groups were used to replace the decanoyl chain at the N-terminus of the daptomycin peptide, with some of these prior synthesized analogs showing better potencies against *S. aureus* than daptomycin. See, Hill et al, U.S. Pat. No. 6,911,525 and Metcalf, III et al., U.S. Pat. No. 8,507,647. In Leese et al., U.S. Pat. No. 6,767,718, the tryptophan residue, the amino acid unit where the acyl chain is attached to, was replaced by several other amino acids while the remaining part of the daptomycin molecule was kept intact, resulting the generation of analogs showing antibacterial potency comparable to daptomycin.

The modification of the daptomycin structure in the present invention adopts a different approach from past modifications to the daptomycin structure. Two important differences from prior approaches are (1) the tryptophan unit in daptomycin is replaced by a substituted tryptophan moiety for the first time, and (2) the structural modifications of the tryptophan residue on the sidechain and the aniline group on the cyclic peptide core are carried out simultaneously. The semisynthetic compounds thus generated significantly enhance the antibacterial activity against methicillin-resistant *S. aureus* (MRSA) and especially Enterococci, including vancomycin-resistant Enterococci (VRE).

Methods for preparing the novel antibacterial lipopeptides of the present invention are described below.

Preparation of Intermediates, Inter-IA, Inter-IB, Inter-IC, Inter-IIA, Inter-IIB, Inter-IIC, Inter-IID, and Inter-IIE Inter-IA, Inter-IB, and Inter-IC may be prepared from daptomycin (1) by protecting the $NH_2$ group in orinithine residue with tert-butyloxycarbonyl protecting group (Boc) using di-tert-dicarbonate, $(Boc)_2O$, followed by reductive amination using reagents such as an aldehyde and sodium cyanoborohydride to alkylate the aniline $NH_2$ group. When each of ethanal, formaldehyde, and propanal is used in the reductive amination, the aniline $NH_2$ is respectively converted to a phNHEt, phNHMe, or phNHPr moiety (Scheme I).

Scheme I

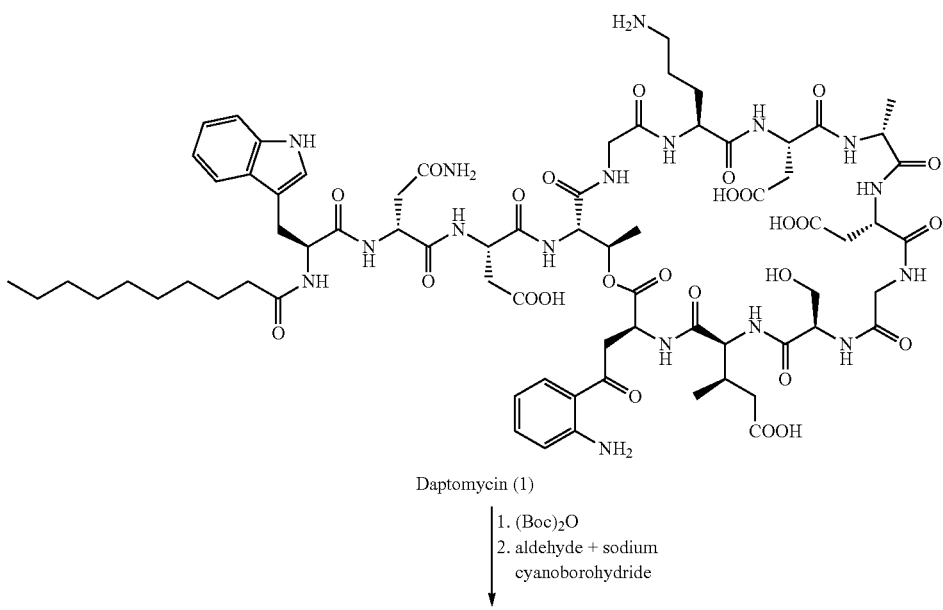

Daptomycin (1)

1. $(Boc)_2O$
2. aldehyde + sodium cyanoborohydride

-continued

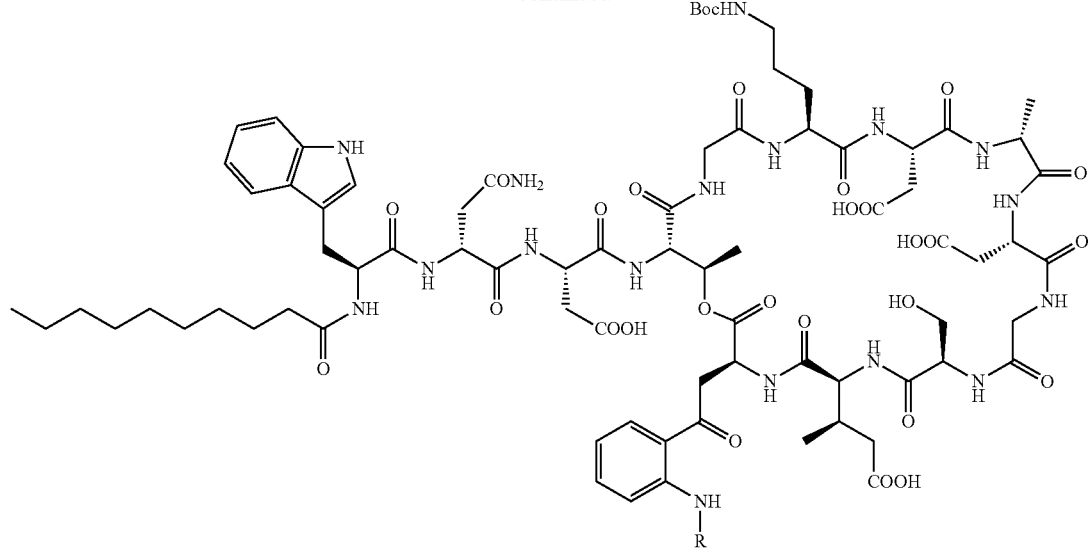

Inter-IA, R = CH₂CH₃ (ethanal is used)
Inter-IB, R = CH₃ (formaldehyde is used)
Inter-IC, R = CH₂CH₂CH₃ (propanal is used)

In the present disclosure, the synthesis of a daptomycin analog that contains an amino acid and acyl group different from the tryptophan and decanoyl group involves a selective cleavage of the amide bond at the C-terminus of the tryptophan residue in Inter-IA, Inter-IB, or Inter-IC, to yield a cyclic peptide of twelve amino acids, Inter-IIA, Inter-IIB, Inter-IIC, Inter-IID, or Inter-IIE under conditions illustrated by Schemes II and III. Each of the resulting products is then coupled to an N-acyl amino acid, Inter-IIIA, Inter-IIIB, Inter-IIIC, Inter-IIID, Inter-IIIE, and Inter-IIIF, followed by removal of the protective Boc group in the orinithine residue to afford the final analog (Scheme IV). See Example 5 for syntheses of these N-acyl amino acids.

There are a number of chemical methods documented in literature for selective cleavage of proteins and peptides, among which the oxidative cleavage of tryptophanyl peptide bonds with o-iodosobenzoic acid is more commonly used. See, Johnson, P.; Stockmal, V.; o-Iodosobenzoic acid: Peptide bond cleavage at tyrosine in addition to tryptophan residues, *Biochemical and Biophysical Research Communications,* 2016, 94 (2), 697-703. The mechanism has been studied and it is believed that the reaction proceeds by a two-step oxidation of the tryptophan residue followed by formation of an iminospirolactone which then hydrolyzes, resulting in the cleavage of the peptide chain. See, Mahoney, W. and Hermodson, M.; High-yield cleavage of tryptophanyl peptide bonds by o-iodosobenzoic acid, *Biochemistry,* 1979, 18 (17), 3810-3814.

The present disclosure describes a novel method to selectively cleave the tryptophanyl C-terminal amide bond for small peptides, daptomycin and its close analogs. Inter-IA, Inter-IB, or Inter-IC may be reacted with o-iodosobenzoic acid in combination with guanidinium monohydrochloride, commonly used as a denaturant in the cleavage of tryptophanyl peptide bond for proteins, to produce novel intermediates Inter-IIA, Inter-IIB or Inter-IIC. In these cases, the guanidinium monohydrochloride not only accelerates the cleavage of the amide bond but also serves as chlorination agent for the aniline group at para- and ortho-positions (Scheme II).

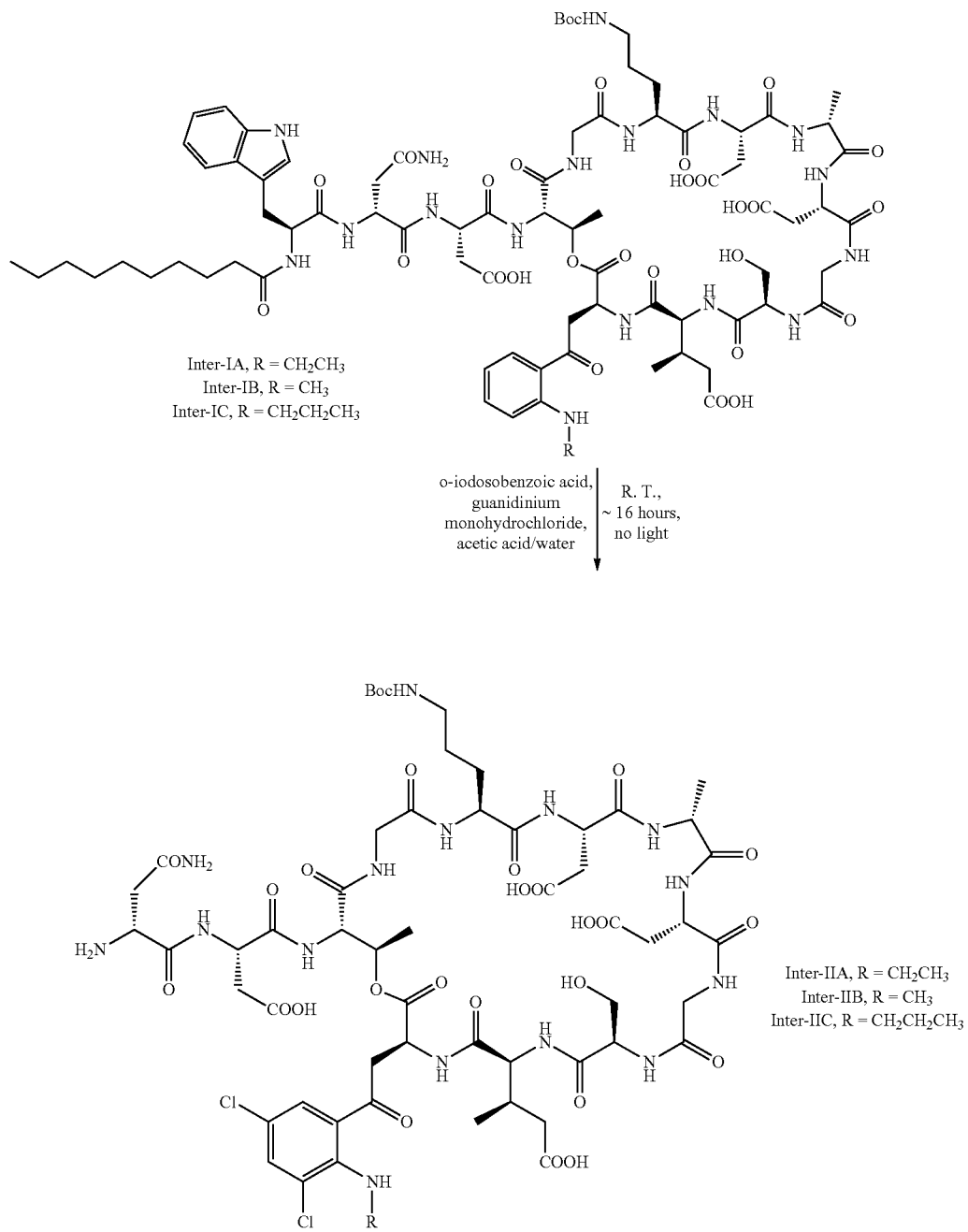

Scheme II

Inter-IA, R = CH₂CH₃
Inter-IB, R = CH₃
Inter-IC, R = CH₂CH₂CH₃ o-iodosobenzoic acid, guanidinium monohydrochloride, acetic acid/water
R. T., ~16 hours, no light Inter-IIA, R = CH₂CH₃
Inter-IIB, R = CH₃
Inter-IIC, R = CH₂CH₂CH₃

The reactions demonstrated in Scheme II may be carried out by a method containing sequential biochemical and chemical procedures. Here, the biochemical procedure employs a deacylase to hydrolyze the decanoyl group (Kreuzman, A J; Hodges, R L; Swartling, J R; Pohl, T E; Ghag, S K; Baker, P J; McGilvray D and Yeh, W K; Membrane-associated echinocandin B deacylase of *Actinoplanes utahensis*: purification, characterization, heterologous cloning and enzymatic deacylation reaction; *J. Industrial Microbiology & Biotechnology;* 2000, 24, 173-180). The chemical procedure uses o-iodosobenzoic acid with guanidinium monohydrochloride to cleave the tryptophanyl C-terminal amide bond and to chlorinate aniline moiety.

In addition, Inter-IID and Inter-IIE may be generated by treating Inter-IA with o-iodosobenzoic acid in combination with a denaturant guanidinium monofluoride or a mixture of denaturants, guanidinium monofluoride (excess quantity) and guanidine monobromide (~1-1.5 equivalence). In the former case, no fluorination at the aniline group was detected, and in the latter case the bromination mainly happens at the para-position to produce a major product Inter-IIE, though a small quantity of bis-bromination product was also detected (LCMS). The reactions are demonstrated in Scheme III.

Scheme III

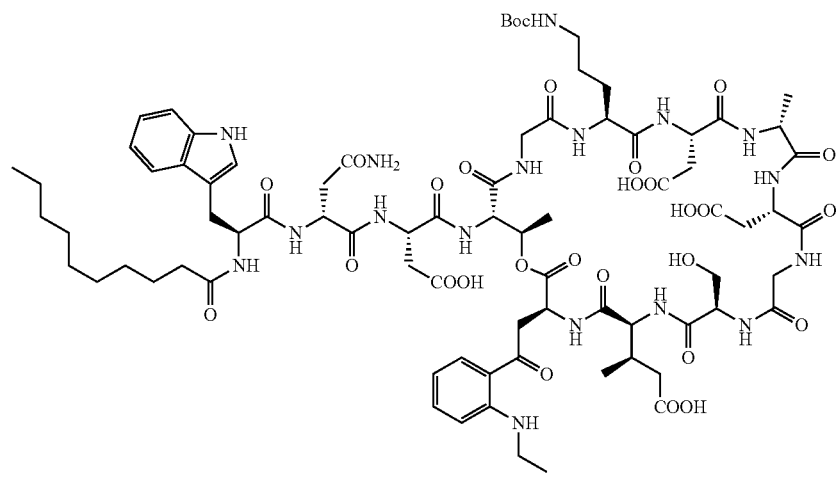

Inter-IA o-iodosobenzoic acid,
guanidinium salt(s),
acetic acid/water
R. T.,
no light

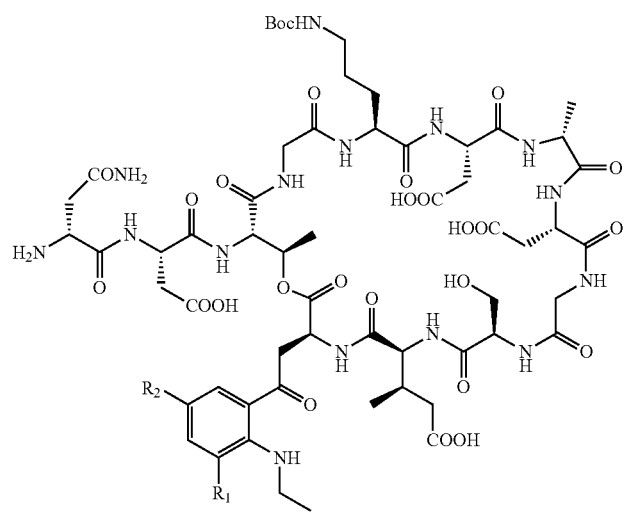

Inter-IID R$_1$ = R$_2$ = H
(guanidinium monohydrofluoride, excess, is used)
Inter-IIE R$_1$ = H, R$_2$ = Br
(guanidinium monohydrofluoride, excess + guanidinium monohydrobromide, ~ 1-1.5 eq are used)

The reactions demonstrated in Scheme III may also be carried out by a method containing sequential biochemical and chemical procedures.

Preparation of Novel Daptomycin Analogs

Preparation of the novel daptomycin analogs may be achieved by direct coupling of an N-acyl-amino acid derivative, such as Inter-IIIB (Example 5) with either Inter-IIA, Inter-IIB, or Inter-IIC in the presence of a coupling agent such as 1-[Bis(dimethylamino)methylene]-1H-1,2,3-triazolo[4,5-b]pyridinium 3-oxide hexafluorophosphate (HATU) and a weak base N,N-diisopropyl ethylamine (Hunig base) or 2,4,6-trimethylpyridine (TMP), followed by removal of the protective Boc group by trifluoroacetic acid (TFA) in dicholomethane (DCM). These reactions are exemplified by Scheme IV, where (S)-2-decanamido-3-(5-fluoro-H-indol-3-yl)propanoic acid (Inter-IIIB) is respectively coupled with Inter-IIA, Inter-IIB, Inter-IIC, Inter-IID, and Inter-IIE, followed by deprotection of Boc in TFA to form compounds RP005, RP018, RP021, RP006, and RP004.

Scheme IV
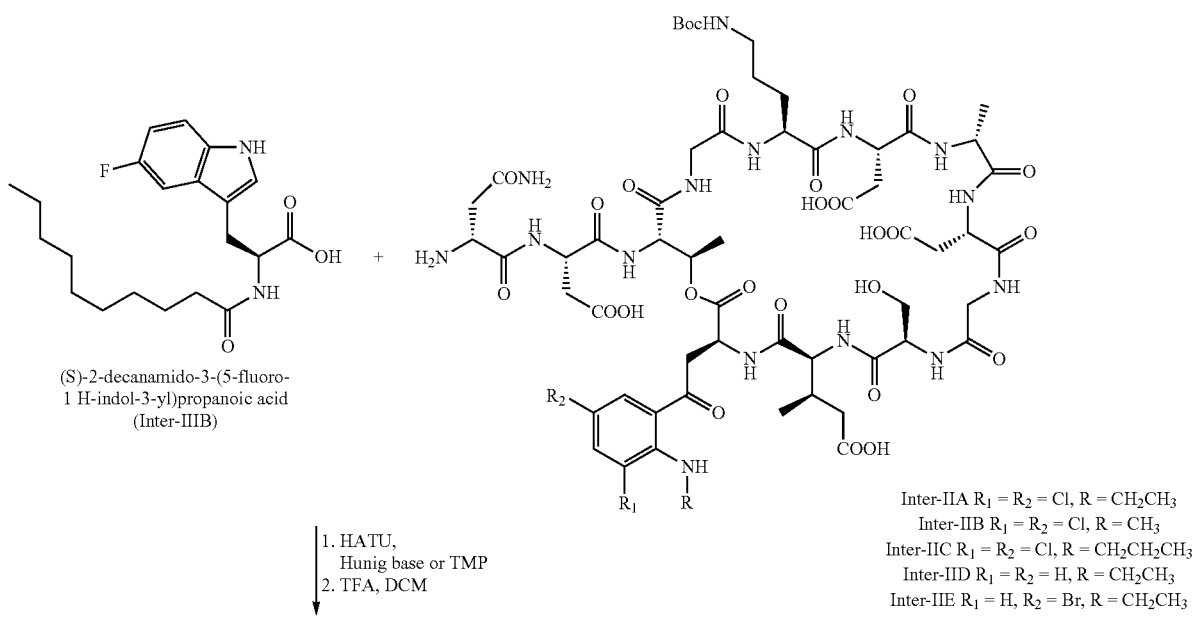
(S)-2-decanamido-3-(5-fluoro-
1H-indol-3-yl)propanoic acid
(Inter-IIIB)
Inter-IIA R₁ = R₂ = Cl, R = CH₂CH₃
Inter-IIB R₁ = R₂ = Cl, R = CH₃
Inter-IIC R₁ = R₂ = Cl, R = CH₂CH₂CH₃
Inter-IID R₁ = R₂ = H, R = CH₂CH₃
Inter-IIE R₁ = H, R₂ = Br, R = CH₂CH₃
1. HATU, Hunig base or TMP
2. TFA, DCM
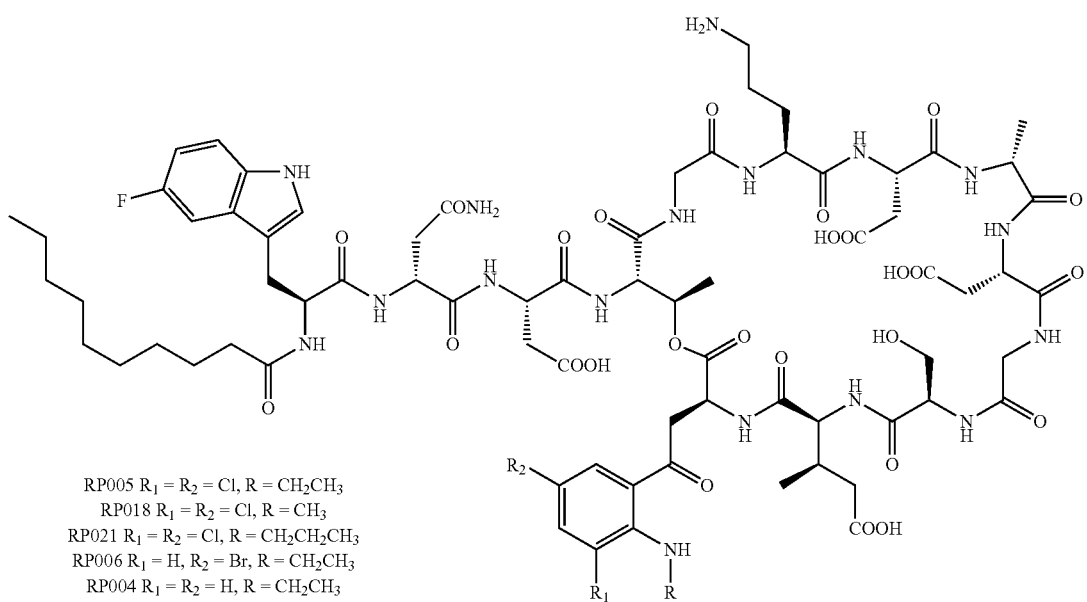
RP005 R₁ = R₂ = Cl, R = CH₂CH₃
RP018 R₁ = R₂ = Cl, R = CH₃
RP021 R₁ = R₂ = Cl, R = CH₂CH₂CH₃
RP006 R₁ = H, R₂ = Br, R = CH₂CH₃
RP004 R₁ = R₂ = H, R = CH₂CH₃

Procedures illustrated in schemes I, II, III, and IV have been shown to be scalable.

Table I lists the novel daptomycin analogs prepared according to above procedures and those similar to IV, in which Inter-IIIB is replaced with Inter-IIIA, Inter-IIIC, Inter-IIID, Inter-IIIE, Inter-IIIF, or decanoic acid.

TABLE I

Novel Daptomycin Analogs.

| ID | Substituents | MW |
|---|---|---|
| RP001-RP013 and RP018-RP022 | (structure shown) | |
| RP001 | $R_1 = CH_2CH_3, R_2 = R_3 = R_4 = R_5 = R_6 = H, R_7 = -(CH_2)_8CH_3$ | 1648.7 |
| RP002 | $R_1 = CH_2CH_3, R_2 = R_3 = R_4 = R_5 = H, R_6 = OCH_3, R_7 = -(CH_2)_8CH_3$ | 1678.8 |
| RP003 | $R_1 = CH_2CH_3, R_2 = Br, R_3 = R_4 = R_5 = H, R_6 = OCH_3, R_7 = -(CH_2)_8CH_3$ | 1757.7 |
| RP004 | $R_1 = CH_2CH_3, R_2 = R_3 = R_4 = R_5 = H, R_6 = F, R_7 = -(CH_2)_8CH_3$ | 1666.7 |
| RP005 | $R_1 = CH_2CH_3, R_2 = R_3 = Cl, R_4 = R_5 = H, R_6 = F, R_7 = -(CH_2)_8CH_3$ | 1735.6 |
| RP006 | $R_1 = CH_2CH_3, R_2 = Br, R_3 = R_4 = R_5 = H, R_6 = F, R_7 = -(CH_2)_8CH_3$ | 1745.6 |
| RP007 | $R_1 = CH_2CH_3, R_2 = R_3 = R_5 = R_6 = H, R_4 = CH_3, R_7 = -(CH_2)_8CH_3$ | 1662.8 |
| RP008 | $R_1 = CH_2CH_3, R_2 = Br, R_3 = R_5 = R_6 = H, R_4 = CH_3, R_7 = -(CH_2)_8CH_3$ | 1741.7 |
| RP009 | $R_1 = CH_2CH_3, R_2 = R_3 = R_4 = R_6 = H, R_5 = CH_3, R_7 = -(CH_2)_8CH_3$ | 1662.8 |
| RP010 | $R_1 = CH_2CH_3, R_2 = R_3 = Cl, R_4 = R_6 = H, R_5 = CH_3, R_7 = -(CH_2)_8CH_3$ | 1731.7 |
| RP011 | $R_1 = CH_2CH_3, R_2 = R_3 = R_4 = R_5 = H, R_6 = CH_3, R_7 = -(CH_2)_8CH_3$ | 1662.8 |
| RP012 | $R_1 = CH_2CH_3, R_2 = R_3 = Cl, R_4 = R_5 = H, R_6 = CH_3, R_7 = -(CH_2)_8CH_3$ | 1731.7 |
| RP013 | $R_1 = CH_2CH_3, R_2 = Br, R_3 = R_4 = R_5 = H, R_6 = CH_3, R_7 = -(CH_2)_8CH_3$ | 1741.7 |
| RP018 | $R_1 = CH_3, R_2 = R_3 = Cl, R_4 = R_5 = H, R_6 = F, R_7 = -(CH_2)_8CH_3$ | 1721.6 |
| RP019 | $R_1 = CH_3, R_2 = R_3 = Cl, R_4 = R_5 = H, R_6 = CH_3, R_7 = -(CH_2)_8CH_3$ | 1717.6 |
| RP020 | $R_1 = CH_2CH_2CH_3, R_2 = R_3 = Cl, R_4 = R_5 = H, R_6 = F, R_7 = -(CH_2)_8CH_3$ | 1749.6 |
| RP021 | $R_1 = CH_2CH_2CH_3, R_2 = R_3 = Cl, R_4 = R_5 = H, R_6 = CH_3, R_7 = -(CH_2)_8CH_3$ | 1745.7 |
| RP022 | $R_1 = CH_2CH_2CH_3, R_2 = R_3 = Cl, R_4 = R_5 = H, R_6 = OCH_3, R_7 = -(CH_2)_8CH_3$ | 1761.7 |

TABLE I-continued

Novel Daptomycin Analogs.

| ID | Substituents | MW |
|---|---|---|
| RP014-RP015 | | |
| RP014 | R₁ = CH₂CH₃ , R₂ = R₃ = H | 1609.7 |
| RP015 | R₁ = CH₂CH₃, R₂ = R₃ = Cl | 1678.6 |
| RP016-RP017 | | |
| RP016 | R₁ = CH₂CH₃, R₂ = R₃ = H | 1462.5 |
| RP017 | R₁ = CH₂CH₃, R₂ = R₃ = Cl | 1531.4 |

TABLE I-continued

Novel Daptomycin Analogs.

| ID | Substituents | MW |
|---|---|---|
| RP023-RP024 | [structure] | |
| RP023 | R$_1$ = H, R$_2$ = CH$_2$CH$_2$NH$_2$ | 1691.8 |
| RP024 | R$_1$ = R$_2$ = CH$_2$CH$_2$NH$_2$ | 1734.9 |

Reactions are performed in a solvent appropriate to the reagents and materials employed and suitable for the transformation being effected. It is understood by those skilled in the art of organic synthesis that the various functionalities present on the molecule must be consistent with the chemical transformations proposed. This may necessitate judgement as to the order of synthetic steps, protecting groups, if required, and deprotection conditions. Substituents on the starting materials may be incompatible with some of the reaction conditions. Such restrictions to the substituents which are compatible with the reaction conditions will be apparent to one skilled in the art.

Some of the compounds of the hereinbefore described schemes have centers of asymmetry. The compounds may, therefore, exist in at least two and often more stereoisomeric forms. The present disclosure encompasses all stereoisomers of the compounds whether free from other stereoisomers or admixed with other stereoisomers in any proportion and thus includes, for instance, racemic mixture of enantiomers as well as the diastereomeric mixture of isomers. The absolute configuration of any compound may be determined by conventional chemical degradation, spectroscopic analysis, X-ray crystallography, or a combination of these methods.

Pharmaceutically acceptable salts of the compounds of the invention may be obtained as metal complexes such as sodium, potassium, aluminum, calcium, iron, magnesium, manganese and complex salts; other inorganic and organic salts and corresponding Mannich base adducts using methods known to those skilled in the art (Richard C. Larock, Comprehensive Organic Transformations, VCH Publishers, 411 415, 1989). The compounds of the invention may be obtained as inorganic salts such as hydrochloric, hydrobromic, hydroiodic, phosphoric, nitric or sulfate; or organic salts such as acetate, benzoate, citrate, cysteine or other amino acids, fumarate, glycolate, maleate, succinate, tartrate alkylsulfonate or arylsulfonate.

BIOLOGICAL ACTIVITY

Method for In Vitro Antibacterial Evaluation

The minimum inhibitory concentration (MIC), the lowest concentration of the antibiotic which inhibits growth of the test organism, was determined by the broth microdilution method using Muller-Hinton Broth (MHB) supplemented with Calcium (25 mg/Liter) following the recommendations of the National Committee for Clinical Laboratory Standards. See, Balouiri, M.; Sadiki, M.; Ibnsouda, S. K.; Methods for In vitro evaluation of antimicrobial activity: review. Journal of Pharmaceutical Analysis, 2016, 6 (2), 71-79; CLSI, Methods for Dilution Antimicrobial Susceptibility Tests for Bacteria that Grow Aerobically, Approved Standard, 9$^{th}$ Ed, CLSI document M07-A9. Approximately 50 µl of the bacterial (MRSA or MSSA) cell suspension (1.0×10$^6$/ml) inoculated in each well (96-micro well plate) containing 50 µl of dosing solution and plates were incubated at 37±+1C for 18 hrs. After the incubation, bacterial growth in each well of 96-well plate were calorimetrically measured by a Biotek microtiter plate reader at 630 nm. The bacterial growth inhibition (GI) is expressed as a percentage relative to the negative control.

Test A

Organisms:

Methicillin-Resistant *Staphylococcus aureus* (MRSA, ATCC33591)

Methicillin-Sensitive *Staphylococcus aureus* (MSSA, ATCC6538)

Dosing Concentrations (μM):
0.039, 0.078, 0.156, 0.313, 0.625, 1.25, 2.50, 5.00 and 10.
Test B
Organisms:
Methicillin-Resistant *Staphylococcus aureus* (MRSA, PBR Lab Culture#1152)
Methicillin-Sensitive *Staphylococcus aureus* (MSSA, ATCC6538)
Dosing Concentrations (μM):
0.005, 0.020, 0.078, 0.312, 1.250, 5.00 and 20.0.
Test C
Organisms:
Vancomycin-Resistant Enterococci *faecium* (VRE, ATCC 700221);
Vancomycin-Resistant Enterococci *faecalis* (VRE, ATCC 51299);
Vancomycin-Sensitive Enterococci *faecalis* (VSE, ATCC 29212);
Vancomycin-Sensitive Enterococci *hirae* (VSE, ATCC 1056).
Dosing Concentrations (μM):
0.156, 0.313, 0.625, 1.250, 2.50, 5.00 and 10.0.

Test Results

Many of the claimed compounds exhibited potent antibacterial activity against drug-resistant *Staphylococcus aureus* and Enterococci strains. For example, compounds RP005 and RP012 were roughly 10 fold as potent as daptomycin against MRSA. In addition, RP005 and RP012 also showed about 10 fold better potency against Vancomycin-Resistant Enterococci (VRE). The potential utility of these compounds in the treatment of infections caused by Gram-positive bacteria is derived from their biological activity. Tables 2 and 3 list the in vitro MIC data (μM) for compounds RP001-RP024 against Methicillin-Resistant *Staphylococcus* (MRSA) and Methicillin-Sensitive *Staphylococcus* (MSSA). Table 4 lists the in vitro MIC data for selected compounds against Vancomycin-Sensitive Enterococci (VSE) and Vancomycin-Resistant Enterococci (VRE).

TABLE 2

MIC Data Obtained According to Test A.

| Test No. | Compound | Minimum Inhibitory Concentration (MIC, μM) | |
|---|---|---|---|
| | | MRSA (ATCC33591) | MSSA (ATCC6538) |
| 1 | RP001 | 0.313 | 0.156 |
| 2 | RP004 | 0.156 | 0.078 |

TABLE 2-continued

MIC Data Obtained According to Test A.

| Test No. | Compound | Minimum Inhibitory Concentration (MIC, μM) | |
|---|---|---|---|
| | | MRSA (ATCC33591) | MSSA (ATCC6538) |
| 3 | RP005 | ≤0.039 | ≤0.039 |
| 4 | RP009 | 1.250 | 0.625 |
| 5 | RP010 | 0.156 | ≤0.039 |
| 6 | RP011 | 0.156 | 0.156 |
| 7 | RP012 | 0.078 | ≤0.039 |
| 8 | RP014 | 2.5 | 2.5 |
| 9 | RP015 | 0.156 | ≤0.039 |
| 10 | RP016 | >10 | >10 |
| 11 | RP017 | 10 | 5 |
| 12 | RP018 | 0.078 | 0.078 |
| 13 | RP019 | 0.078 | 0.078 |
| 14 | RP020 | 0.313 | 0.313 |
| 15 | RP021 | 0.313 | 0.313 |
| 16 | RP022 | 0.313 | 0.313 |
| 17 | RP023 | 0.313 | 0.313 |
| 18 | RP024 | 0.313 | 0.313 |
| 19 | Daptomycin | 0.625 | 0.313 |
| 20 | Methicillin | >64 μg/ml | <1 μg/ml |

TABLE 3

MIC Data Obtained According to Test B.

| Test No. | Compound | Minimum Inhibitory Concentration (MIC, μM) | |
|---|---|---|---|
| | | MRSA (PBR1152)* | MSSA (ATCC6538) |
| 1 | RP002 | 1.25 | 1.25 |
| 2 | RP003 | 0.313 | 0.313 |
| 3 | RP006 | 0.078 | 0.313 |
| 4 | RP007 | 1.25 | 1.25 |
| 5 | RP008 | 0.078 | 0.078 |
| 6 | RP013 | 0.313 | 0.078 |
| 7 | Daptomycin | 1.25 | 1.25 |
| 8 | Methicillin | >64 μg/ml | <1 μg/ml |

*Methicillin-Resistant *Staphylococcus aureus*, internal culture from PBR Laboratory, Inc., Edmonton, AB, Canada.

TABLE 4

MIC Data Obtained According to Test C.

| No. | Test compound | Minimum Inhibitory Concentration (MIC, μM) | | | |
|---|---|---|---|---|---|
| | | VRE (ATCC 700221) | VRE (ATCC 51299) | VSE (ATCC 29212) | VSE (ATCC 1056) |
| 1 | RP001 | 1.25 | 0.625 | 0.625 | 5.0 |
| 2 | RP005 | ≤0.156 | ≤0.156 | ≤0.156 | ≤0.156 |
| 3 | RP008 | 0.313 | ≤0.156 | ≤0.156 | 0.313 |
| 4 | RP011 | 0.625 | ≤0.156 | 0.313 | 1.25 |
| 5 | RP012 | ≤0.156 | ≤0.156 | ≤0.156 | ≤0.156 |
| 6 | Daptomycin | 2.5 | 1.25 | 1.25 | 5.0 |
| 7 | Vacomycin | >10 | >10 | 1.25 | 0.313 |

EXAMPLES

The following non-limiting examples are provided.

Protocol A1-Neg (LCMS analysis).

Instrument: Agilent 1100 LC-G1956B MSD, negative polarity

Column: YMC ODS-A 150×4.6 mm, 5 uM, 120 A.
Solvent system: (20-100% acetonitrile/water)+0.025% formic acid, 0.5 ml/min in 15 min.
Protocol A1-Pos (LCMS analysis).
Instrument: Agilent 1100 LC-G1956B MSD, positive polarity
Column: YMC ODS-A 150×4.6 mm, 5 uM, 120 A.
Solvent system: (20-100% acetonitrile/water)+0.025% formic acid, 0.5 ml/min in 15 min.
Protocol A2 (LCMS analysis).
Instrument: Agilent 1100 LC-G1956B MSD, positive polarity
Column: YMC ODS-A, 150×4.6 mm, 5 uM, 120 A.
Solvent system: (40-100% acetonitrile/water)+0.1% formic acid, 0.5 ml/min in 15 min.
Protocol B1 (preparative HPLC).
Instrument: Rainin Dynamax SD-200, UV-1
Column: YMC ODS-A, 250×30 mm, 10 uM, 120 A.
Solvent system: (50% acetonitrile/water)+0.025% formic acid, 3 min, (50-85% acetonitrile/water)+0.025% formic acid in 17 min, 20 ml/min flowrate, monitoring wavelength 395 nm.
Protocol B2 (preparative HPLC).
Instrument: Rainin Dynamax SD-200, UV-1
Column: YMC ODS-A, 250×30 mm, 10 uM, 120 A.
Solvent system: (30% acetonitrile/water)+0.025% formic acid, 3 min, (30-80% acetonitrile/water)+0.025% formic acid in 17 min, 20 ml/min flowrate, monitoring wavelength 395 nm.
Protocol B3 (preparative HPLC).
Instrument: Rainin Dynamax SD-200, UV-1
Column: YMC ODS-A, 250×30 mm, 10 uM, 120 A.
Solvent system: (60% acetonitrile/water)+0.025% formic acid, 3 min, (60-95% acetonitrile/water)+0.025% acetic acid in 17 min, 20 ml/min flowrate, monitoring wavelength 270 nm.

Example 1a

Preparation of Inter-IA

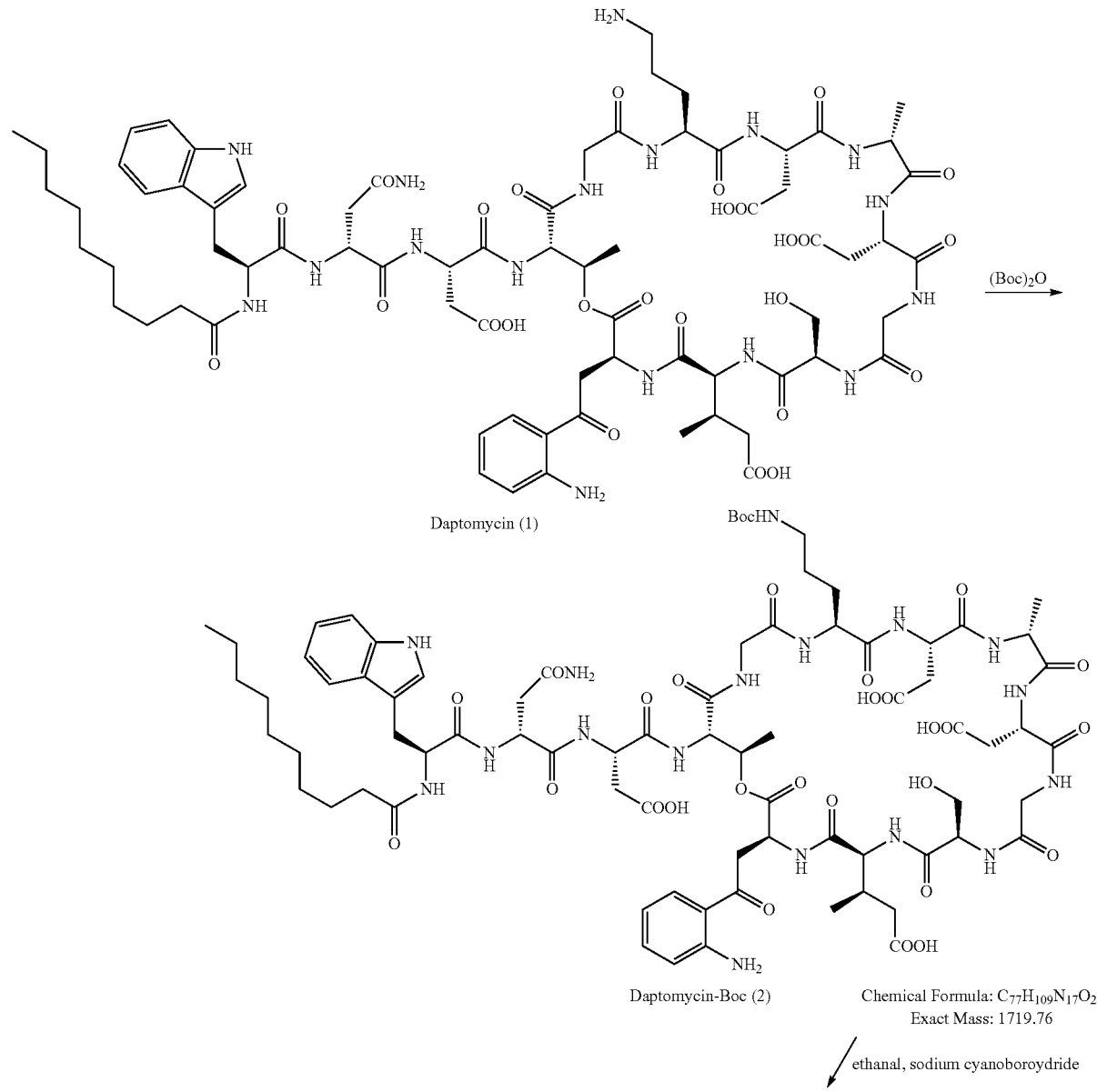

Daptomycin (1)

Daptomycin-Boc (2)  Chemical Formula: $C_{77}H_{109}N_{17}O_{28}$
Exact Mass: 1719.76 ethanal, sodium cyanoboroydride

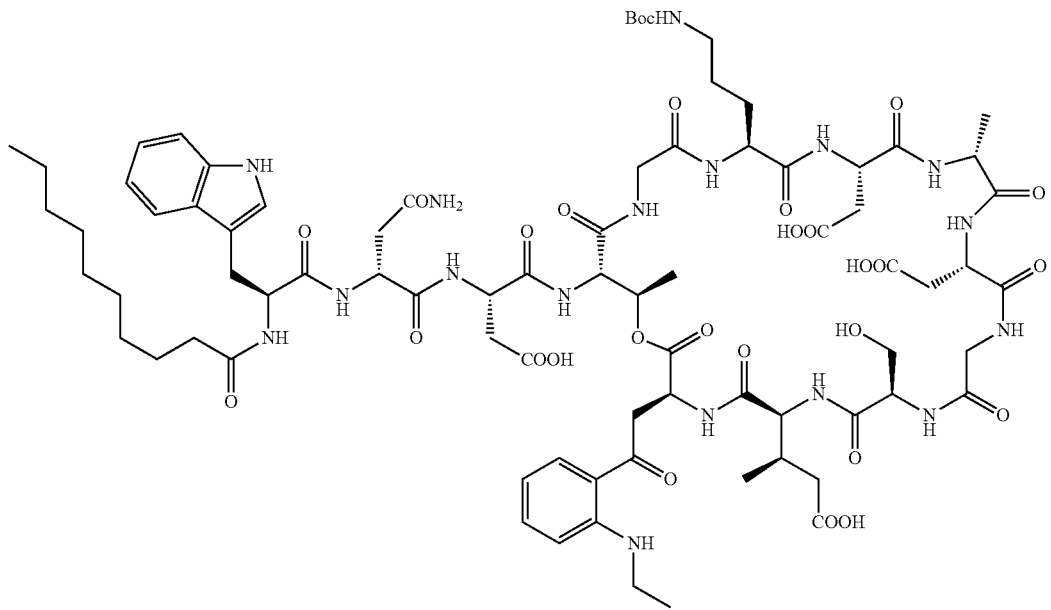

Inter-IA
Chemical Formula: $C_{79}H_{113}N_{17}O_{28}$
Exact Mass: 1747.79

Step 1. Boc Protection of Orinithine Amino Group to Generate Daptomycin-Boc (2)

A mixture of daptomycin (1.0 g) in water (6 ml) was stirred for 1 hour at ambient temperature and the solid was gradually dissolved. To this solution was added triethylamine (600 ul) followed by a solution of (Boc)$_2$CO (500 mg) in DMSO (2 ml). The resulting suspension was stirred vigorously for one hour and it became a yellowish solution. LCMS analysis indicated that daptomycin was completely converted to 2. Positive ESIMS m/z 1720.7 (MH)$^+$, theoretical mass for $C_{77}H_{110}N_{17}O_{28}$, 1720.77 (Protocol A2). The reaction mixture was extracted with ethyl acetate (5 mL). The aqueous layer was acidified by acetic acid (800 uL) and then extracted with n-butanol (2×5 mL). The combined butanol solution was evaporated under reduced pressure to yield a light yellow film, which was then purified by preparative HPLC (Protocol B 1, 3 injections). The peak at 14 minutes was collected, evaporated under reduced pressure and dried in vacuo to yield daptomycin-Boc (2) as a powder, 1.12 g. The above reaction was repeated.

Step 2. Alkylation of Aniline Amino Group by Reductive Animation

To a solution of daptomycin-Boc (2, 900 mg) in methanol (5 mL) was added acetic acid (360 uL), followed by 40% ethanal in water (900 uL). The resulting mixture was stirred at ambient temperature for 5 min and then mixed with a solution of sodium cyanoborohydride (360 mg) in methanol (2 mL). The reaction solution was stirred at ambient temperature for 20 min and the product purified by preparative HPLC (Protocol B 1). The peak at 16 min was collected, and evaporated in vacuo to afford Inter-IA as a yellow powder (954 mg). Positive ESIMS m/z 1748.6 MH$^+$, theoretical mass for $C_{79}H_{114}N_{17}O_{28}$, 1748.80 (Protocol A2).

Example 1b

Preparation of Inter-IB

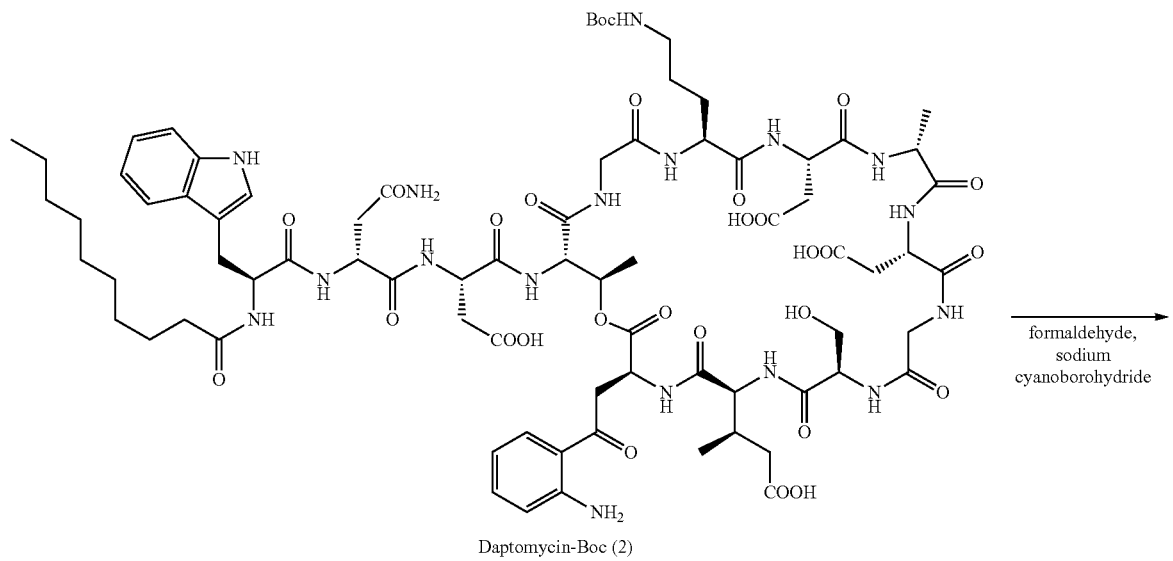

Daptomycin-Boc (2)

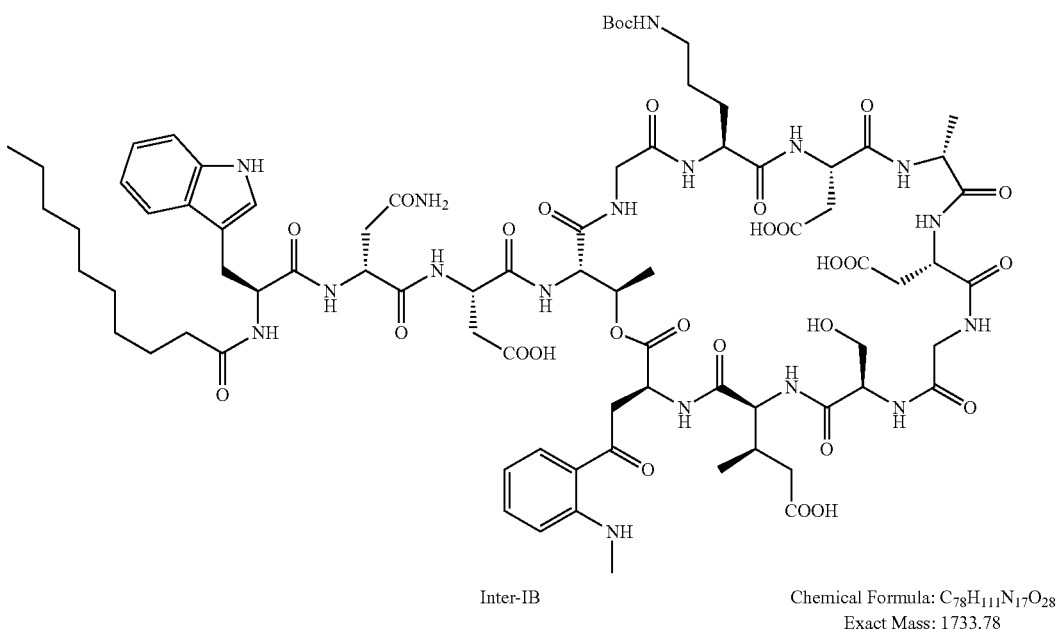

Inter-IB    Chemical Formula: $C_{78}H_{111}N_{17}O_{28}$
Exact Mass: 1733.78

To a solution of daptomycin-Boc (2, 0.5 g) in methanol (5 mL) was added acetic acid (360 uL), followed by 40% formaldehyde in water (900 uL). The resulting mixture was stirred at ambient temperature for 5 min and then mixed with a solution of sodium cyanoborohydride (360 mg) in methanol (2 mL). The reaction solution was stirred at ambient temperature for 20 min and the product purified by preparative HPLC (Protocol B 1). The peak at 16 min was collected, and evaporated in vacuo to afford Inter-IB as a yellow powder (255 mg). Negative ESIMS m/z 1732.6 (M-H)$^-$, theoretical mass for $C_{78}H_{110}N_{17}O_{28}$, 1732.77 (Protocol A1-Neg).

Example 1c

Preparation of Inter-IC

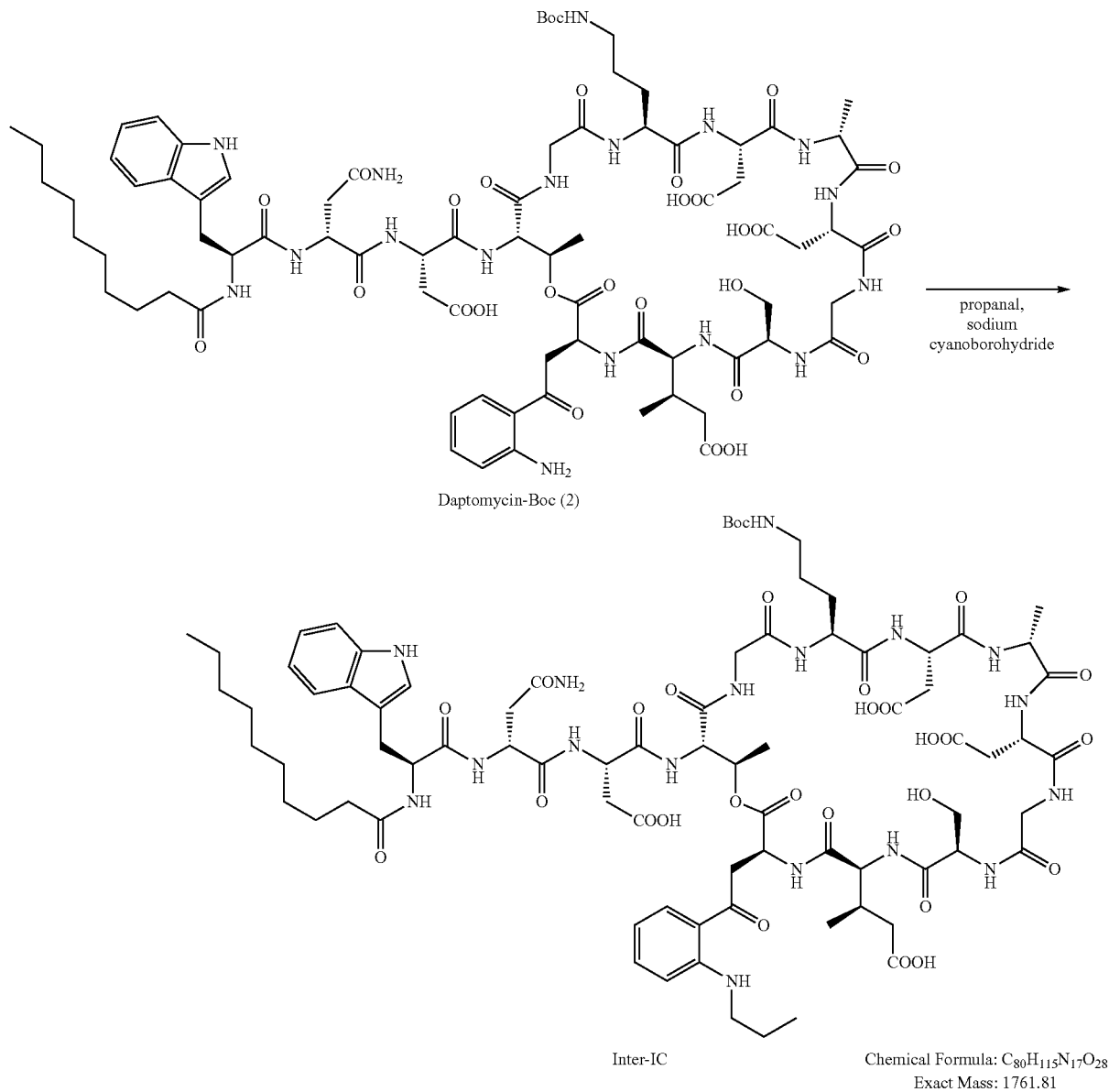

To a solution of daptomycin-Boc (2, 500 mg) in methanol (2.5 mL) was added acetic acid (180 uL), followed by 97% propanal (60 uL). The resulting mixture was stirred at ambient temperature for 5 min and then mixed with a solution of sodium cyanoborohydride (50 mg) in methanol (1 mL). The reaction solution was stirred at ambient temperature for 20 min and the product purified by preparative HPLC (Protocol B 1). The peak at 16 min was collected, and evaporated in vacuo to afford Inter-IC as a yellow powder (440 mg). Negative ESIMS m/z 1760.7 (M-H)$^-$, theoretical mass for $C_{80}H_{114}N_{17}O_{28}$, 1760.8 (Protocol A1-Neg).

Example 2a

Preparation of Inter-IIA

To a mixed powder of Inter-IA (498 mg) and o-iodosobenzoic acid (1.0 g) in a 100 ml brown bottle was added a solution of guanidinium monohydrochloride (1.0 g) in acetic acid (40 mL) and water (10 mL). The resulting suspension was stirred at ambient temperature for 16 hours without light.

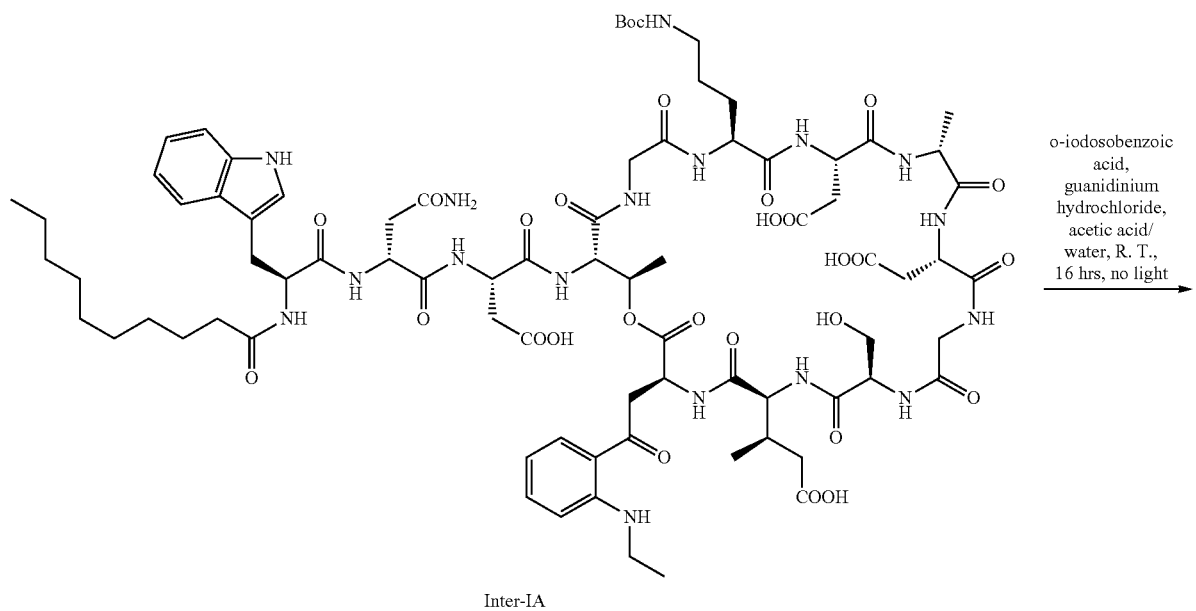

Inter-IA

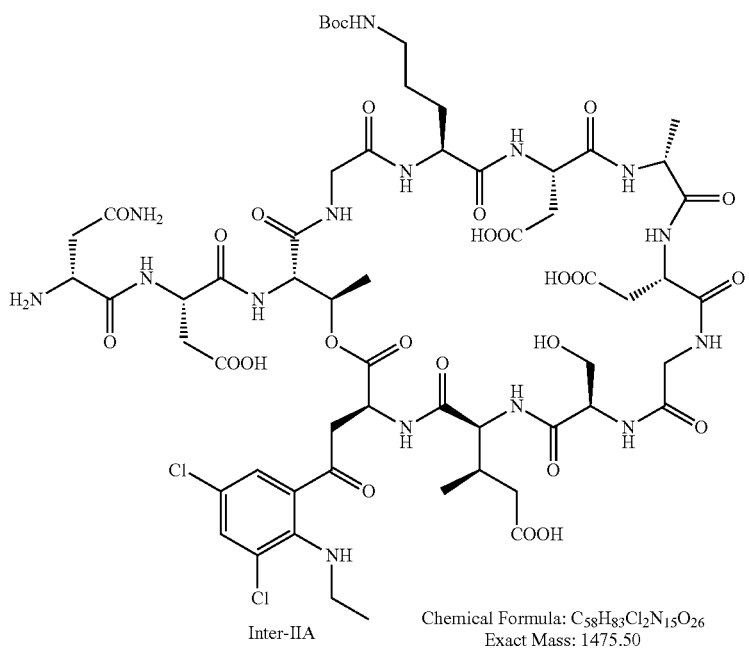

Inter-IIA

Chemical Formula: $C_{58}H_{83}Cl_2N_{15}O_{26}$
Exact Mass: 1475.50

At the end of reaction, the reactant was filtered and the yellow filtrate was loaded on a glass chromatography column containing Sephadex LH-20 resin (100 g) in methanol (350 mL). The column was eluted with methanol to obtain a yellow fraction (~150 mL). Upon evaporation under reduced pressure, the residue (~380 mg) was further purified by preparative HPLC (Protocol B2). The peak at 13 minutes was collected and freeze-dried to produce Inter-IIA as a bright yellow solid upon freeze-drying (55.0 mg). Negative ESIMS m/z 1474.3 (M-H)⁻, theoretical mass for $C_{58}H_{82}Cl_2N_{15}O_{26}$, 1474.49 (Protocol A1-Neg).

Example 2b

Preparation of Inter-IIB

To a mixed powder of Inter-IB (300 mg) and o-iodosobenzoic acid (300 mg) in a 100 ml brown bottle was added a solution of guanidinium monohydrochloride (362 mg) in acetic acid (13 mL) and water (3 mL). The resulting suspension was stirred at ambient temperature for 16 hours without light.

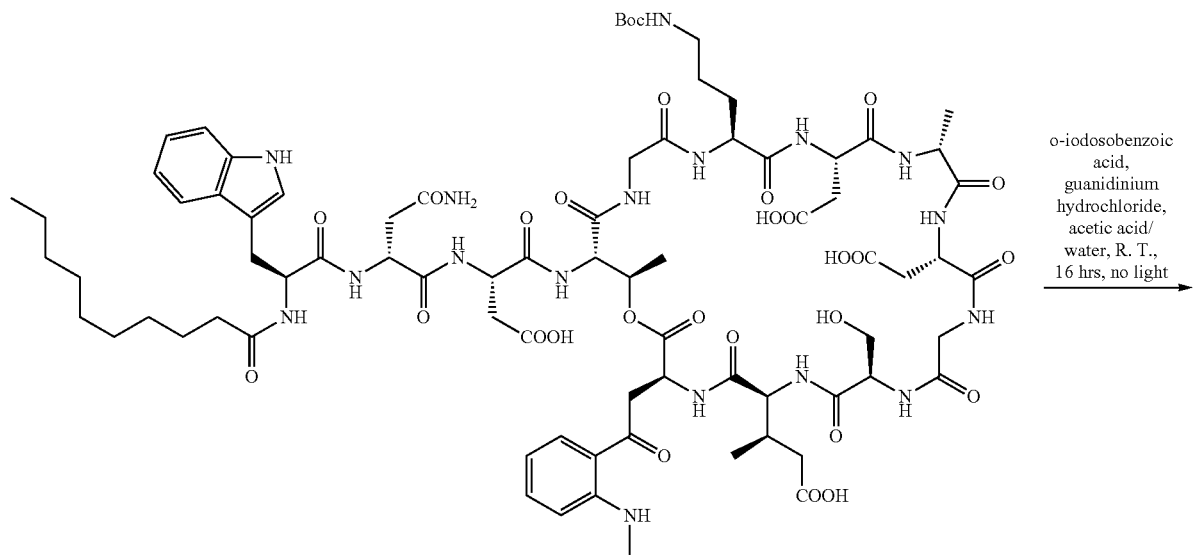

Inter-IB

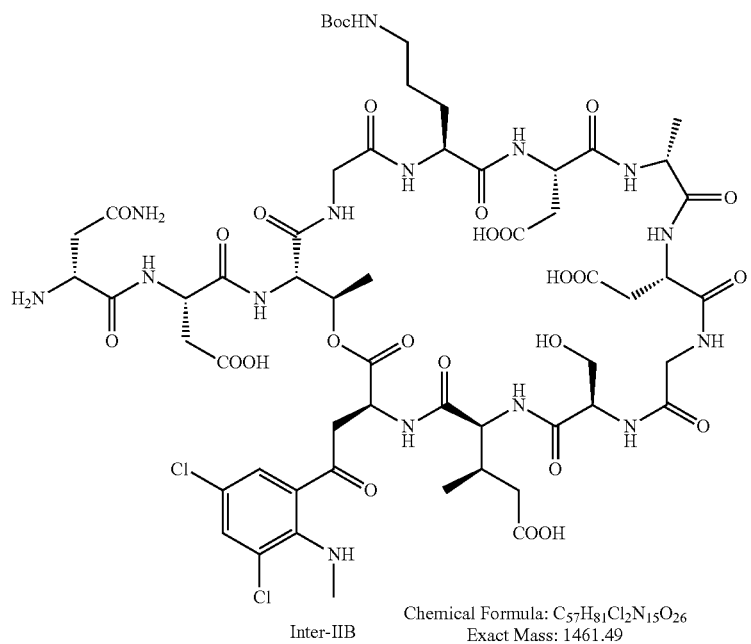

Inter-IIB

Chemical Formula: $C_{57}H_{81}Cl_2N_{15}O_{26}$
Exact Mass: 1461.49

At the end of reaction, the reactant was filtered and the yellow filtrate was loaded on a glass chromatography column containing Sephadex LH-20 resin (100 g) in methanol (350 mL). The column was eluted with methanol to obtain a yellow fraction (~150 mL). Upon evaporation under reduced pressure, the residue (~100 mg) was further purified by preparative HPLC (Protocol B2). The peak at 13 minutes was collected and freeze-dried to produce Inter-IIB as a bright yellow solid upon freeze-drying (30.5 mg). Negative ESIMS m/z 1460.3 (M-H)⁻, theoretical mass for $C_{57}H_{80}Cl_2N_{15}O_{26}$, 1460.48 (Protocol A1-Neg).

Example 2c

Preparation of Inter-IIC

To a mixed powder of Inter-IC (444 mg) and o-iodosobenzoic acid (300 mg) in a 100 ml brown bottle was added a solution of guanidinium monohydrochloride (605 mg) in acetic acid (16 mL) and water (4 mL). The resulting suspension was stirred at R. T. for 16 hours without light.

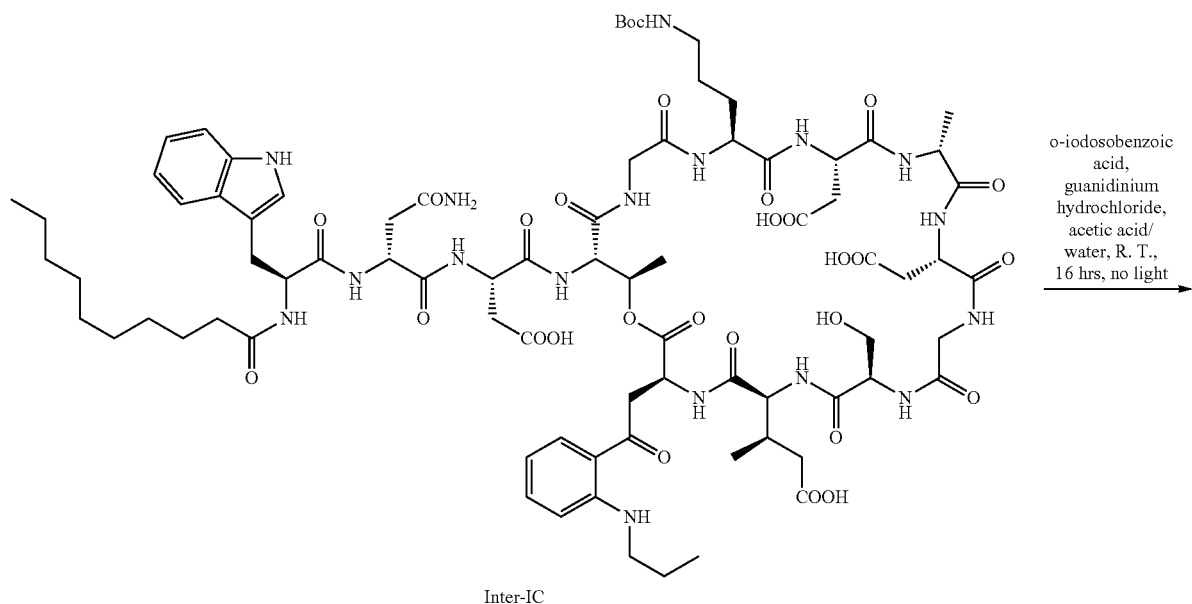
Inter-IC
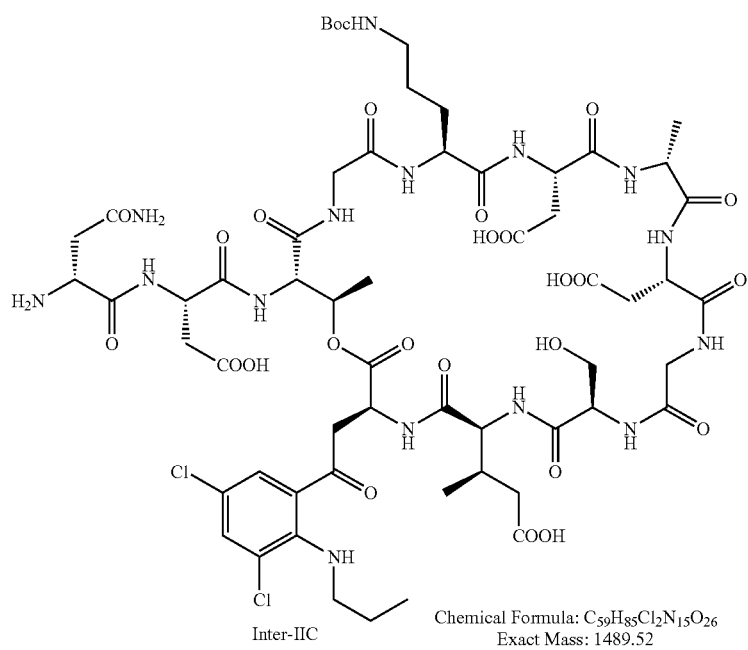
Inter-IIC
Chemical Formula: $C_{59}H_{85}Cl_2N_{15}O_{26}$
Exact Mass: 1489.52

At the end of reaction, the reactant was filtered and the yellow filtrate was loaded on a glass chromatography column containing Sephadex LH-20 resin (100 g) in methanol (350 mL). The column was eluted with methanol to obtain a yellow fraction (~150 mL). Upon evaporation under reduced pressure, the residue (~380 mg) was further purified by preparative HPLC (Protocol B2). The peak at 13 minutes was collected and freeze-dried to produce Inter-IIC as a bright yellow solid upon freeze-drying (79.0 mg). Negative ESIMS m/z 1488.4 (M-H)$^-$, theoretical mass for $C_{59}H_{84}Cl_2N_{15}O_{26}$, 1488.50 (Protocol A1-Neg).

Example 3

Preparation of Inter-IID

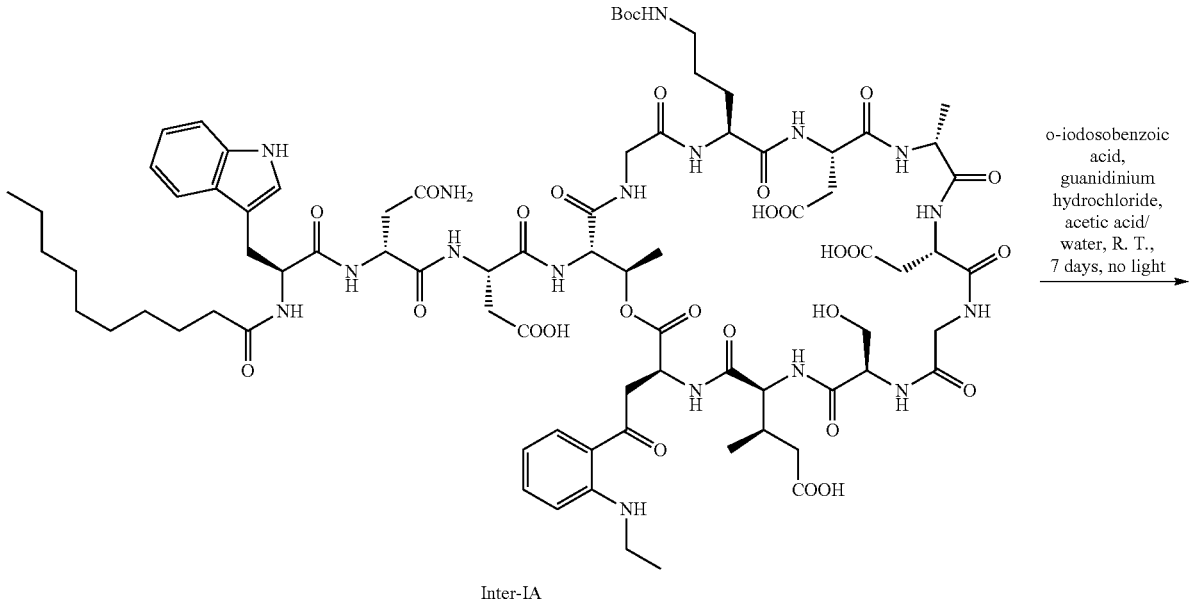

Inter-IA

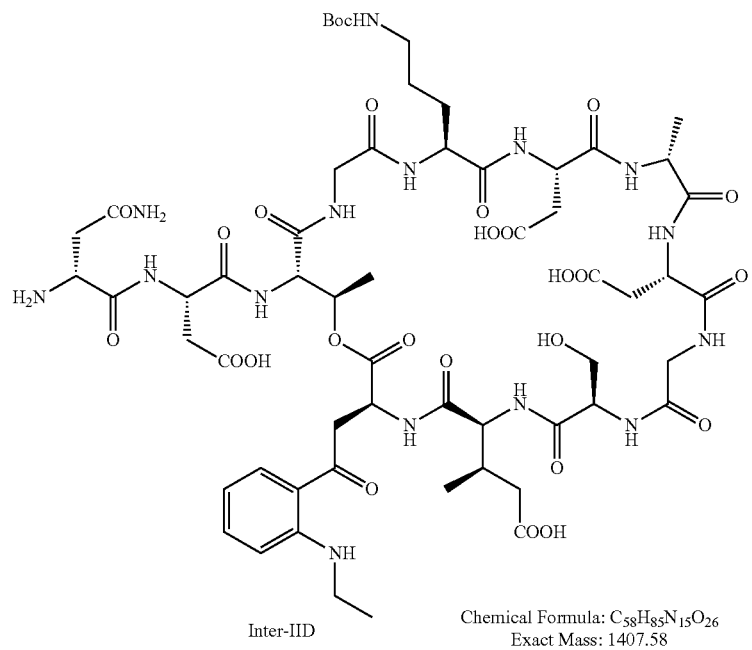

Inter-IID

Chemical Formula: $C_{58}H_{85}N_{15}O_{26}$
Exact Mass: 1407.58

To a mixed powder of Inter-IA (508 mg) and o-iodosobenzoic acid (1.0 g) in a 100 ml brown bottle was added a solution of guanidinium monohydrofluoride (1.0 g) in acetic acid (40 mL) and water (10 mL). The resulting suspension was stirred at ambient temperature for 7 days without light.

At the end of reaction, the mixture was filtered and the yellow filtrate was loaded onto a glass chromatography column containing Sephadex LH-20 resin (100 g) in methanol (350 mL). The column was eluted with methanol to obtain a light yellow fraction (~150 mL). Upon evaporation under reduced pressure, the residue (~360 mg) was further purified by preparative HPLC (Protocol B2). The peak at 11 minutes was collected and freeze-dried to produce Inter-IID as a yellow solid upon freeze-drying (70.3 mg). Negative ESIMS m/z 1406.4 (M-H)$^-$, theoretical mass for $C_{58}H_{84}N_{15}O_{26}$, 1406.57 (Protocol A1-Neg).

Example 4

Preparation of Inter-IIE

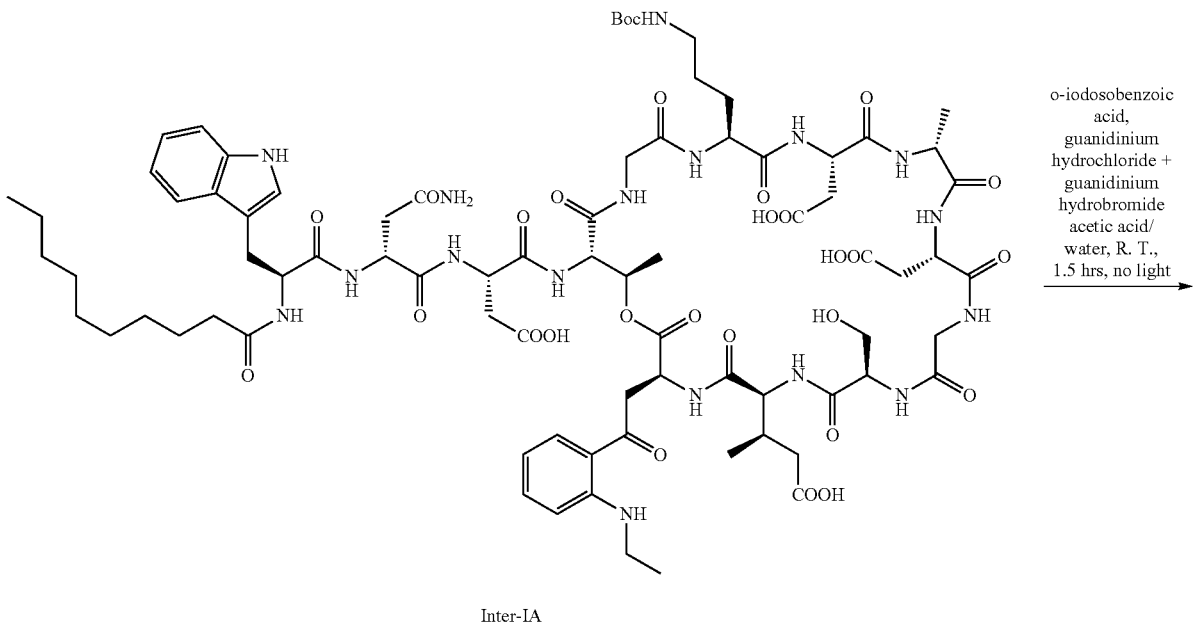

Inter-IA

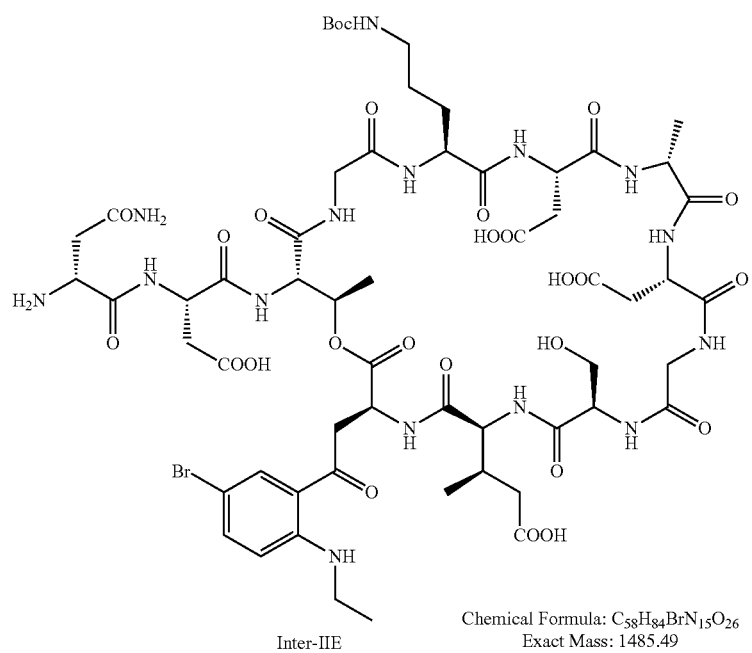

Inter-IIE

Chemical Formula: $C_{58}H_{84}BrN_{15}O_{26}$
Exact Mass: 1485.49

To a mixed powder of Inter-IA (422 mg) and o-iodosobenzoic acid (410 mg) in a 100 ml brown bottle was added a solution of guanidinium monohydrofluoride (400 mg, excess) and guanidinium monohydrobromide (43 mg, 1.3 eq) in acetic acid (16 mL) and water (4 mL). The resulting suspension was stirred at ambient temperature for 1.5 hours without light.

The reaction mixture was filtered and the yellow filtrate was loaded onto a glass chromatography column containing Sephadex LH-20 resin (100 g) in methanol (350 mL). The column was eluted with methanol to obtain a light yellow fraction (~150 mL). Upon evaporation under reduced pressure, the residue (~360 mg) was further purified by preparative HPLC (Protocol B2). The peak at 13 minutes was collected and freeze-dried to produce Inter-IID as a yellow solid upon freeze-drying (127.0 mg). Negative ESIMS m/z 1484.3 (M-H)$^-$, theoretical mass for $C_{58}H_{83}BrN_{15}O_{26}$, 1484.48 (Protocol A1-Neg).

Example 5

Preparation of Intermediates, 3H-[1,2,3]triazolo[4,5-b]pyridin-3-yl decanoate (3), 3H-[1,2,3]triazolo[4,5-b]pyridin-3-yl dodecanoate (4), Inter-IIIA, Inter-IIIB, Inter-IIIC, Inter-IIID, Inter-IIIE, and Inter-IIIF Step 1. Preparation of 3H-[1,2,3]triazolo[4,5-b]pyridin-3-yl decanoate (3)

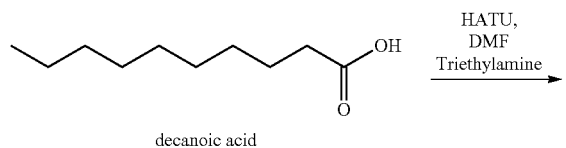

decanoic acid

3H-[1,2,3]triazolo[4,5-b]pyridin-3-yl decanoate
(3)

To a solution of decanoic acid (200 mg) and 1-[Bis(dimethylamino)methylene]-1H-1,2,3-triazolo[4,5-b]pyridinium 3-oxide hexafluorophosphate (HATU, 211 mg) in anhydrous DMF (2 ml) was added triethylamine (200 uL) with stirring. The resulting solution was further stirred at ambient temperature for 16 hours. At the end of reaction, the reactant was purified by HPLC (Protocol B3) and freeze-dried to yield the 3H-[1,2,3]triazolo[4,5-b]pyridin-3-yl decanoate (3) as a wax-like solid (160.5 mg).

Step 2. Preparation of 3H-[1,2,3]triazolo[4,5-b]pyridin-3-yl dodecanoate (4)

dodecanoic acid

3H-[1,2,3]triazolo[4,5-b]pyridin-3-yl dodecanoate
(4)

To a solution of dodecanoic acid (100 mg) and 1-[Bis(dimethylamino)methylene]-1H-1,2,3-triazolo[4,5-b]pyridinium 3-oxide hexafluorophosphate (HATU, 107 mg) in anhydrous DMF (1 mL) was added triethylamine (150 uL) with stirring. The resulting solution was further stirred at ambient temperature for 16 hours. At the end of reaction, the reactant was purified by HPLC (Protocol B3) and freeze-dried to yield the 3H-[1,2,3]triazolo[4,5-b]pyridin-3-yl dodecanoate (4) as a wax-like solid (73 mg).

Step 3. Couplings of amino acids with 3 to prepare Inter-IIIA, Inter-IIIB, Inter-IIIC, Inter-IIID, Inter-IIIE, and Inter-IIIF The amino acids used in these preparation procedures was each dissolved in 5% trifluoroacetic acid (TFA) aqueous solution (10 mg/mL). Each of the resulting solution was then freeze dried to yield an amino acid TFA salt as a white powder, which was more soluble in N,N-dimethylformamide (DMF).

To a solution an aforementioned amino acid TFA salt (reactant A) with 3 (reactant B) in anhydrous DMF (1 mL) was added trimethylamine (50 uL) with stirring. The resulting solution was stirred at ambient temperature for 1.5 hours and analyzed by LCMS (Protocol A2). The products was then purified by HPLC (Protocol B 1). The reactants, products, and experimental data are listed in Table 5.

TABLE 5

Conditions for the preparation of Inter-IIIA, Inter-IIIB, Inter-IIIC, Inter-IIID, Inter-IIIE, and Inter-IIIF.

| reactant (mg) | | product | theorectical | observed |
|---|---|---|---|---|
| A* | B | (mg) | (MH)+ | (MH)+ |
| 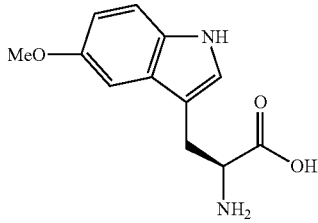<br>5-methoxy-L-tryptopan<br>(26.0 mg) | 3<br>(26.2 mg) | 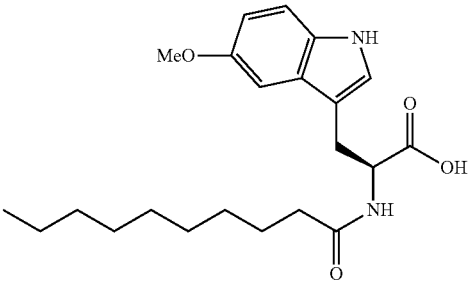 [SMILES: CCCCCCCCCC(=O)N[C@@H](Cc1c[nH]c2ccc(OC)cc12)C(=O)O]<br>Inter-IIIA (39.4 mg) | 389.24 | 389.1 |
| 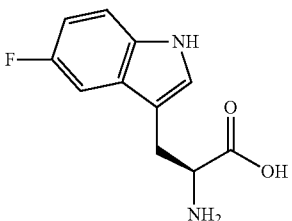<br>5-fluoro-L-tryptopan<br>(26.5 mg) | 3<br>(26.5 mg) | 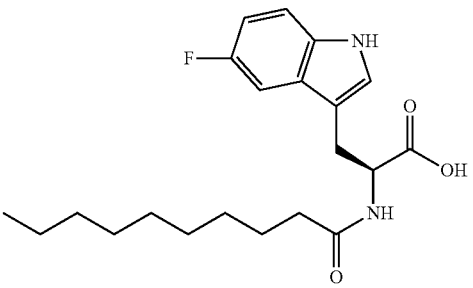<br>Inter-IIIB (34.0 mg) | 377.22 | 377.1 |
| 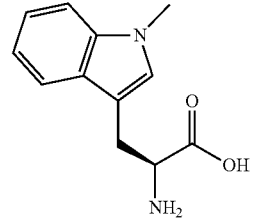<br>1-methyl-L-tryptophan<br>(26.4 mg) | 3<br>(27.1 mg) | 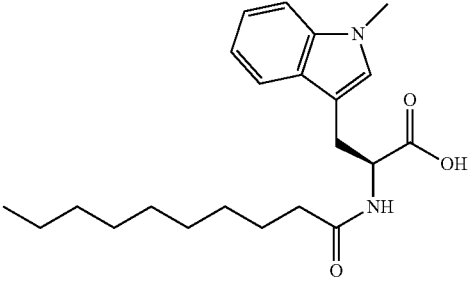 [SMILES: CCCCCCCCCC(=O)N[C@@H](Cc1cn(C)c2ccccc12)C(=O)O]<br>Inter-IIIC (30.9 mg) | 373.25 | 373.1 |
| 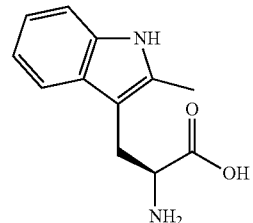<br>2-methyl-L-tryptophan<br>(26.5 mg) | 3<br>(27.2 mg) | 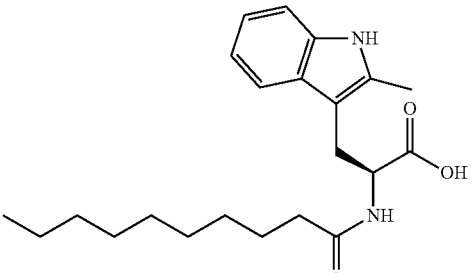<br>Inter-IIID (27.7 mg) | 373.25 | 373.1 |

TABLE 5-continued
Conditions for the preparation of Inter-IIIA, Inter-IIIB, Inter-IIIC, Inter-IIID, Inter-IIIE, and Inter-IIIF.
| reactant (mg) | | product | theorectical | observed |
|---|---|---|---|---|
| A* | B | (mg) | (MH)+ | (MH)+ |
| 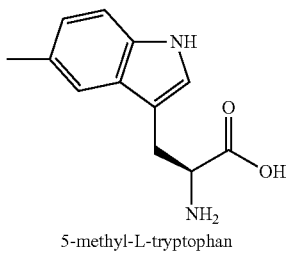<br>5-methyl-L-tryptophan<br>(25.8 mg) | 3<br>(27.0 mg) | 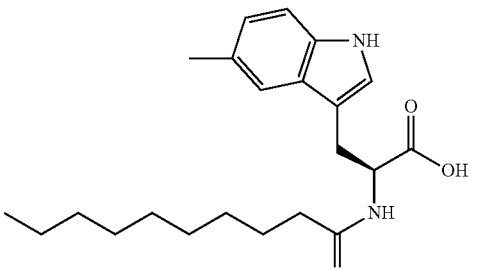<br>Inter-IIIE (41.0 mg) | 373.25 | 373.1 |
| L-phenylalanine<br>(26.4 mg) | 3<br>(27.1 mg) | 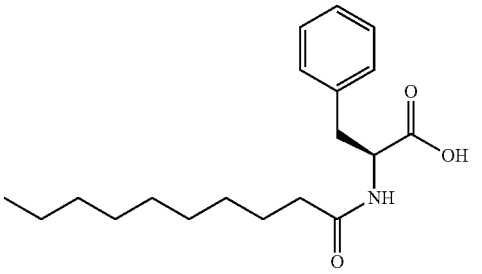 [SMILES: CCCCCCCCCC(=O)N[C@@H](Cc1ccccc1)C(=O)O]<br>Inter-IIIF (28.2 mg) | 320.22 | 320.1 |
*TFA salts of these amino acids were used in the reactions.

Example 6

Preparation of RP001

A solution of Inter-IA (10.1 mg) in (1:9) trifluoroacetic acid (TFA)/dichloromethane (DCM) (500 uL total) was stirred at ambient temperature for 10 minutes. Acetonitrile (1 mL) was then added and the solution was evaporated under reduced pressure to a volume of about 200 uL. The concentrated solution was then purified by HPLC (Protocol B2) to obtain RP001 as a yellow powder (7.7 mg) upon freeze-drying. Positive ESIMS m/z 1648.4 (MH)$^+$, theoretical mass for $C_{74}H_{106}N_{17}O_{26}$, 1648.74 (Protocol A2).

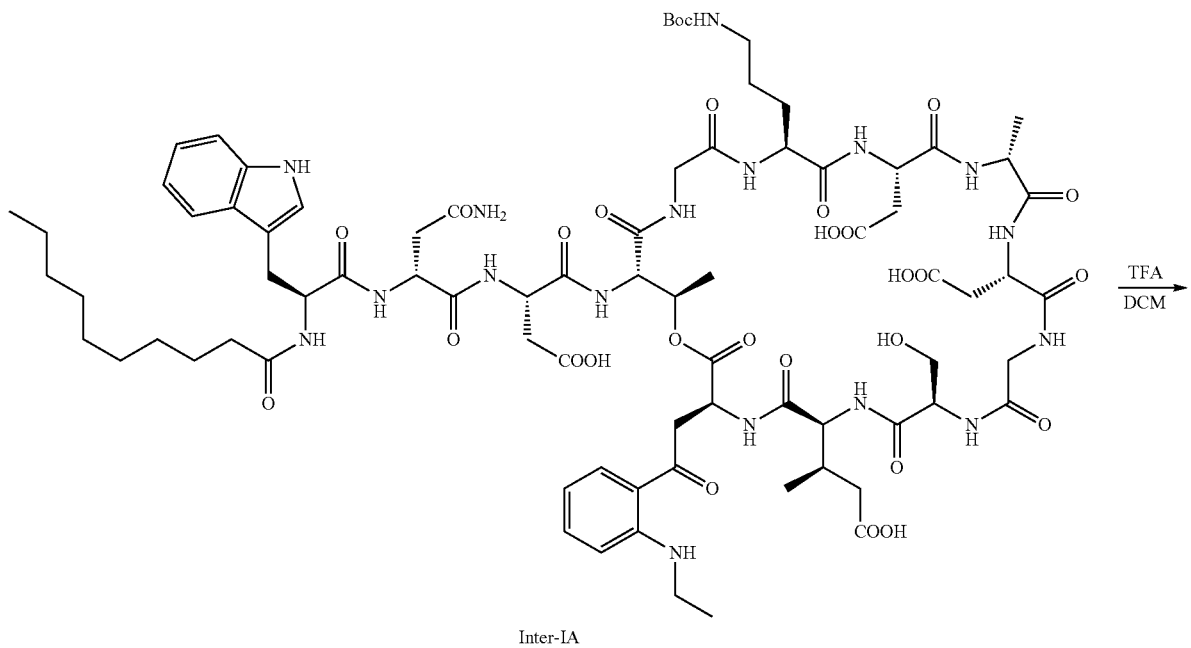

Inter-IA

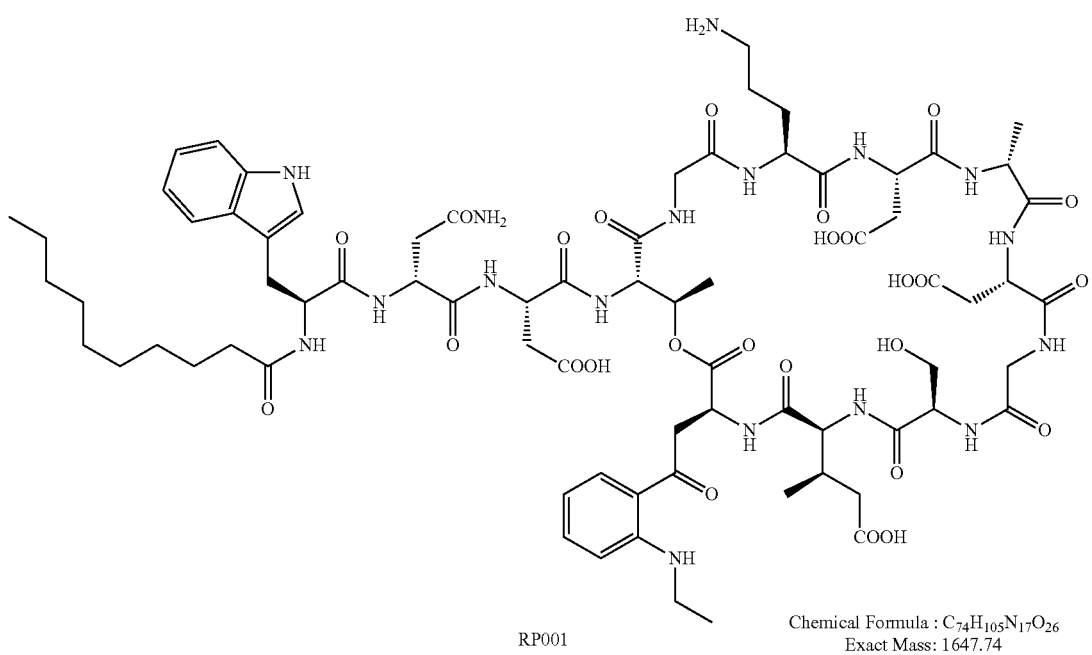

RP001

Chemical Formula: $C_{74}H_{105}N_{17}O_{26}$
Exact Mass: 1647.74

Example 7

Preparation of RP002

Step 1. Preparation of RP002-Boc

A solution of (S)-2-decanamido-3-(5-methoxy-H-indol-3-yl)propanoic acid (Inter-IIIA, 5.0 mg), 1-[Bis(dimethylamino)methylene]-1H-1,2,3-triazolo[4,5-b]pyridinium 3-oxide hexafluorophosphate (HATU, 4.1 mg), and N,N-Diisopropylethylamine (Hunig base, 20 uL) in N,N-dimethylformamide (150 uL) was stirred at ambient temperature for 10 minutes, and then mixed with Inter-IID (8.2 mg) in DMF (150 uL). The resulting solution was further stirred for 15 minutes until the coupling reaction was complete. The product RP002-Boc was purified by HPLC (Protocol B1) as a yellow powder (4.2 mg) upon freeze-drying.

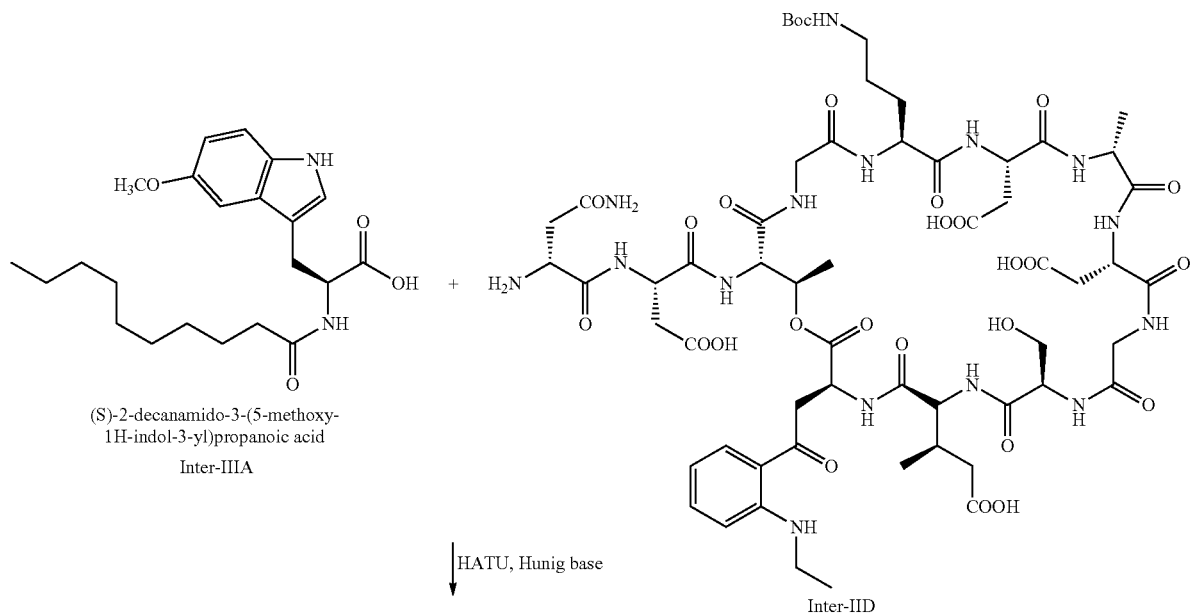

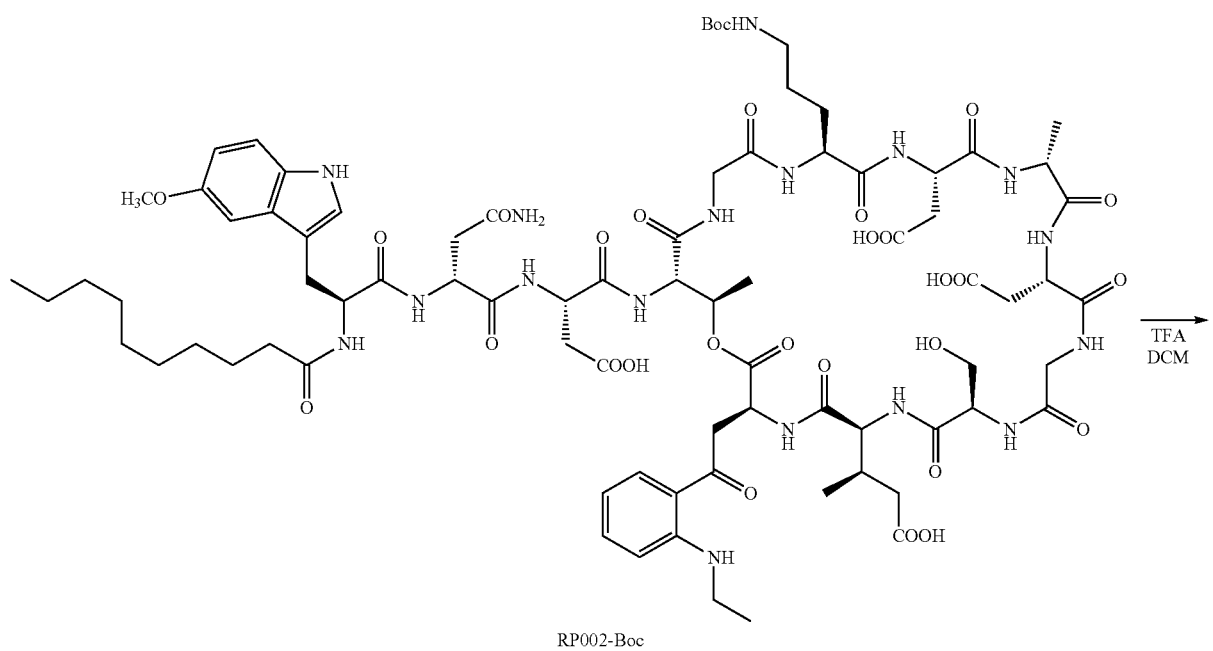

-continued

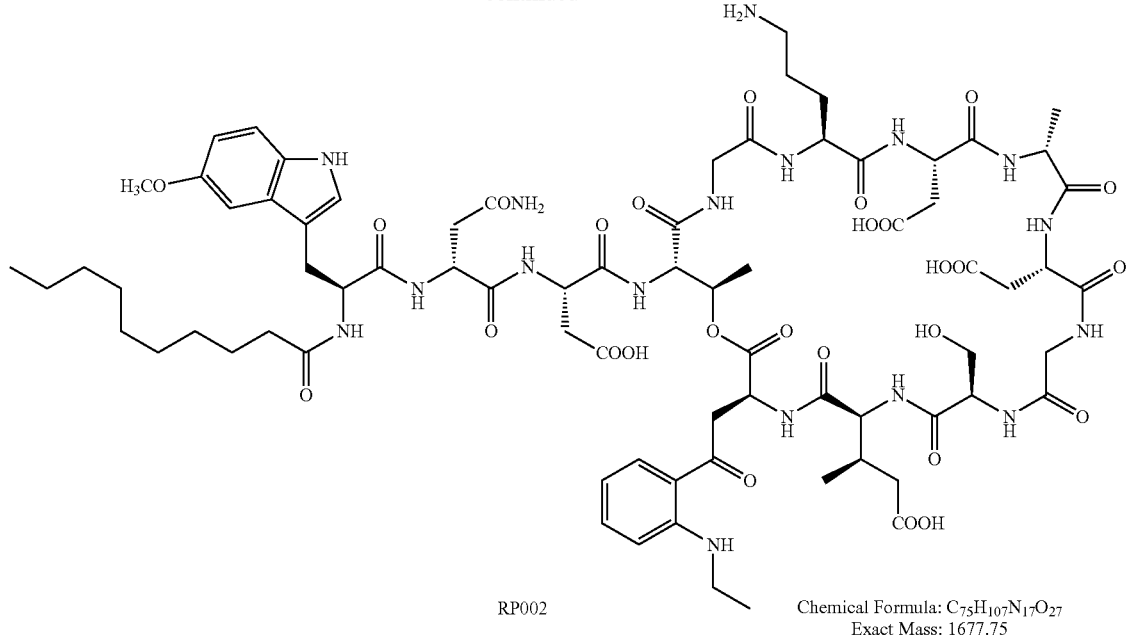 [SMILES: CCCCCCCCCC(=O)N[C@@H](Cc1c[nH]c2ccc(OC)cc12)C(=O)N[C@H](CC(N)=O)C(=O)N[C@@H](CC(=O)O)C(=O)N[C@@H]1C(=O)NCC(=O)N[C@@H](CCCN)C(=O)N[C@@H](CC(=O)O)C(=O)N[C@H](C)C(=O)N[C@@H](CC(=O)O)C(=O)NCC(=O)N[C@H](CO)C(=O)N[C@@H]([C@H](C)CC(=O)O)C(=O)N[C@@H](CC(=O)c2ccccc2NCC)C(=O)O[C@@H]1C]

RP002

Chemical Formula: $C_{75}H_{107}N_{17}O_{27}$
Exact Mass: 1677.75

Step 2. Preparation of RP002

RP002-Boc (4.2 mg) in (1:9) trifluoroacetic acid (TFA)/dichloromethane (DCM) (250 uL total) was stirred at ambient temperature for 10 minutes. Acetonitrile (1 mL) was then added and the solution was evaporated under reduced pressure to a volume of about 100 uL. The concentrated solution was then purified by HPLC (Protocol B2) to obtain RP002 as a yellow powder (3.1 mg) upon freeze-drying. Positive ESIMS m/z 1678.6 (MH)$^+$, theoretical mass for $C_{75}H_{108}N_{17}O_{27}$, 1678.76 (Protocol A2).

Example 8

Preparation of RP003

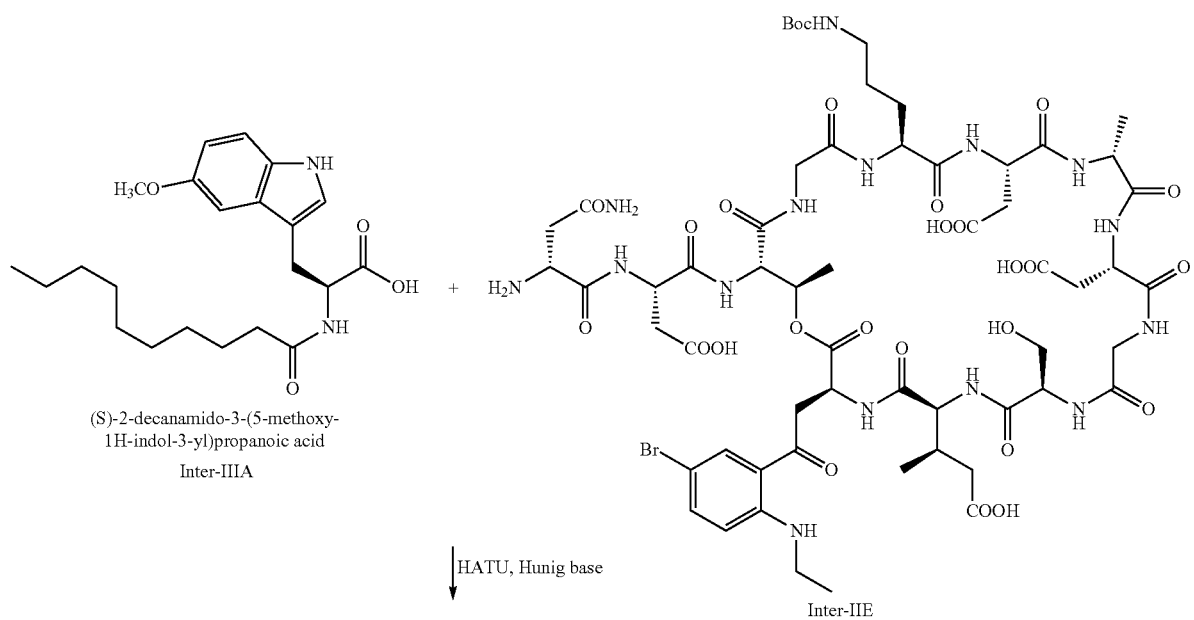

(S)-2-decanamido-3-(5-methoxy-1H-indol-3-yl)propanoic acid
Inter-IIIA

Inter-IIE

HATU, Hunig base

-continued

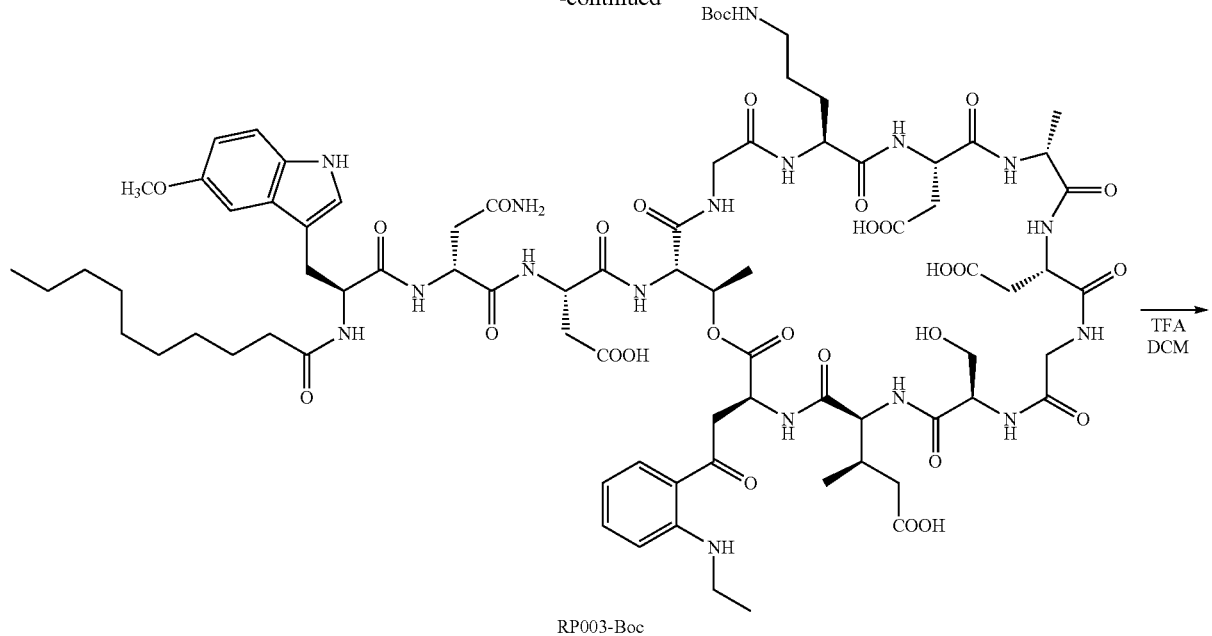

RP003-Boc

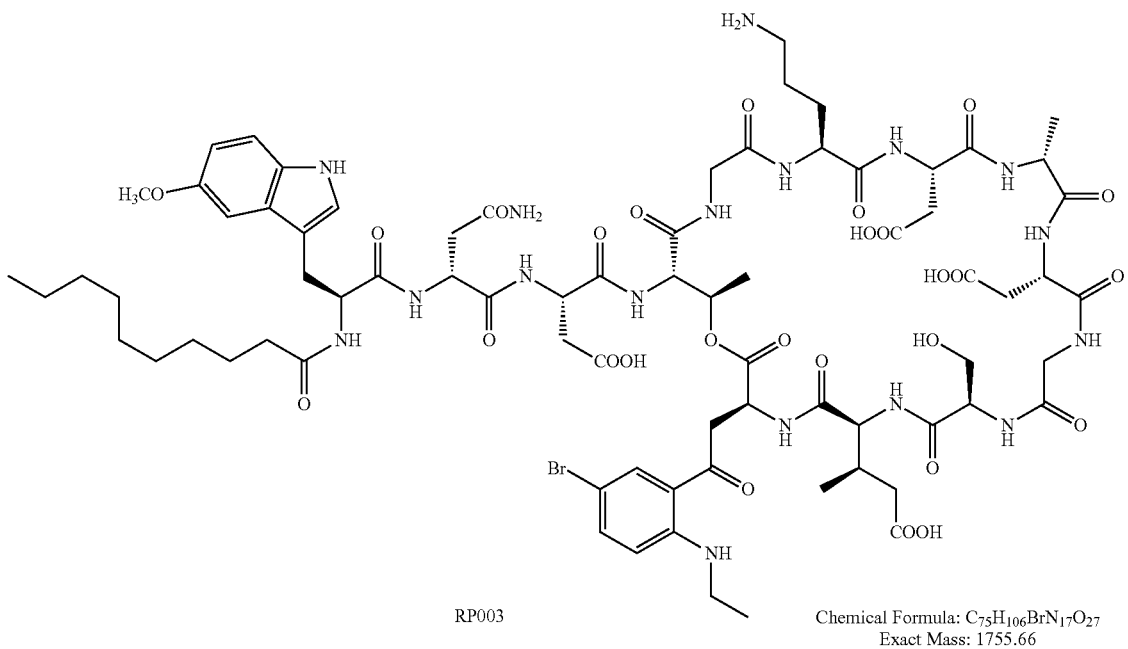 [SMILES: CCCCCCCCCC(=O)N[C@@H](Cc1c[nH]c2ccc(OC)cc12)C(=O)N[C@H](CC(N)=O)C(=O)N[C@@H](CC(=O)O)C(=O)N[C@@H]1C(=O)NCC(=O)N[C@@H](CCCN)C(=O)N[C@@H](CC(=O)O)C(=O)N[C@H](C)C(=O)N[C@@H](CC(=O)O)C(=O)NCC(=O)N[C@H](CO)C(=O)N[C@@H]([C@H](C)CC(=O)O)C(=O)N[C@@H](CC(=O)c2cc(Br)ccc2NCC)C(=O)O[C@@H]1C]

RP003

Chemical Formula: $C_{75}H_{106}BrN_{17}O_{27}$
Exact Mass: 1755.66

Step 1. Preparation of RP003-Boc

A solution of (S)-2-decanamido-3-(5-methoxy-H-indol-3-yl)propanoic acid (Inter-IIIA, 5.3 mg), 1-[Bis(dimethylamino)methylene]-1H-1,2,3-triazolo[4,5-b]pyridinium 3-oxide hexafluorophosphate (HATU, 4.5 mg), and N,N-Diisopropylethylamine (Hunig base, 20 uL) in N,N-dimethylformamide (150 uL) was stirred at ambient temperature for 10 minutes, and then transferred to Inter-IIE (8.0 mg) in DMF (150 uL). The resulting solution was further stirred for 15 minutes until the coupling reaction was complete. The product, RP003-Boc, was purified by HPLC (Protocol B1) as a yellow powder (4.8 mg) upon freeze-drying.

Step 2. Preparation of RP003

RP003-Boc (4.7 mg) in (1:9) trifluoroacetic acid (TFA)/dichloromethane (DCM) (250 uL) was stirred at ambient temperature for 10 minutes. Acetonitrile (1 mL) was then added and the solution was evaporated under reduced pressure to a volume of about 100 uL. The concentrated solution was then purified by HPLC (Protocol B2) to obtain RP003 as a yellow powder (3.7 mg) upon freeze-drying. Positive ESIMS m/z 1756.4 (MH)$^+$, theoretical mass for $C_{75}H_{107}BrN_{17}O_{27}$, 1756.67 (Protocol A2).

Example 9

Preparation of RP004

Step 1. Preparation of RP004-Boc

A mixture of (S)-2-decanamido-3-(5-fluoro-1H-indol-3-yl)propanoic acid (Inter-IIIB, 5.0 mg), 1-[Bis(dimethylamino)methylene]-1H-1,2,3-triazolo [4,5-b]pyridinium 3-oxide hexafluorophosphate (HATU, 4.2 mg), and N,N-Diisopropylethylamine (Hunig base, 20 uL) in N,N-dimethylformamide (150 uL) was stirred at ambient temperature for 10 minutes, and then transferred to a solution of Inter-IID (8.0 mg) in DMF (150 uL). The resulting solution was further stirred for 15 minutes until the coupling reaction was complete. The product, RP004-Boc, was purified by HPLC (Protocol B1) as a yellow powder (4.9 mg) upon freeze-drying.

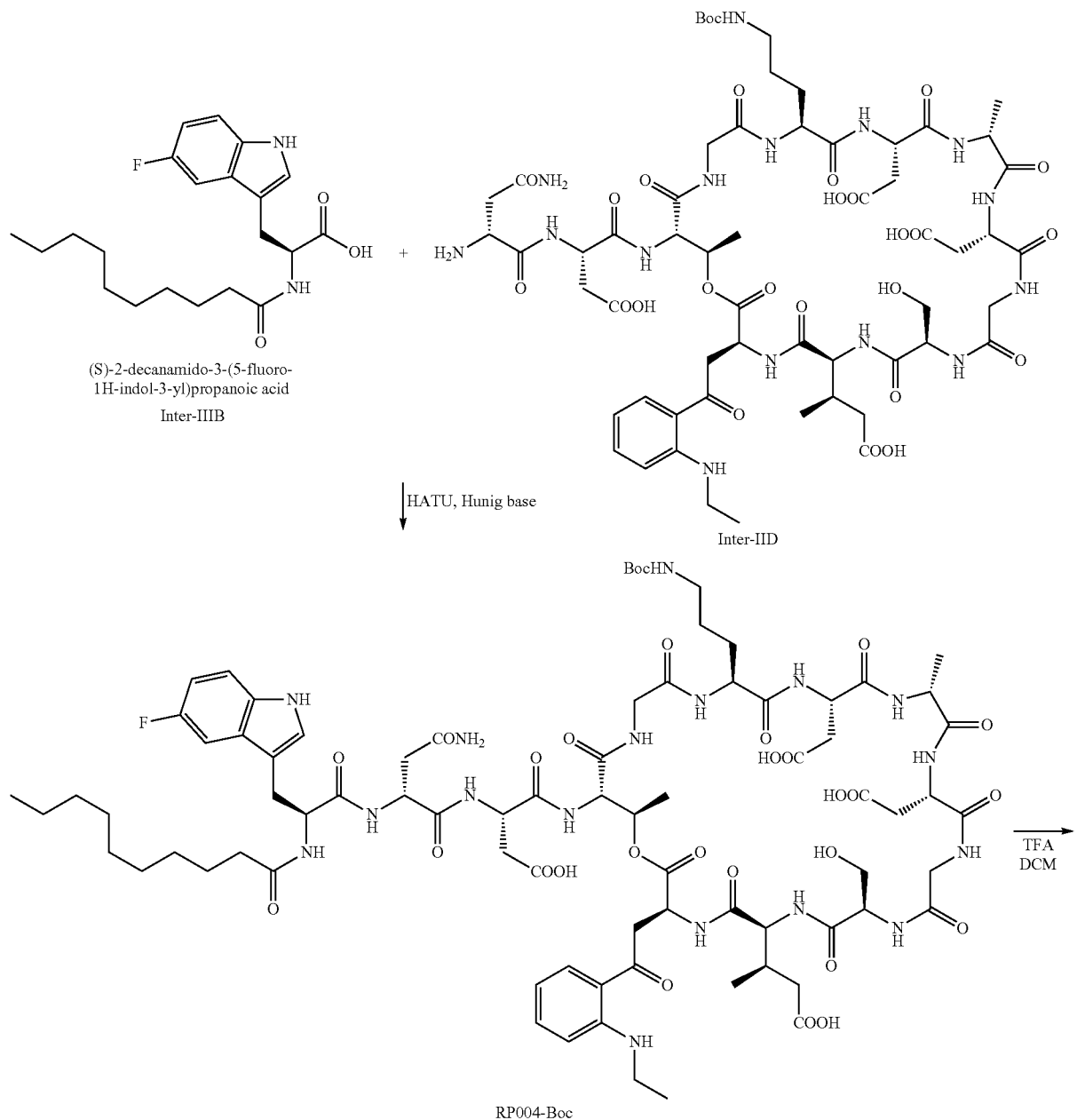

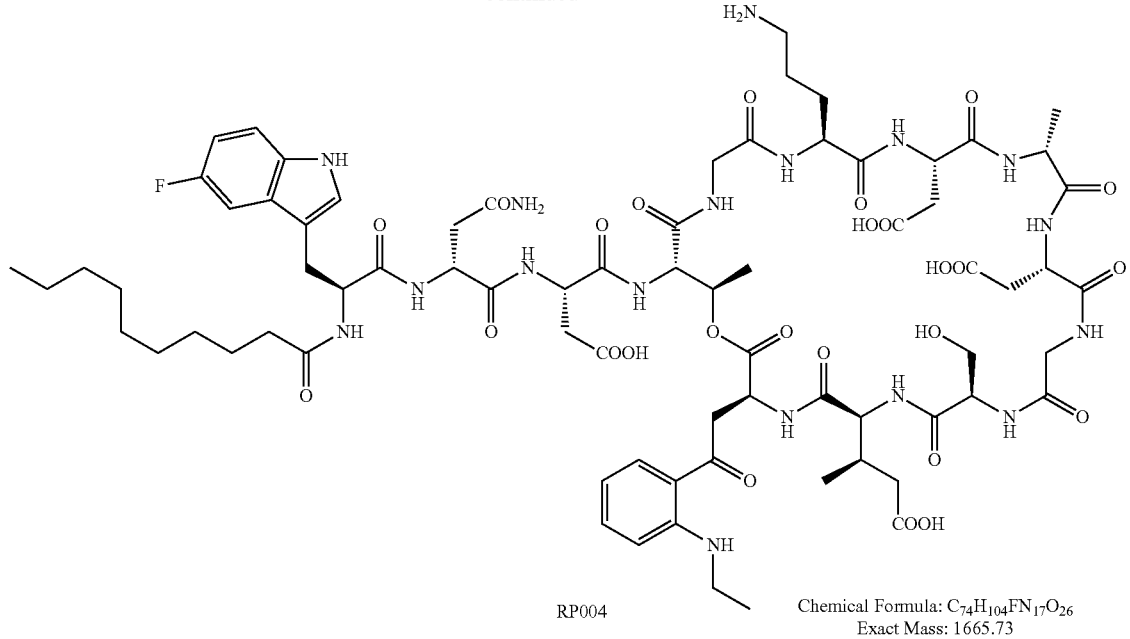 [SMILES: CCCCCCCCCC(=O)N[C@@H](Cc1c[nH]c2ccc(F)cc12)C(=O)N[C@H](CC(N)=O)C(=O)N[C@@H](CC(=O)O)C(=O)N[C@@H]1C(=O)NCC(=O)N[C@@H](CCCN)C(=O)N[C@@H](CC(=O)O)C(=O)N[C@H](C)C(=O)N[C@@H](CC(=O)O)C(=O)NCC(=O)N[C@H](CO)C(=O)N[C@@H]([C@H](C)CC(=O)O)C(=O)N[C@@H](CC(=O)c2ccccc2NCC)C(=O)O[C@@H]1C]

RP004

Chemical Formula: $C_{74}H_{104}FN_{17}O_{26}$
Exact Mass: 1665.73

Step 2. Preparation of RP004

RP004-Boc (3.9 mg) in (1:9) trifluoroacetic acid (TFA)/dichloromethane (DCM) (250 uL total) was stirred at ambient temperature for 10 minutes. Acetonitrile (1 mL) was then added and the solution was evaporated under reduced pressure to a volume of about 100 uL. The concentrated solution was then purified by HPLC (Protocol B2) to obtain RP004 as a yellow powder (2.9 mg) upon freeze-drying. Positive ESIMS m/z 1666.5 (MH)$^+$, theoretical mass for $C_{74}H_{105}N_{17}O_{26}$, 1666.74 (Protocol A2).

Example 10

Preparation of RP005

The procedure in this example is similar to what is described in Example 9, except that Inter-IID was replaced by Inter-IIA. Therefore, Inter-IIIB (5.0 mg) and Inter-IIA (7.1 mg) were coupled and then the protective Boc group was removed to yield RP005 as a yellow powder (2.8 mg). Positive ESIMS m/z 1734.3 (MH)$^+$, theoretical mass for $C_{74}H_{103}Cl_2FN_{17}O_{26}$, 1734.66 (Protocol A2).

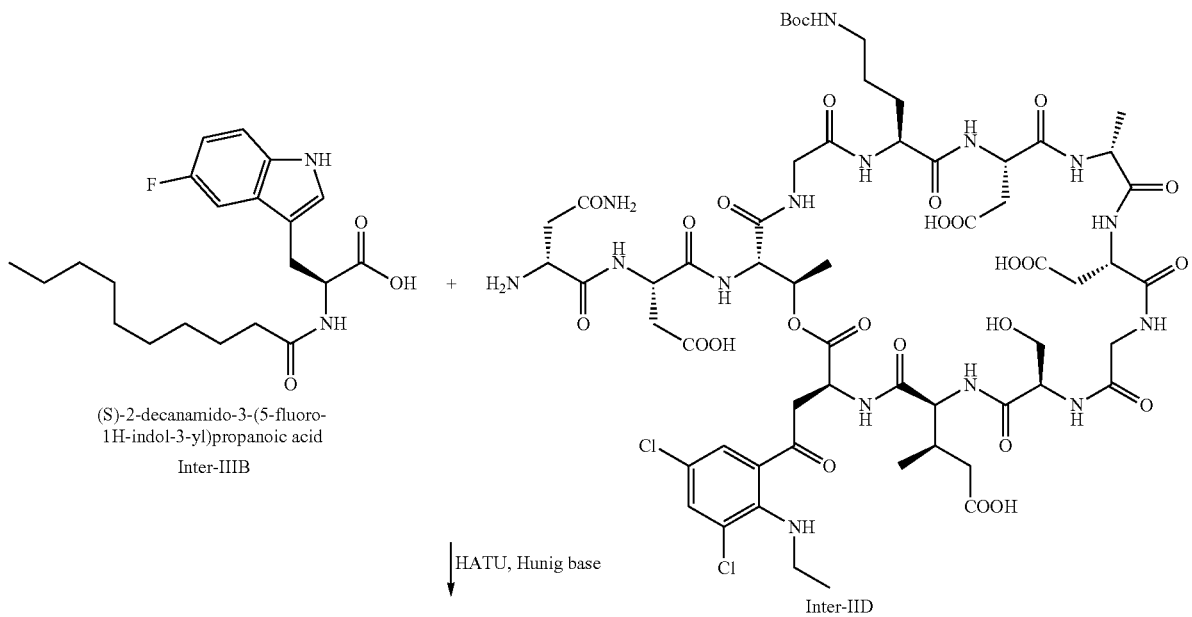

(S)-2-decanamido-3-(5-fluoro-1H-indol-3-yl)propanoic acid
Inter-IIIB

HATU, Hunig base

Inter-IID

-continued
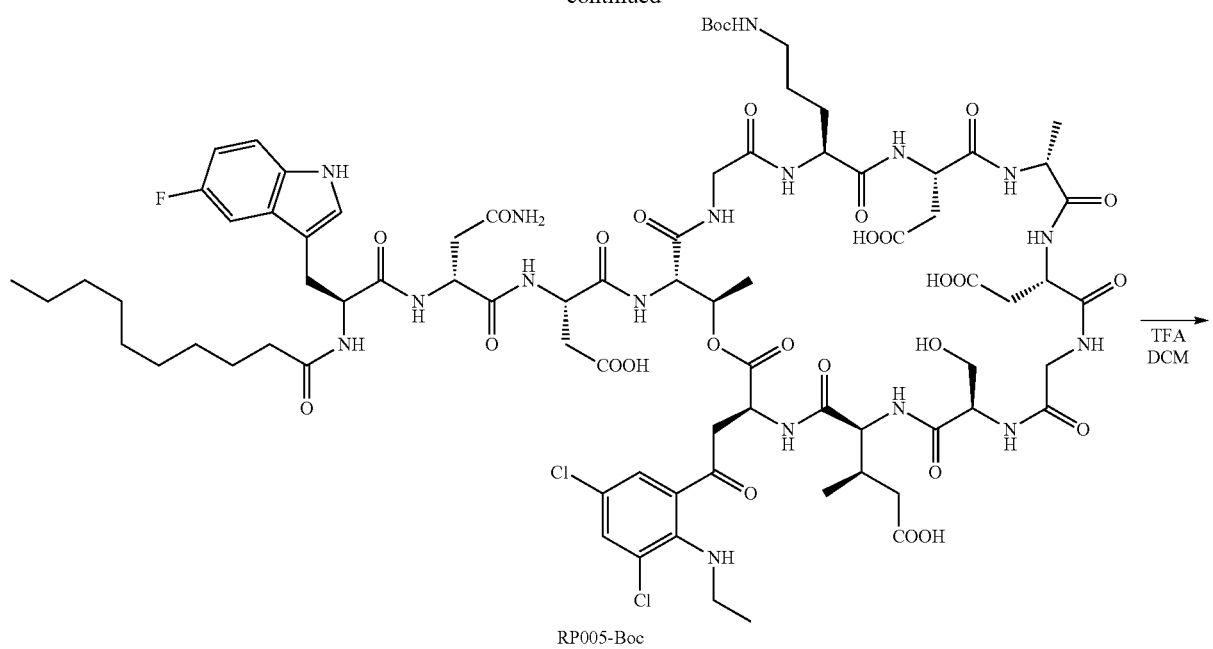
RP005-Boc
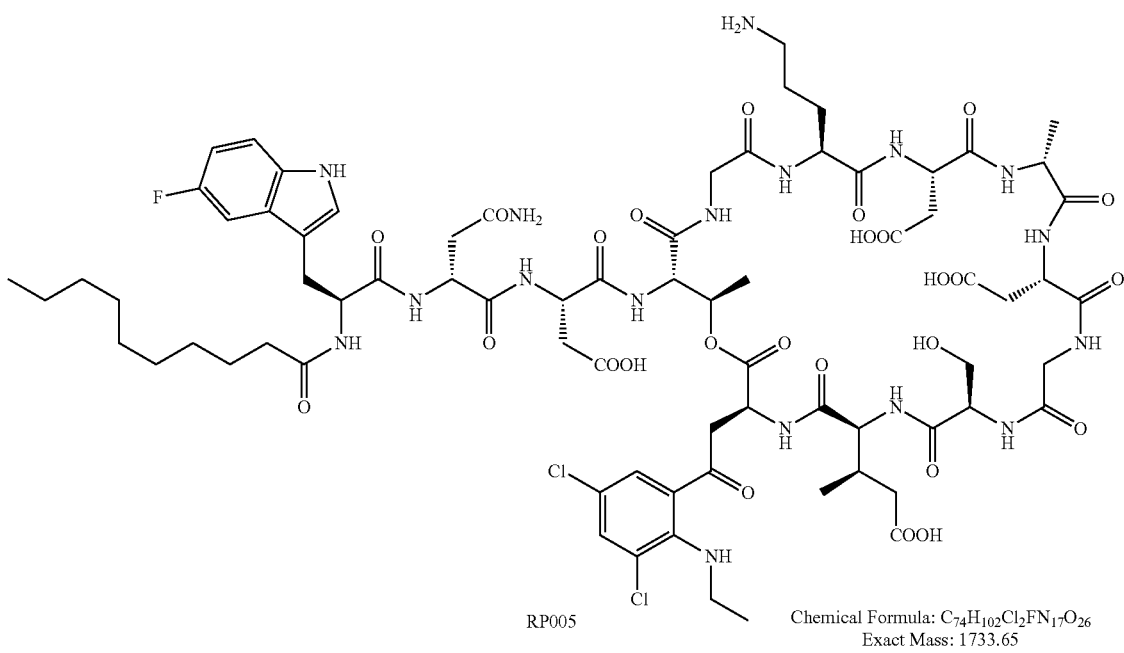 [SMILES: CCCCCCCCCC(=O)N[C@@H](Cc1c[nH]c2ccc(F)cc12)C(=O)N[C@H](CC(N)=O)C(=O)N[C@@H](CC(=O)O)C(=O)N[C@@H]1C(=O)NCC(=O)N[C@@H](CCCN)C(=O)N[C@@H](CC(=O)O)C(=O)N[C@H](C)C(=O)N[C@@H](CC(=O)O)C(=O)NCC(=O)N[C@H](CO)C(=O)N[C@@H]([C@H](C)CC(=O)O)C(=O)N[C@@H](CC(=O)c2cc(Cl)cc(Cl)c2NCC)C(=O)O[C@@H]1C]
RP005
Chemical Formula: $C_{74}H_{102}Cl_2FN_{17}O_{26}$
Exact Mass: 1733.65

Example 11
Preparation of RP006
The procedure in this example is similar to what is described in Example 9, except that Inter-IID was replaced by Inter-IIE. Therefore, Inter-IIIB (5.2 mg) and Inter-IIE (8.0 mg) were coupled and the protective Boc group was removed to yield RP006 as a yellow powder (3.8 mg). Positive ESIMS m/z 1744.4 (MH)$^+$, theoretical mass for $C_{74}H_{104}BrFN_{17}O_{26}$, 1744.65 (Protocol A2).
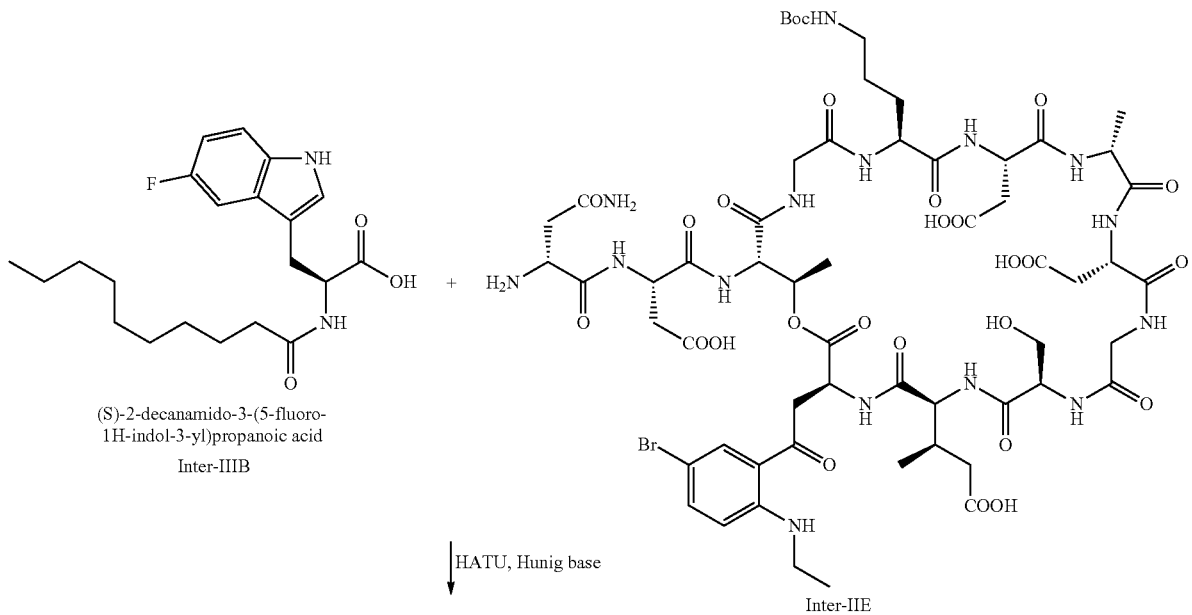
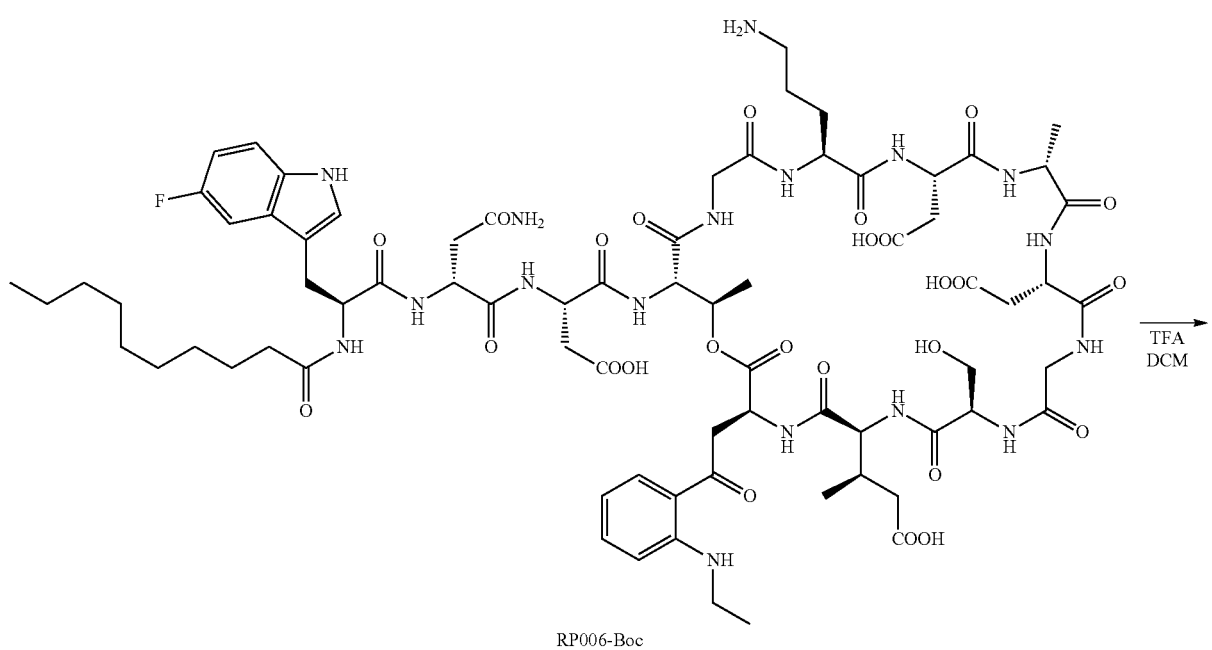

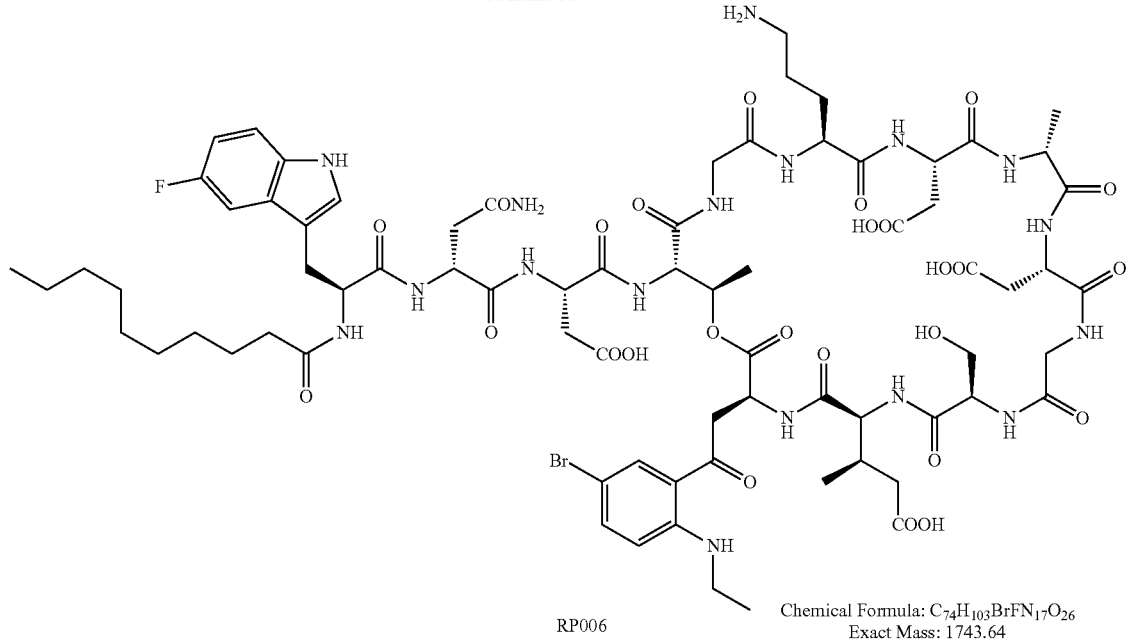 [SMILES: CCCCCCCCCC(=O)N[C@@H](Cc1c[nH]c2ccc(F)cc12)C(=O)N[C@H](CC(N)=O)C(=O)N[C@@H](CC(=O)O)C(=O)N[C@@H]1C(=O)NCC(=O)N[C@@H](CCCN)C(=O)N[C@@H](CC(=O)O)C(=O)N[C@H](C)C(=O)N[C@@H](CC(=O)O)C(=O)NCC(=O)N[C@H](CO)C(=O)N[C@@H]([C@H](C)CC(=O)O)C(=O)N[C@@H](CC(=O)c2cc(Br)ccc2NCC)C(=O)O[C@@H]1C]

RP006

Chemical Formula: $C_{74}H_{103}BrFN_{17}O_{26}$
Exact Mass: 1743.64

Example 12

Preparation of RP007

The procedure in this example is similar to what is described in Example 9, except that Inter-IIIB was replaced by Inter-IIIC. Therefore, Inter-IIIC (5.0 mg) and Inter-IID (8.1 mg) were coupled and then the protective Boc group was removed to yield RP007 as a yellow powder (3.2 mg). Positive ESIMS m/z 1662.6 (MH)$^+$, theoretical mass for $C_{75}H_{108}N_{17}O_{26}$, 1662.77 (Protocol A2).

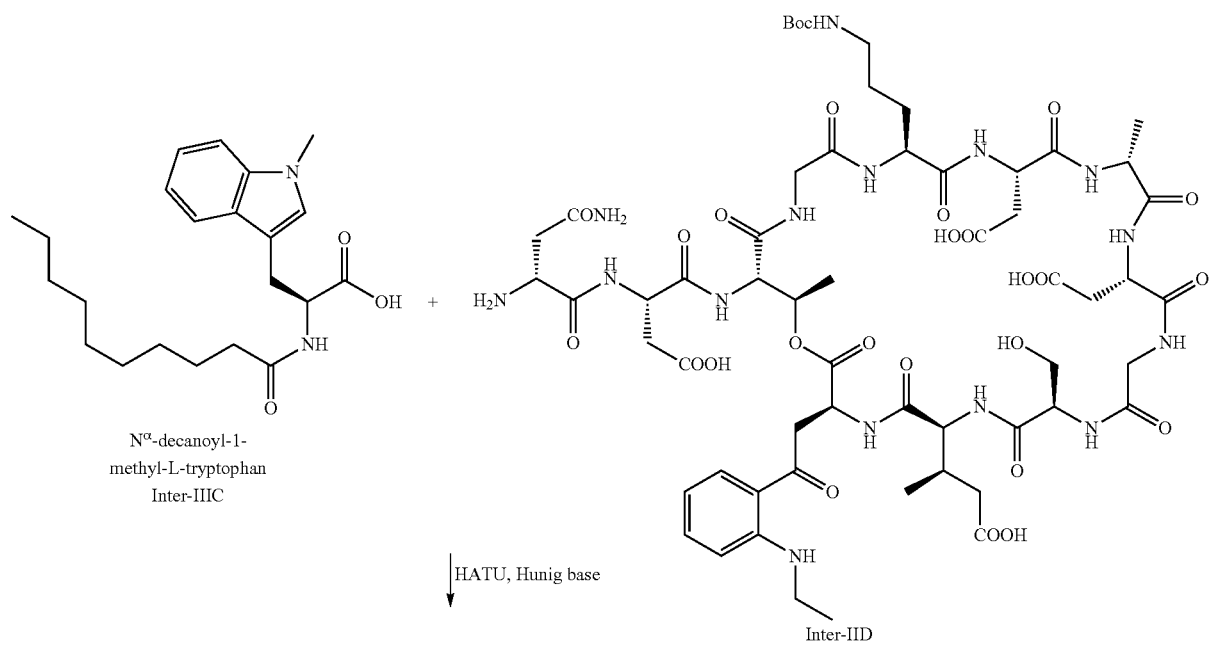

N$^\alpha$-decanoyl-1-methyl-L-tryptophan
Inter-IIIC

Inter-IID

HATU, Hunig base

-continued

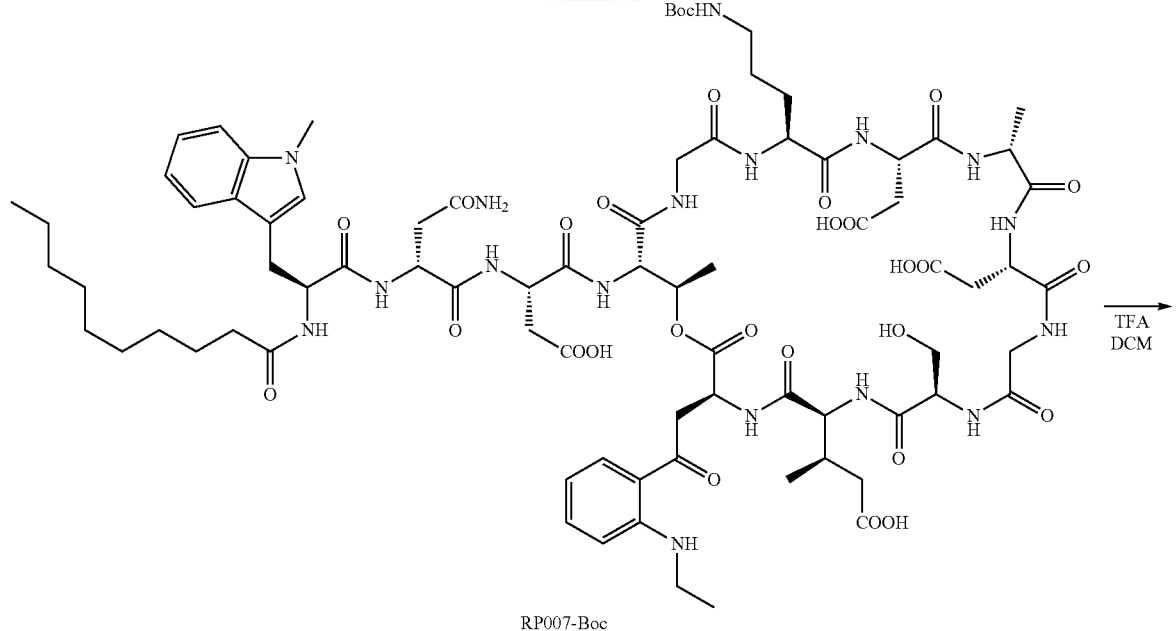

RP007-Boc

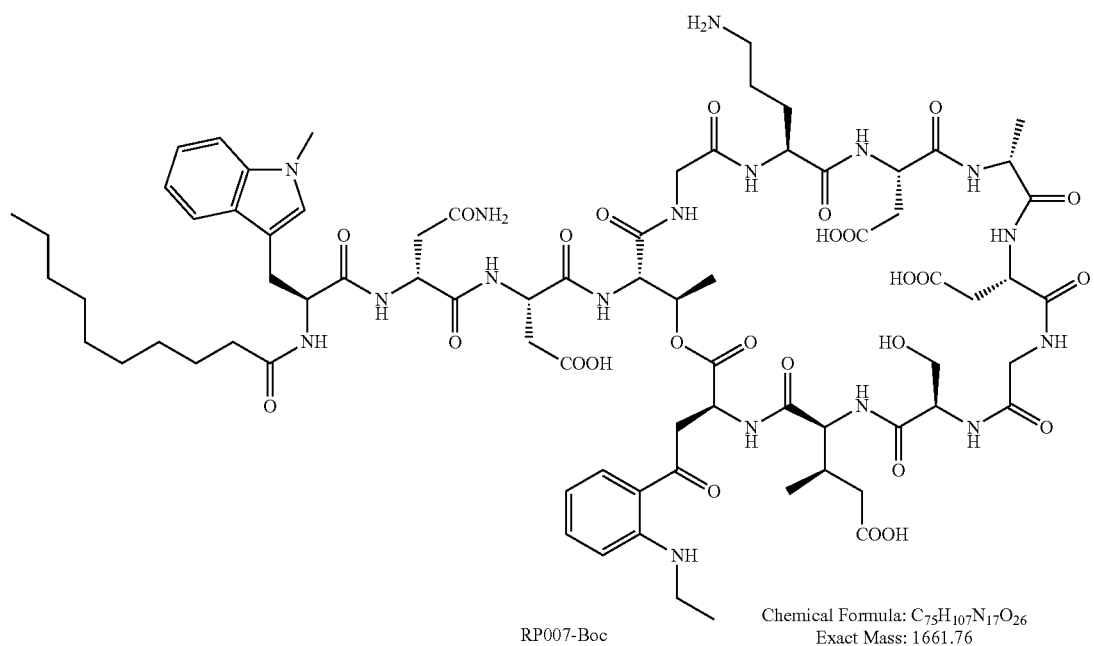 [SMILES: CCCCCCCCCC(=O)N[C@@H](Cc1cn(C)c2ccccc12)C(=O)N[C@H](CC(N)=O)C(=O)N[C@@H](CC(=O)O)C(=O)N[C@@H]1C(=O)NCC(=O)N[C@@H](CCCN)C(=O)N[C@@H](CC(=O)O)C(=O)N[C@H](C)C(=O)N[C@@H](CC(=O)O)C(=O)NCC(=O)N[C@H](CO)C(=O)N[C@@H]([C@H](C)CC(=O)O)C(=O)N[C@@H](CC(=O)c2ccccc2NCC)C(=O)O[C@@H]1C]

RP007-Boc

Chemical Formula: $C_{75}H_{107}N_{17}O_{26}$
Exact Mass: 1661.76

Example 13

Preparation of RP008

The procedure in this example is similar to what is described in Example 12, except that Inter-IID was replaced by Inter-IIE. Therefore, Inter-IIIC (6.0 mg) and Inter-IIE (7.4 mg) were coupled and then the protective Boc group was removed to yield RP008 as a yellow powder (4.4 mg). Positive ESIMS m/z 1740.4 (MH)$^+$, theoretical mass for $C_{75}H_{107}BrN_{17}O_{26}$, 1740.68 (Protocol A2).

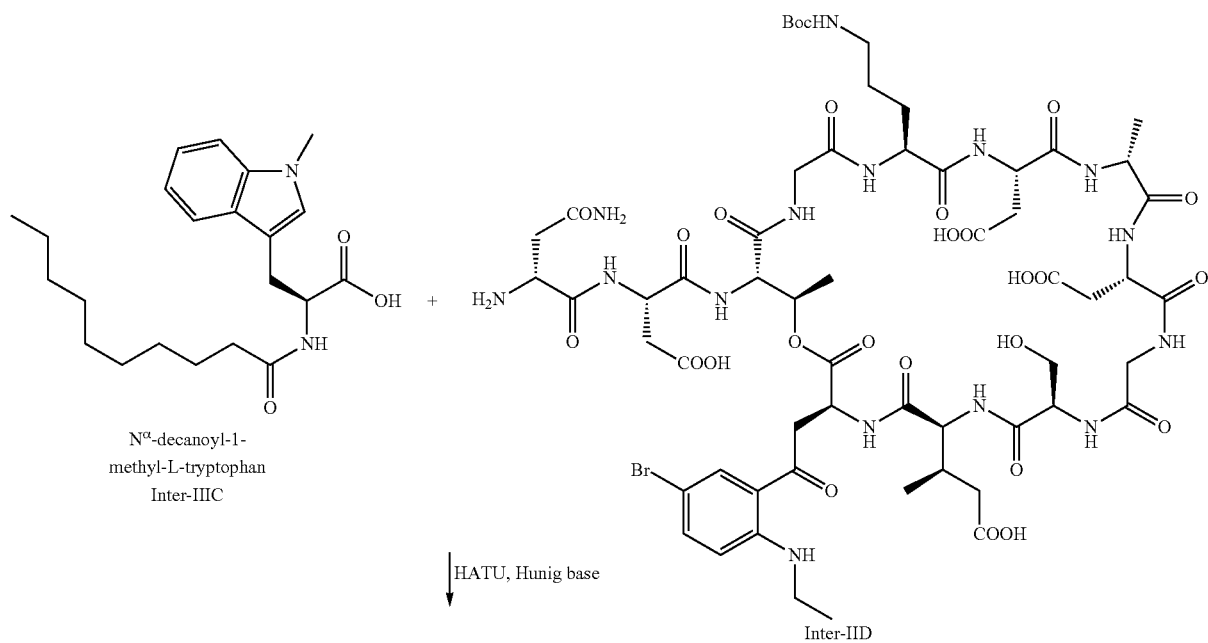
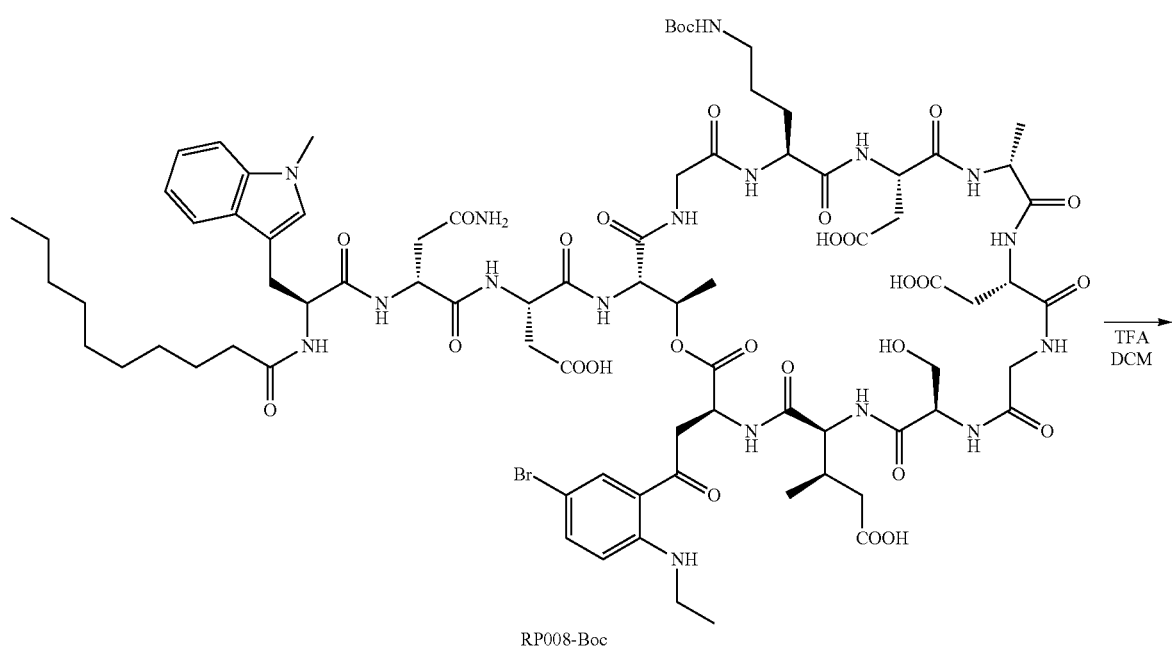

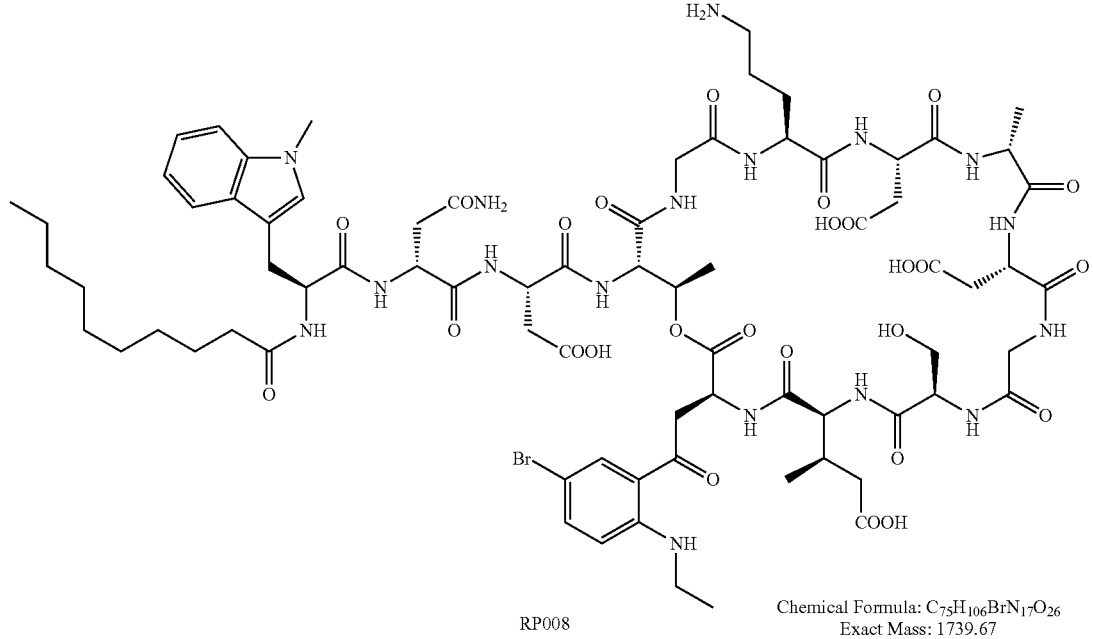 [SMILES: CCCCCCCCCC(=O)N[C@@H](Cc1cn(C)c2ccccc12)C(=O)N[C@H](CC(N)=O)C(=O)N[C@@H](CC(=O)O)C(=O)N[C@@H]1C(=O)NCC(=O)N[C@@H](CCCN)C(=O)N[C@@H](CC(=O)O)C(=O)N[C@H](C)C(=O)N[C@@H](CC(=O)O)C(=O)NCC(=O)N[C@H](CO)C(=O)N[C@@H]([C@H](C)CC(=O)O)C(=O)N[C@@H](CC(=O)c2cc(Br)ccc2NCC)C(=O)O[C@@H]1C]

RP008

Chemical Formula: C$_{75}$H$_{106}$BrN$_{17}$O$_{26}$
Exact Mass: 1739.67

Example 14

Preparation of RP009

The procedure in this example is similar to what is described in Example 9, except that Inter-IIIB was replaced by Inter-IIID. Therefore, Inter-IIID (5.0 mg) and Inter-IID (8.6 mg) were coupled and then the protective Boc group was removed to yield RP009 as a yellow powder (3.0 mg). Positive ESIMS m/z 1662.5 (MH)$^+$, theoretical mass for C$_{75}$H$_{108}$N$_{17}$O$_{26}$, 1662.77 (Protocol A2).

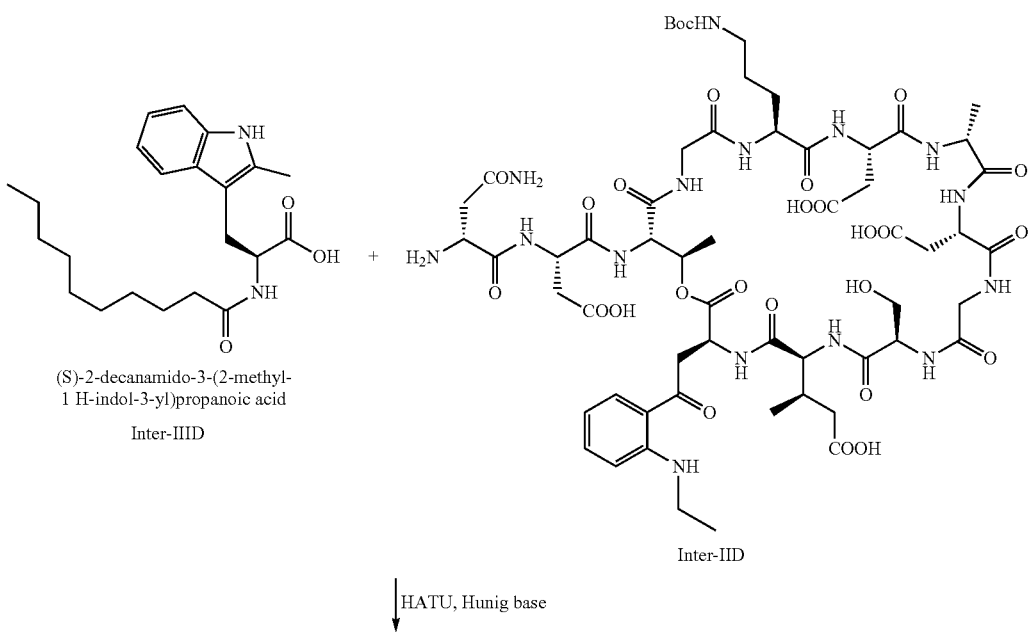

-continued
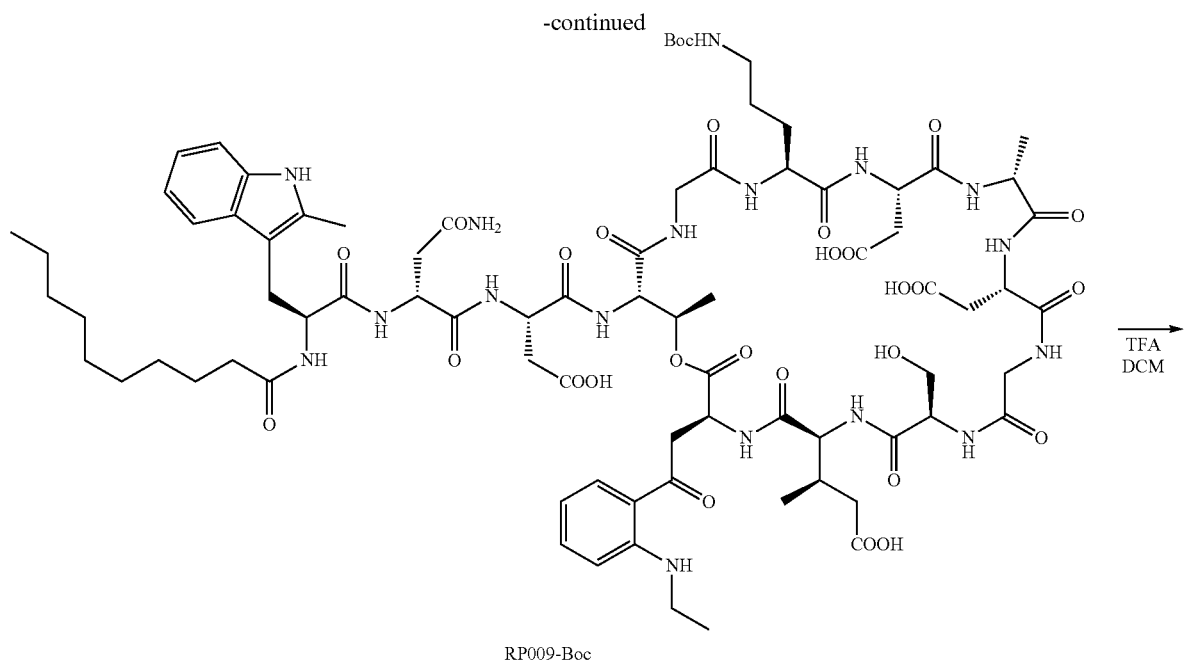
RP009-Boc
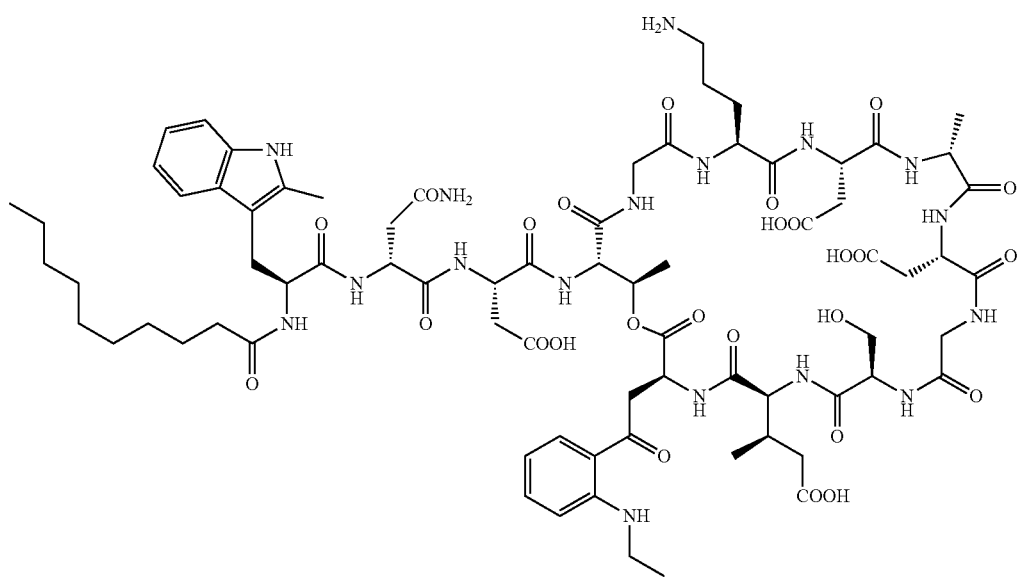
RP009     Chemical Formula: $C_{75}H_{107}N_{17}O_{26}$
Exact Mass: 1661.76

Example 15
Preparation of RP010
The procedure in this example is similar to what is described in Example 14, except that Inter-IID was replaced by Inter-IIA. Therefore, Inter-IIID (5.0 mg) and Inter-IIA (8.1 mg) were coupled and then the protective Boc group was removed to yield RP010 as a yellow powder (3.1 mg). Positive ESIMS m/z 1730.4 (MH)$^+$, theoretical mass for $C_{75}H_{106}Cl_2N_{17}O_{26}$, 1730.69 (Protocol A2).
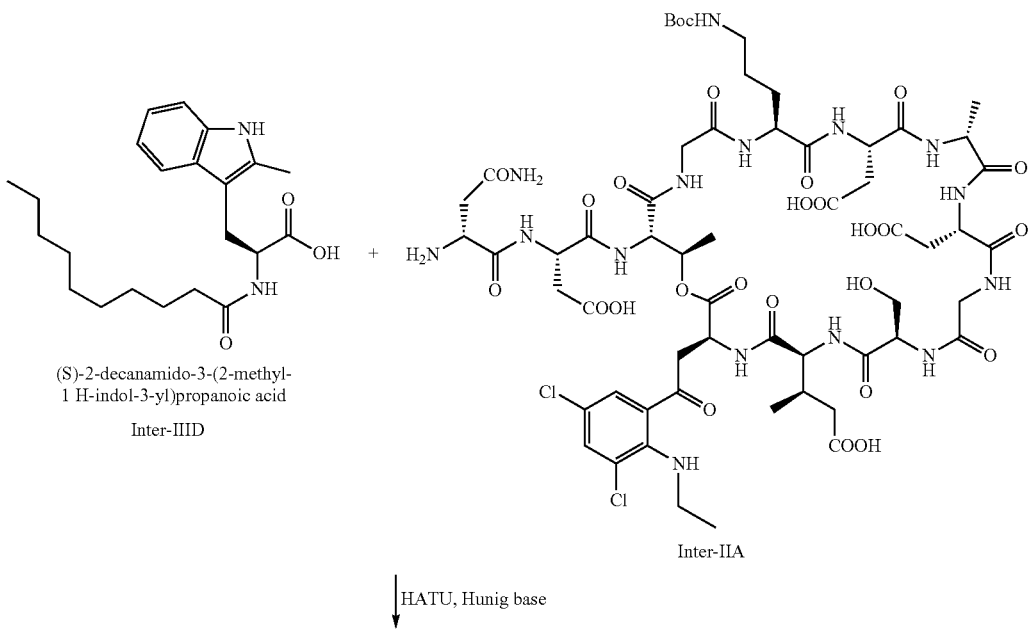
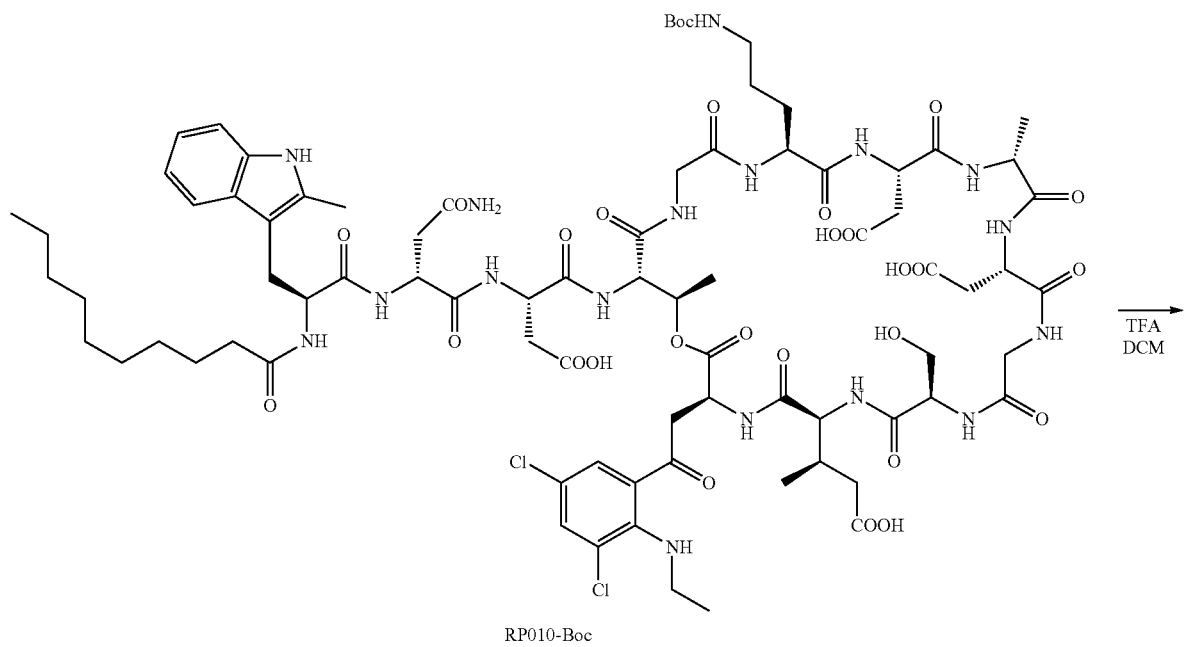

-continued

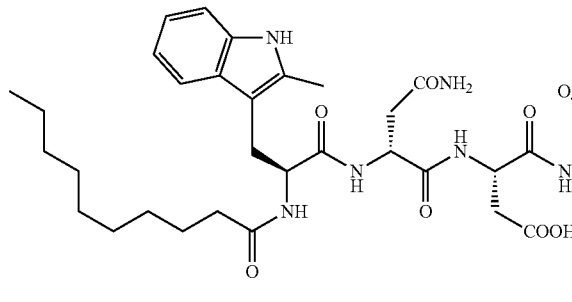

RP010

Chemical Formula: $C_{75}H_{105}Cl_2N_{17}O_{26}$
Exact Mass: 1729.68

Example 16

Preparation of RP011

The procedure in this example is similar to what is described in Example 9, except that IIIB was replaced by Inter-IIIE. Therefore, Inter-IIIE (5.2 mg) and Inter-IID (8.4 mg) were coupled and then the protective Boc group was removed to yield RP011 as a yellow powder (3.2 mg) upon freeze-drying. Positive ESIMS m/z 1662.5 (MH)$^+$, theoretical mass for $C_{75}H_{108}N_{17}O_{26}$, 1662.77 (Protocol A2).

107
108
-continued
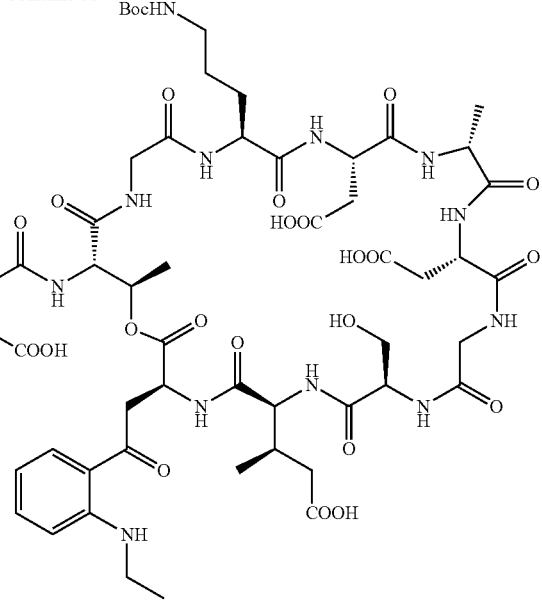
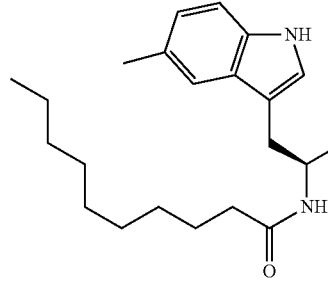
RP011-Boc
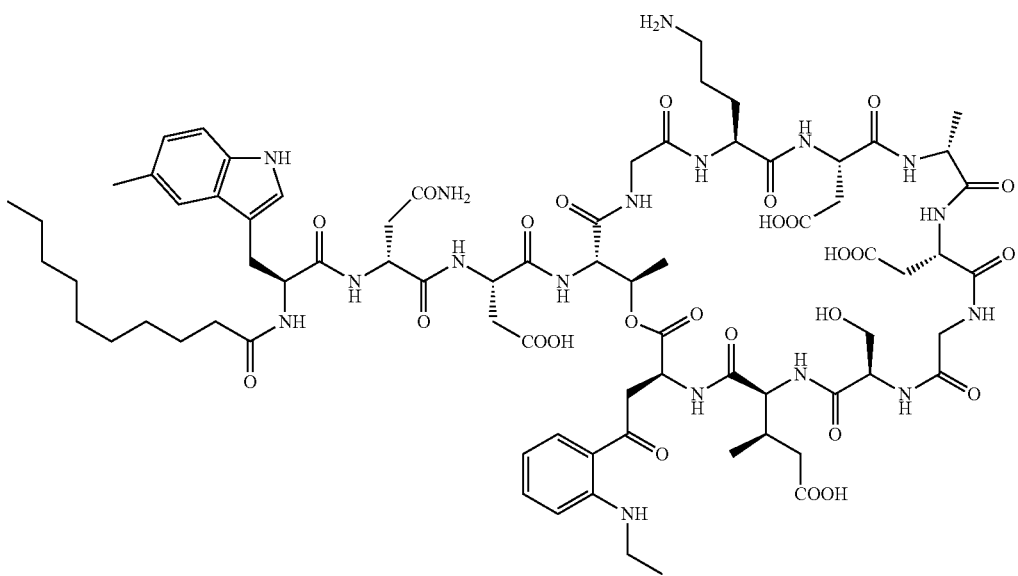
RP011
Chemical Formula: $C_{75}H_{107}N_{17}O_{26}$
Exact Mass: 1661.76

Example 17
Preparation of RP012
The procedure in this example is similar to what is described in Example 16, except that Inter-IID was replaced by Inter-IIA. Therefore, Inter-IIIE (5.2 mg) and Inter-IIA (8.0 mg) were coupled and then the protective Boc group was removed to yield RP012 as a yellow powder (3.8 mg). Positive ESIMS m/z 1730.4 (MH)$^+$, theoretical mass for $C_{75}H_{106}Cl_2N_{17}O_{26}$, 1730.69 (Protocol A2).
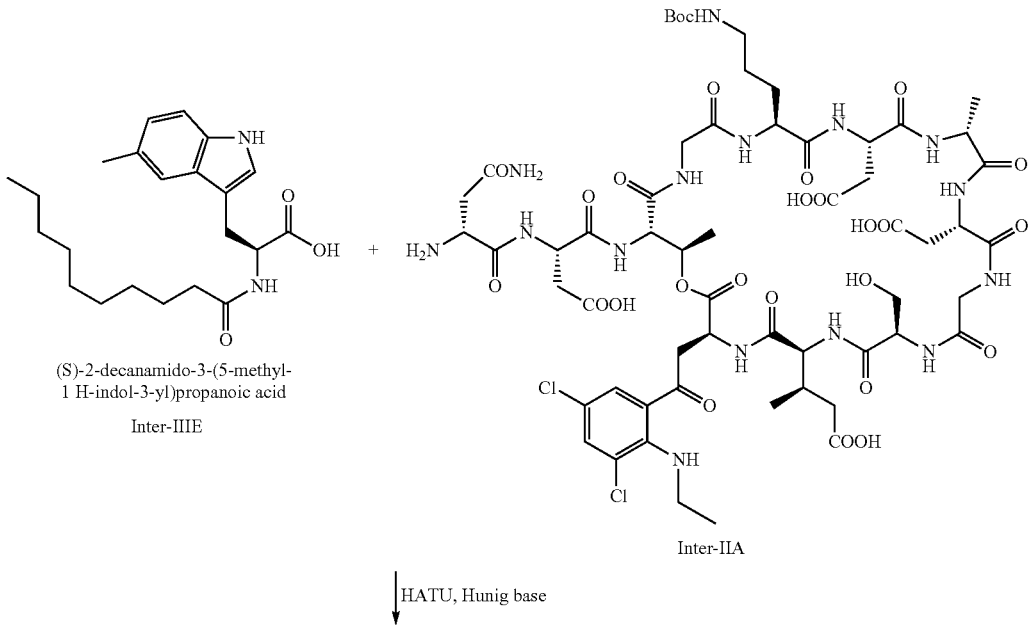
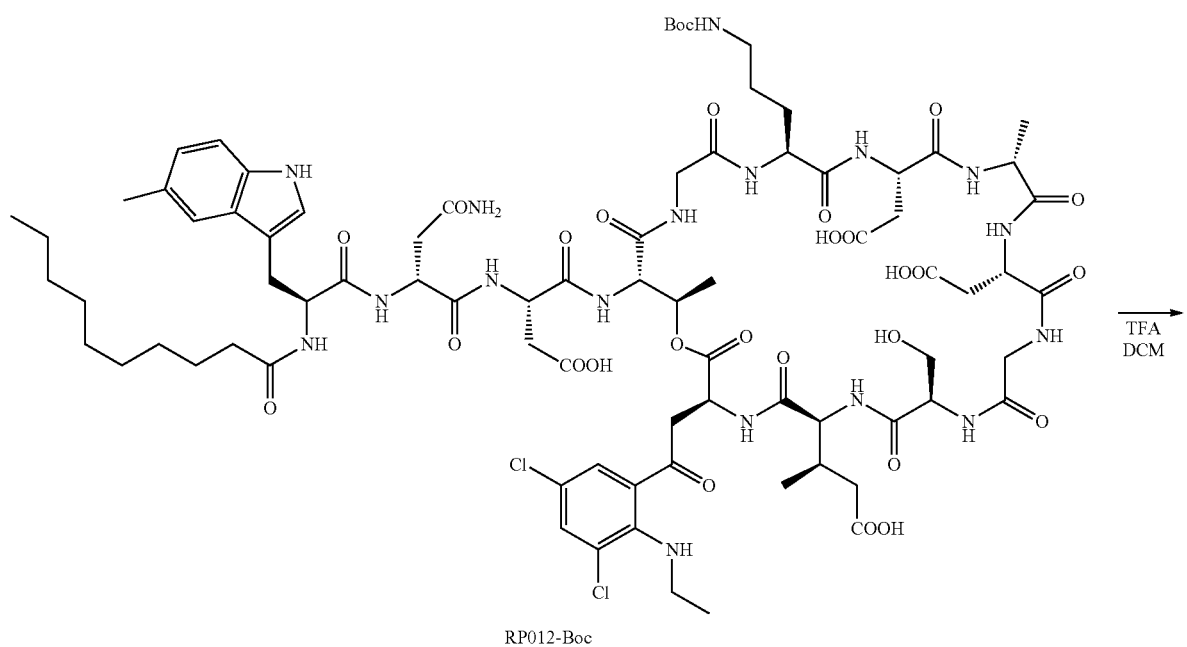

-continued

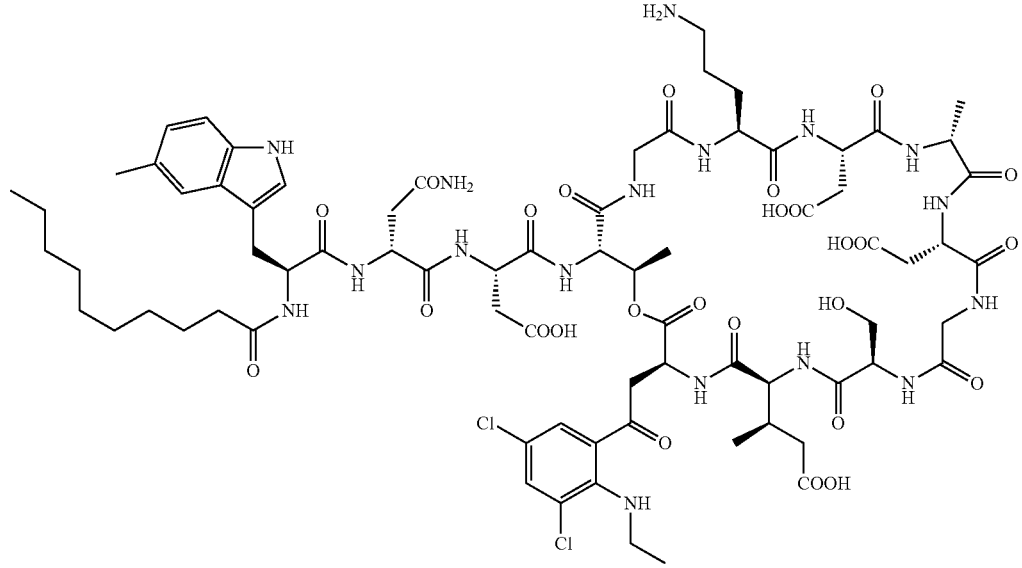

RP012  
Chemical Formula: $C_{75}H_{107}Cl_2N_{17}O_{26}$  
Exact Mass: 1729.68

Example 18

Preparation of RP013

The procedure in this example is similar to what is described in Example 16, except that Inter-IID was replaced by Inter-IIE. Therefore, Inter-IIIE (10.4 mg) and Inter-IIE (14.0 mg) were coupled and then the protective Boc group was removed to yield RP013 as a yellow powder (6.7 mg). Positive ESIMS m/z 1740.4 (MH)⁺, theoretical mass for $C_{75}H_{107}BrN_{17}O_{26}$, 1740.68 (Protocol A2).

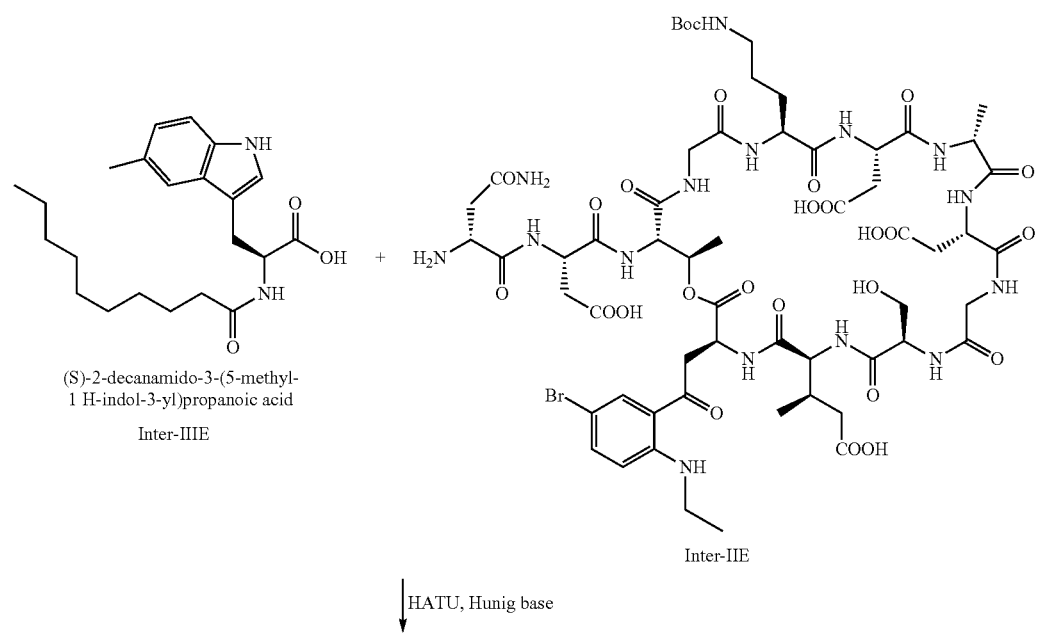

(S)-2-decanamido-3-(5-methyl-1H-indol-3-yl)propanoic acid  
Inter-IIIE

Inter-IIE

↓ HATU, Hunig base 113
114
-continued
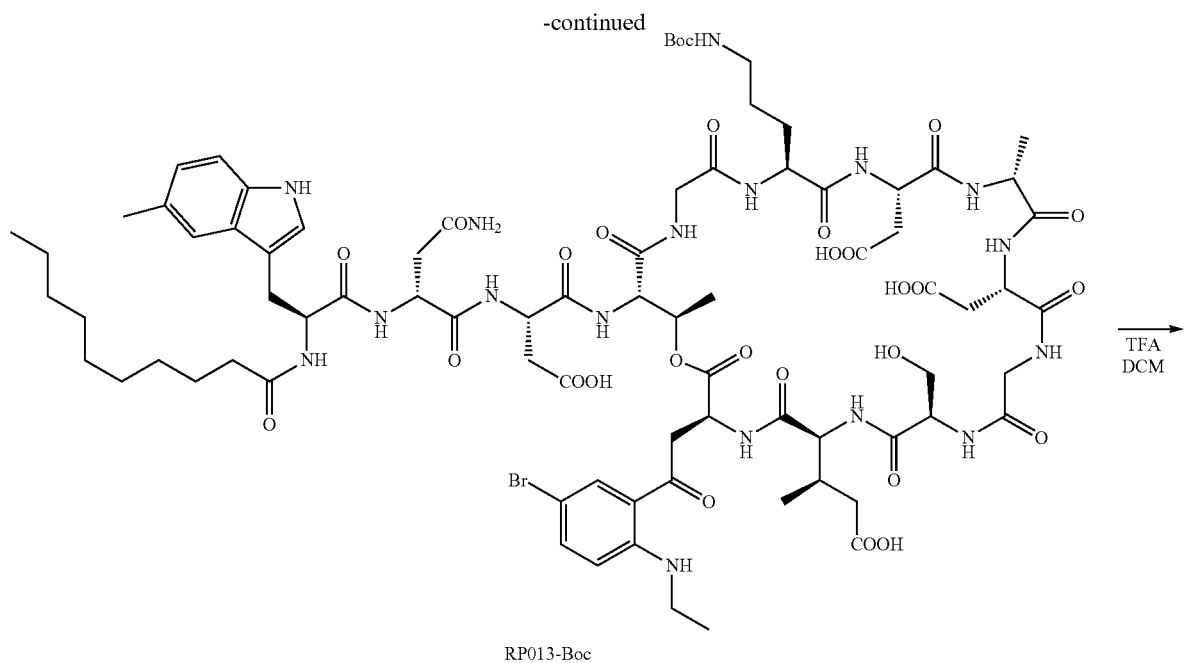
RP013-Boc
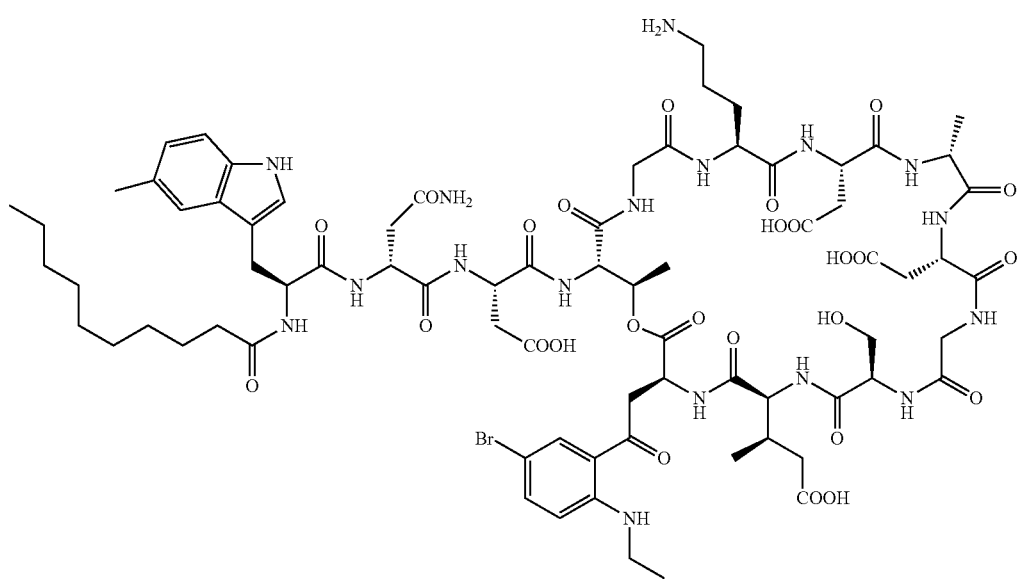
RP013      Chemical Formula: $C_{75}H_{106}BrN_{17}O_{26}$
Exact Mass: 1739.67

Example 19

Preparation of RP014

The procedure in this example is similar to what is described in Example 16, except that Inter-IIIE was replaced by Inter-IIIF. Therefore, Inter-IIIF (10.0 mg) and Inter-IID (8.9 mg) were coupled and then the protective Boc group was removed to yield RP014 as a yellow powder (3.9 mg) upon freeze-drying. Positive ESIMS m/z 1609.4 (MH)$^+$, theoretical mass for $C_{72}H_{105}N_{16}O_{26}$, 1609.74 (Protocol A2).

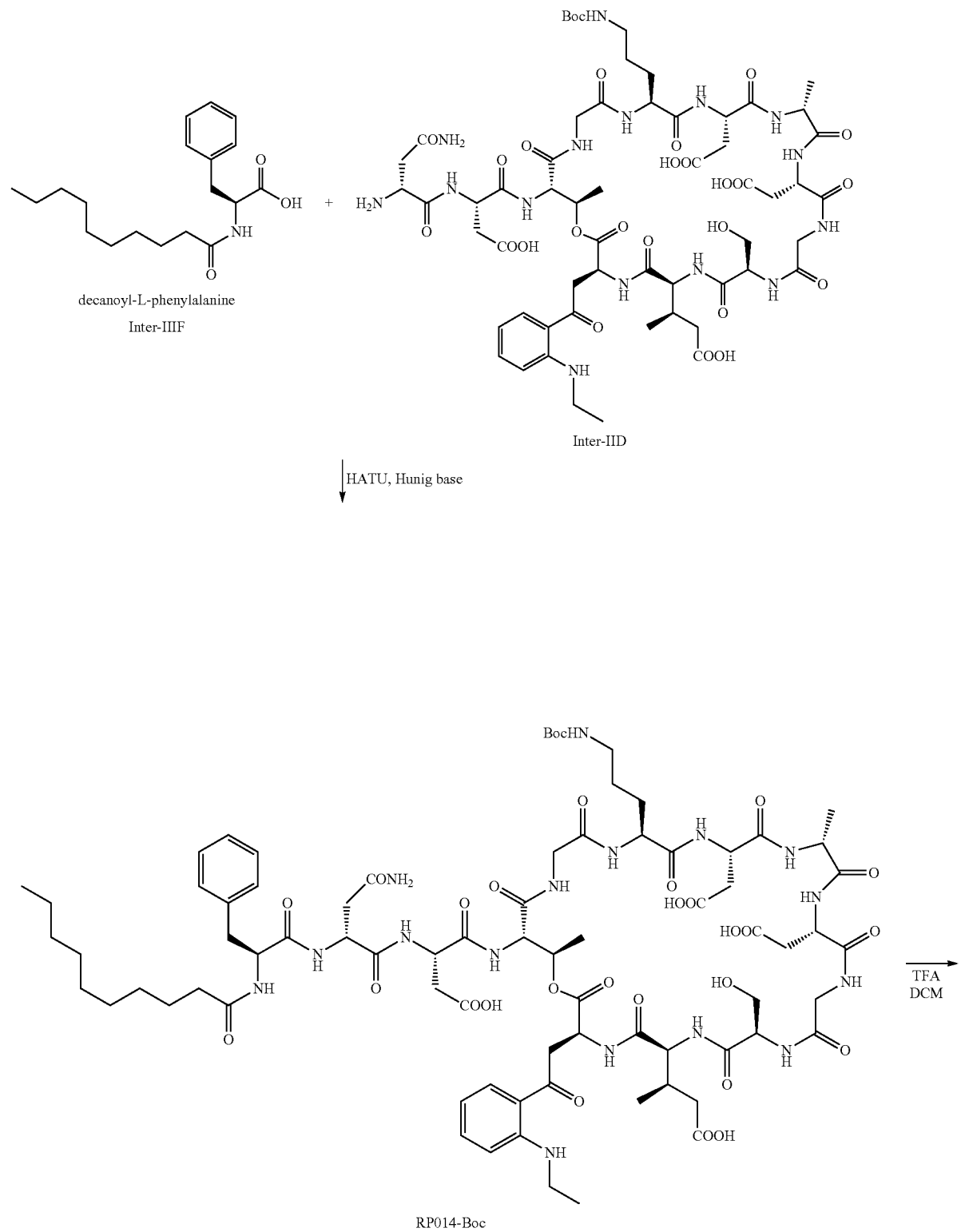

-continued

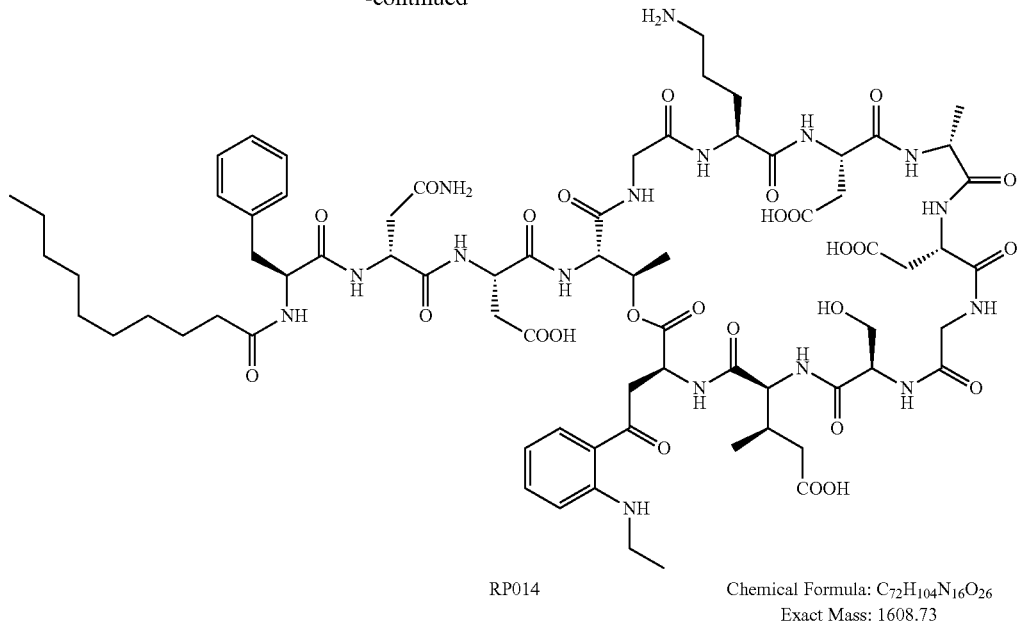

RP014

Chemical Formula: $C_{72}H_{104}N_{16}O_{26}$
Exact Mass: 1608.73

Example 20

Preparation of RP015

The procedure in this example is similar to what is described in Example 19, except that Inter-IID was replaced by Inter-IIA. Therefore, Inter-IIIF (5.9 mg) and Inter-IIA (8.4 mg) were coupled and then the protective Boc group was removed to yield RP015 as a yellow powder (3.4 mg). Positive ESIMS m/z 1677.3 (MH)$^+$, theoretical mass for $C_{72}H_{103}Cl_2N_{16}O_{26}$, 1677.66 (Protocol A2).

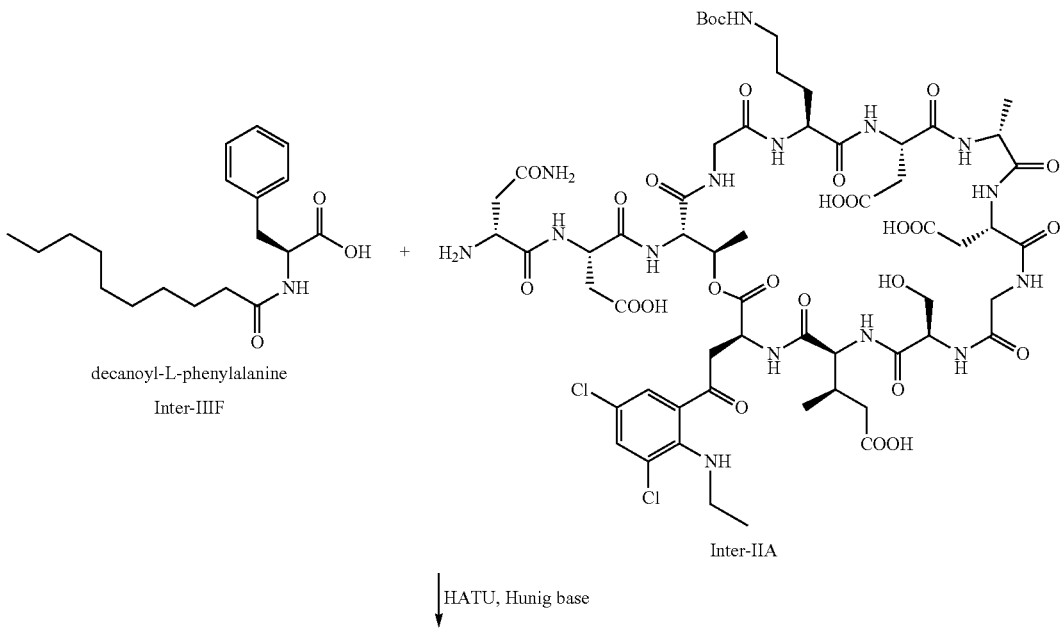

decanoyl-L-phenylalanine
Inter-IIIF

Inter-IIA

HATU, Hunig base

-continued
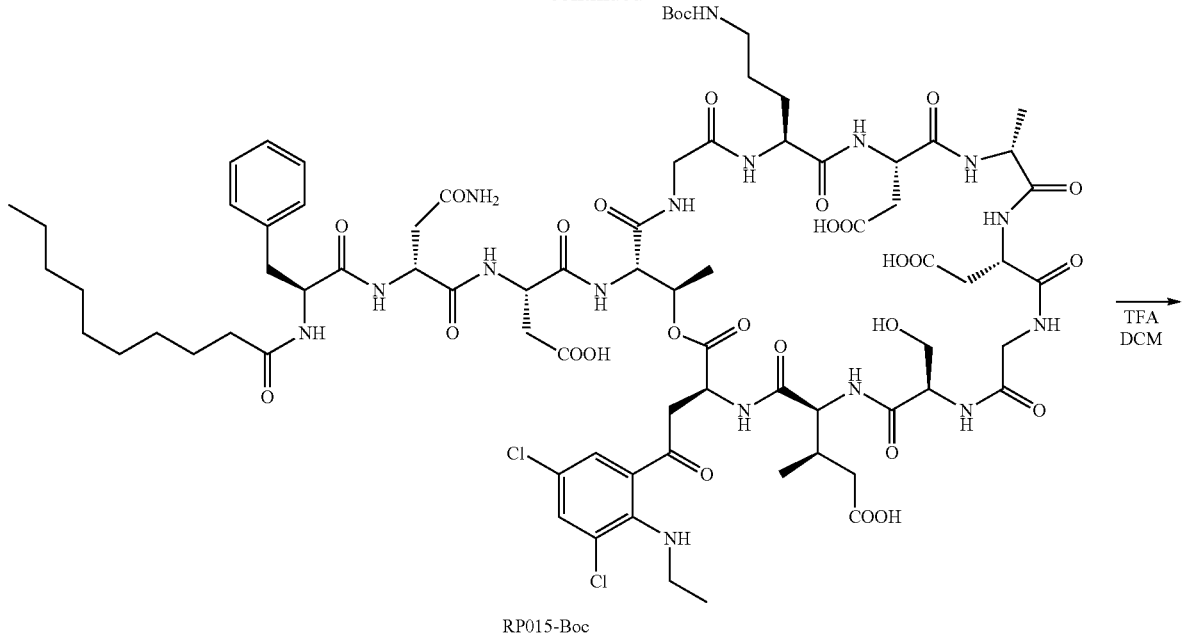
RP015-Boc
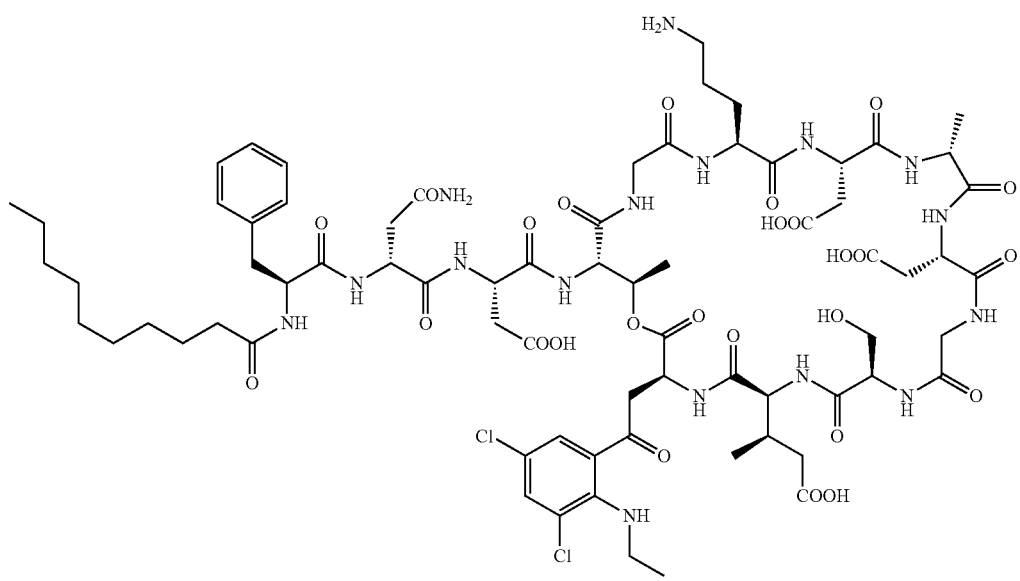
RP015  Chemical Formula: $C_{72}H_{102}Cl_2N_{16}O_{26}$
Exact Mass: 1676.65

Example 21

Preparation of RP016

Step 1. Preparation of RP016-Boc

To a solution of 3H-[1,2,3]triazolo[4,5-b]pyridin-3-yl decanoate (3, 10.1 mg), Inter-IID (5.2 mg) in DMF (200 uL) was added trimethylamine (20 uL). The resulting solution was stirred for 15 minutes until the coupling reaction was complete. The product, RP016-Boc, was purified by HPLC (Protocol B 1) as a yellow powder (3.8 mg) upon freeze-drying.

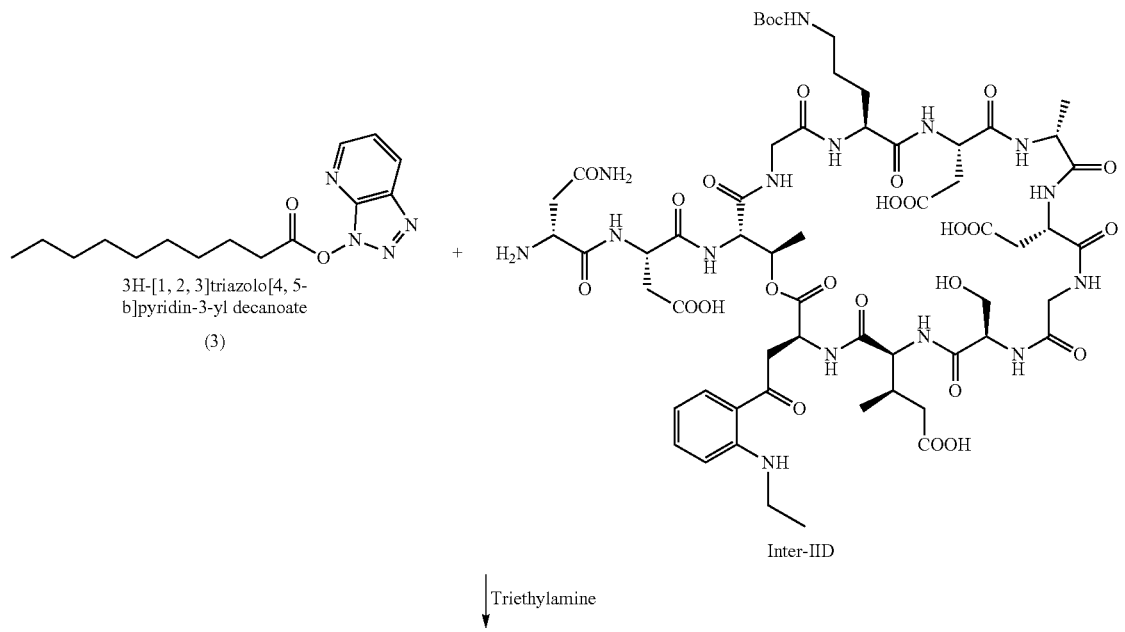

3H-[1, 2, 3]triazolo[4, 5-b]pyridin-3-yl decanoate
(3)

Inter-IID

Triethylamine

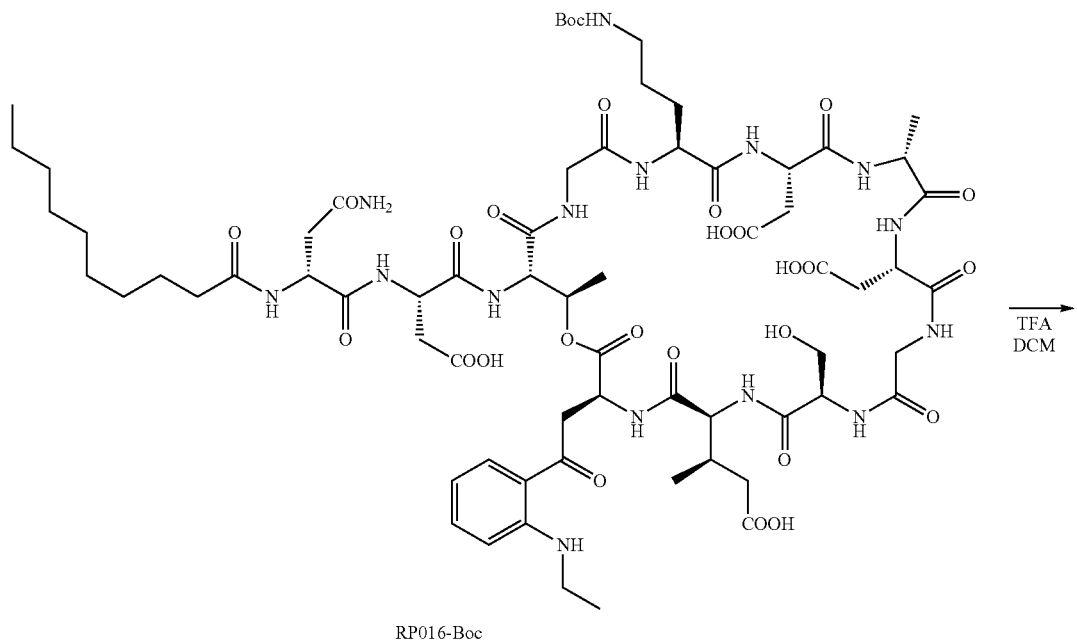

RP016-Boc

TFA
DCM 123 124

-continued

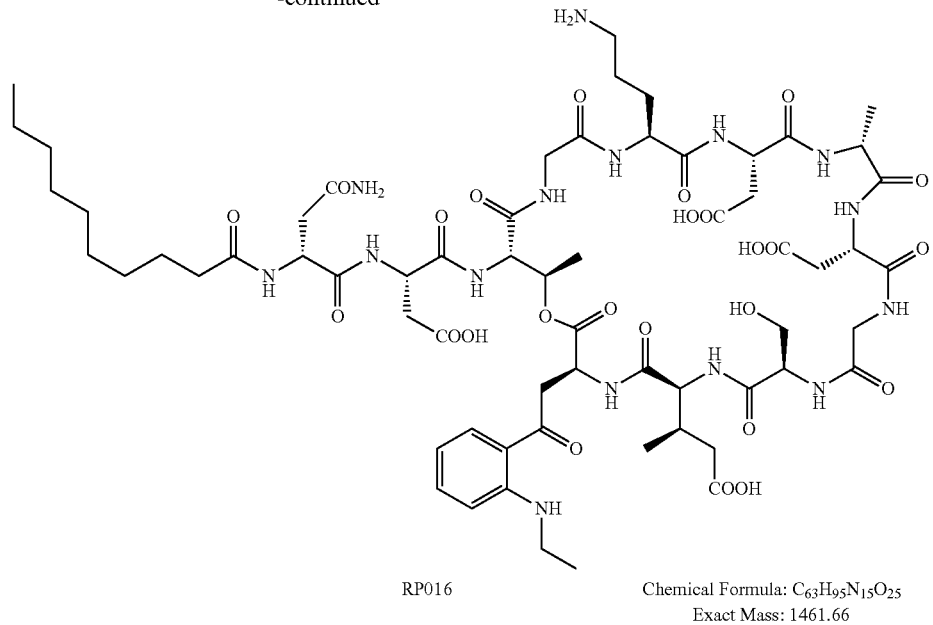

RP016

Chemical Formula: $C_{63}H_{95}N_{15}O_{25}$
Exact Mass: 1461.66

Step 2. Preparation of RP016.

RP016-Boc (3.5 mg) in 1:9 trifluoroacetic acid (TFA)/dichloromethane (DCM) (250 uL total) was stirred at ambient temperature for 10 minutes. Acetonitrile (1 mL) was then added and the solution was evaporated under reduced pressure to a volume of about 100 uL. The concentrated solution was then purified by HPLC (Protocol B2) to obtain RP016 as a yellow powder (3.0 mg) upon freeze-drying. Positive ESIMS m/z 1462.4 (MH)$^+$, theoretical mass for $C_{63}H_{96}N_{15}O_{25}$, 1462.67 (Protocol A2).

Example 22

Preparation of RP017

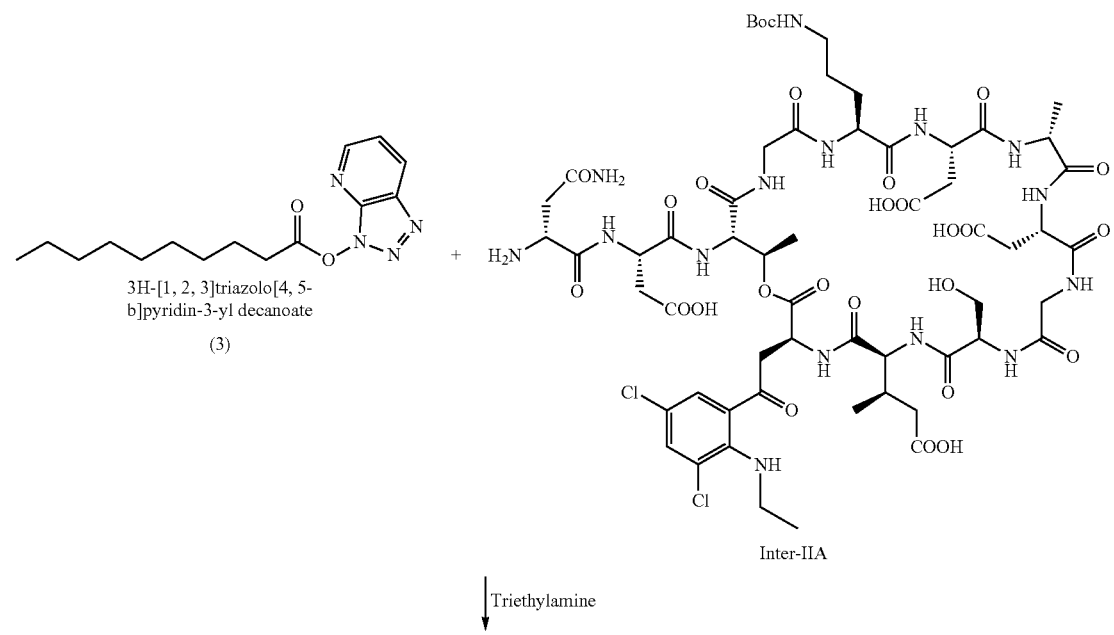

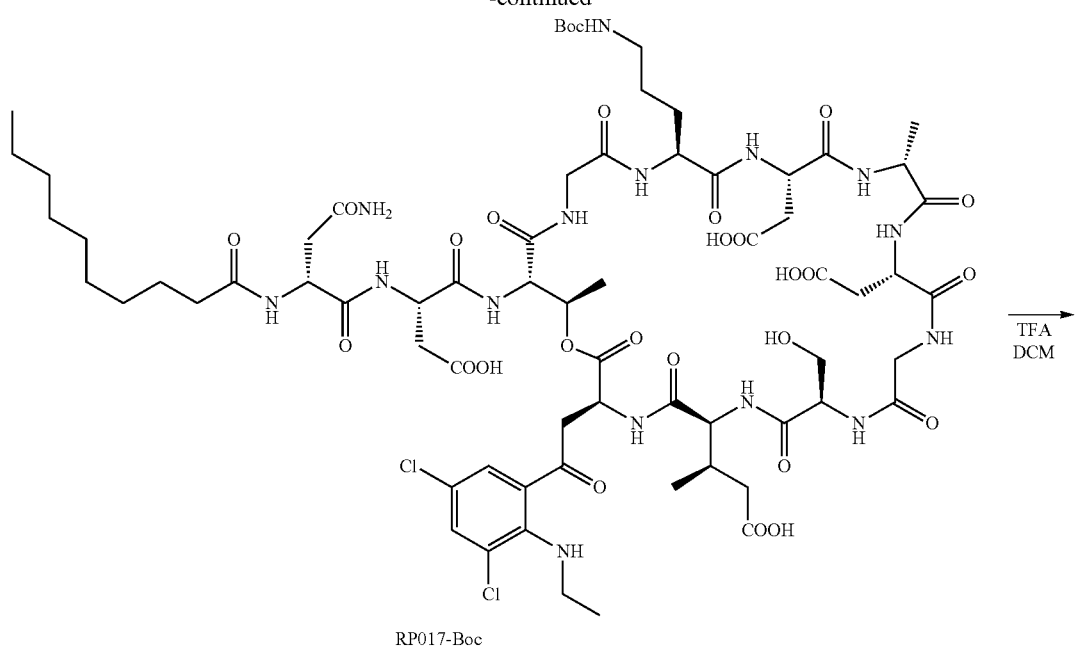
RP017-Boc
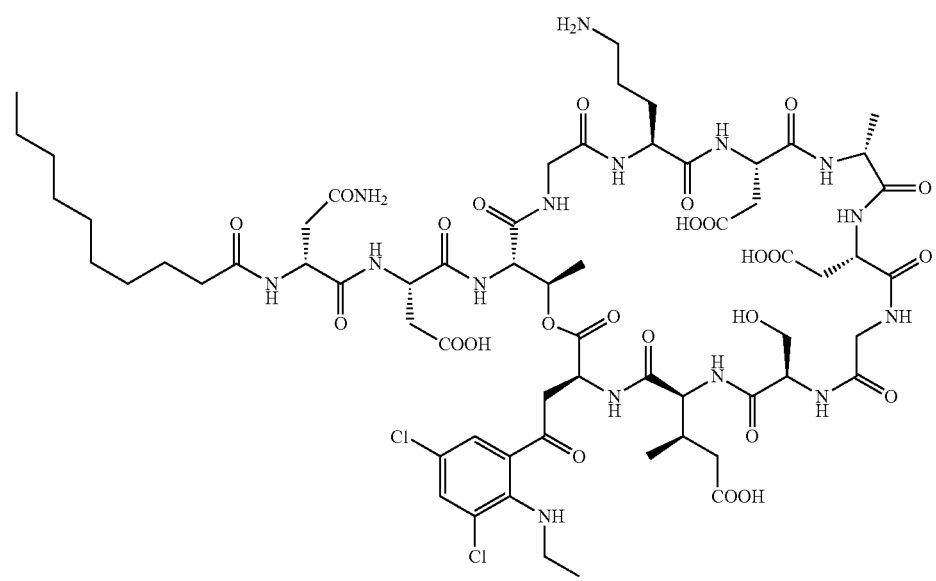
RP017      Chemical Formula: $C_{63}H_{93}Cl_2N_{15}O_{25}$
Exact Mass: 1529.58

The procedure in this example is similar to what is described in Example 21, except that Inter-IID is replaced by Inter-IIA. Thus, the activated fatty acid, 3H-[1,2,3]triazolo[4,5-b]pyridin-3-yl decanoate (3, 10.5 mg) and Inter-IIA (5.5 mg) were coupled and the protective Boc group was removed to yield RP017 as a yellow powder (3.7 mg). Positive ESIMS m/z 1530.3 (MH)$^+$, theoretical mass for $C_{63}H_{94}Cl_2N_{15}O_{25}$, 1530.59 (Protocol A2).

Example 23
Preparation of RP018

The procedures in this example are similar to what are described in Example 10, except that Inter-IIA and Hunig base were respectively replaced by Inter-IIB and 2,4,6-trimethylpyridine (TMP). Therefore, Inter-IIIB (5.0 mg) and Inter-IIB (10.1 mg) were coupled in the presence of HATU and TMP to yield RP018-Boc (5.5 mg). The protective Boc group was then removed by TFA to yield RP018 as a yellow powder (4.0 mg). Negative ESIMS m/z 858.8 (M-2H)$^{2-}$, theoretical value of (M-2H)$^{2-}$ for $C_{73}H_{100}Cl_2FN_{17}O_{26}$, 858.81 (Protocol A1-Neg).

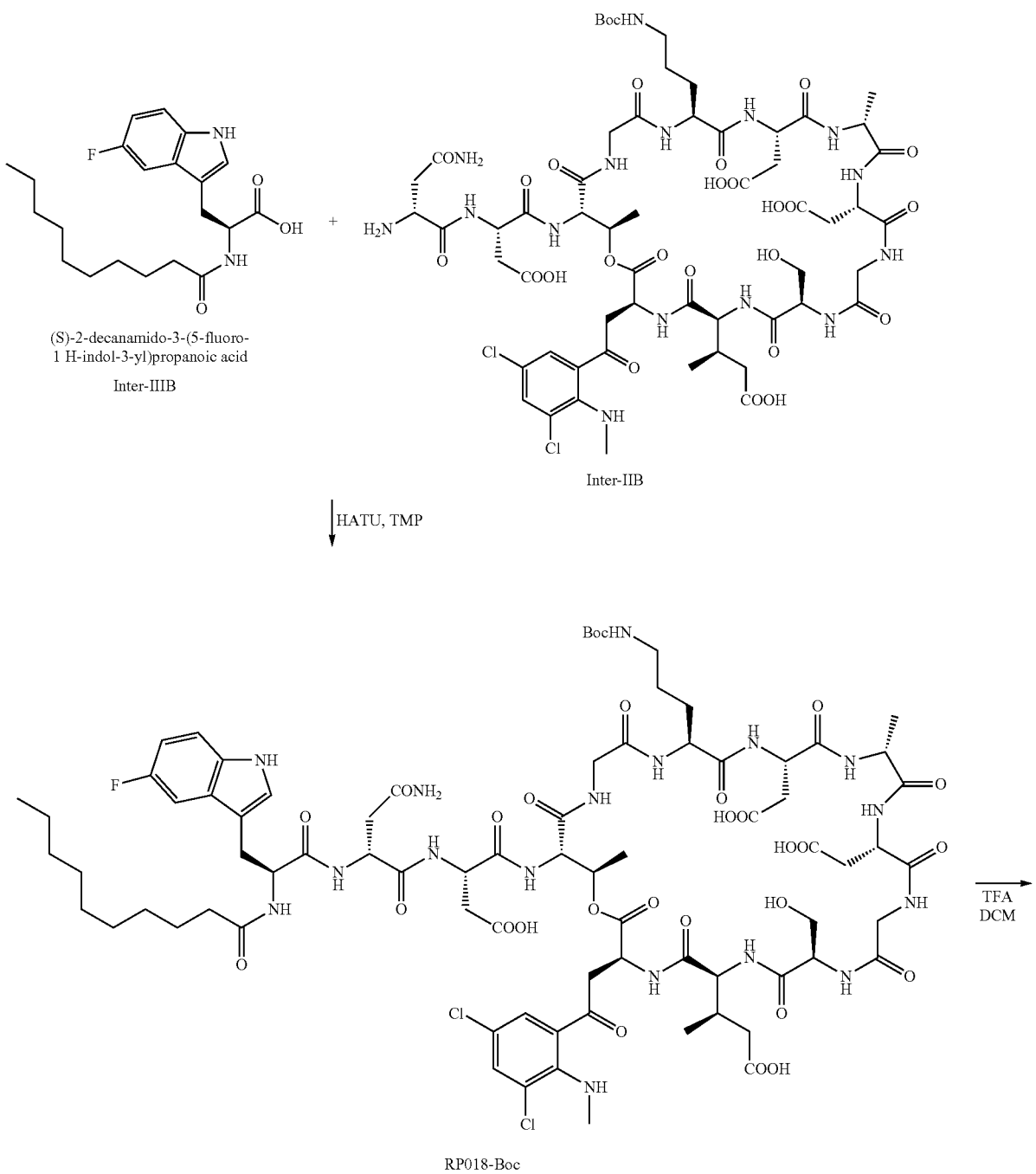

-continued
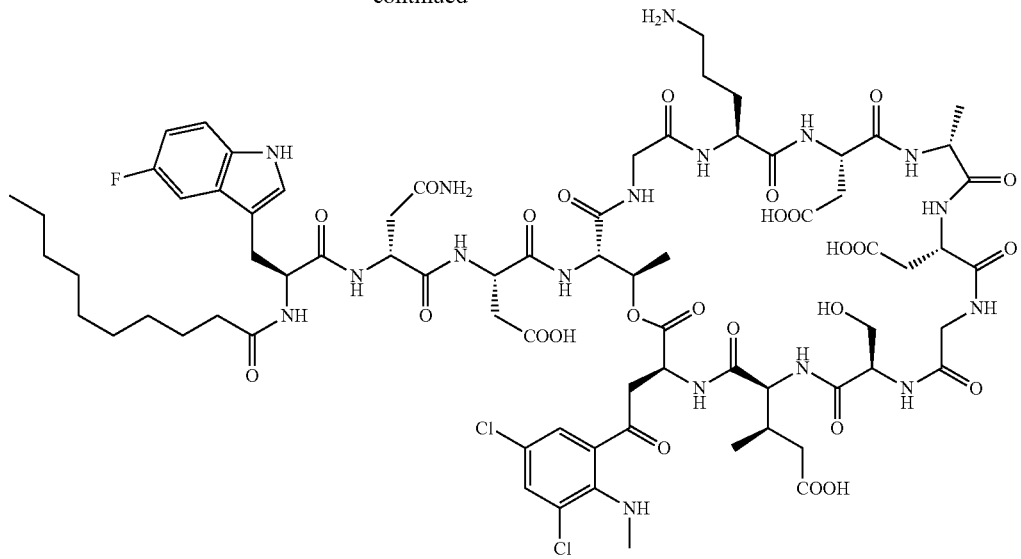
RP018
Chemical Formula: $C_{73}H_{100}Cl_2N_{17}O_{26}$
Exact Mass: 1719.64
Example 24
Preparation of RP019
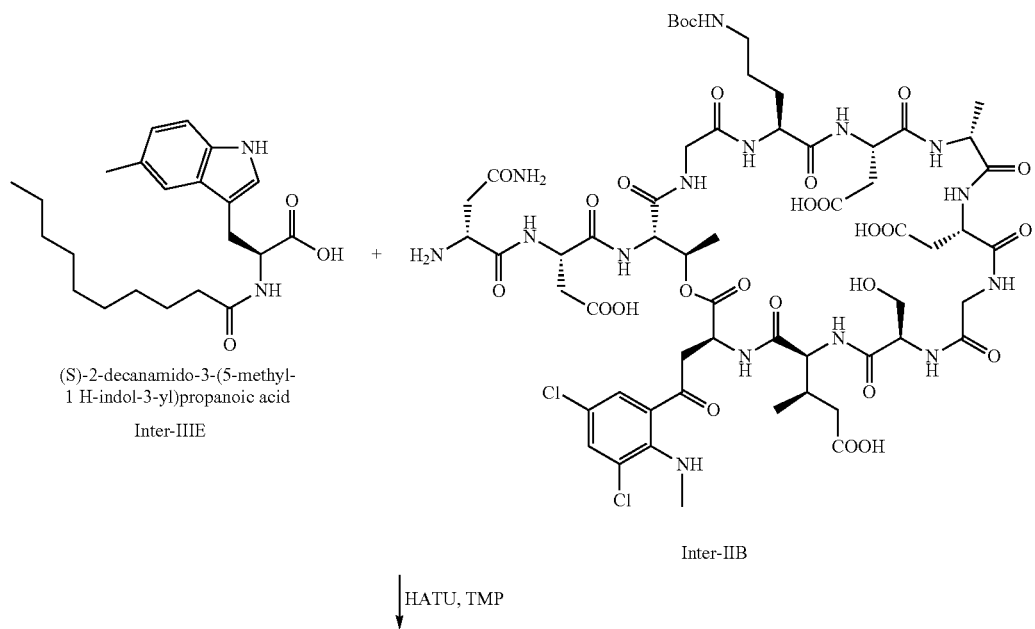
(S)-2-decanamido-3-(5-methyl-
1H-indol-3-yl)propanoic acid
Inter-IIIE
Inter-IIB
HATU, TMP -continued

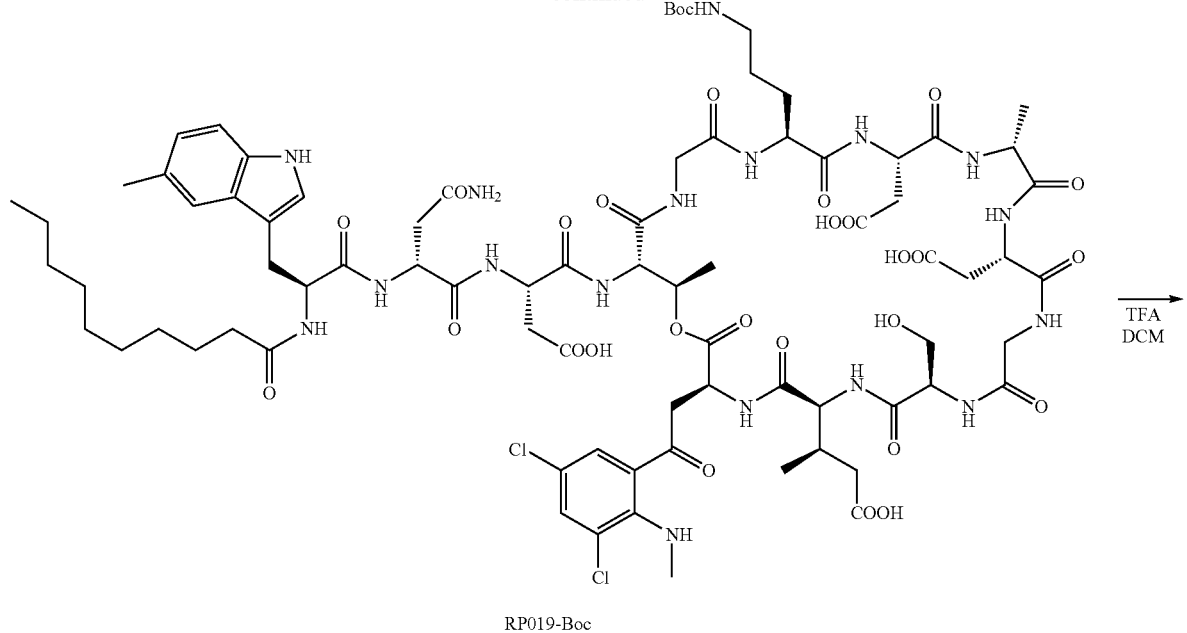

RP019-Boc

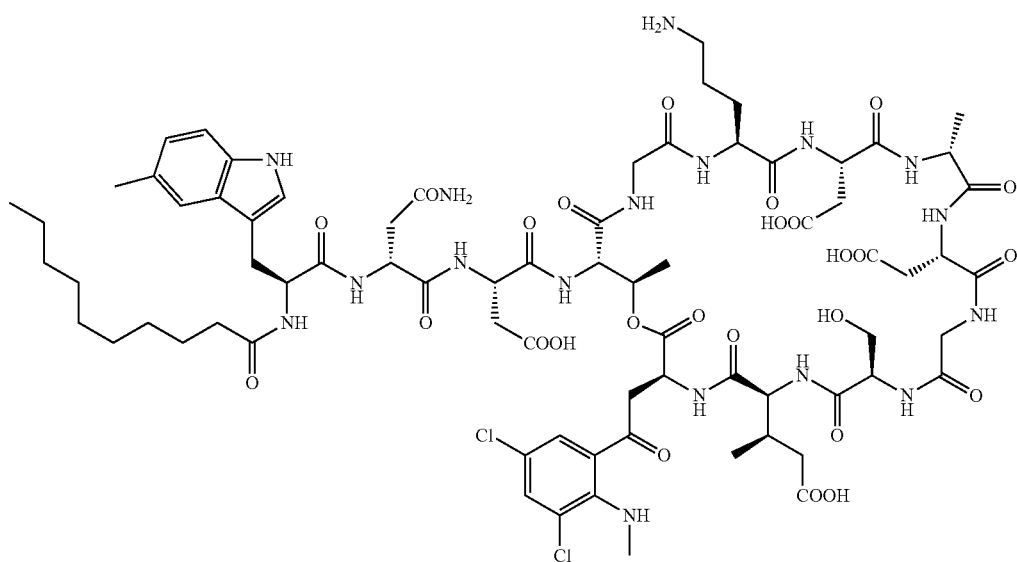

RP019  Chemical Formula: $C_{74}H_{103}Cl_2N_{17}O_{26}$
Exact Mass: 1715.66

The procedure in this example is similar to what is described in Example 17, except that Inter-IIA was replaced by Inter-IIB, and Hunig base replaced by TMP. Therefore, Inter-IIIE (5.2 mg) and Inter-IIB (10.0 mg) were coupled and then the protective Boc group was then removed to yield RP019 as a yellow powder (3.5 mg). Negative ESIMS m/z 856.8 $(M-2H)^{2-}$, theoretical value of $(M-2H)^{2-}$ for $C_{74}H_{103}Cl_2N_{17}O_{26}$, 856.82 (Protocol Al-Neg).

Example 25
Preparation of RP020
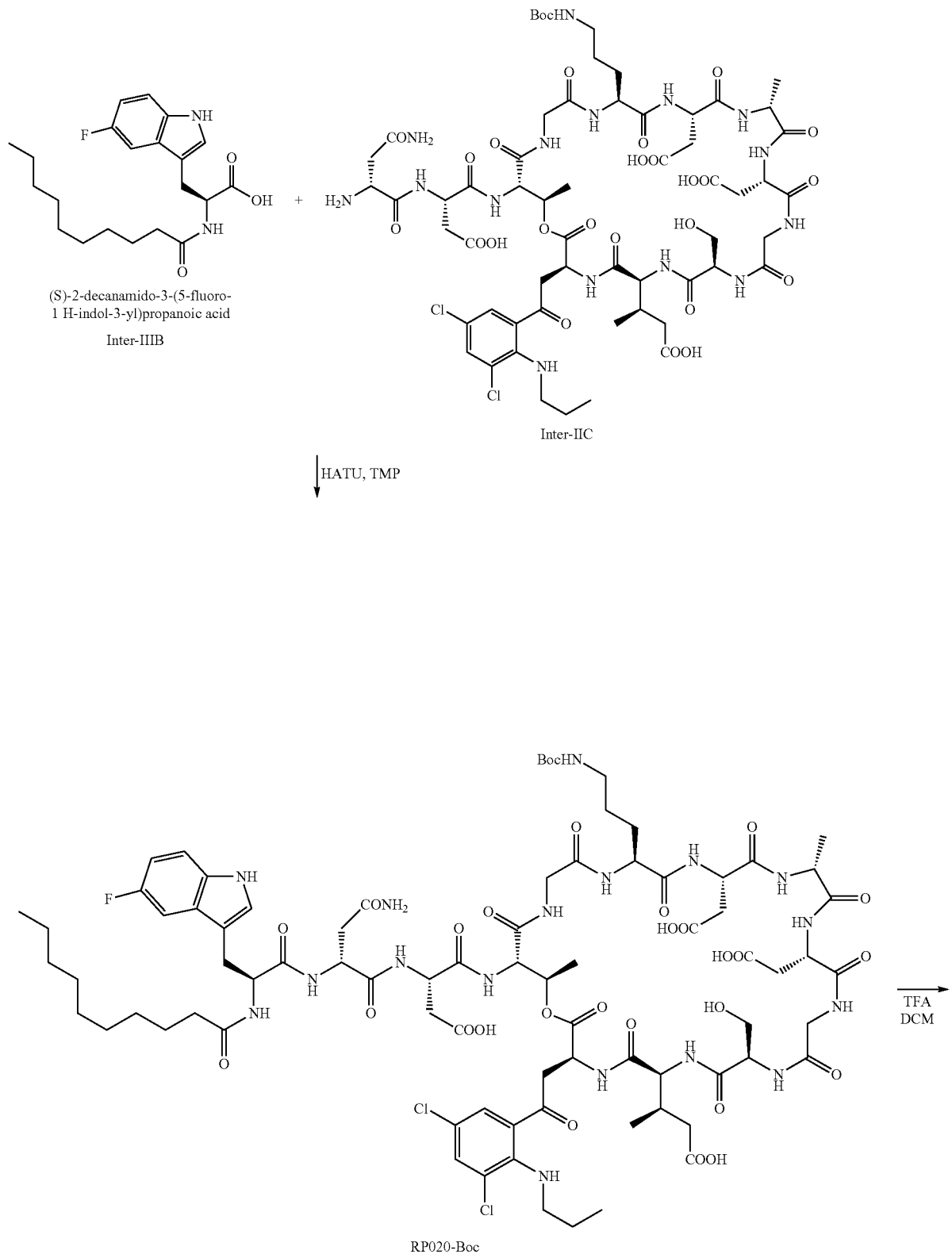

-continued

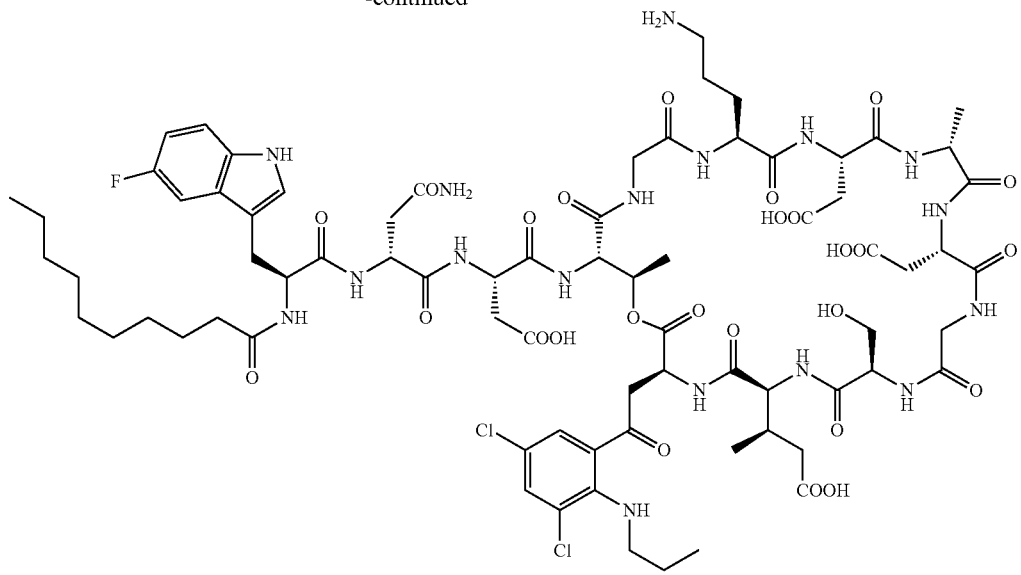

RP020  
Chemical Formula: $C_{75}H_{104}Cl_2FN_{17}O_{26}$  
Exact Mass: 1747.67

The procedures in this example are similar to what are described in Example 23, except that Inter-IIB was replaced by Inter-IIC. Therefore, Inter-IIIB (5.3 mg) and Inter-IIC (10.0 mg) were coupled in the presence of HATU and TMP and the protective Boc group was then removed by TFA to yield RP020 as a yellow powder (5.2 mg). Negative ESIMS m/z 872.8 $(M-2H)^{2-}$, theoretical value of $(M-2H)^{2-}$ for $C_{75}H_{104}Cl_2FN_{17}O_{26}$, 872.83 (Protocol A1-Neg).

Example 26

Preparation of RP021

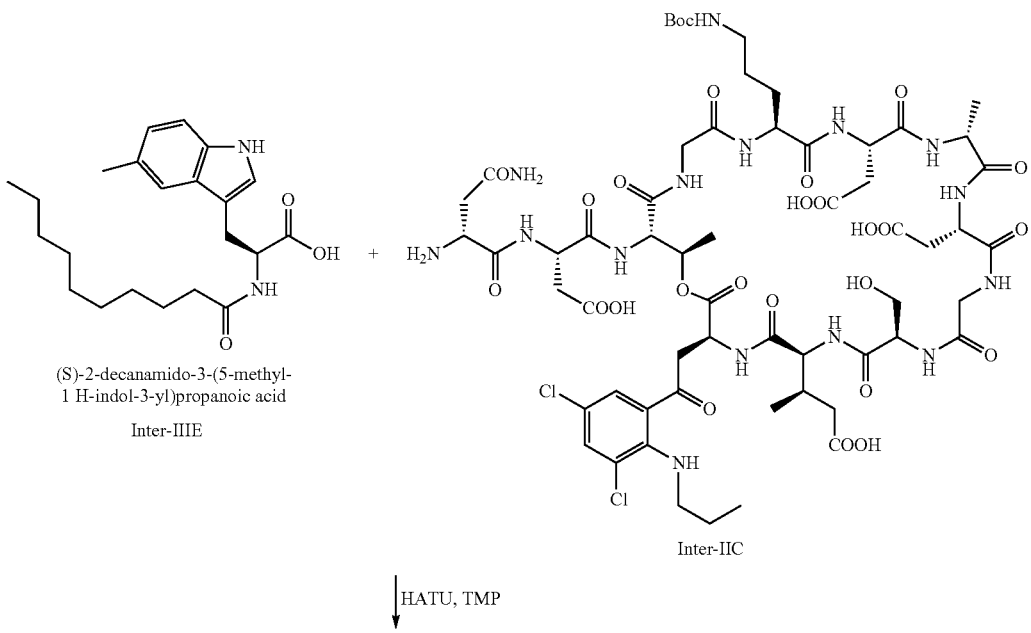

(S)-2-decanamido-3-(5-methyl-1H-indol-3-yl)propanoic acid
Inter-IIIE

Inter-IIC

HATU, TMP

-continued
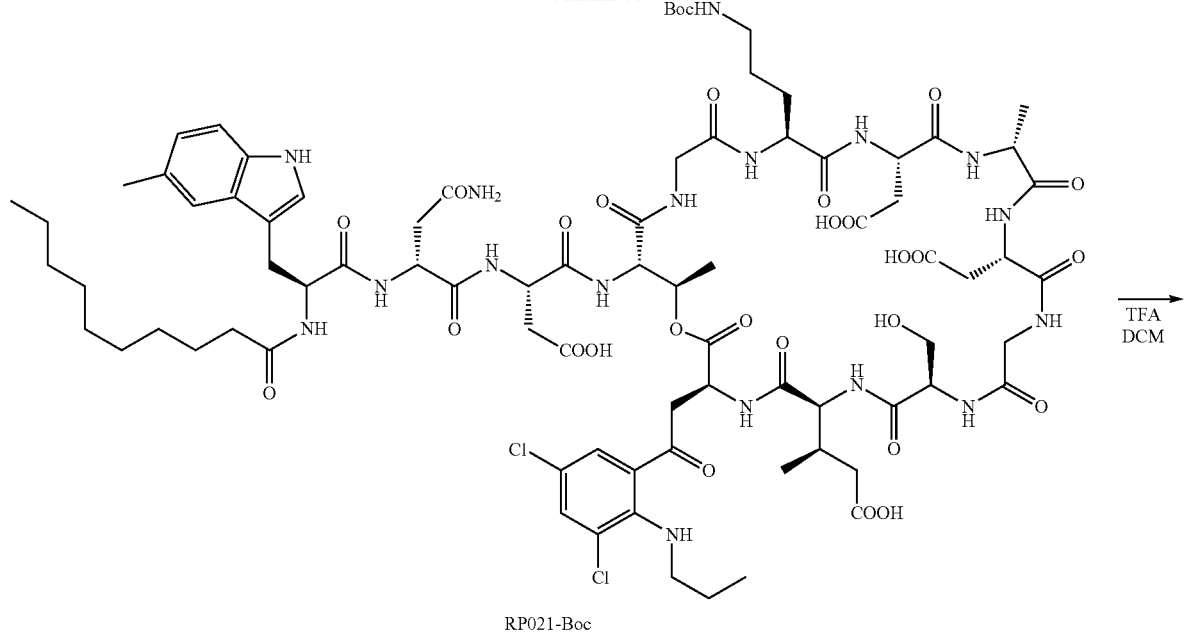
RP021-Boc
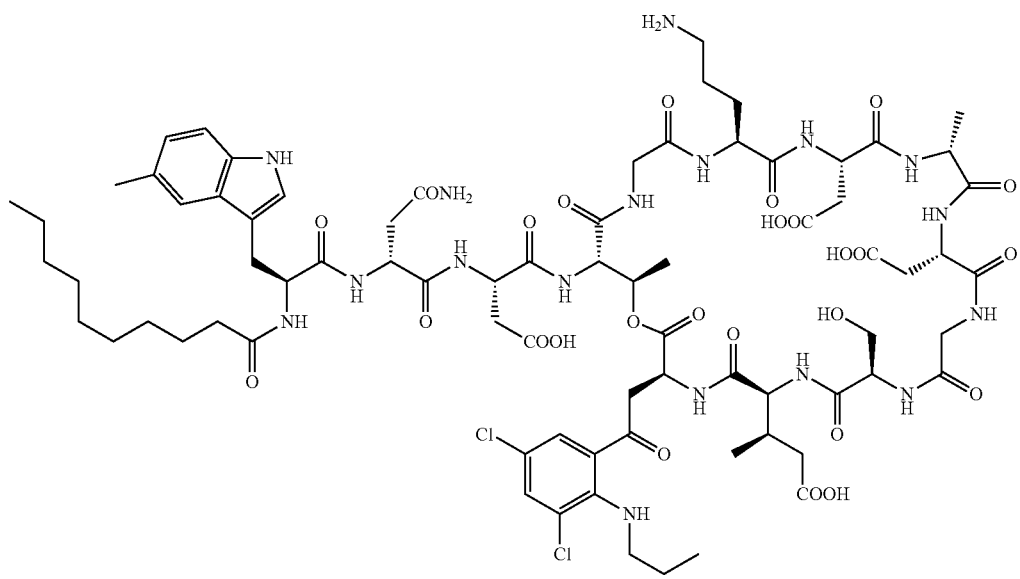
RP021      Chemical Formula: $C_{76}H_{107}Cl_2N_{17}O_{26}$
Exact Mass: 1743.70

The procedure in this example is similar to what is described in Example 24, except that Inter-IIB was replaced by Inter-IIC. Therefore, Inter-IIIE (5.2 mg) and Inter-IIC (9.8 mg) were coupled and the protective Boc group was then removed to yield RP021 as a yellow powder (4.2 mg).
Negative ESIMS m/z 870.8 (M-2H)$^{2-}$, theoretical value of (M-2H)$^{2-}$ for $C_{76}H_{107}Cl_2N_{17}O_{26}$, 870.84 (Protocol A1-Neg).
Example 27
Preparation of RP022
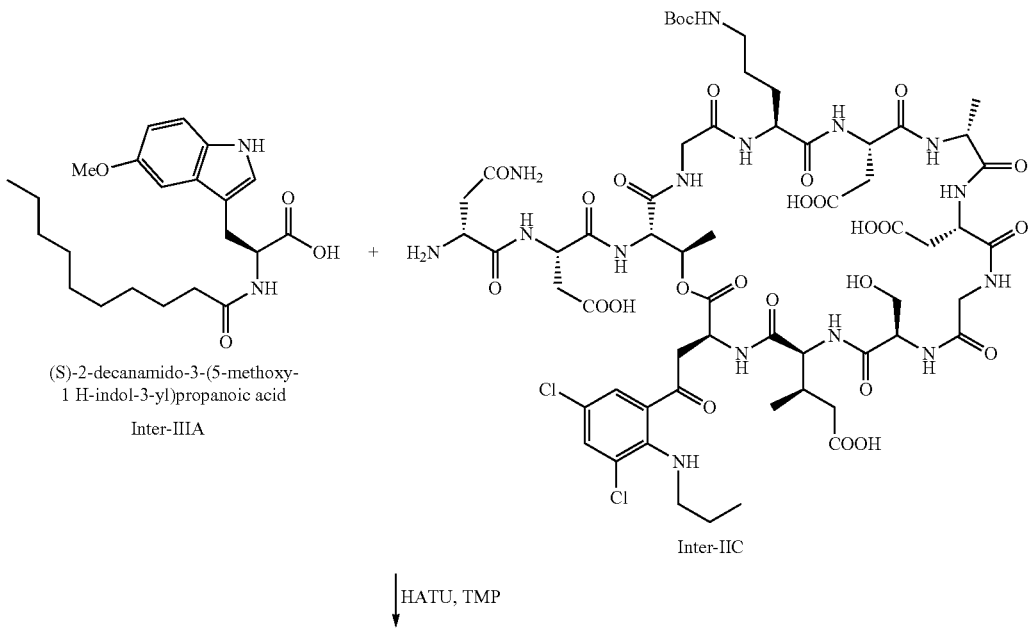
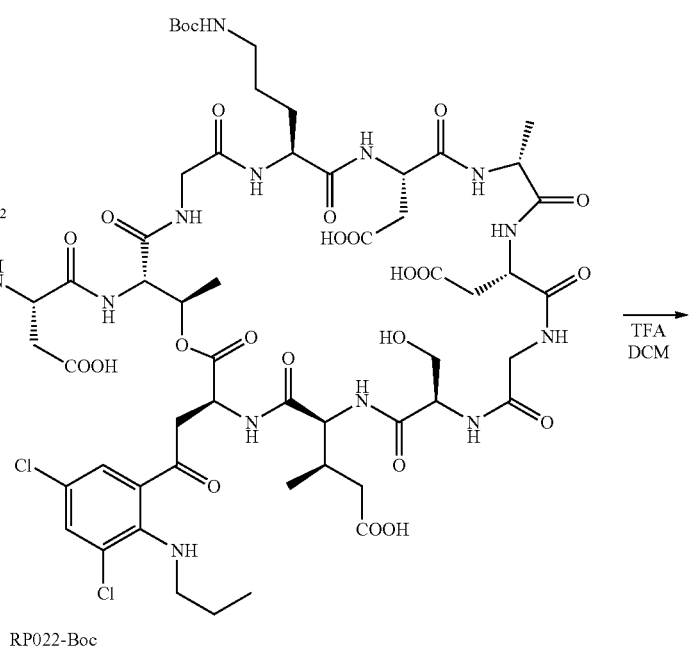

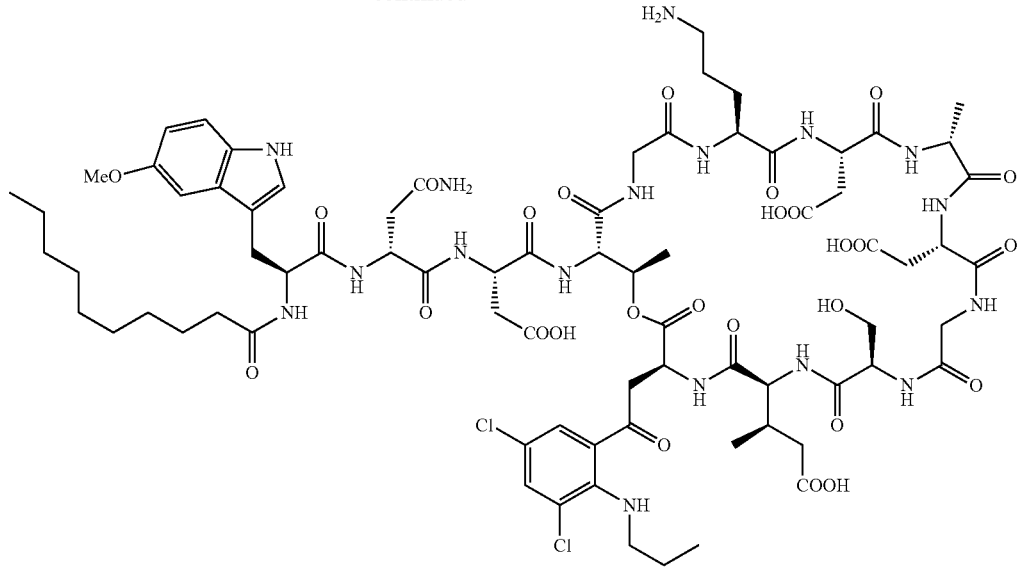

RP022  
Chemical Formula: $C_{76}H_{107}Cl_2N_{17}O_{27}$  
Exact Mass: 1759.69

The procedure in this example is similar to what is described in Example 26, except that Inter-IIIE was replaced by Inter-IIIA. Therefore, Inter-IIIA (3.9 mg) and Inter-IIC (10.2 mg) were coupled and its protective Boc group was then removed to yield RP022 as a yellow powder (5.9 mg). Negative ESIMS m/z 878.8 $(M-2H)^{2-}$, theoretical value of $(M-2H)^{2-}$ for $C_{76}H_{107}C_{12}N_{17}O_{27}$, 878.84 (Protocol A1-Neg).

Example 28

Preparation of RP023 and RP024

A solution of RP001 (12.2 mg), acetic acid (10 uL) and tert-butyl(2-oxoethyl)carbamate (21.0 mg) in methanol (300 uL) was stirred for 5 min and then mixed with sodium cyanoborohydride (12.5 mg) in methanol (150 uL). The resulting mixture was further stirred at 0° C. for 30 min and the product purified by preparative HPLC (Protocol B1) to obtain RP023-Boc (4.6 mg) and RP024-bis-Boc (6.5 mg). RP023-Boc and RP024-bis-Boc were respectively treated with 10% TFA in DCM for 15 minutes and then purified by HPLC (Protocol B2) to obtain RP023 (2.6 mg) and RP024 (3.7 mg). RP023: negative ESIMS m/z 844.3 $(M-2H)^{2-}$, theoretical value for $(M-2H)^{2-}$, 844.38 (Protocol A1-Neg). RP024: negative ESIMS m/z 865.9 $(M-2H)^{2-}$, theoretical value for $(M-2H)^{2-}$, 865.91 (Protocol A1-Neg).

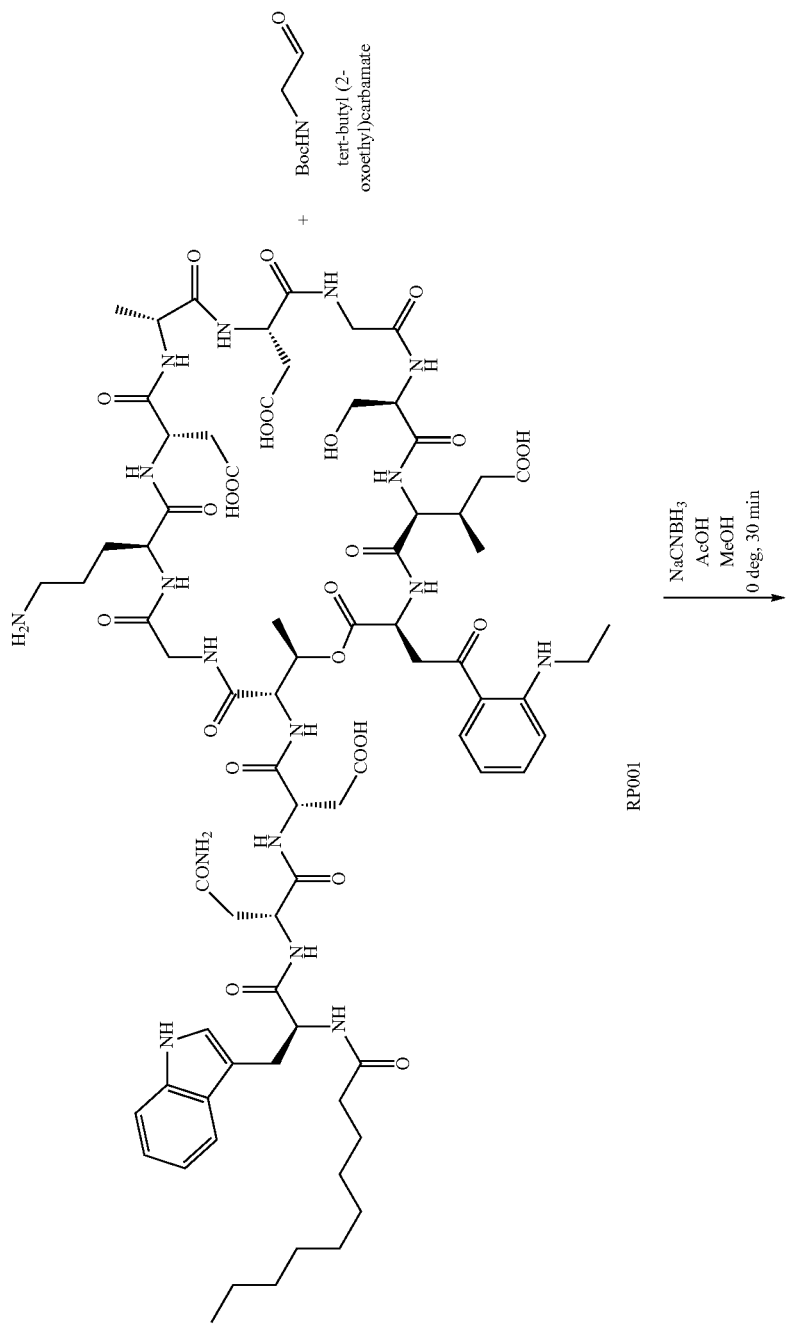

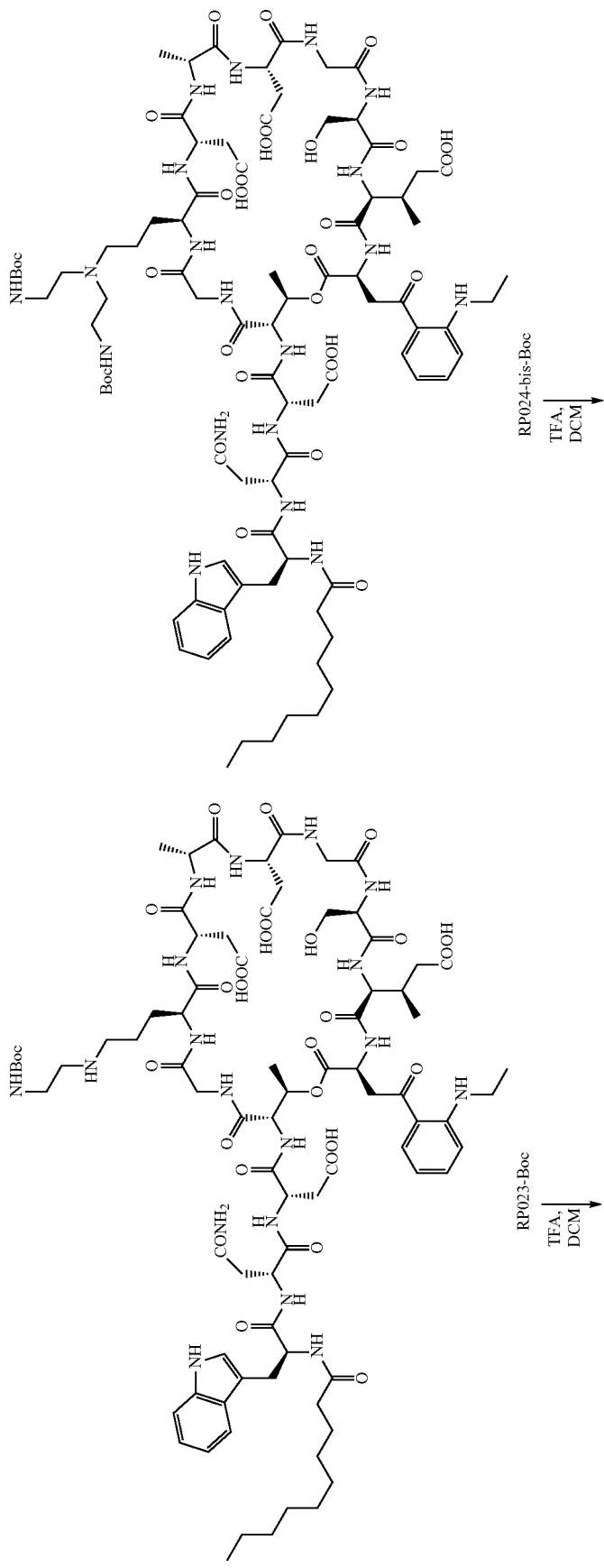

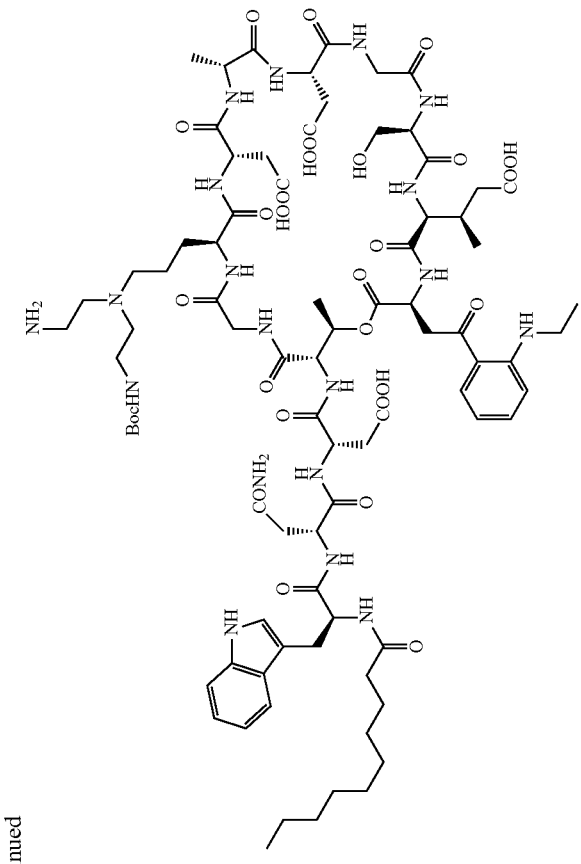
RP024
Chemical Formula: $C_{78}H_{115}N_{19}O_{26}$
Exact Mass: 1733.83
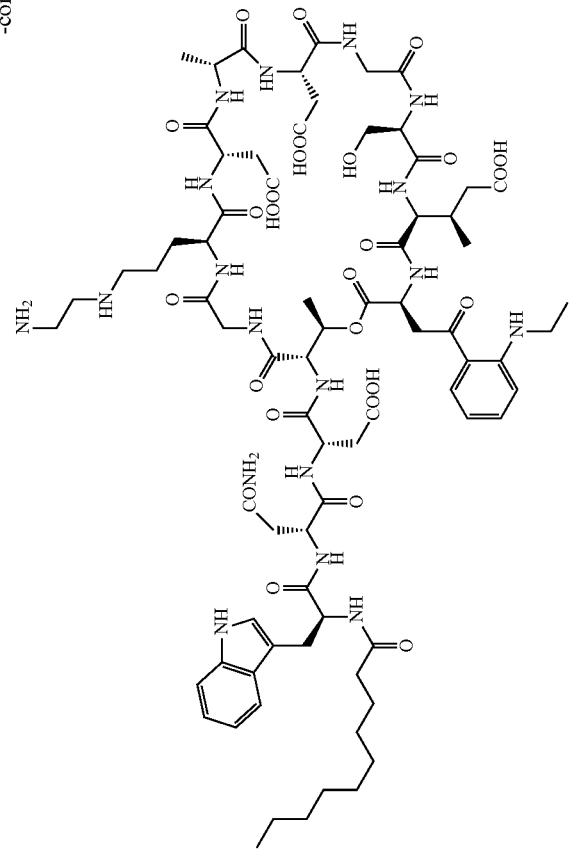
RP023
Chemical Formula: $C_{76}H_{110}N_{18}O_{26}$
Exact Mass: 1690.78

The invention is not to be limited in scope by the specific embodiments described herein. Indeed, various modifications of the invention in addition to those described will become apparent to those skilled in the art from the foregoing description. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

Exemplary Compounds, Compositions and Methods are Set Out in the Following Items:

Item 1. A compound comprising Formula I,

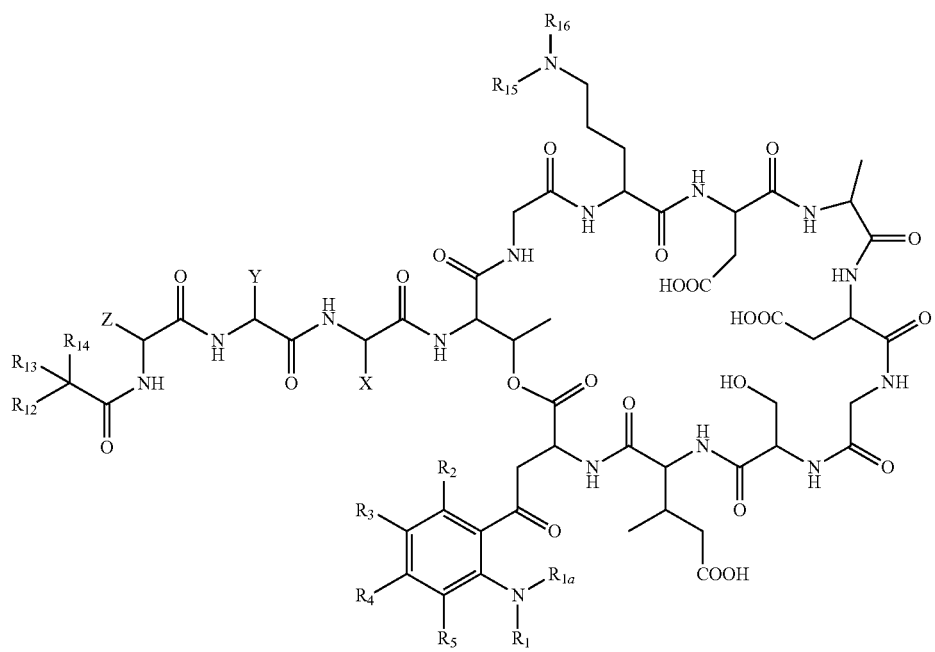

Formula I wherein:

X and Y are independently selected from hydrogen, alkyl, alkenyl, cycloalkyl, cycloalkenyl, alkynyl, aryl, heteroaryl group,

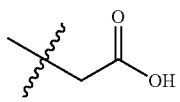 [SMILES: *CC(=O)O]

and

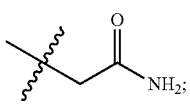 [SMILES: *CC(N)=O]

Z is selected from hydrogen, alkyl, cycloalkyl, alkenyl, cycloalkenyl, alkynyl, aryl, heteroaryl group, and an indolylmethyl moiety having the following structure:

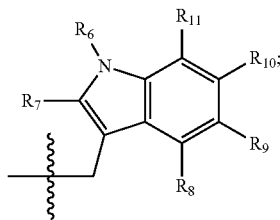

$R_1$, $R_{1a}$, and $R_6$ are each independently selected from hydrogen, alkyl, alkenyl, alkynyl, cycloalkyl, cycloalkenyl, aryl, heteroaryl, acyl, OH, OR, NHR, or $NR_2$ group; wherein R is a $C_1$-$C_6$ alkyl, $C_2$-$C_6$ alkenyl, $C_2$-$C_6$ alkynyl, cycloalkyl, cycloalkenyl, aryl, or heteroaryl group;

$R_2$, $R_3$, $R_4$, $R_5$, $R_7$, $R_8$, $R_9$, $R_{10}$, and $R_{11}$ are each independently selected from hydrogen, halogen, alkyl, alkenyl, alkynyl, cycloalkyl, cycloalkenyl, aryl, heteroaryl, cyano, isocyano, thiocyano, isothiocyano, phosphate, phosphoryl, sulfate, sulfinyl, sulfonyl, formyl, acyl, amino, acylamino, acyloxy, thiocarbonyl, imino, carboalkoxy, carboxy, carboxyamido, hydroxyl, nitro, thio, alkoxy, aryloxy, OC=$OR_a$, OC=$OOR_a$, OC=$ONHR_a$, OC=$ON(R_a)_2$, $NHR_a$, or $N(R_a)_2$ group; wherein $R_a$ is selected from a $C_1$-$C_6$ alkyl, $C_2$-$C_6$ alkenyl, $C_2$-$C_6$ alkynyl, cycloalkyl, cycloalkenyl, aryl or heteroaryl group;

$R_{12}$, $R_{13}$, $R_{14}$ are each independently selected from hydrogen, $C_1$-$C_{25}$ alkyl, $C_2$-$C_{25}$ alkenyl, $C_2$-$C_{25}$ alkynyl, aryl, heteroaryl, cycloalkyl, cycloalkenyl, or a group containing branched or unbranched poly ethylene —$(OCH_2CH_2)_n$—, or poly propylene —$(OCH_2CH_2CH_2)_m$— group, wherein each n and m is an integer between 1 and 10;

$R_{15}$ and $R_{16}$ are each selected from H or —(P'Q'), whereas P' is an alkyl, alkenyl, cycloalkyl, or cycloalkenyl moiety, and Q' is a primary, secondary, tertiary, or quaternary amino group;

provided that at least one of $R_1$, $R_{1a}$, $R_2$, $R_3$, $R_4$, and $R_5$ is not H;

and further provided that when Z is the following indolylmethyl group

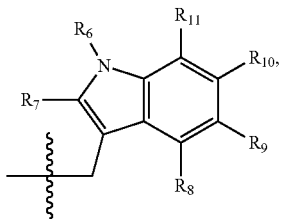

at least one of $R_6$, $R_7$, $R_8$, $R_9$, $R_{10}$, and $R_{11}$ is not H;

and pharmaceutically acceptable salts thereof.

Item 2. A compound according to item 1, wherein Z is the following indolylmethyl group

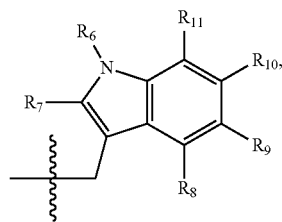

provided that at least one of $R_1$, $R_{1a}$, $R_2$, $R_3$, $R_4$, and $R_5$ is not H;

and further provided that at least one of $R_6$, $R_7$, $R_8$, $R_9$, $R_{10}$, and $R_{11}$ is not H;

and pharmaceutically acceptable salts thereof.

Item 3. A compound comprising Formula II,

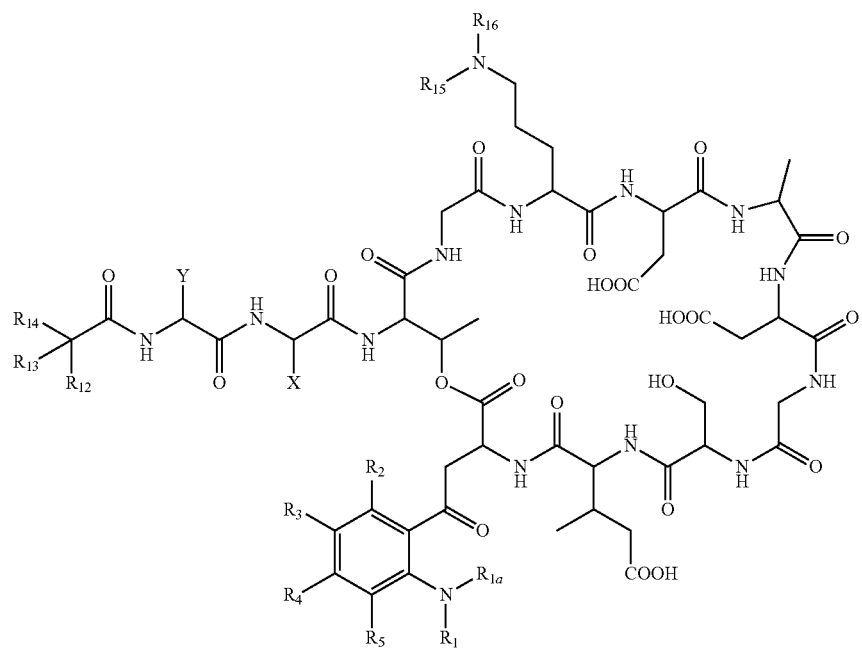

Formula II wherein:

X and Y are independently selected from hydrogen, alkyl, cycloalkyl, alkenyl, cycloalkenyl, alkynyl, aryl, heteroaryl group,

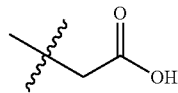 [SMILES: *CC(=O)O]

and poly propylene —(OCH$_2$CH$_2$CH$_2$)$_m$— group, wherein each n and m is an integer between 1 and 10;

R$_{15}$ and R$_{16}$ are each selected from H or —(P'Q'), whereas P' is an alkyl, alkenyl, cycloalkyl, or cycloalkenyl moiety, and Q' is a primary, secondary, tertiary, or quaternary amino group;

provided that at least one of R$_1$ and R$_{1a}$ is not H;

or pharmaceutically acceptable salts thereof.

Item 4. A compound comprising Formula III,

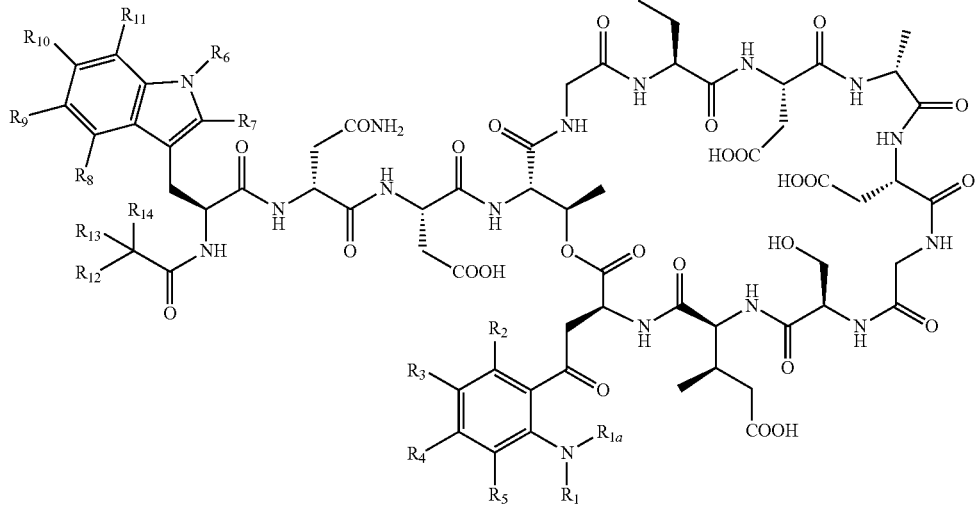

Formula III

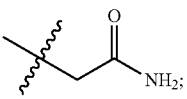

R$_1$ and R$_{1a}$ are each independently selected from hydrogen, alkyl, alkenyl, alkynyl, cycloalkyl, cycloalkenyl, aryl, heteroaryl, acyl, OH, OR, NHR, or NR$_2$ group; wherein R is a C$_1$-C$_6$ alkyl, C$_2$-C$_6$ alkenyl, C$_2$-C$_6$ alkynyl, cycloalkyl, cycloalkenyl, aryl, or heteroaryl group;

R$_2$, R$_3$, R$_4$, R$_5$ are each independently selected from hydrogen, halogen, alkyl, alkenyl, alkynyl, cycloalkyl, cycloalkenyl, aryl, heteroaryl, cyano, isocyano, thiocyano, isothiocyano, phosphate, phosphoryl, sulfate, sulfinyl, sulfonyl, formyl, acyl, amino, acylamino, acyloxy, thiocarbonyl, imino, carboalkoxy, carboxy, carboxyamido, hydroxyl, nitro, thio, alkoxy, aryloxy, OC=OR$_a$, OC=OOR$_a$, OC=ONHR$_a$, OC=ON(R$_a$)$_2$, NHR$_a$, or N(R$_a$)$_2$ group; wherein R$_a$ is selected from a C$_1$-C$_6$ alkyl, C$_2$-C$_6$ alkenyl, C$_2$-C$_6$ alkynyl, cycloalkyl, cycloalkenyl, aryl or heteroaryl group;

R$_{12}$, R$_{13}$, R$_{14}$ are each independently selected from hydrogen, C$_1$-C$_{25}$ alkyl, C$_2$-C$_{25}$ alkenyl, C$_2$-C$_{25}$ alkynyl, aryl, heteroaryl, cycloalkyl, cycloalkenyl, or a group containing branched or unbranched poly ethylene —(OCH$_2$CH$_2$)$_n$—, or wherein:

R$_1$, R$_{1a}$, and R$_6$ are each independently selected from hydrogen, alkyl, alkenyl, alkynyl, cycloalkyl, cycloalkenyl, aryl, heteroaryl, acyl, OH, OR, NHR, or NR$_2$ group; wherein R is a C$_1$-C$_6$ alkyl, C$_2$-C$_6$ alkenyl, C$_2$-C$_6$ alkynyl, cycloalkyl, cycloalkenyl, aryl, or heteroaryl group; R$_2$, R$_3$, R$_4$, R$_5$, R$_7$, R$_8$, R$_9$, R$_{10}$, and R$_{11}$ are each independently selected from hydrogen, halogen, alkyl, alkenyl, alkynyl, cycloalkyl, cycloalkenyl, aryl, heteroaryl, cyano, isocyano, thiocyano, isothiocyano, phosphate, phosphoryl, sulfate, sulfinyl, sulfonyl, formyl, acyl, amino, acylamino, acyloxy, thiocarbonyl, imino, carboalkoxy, carboxy, carboxyamido, hydroxyl, nitro, thio, alkoxy, aryloxy, OC=OR$_a$, OC=OOR$_a$, OC=ONHR$_a$, OC=ON(R$_a$)$_2$, NHR$_a$, or N(R$_a$)$_2$ group; wherein R$_a$ is selected from a C$_1$-C$_6$ alkyl, C$_2$-C$_6$ alkenyl, C$_2$-C$_6$ alkynyl, cycloalkyl, cycloalkenyl, aryl or heteroaryl group;

R$_{12}$, R$_{13}$, R$_{14}$ are each independently selected from hydrogen, substituted, unsubstituted, branched, unbranched C$_1$-C$_{25}$ alkyl, C$_2$-C$_{25}$ alkenyl, C$_2$-C$_{25}$ alkynyl, aryl, heteroaryl, cyclic alkyl, cyclic alkenyl, cyclic alkynyl, or a group containing branched or unbranched poly ethylene —(OCH$_2$CH$_2$)$_n$—, or poly propylene —(OCH$_2$CH$_2$CH$_2$)$_m$— group, wherein each n and m is an integer between 1 and 10;

$R_{15}$ and $R_{16}$ are each selected from H or —(P'Q'), whereas P' is an alkyl, alkenyl, cycloalkyl, or cycloalkenyl moiety, and Q' is a primary, secondary, tertiary, or quaternary amino group;

provided that at least one of $R_1$, $R_{1a}$, $R_2$, $R_3$, $R_4$, and $R_5$ is not H;

and further provided that at least one of $R_6$, $R_7$, $R_8$, $R_9$, $R_{10}$, and $R_{11}$ is not H;

and pharmaceutically acceptable salts and prodrugs thereof.

Item 5. A compound having antibacterial activity selected from the group consisting of compounds designated RP002, RP003, RP004, RP005, RP006, RP007, RP008, RP009, RP010, RP011, RP012, RP013, RP014, RP015, RP016, RP017, RP018, RP019, RP020, RP021, and RP022, and having the following formulas:

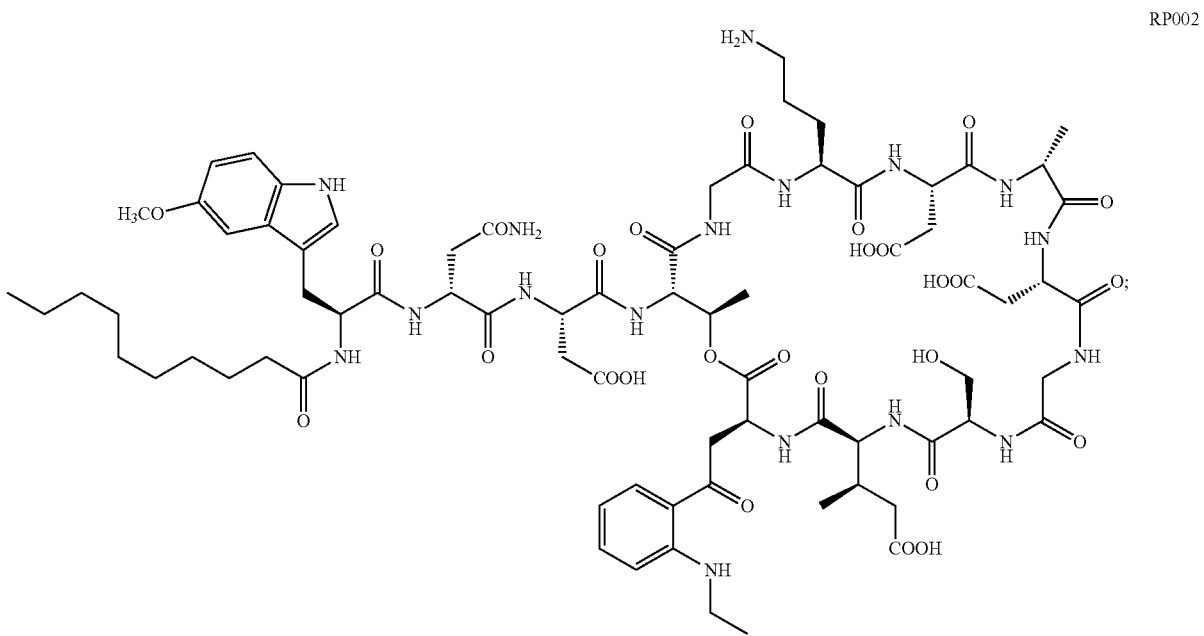

RP002

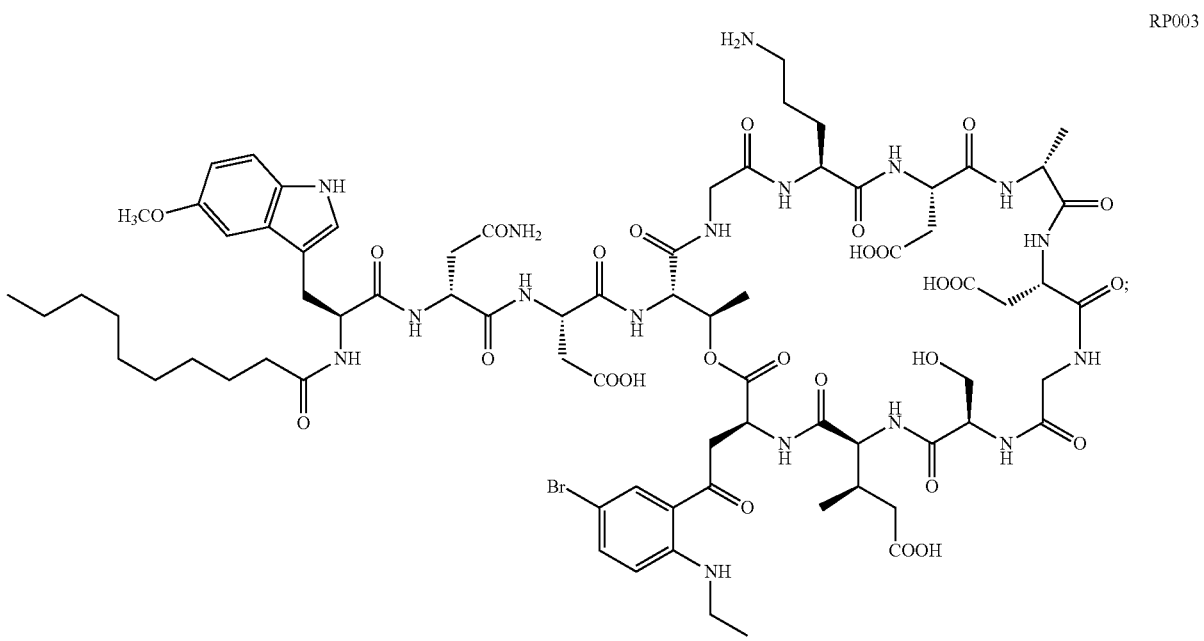

RP003

-continued
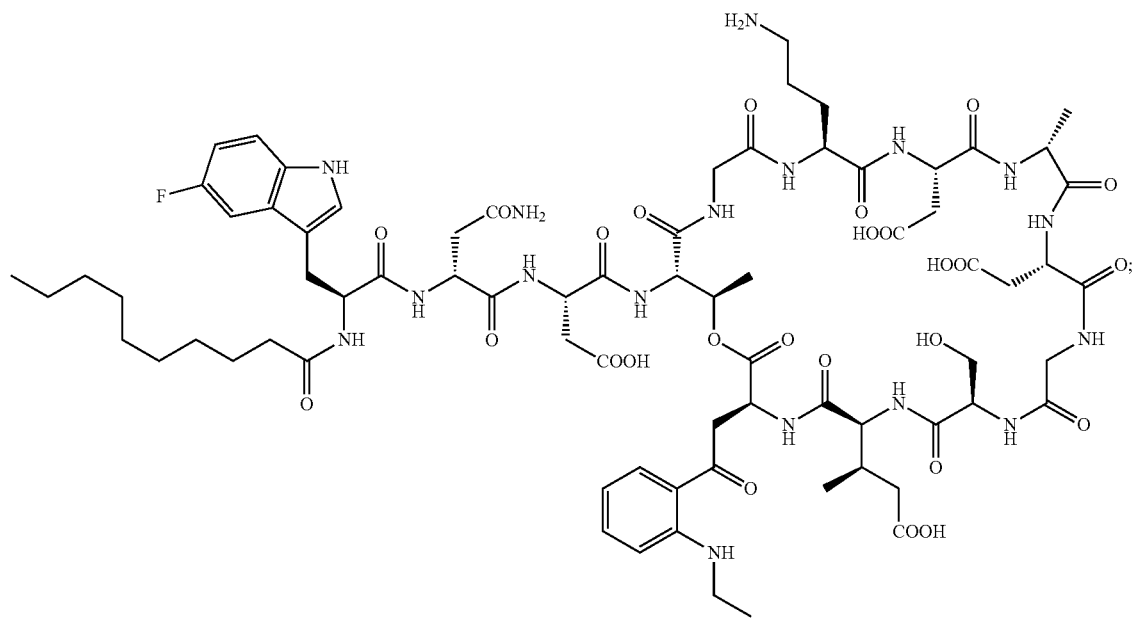
RP004
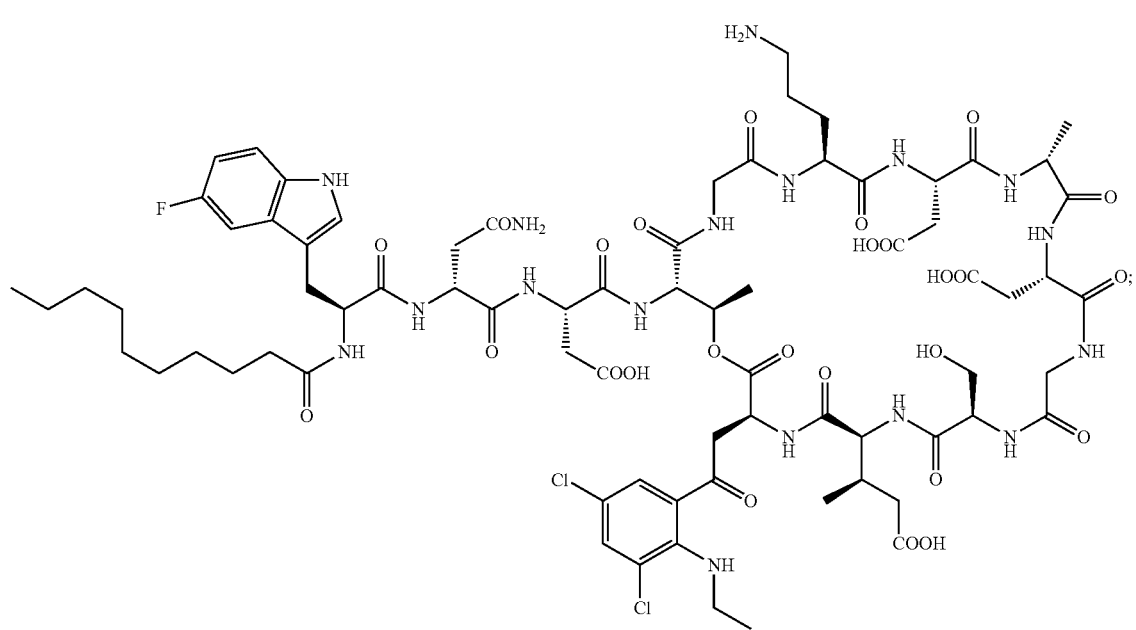
RP005

-continued
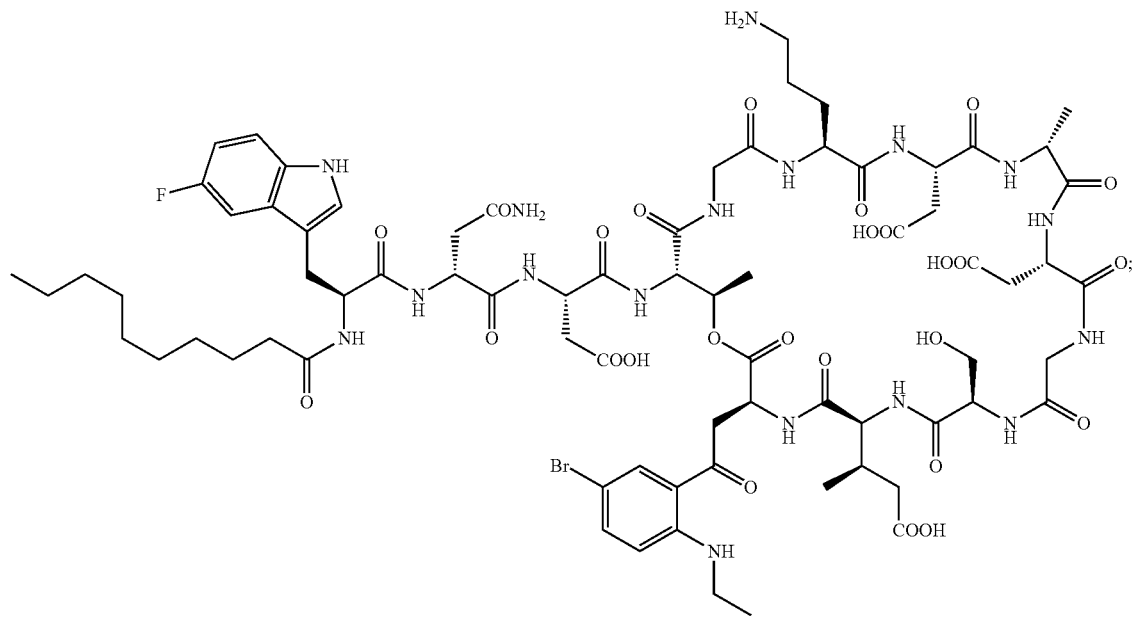
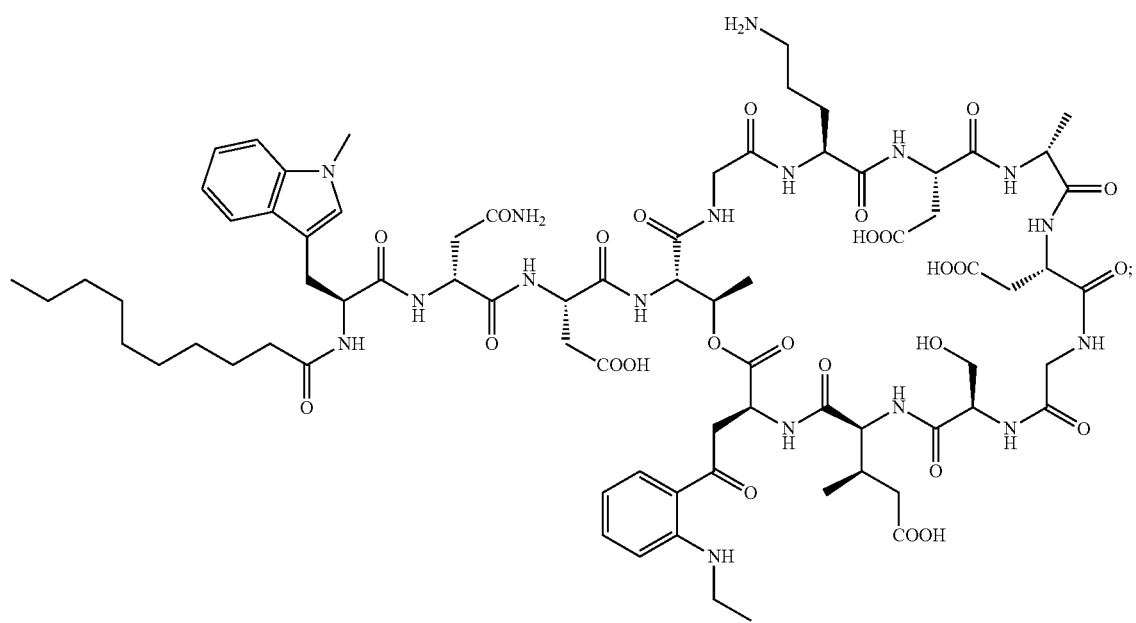

-continued
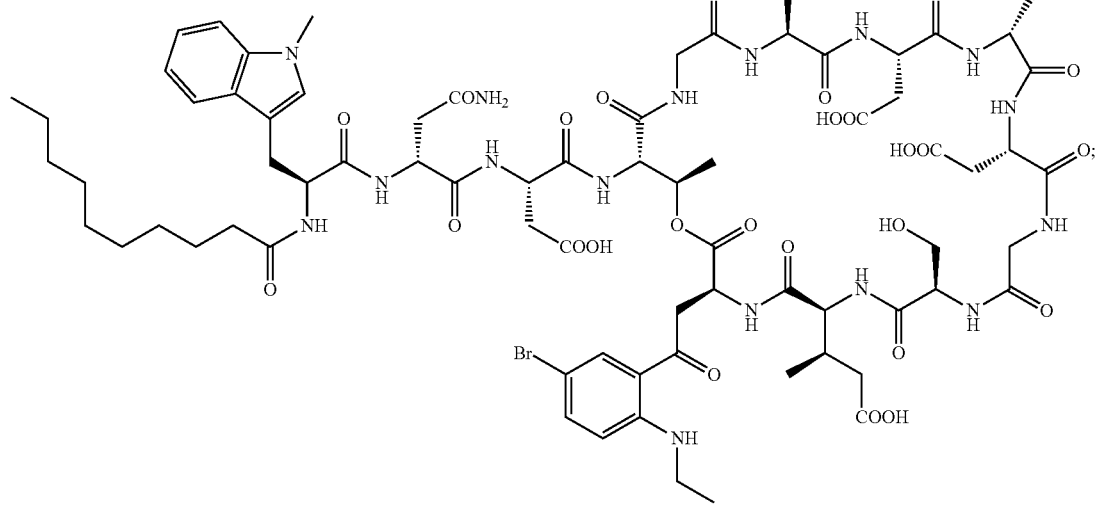
RP008
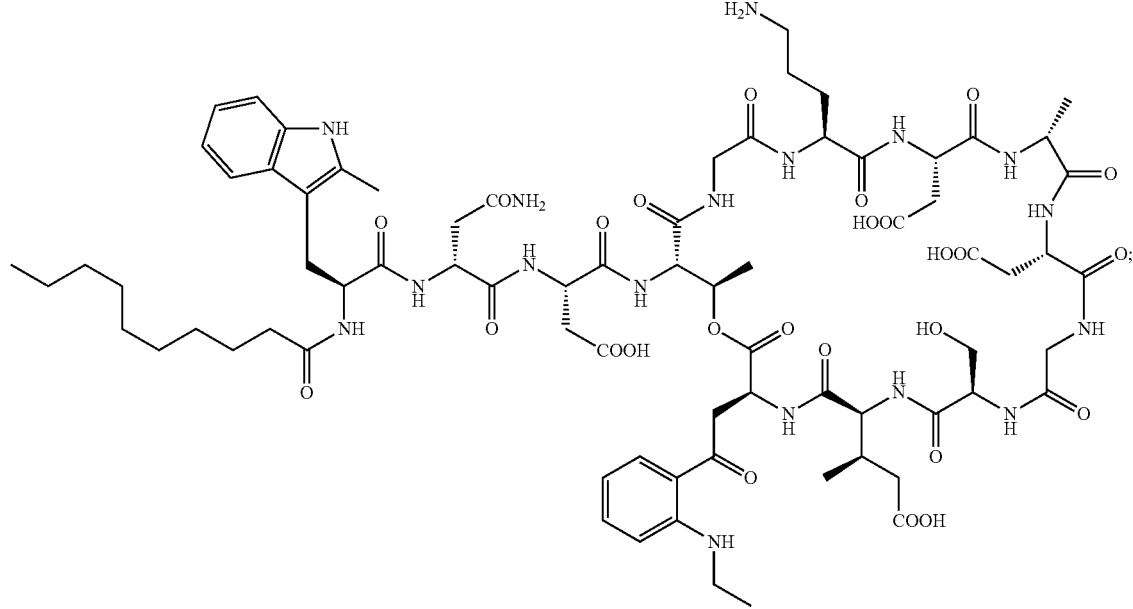
RP009

-continued
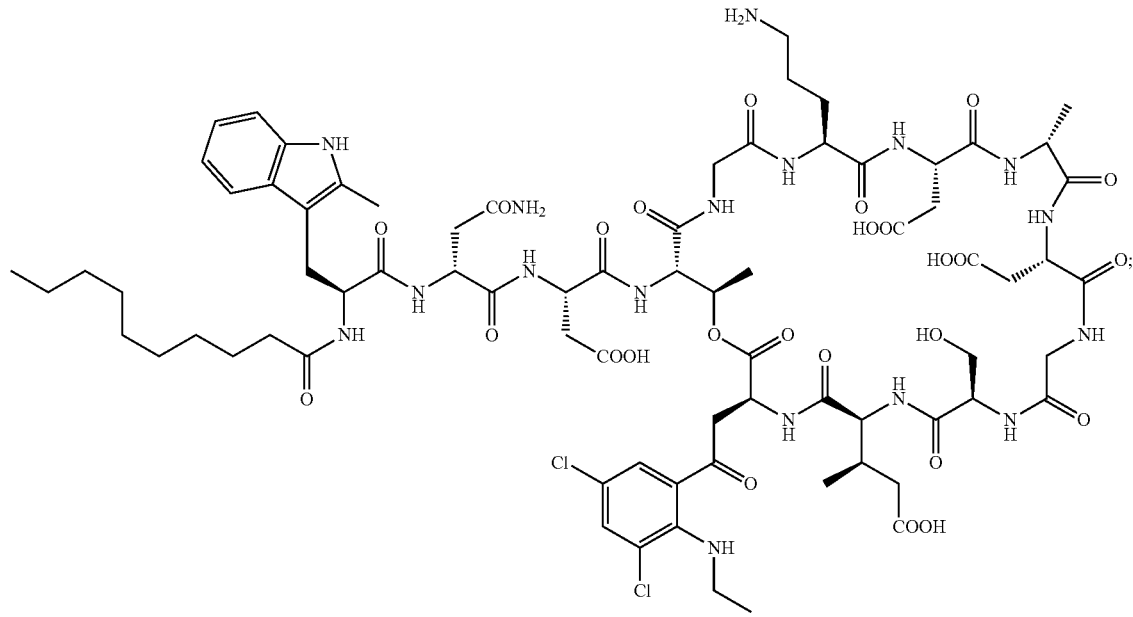
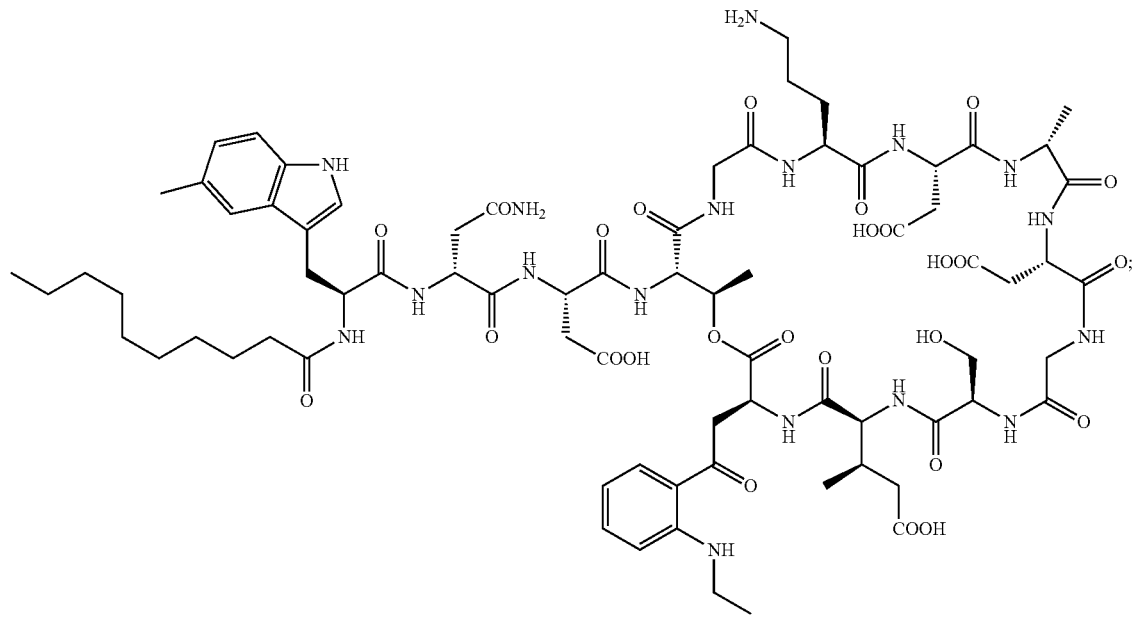

-continued
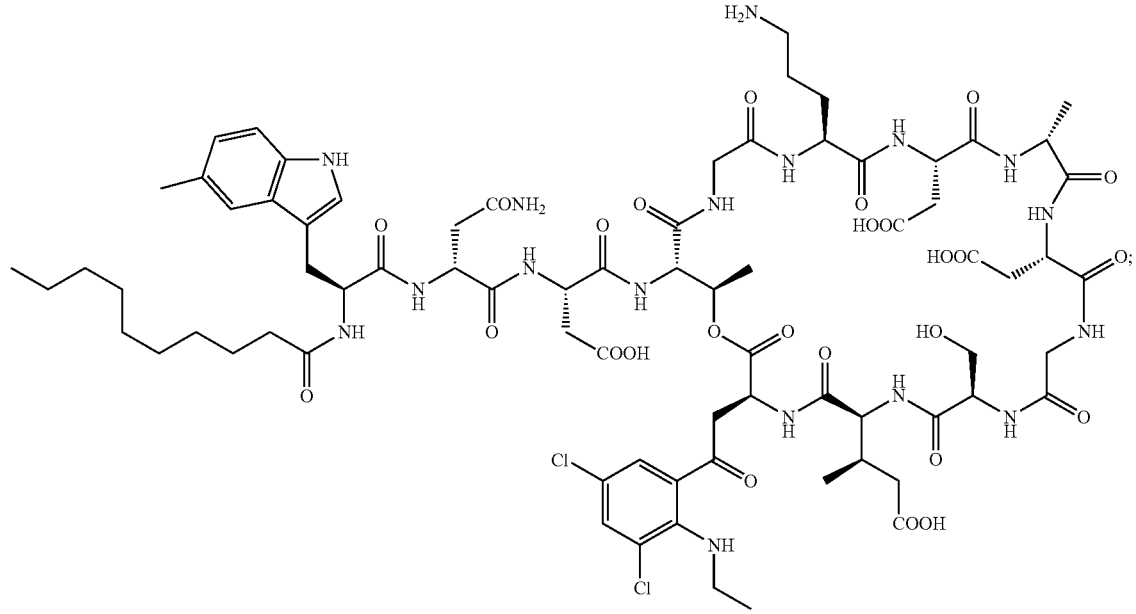
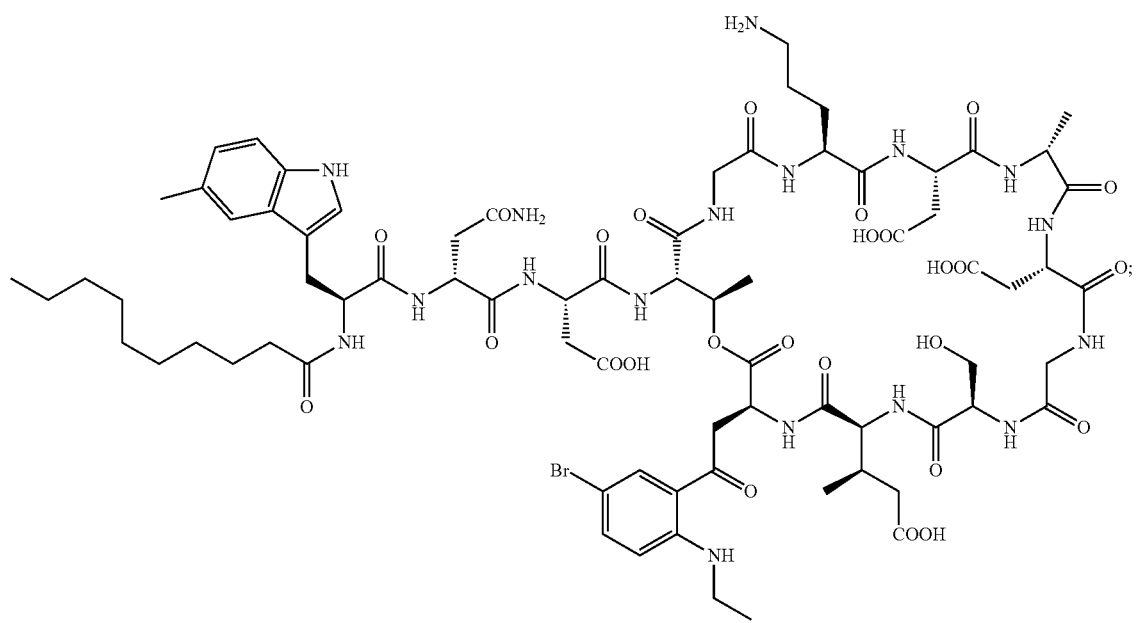

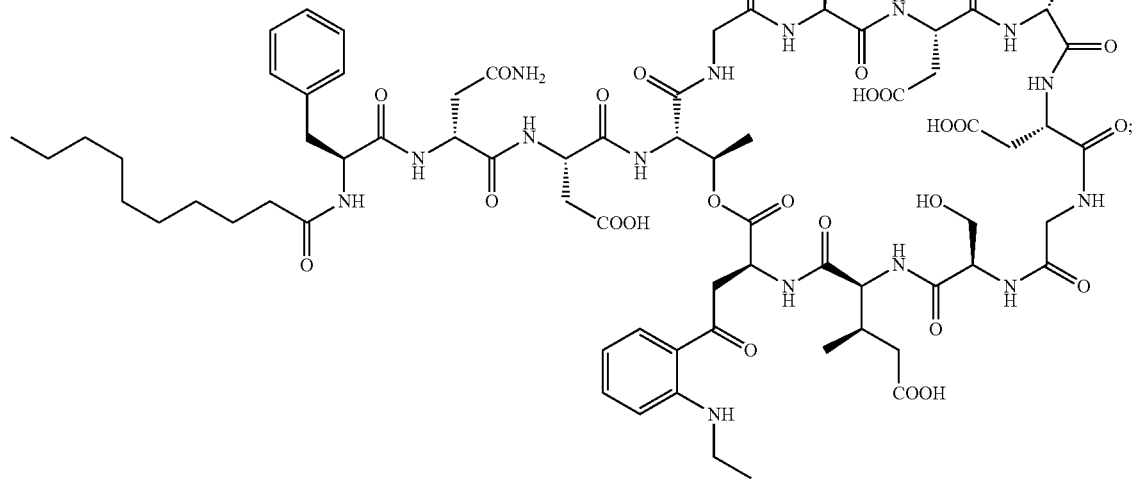
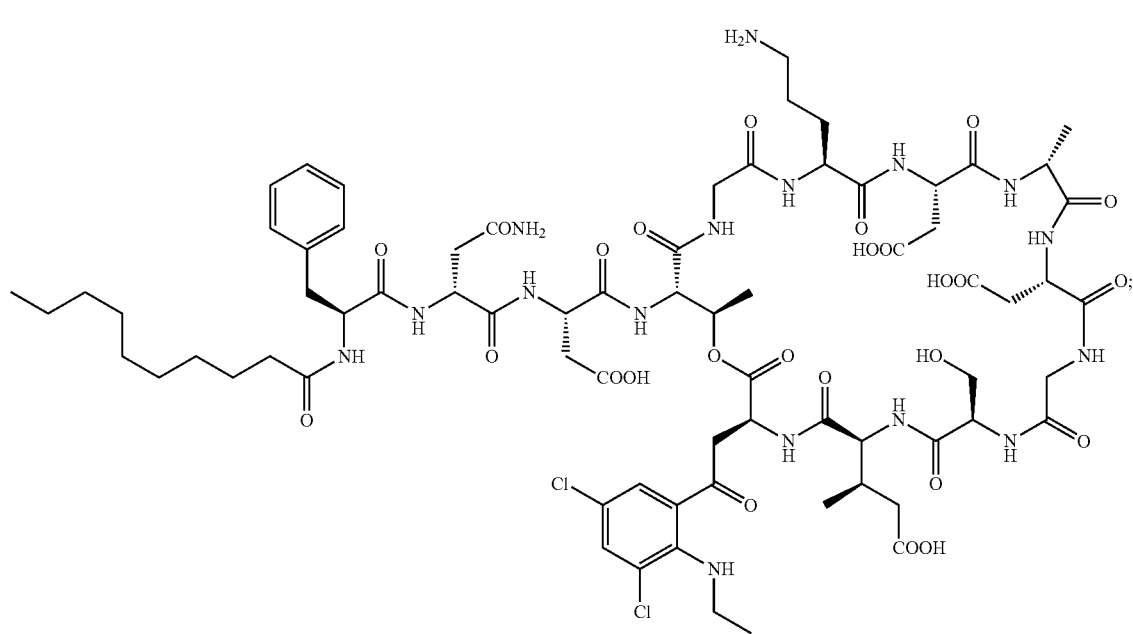

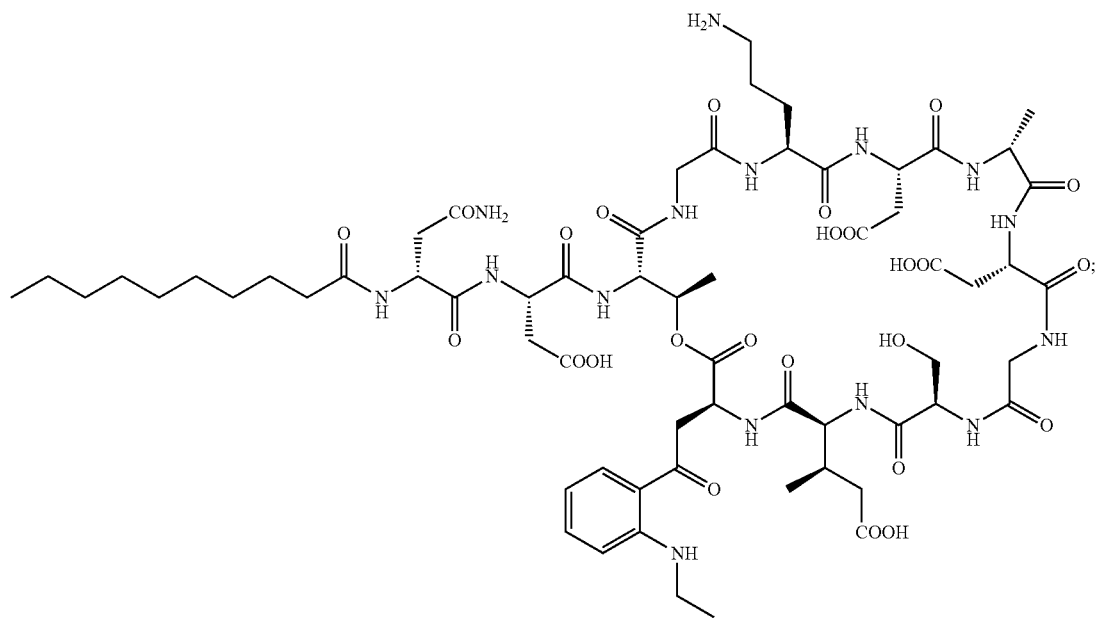
RP016
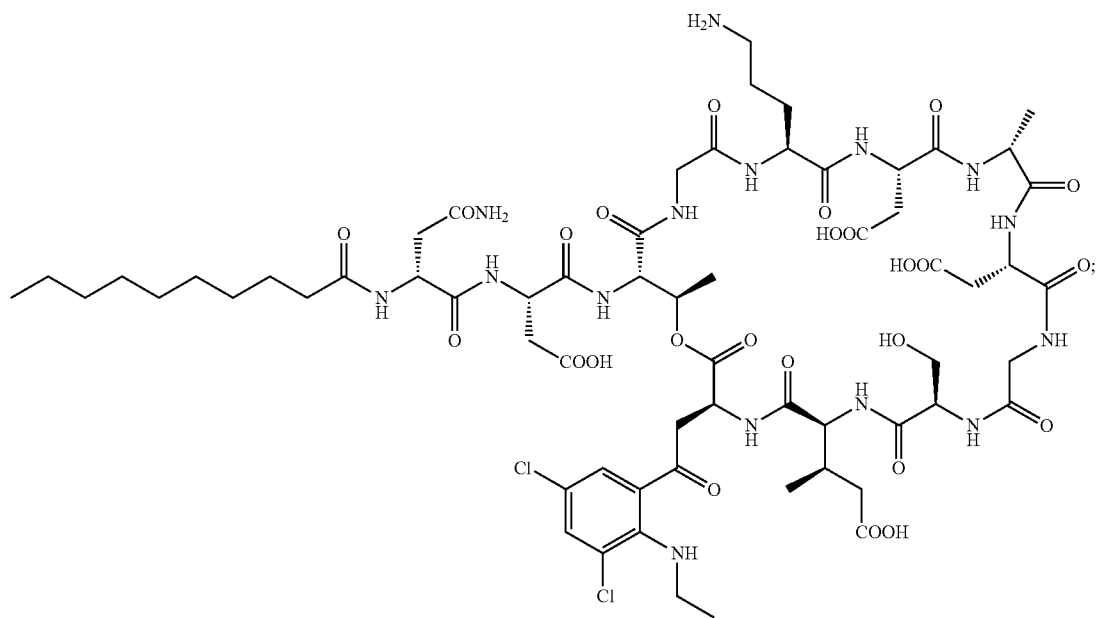
RP017

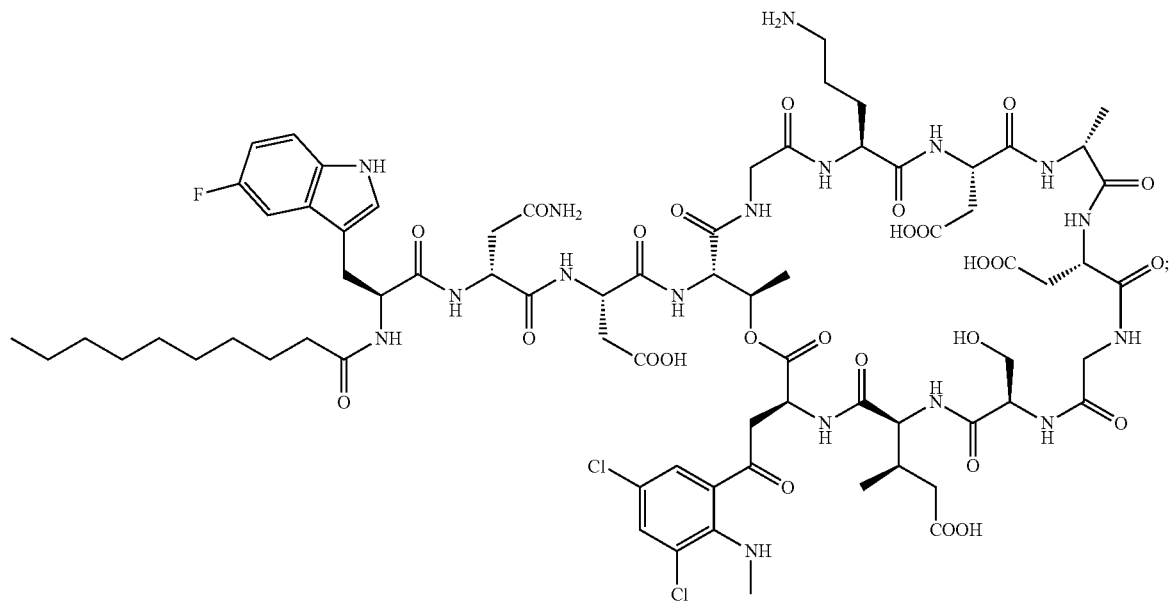
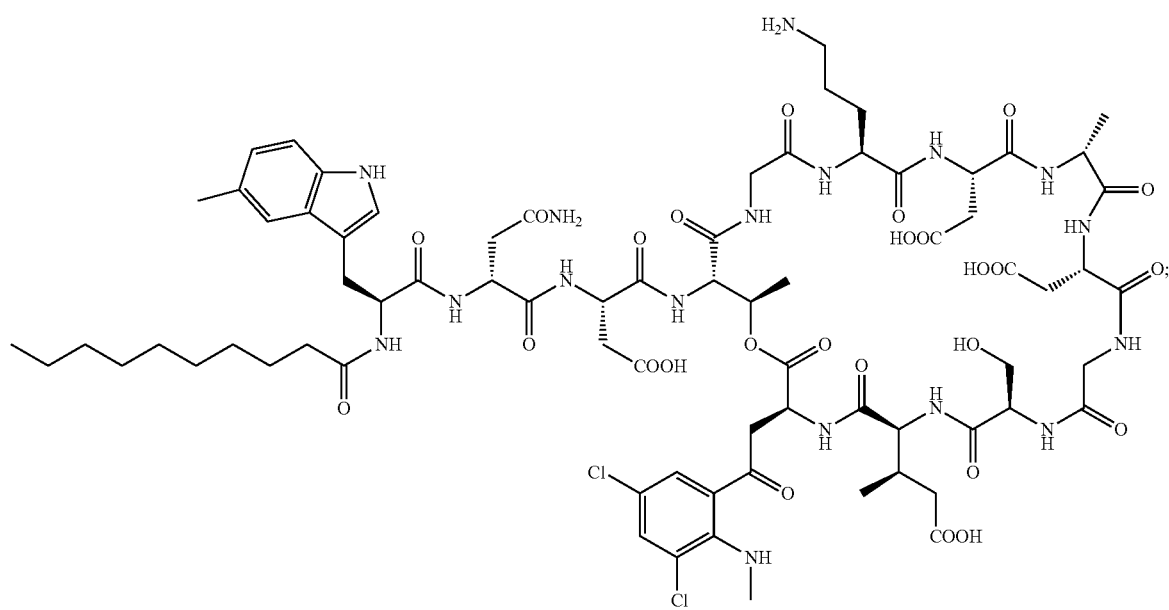

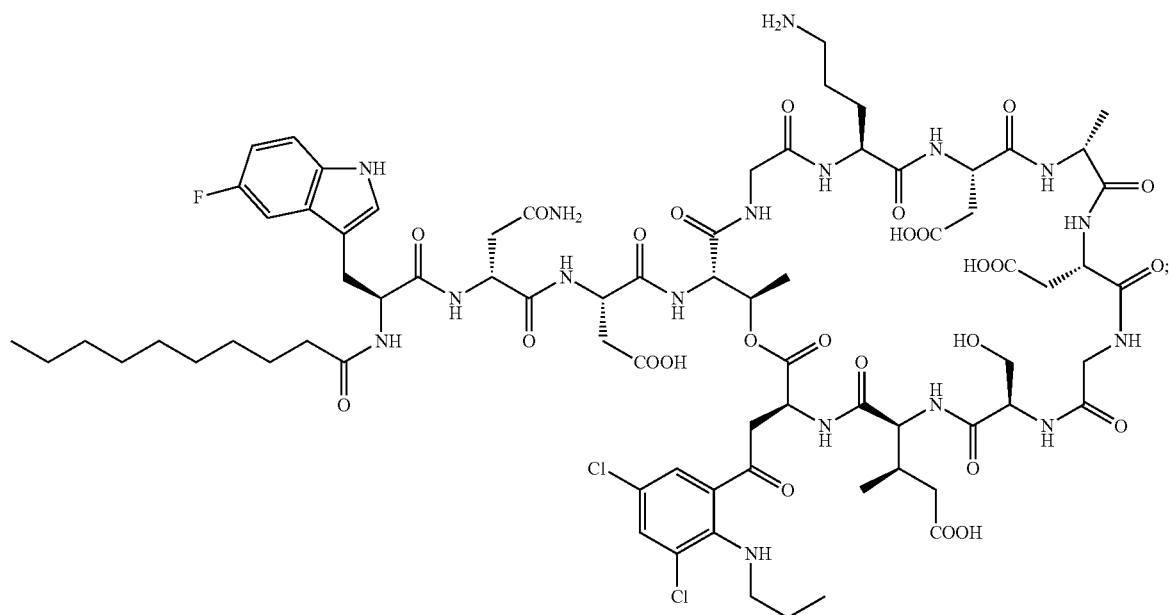
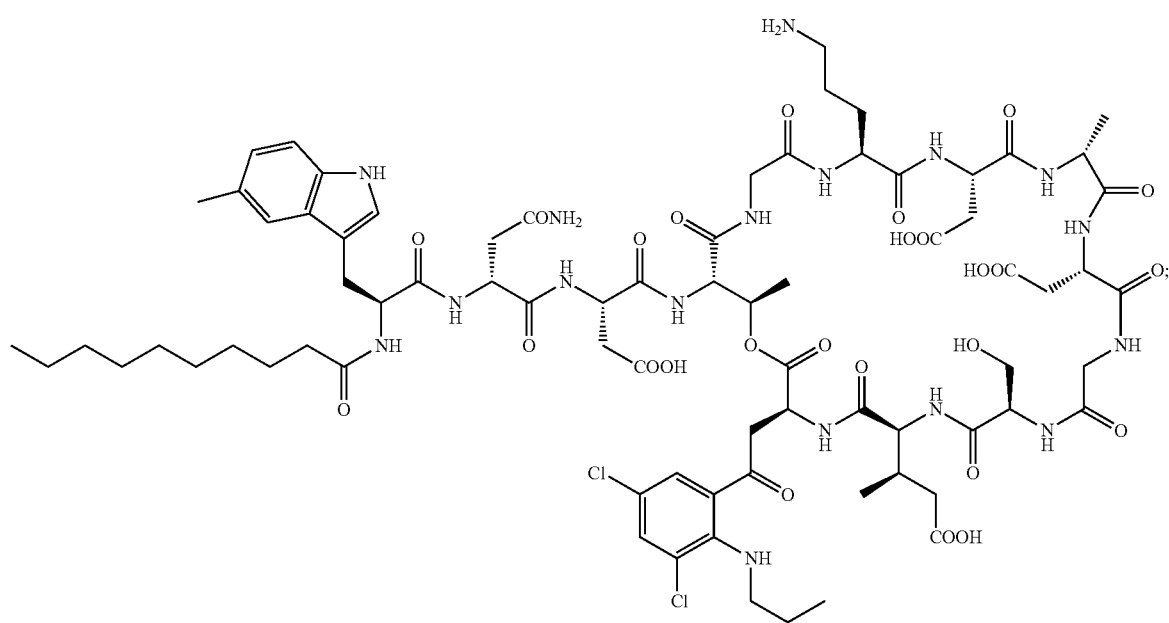

RP022

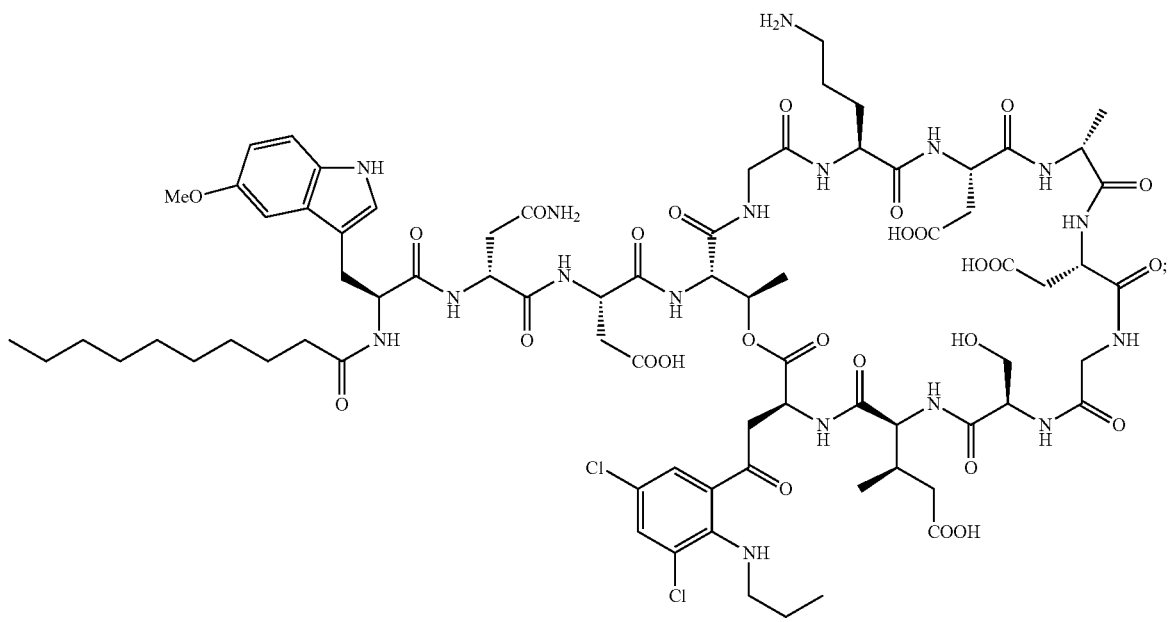

and pharmaceutically acceptable salts thereof.

Item 6. A pharmaceutical composition comprising a compound or a pharmaceutically acceptable salt according to item 1, and a pharmaceutically acceptable carrier.

Item 7. A pharmaceutical composition comprising a compound or a pharmaceutically acceptable salt according to item 3, and a pharmaceutically acceptable carrier.

Item 8. A pharmaceutical composition comprising a compound or a pharmaceutically acceptable salt according to item 4, and a pharmaceutically acceptable carrier.

Item 9. A pharmaceutical composition comprising a compound or a pharmaceutically acceptable salt according to item 5, and a pharmaceutically acceptable carrier.

Item 10. A method of treating a mammal affected by bacterial infections, comprising administering to the mammal an effective amount of a compound of item 1 or a pharmaceutically acceptable salt thereof, wherein the amount of the compound of item 1 may be from 0.1 to 50 mg/kg per day, and wherein the compound of item 1 may be administered in a single dose or multiple doses per day.

Item 11. A method of treating a mammal affected by bacterial infections, comprising administering to the mammal an effective amount of a compound of item 3 or a pharmaceutically acceptable salt thereof, wherein the amount of the compound of item 3 may be from 0.1 to 50 mg/kg per day, and wherein the compound of item 3 may be administered in a single dose or multiple doses per day.

Item 12. A method of treating a mammal affected by bacterial infections, comprising administering to the mammal an effective amount of a compound of item 4 or a pharmaceutically acceptable salt thereof, wherein the amount of the compound of item 4 may be from 0.1 to 50 mg/kg per day, and wherein the compound of item 4 may be administered in a single dose or multiple doses per day.

Item 13. A method of treating a mammal affected by bacterial infections, comprising administering to the mammal an effective amount of a compound of item 5 or a pharmaceutically acceptable salt thereof, wherein the amount of the compound of item 5 may be from 0.1 to 50 mg/kg per day, and wherein the compound of item 5 may be administered in a single dose or multiple doses per day.

Item 14. A compound of formula Inter-II and its use in the synthesis of a lipopeptide having antibacterial activity.

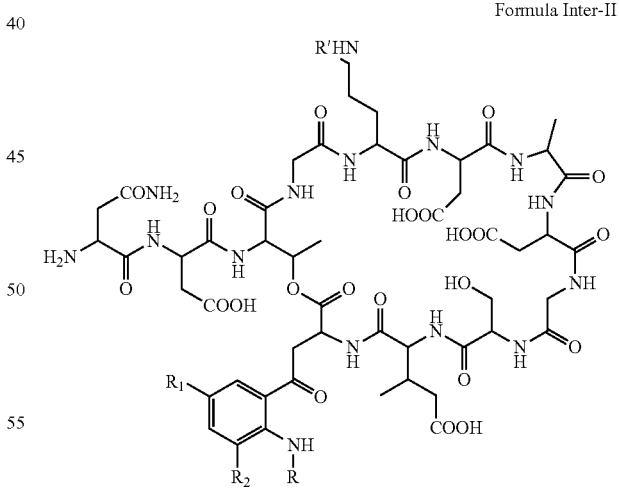

Formula Inter-II wherein:

R is selected from acyl, alkyl, alkenyl, alkynyl, cycloalkyl, cycloalkenyl, aryl, or heteroaryl; R' is an amino protective group, such as Boc; $R_1$ and $R_2$ are independently selected from hydrogen or halogen;

provided that at least one of R, $R_1$, and $R_2$ is not H;

and their salts thereof.

What is claimed is:

1. A compound comprising Formula I,

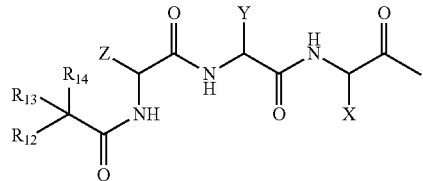

Formula I wherein:

X and Y are independently selected from hydrogen, alkyl, alkenyl, cycloalkyl, cycloalkenyl, alkynyl, aryl, heteroaryl group,

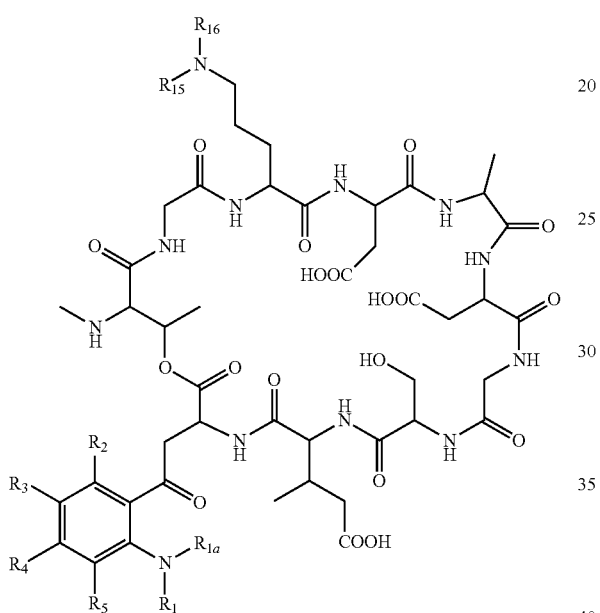

and

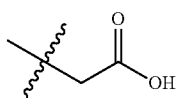 [SMILES: *CC(=O)O]

and

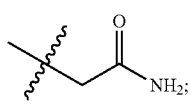 [SMILES: *CC(N)=O]

Z is selected from hydrogen, alkyl, cycloalkyl, alkenyl, cycloalkenyl, alkynyl, aryl, heteroaryl group, and an indolylmethyl moiety having the following structure:

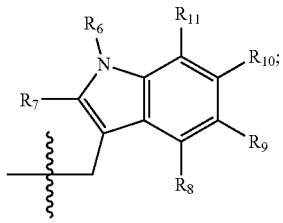

$R_1$, $R_{1a}$, and $R_6$ are each independently selected from hydrogen, alkyl, alkenyl, alkynyl, cycloalkyl, cycloalkenyl, aryl, heteroaryl, acyl, OH, OR, NHR, or $NR_2$ group; wherein R is a $C_1$-$C_6$ alkyl, $C_2$-$C_6$ alkenyl, $C_2$-$C_6$ alkynyl, cycloalkyl, cycloalkenyl, aryl, or heteroaryl group;

$R_2$, $R_3$, $R_4$, $R_5$, $R_7$, $R_8$, $R_9$, $R_{10}$, and $R_{11}$ are each independently selected from hydrogen, halogen, alkyl, alkenyl, alkynyl, cycloalkyl, cycloalkenyl, aryl, heteroaryl, cyano, isocyano, thiocyano, isothiocyano, phosphate, phosphoryl, sulfate, sulfinyl, sulfonyl, formyl, acyl, amino, acylamino, acyloxy, thiocarbonyl, imino, carboalkoxy, carboxy, carboxyamido, hydroxyl, nitro, thio, alkoxy, aryloxy, OC=$OR_a$, OC=$OOR_a$, OC=$ONHR_a$, OC=$ON(R_a)_2$, $NHR_a$, or $N(R_a)_2$ group; wherein $R_a$ is selected from a $C_1$-$C_6$ alkyl, $C_2$-$C_6$ alkenyl, $C_2$-$C_6$ alkynyl, cycloalkyl, cycloalkenyl, aryl or heteroaryl group;

$R_{12}$, $R_{13}$, $R_{14}$ are each independently selected from hydrogen, $C_1$-$C_{25}$ alkyl, $C_2$-$C_{25}$ alkenyl, $C_2$-$C_{25}$ alkynyl, aryl, heteroaryl, cycloalkyl, cycloalkenyl, or a group containing branched or unbranched poly ethylene —$(OCH_2CH_2)_n$—, or poly propylene —$(OCH_2CH_2CH_2)_m$— group, wherein each n and m is an integer between 1 and 10;

$R_{15}$ and $R_{16}$ are each selected from H or —(P'Q'), whereas P' is an alkyl, alkenyl, cycloalkyl, or cycloalkenyl moiety, and Q' is a primary, secondary, tertiary, or quaternary amino group;

provided that at least one of $R_1$, $R_{1a}$, $R_2$, $R_3$, $R_4$, and $R_5$ is not H;

and further provided that when Z is the following indolylmethyl group

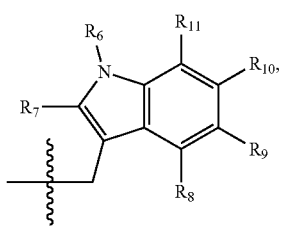

at least one of $R_6$, $R_7$, $R_8$, $R_9$, $R_{10}$, and $R_{11}$ is not H;

and pharmaceutically acceptable salts thereof.

2. A compound according to claim 1, wherein Z is the following indolylmethyl group,

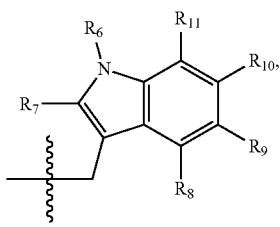

provided that at least one of $R_1$, $R_{1a}$, $R_2$, $R_3$, $R_4$, and $R_5$ is not H;
and further provided that at least one of $R_6$, $R_7$, $R_8$, $R_9$, $R_{10}$, and $R_{11}$ is not H;
and pharmaceutically acceptable salts thereof.

3. A compound comprising Formula II,

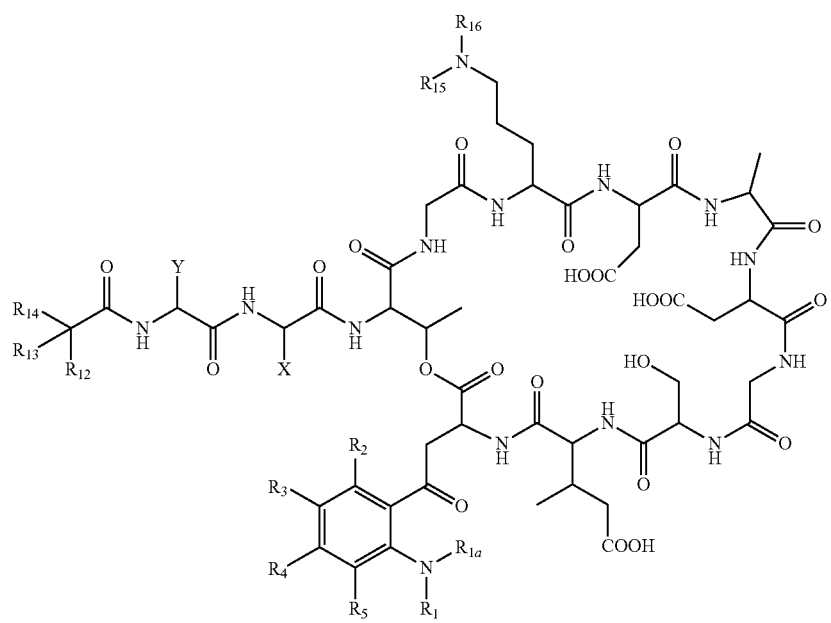

Formula II wherein:
X and Y are independently selected from hydrogen, alkyl, cycloalkyl, alkenyl, cycloalkenyl, alkynyl, aryl, heteroaryl group,

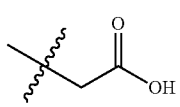 [SMILES: *CC(=O)O]

and

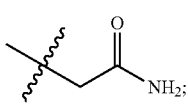

$R_1$ and $R_{1a}$ are each independently selected from hydrogen, alkyl, alkenyl, alkynyl, cycloalkyl, cycloalkenyl, aryl, heteroaryl, acyl, OH, OR, NHR, or $NR_2$ group; wherein R is a $C_1$-$C_6$ alkyl, $C_2$-$C_6$ alkenyl, $C_2$-$C_6$ alkynyl, cycloalkyl, cycloalkenyl, aryl, or heteroaryl group;

$R_2$, $R_3$, $R_4$, $R_5$ are each independently selected from hydrogen, halogen, alkyl, alkenyl, alkynyl, cycloalkyl, cycloalkenyl, aryl, heteroaryl, cyano, isocyano, thiocyano, isothiocyano, phosphate, phosphoryl, sulfate, sulfinyl, sulfonyl, formyl, acyl, amino, acylamino, acyloxy, thiocarbonyl, imino, carboalkoxy, carboxy, carboxyamido, hydroxyl, nitro, thio, alkoxy, aryloxy, OC=$OR_a$, OC=$OOR_a$, OC=$ONHR_a$, OC=$ON(R_a)_2$, $NHR_a$, or $N(R_a)_2$ group; wherein $R_a$ is selected from a $C_1$-$C_6$ alkyl, $C_2$-$C_6$ alkenyl, $C_2$-$C_6$ alkynyl, cycloalkyl, cycloalkenyl, aryl or heteroaryl group;

$R_{12}$, $R_{13}$, $R_{14}$ are each independently selected from hydrogen, $C_1$-$C_{25}$ alkyl, $C_2$-$C_{25}$ alkenyl, $C_2$-$C_{25}$ alkynyl, aryl, heteroaryl, cycloalkyl, cycloalkenyl, or a group containing branched or unbranched poly ethylene —(OCH$_2$CH$_2$)$_n$—, or poly propylene —(OCH$_2$CH$_2$CH$_2$)$_m$— group, wherein each n and m is an integer between 1 and 10;

$R_{15}$ and $R_{16}$ are each selected from H or —(P'Q'), whereas P' is an alkyl, alkenyl, cycloalkyl, or cycloalkenyl moiety, and Q' is a primary, secondary, tertiary, or quaternary amino group;

provided that at least one of $R_1$ and $R_{1a}$ is not H;

or pharmaceutically acceptable salts thereof.

4. A compound comprising Formula III,

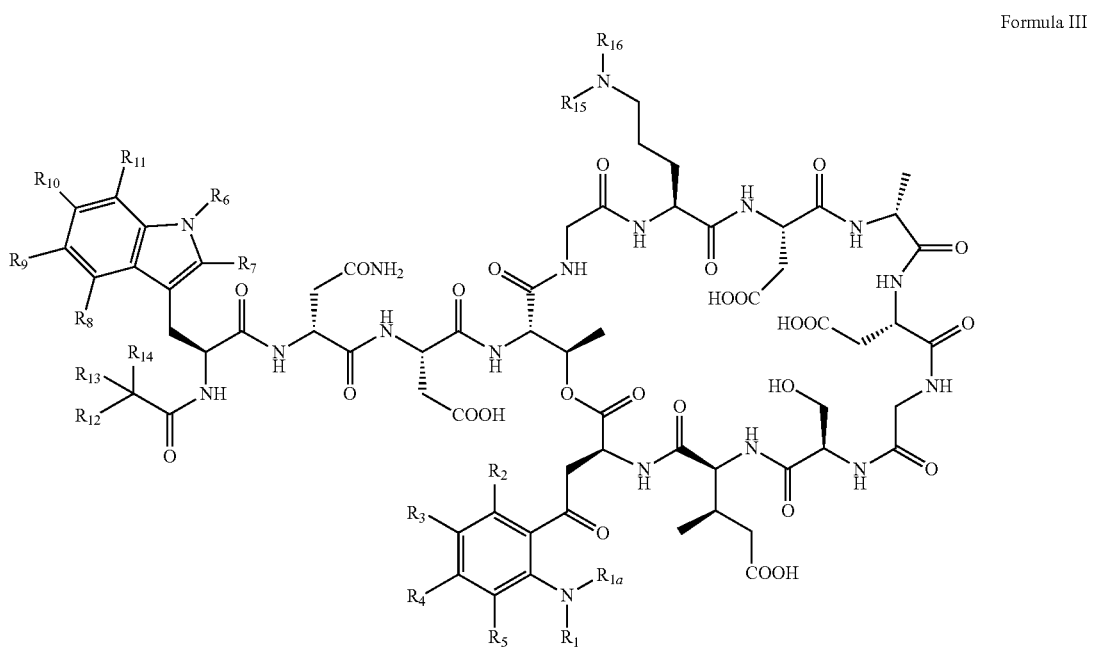

Formula III wherein:

$R_1$, $R_{1a}$, and $R_6$ are each independently selected from hydrogen, alkyl, alkenyl, alkynyl, cycloalkyl, cycloalkenyl, aryl, heteroaryl, acyl, OH, OR, NHR, or $NR_2$ group; wherein R is a $C_1$-$C_6$ alkyl, $C_2$-$C_6$ alkenyl, $C_2$-$C_6$ alkynyl, cycloalkyl, cycloalkenyl, aryl, or heteroaryl group;

$R_2$, $R_3$, $R_4$, $R_5$, $R_7$, $R_8$, $R_9$, $R_{10}$, and $R_{11}$ are each independently selected from hydrogen, halogen, alkyl, alkenyl, alkynyl, cycloalkyl, cycloalkenyl, aryl, heteroaryl, cyano, isocyano, thiocyano, isothiocyano, phosphate, phosphoryl, sulfate, sulfinyl, sulfonyl, formyl, acyl, amino, acylamino, acyloxy, thiocarbonyl, imino, carboalkoxy, carboxy, carboxyamido, hydroxyl, nitro, thio, alkoxy, aryloxy, $OC=OR_a$, $OC=OOR_a$, $OC=ONHR_a$, $OC=ON(R_a)_2$, $NHR_a$, or $N(R_a)_2$ group; wherein $R_a$ is selected from a $C_1$-$C_6$ alkyl, $C_2$-$C_6$ alkenyl, $C_2$-$C_6$ alkynyl, cycloalkyl, cycloalkenyl, aryl or heteroaryl group;

$R_{12}$, $R_{13}$, $R_{14}$ are each independently selected from hydrogen, substituted, unsubstituted, branched, unbranched $C_1$-$C_{25}$ alkyl, $C_2$-$C_{25}$ alkenyl, $C_2$-$C_{25}$ alkynyl, aryl, heteroaryl, cyclic alkyl, cyclic alkenyl, cyclic alkynyl, or a group containing branched or unbranched poly ethylene $—(OCH_2CH_2)_n—$, or poly propylene $—(OCH_2CH_2CH_2)_m—$ group, wherein each n and m is an integer between 1 and 10;

$R_{15}$ and $R_{16}$ are each selected from H or $—(P'Q')$, whereas P' is an alkyl, alkenyl, cycloalkyl, or cycloalkenyl moiety, and Q' is a primary, secondary, tertiary, or quaternary amino group;

provided that at least one of $R_1$, $R_{1a}$, $R_2$, $R_3$, $R_4$, and $R_5$ is not H;

and further provided that at least one of $R_6$, $R_7$, $R_8$, $R_9$, $R_{10}$, and $R_{11}$ is not H;

and pharmaceutically acceptable salts thereof.

5. A compound having antibacterial activity selected from the group consisting of compounds designated RP002, RP003, RP004, RP005, RP006, RP007, RP008, RP009, RP010, RP011, RP012, RP013, RP014, RP015, RP016, RP017, RP018, RP019, RP020, RP021 and RP022, and having the following formulas:

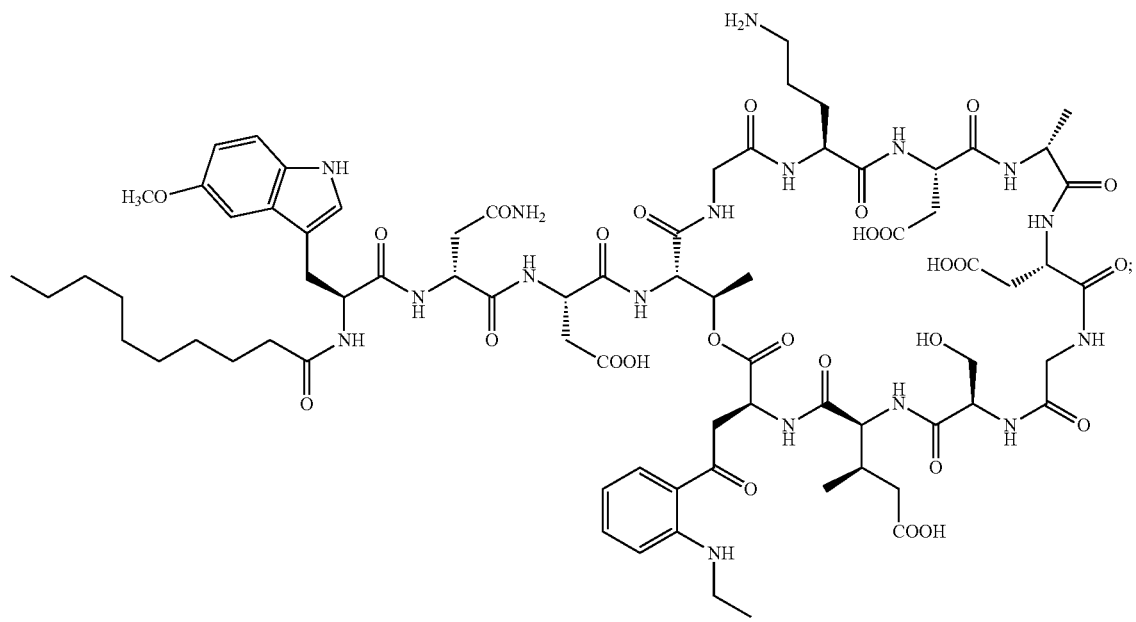
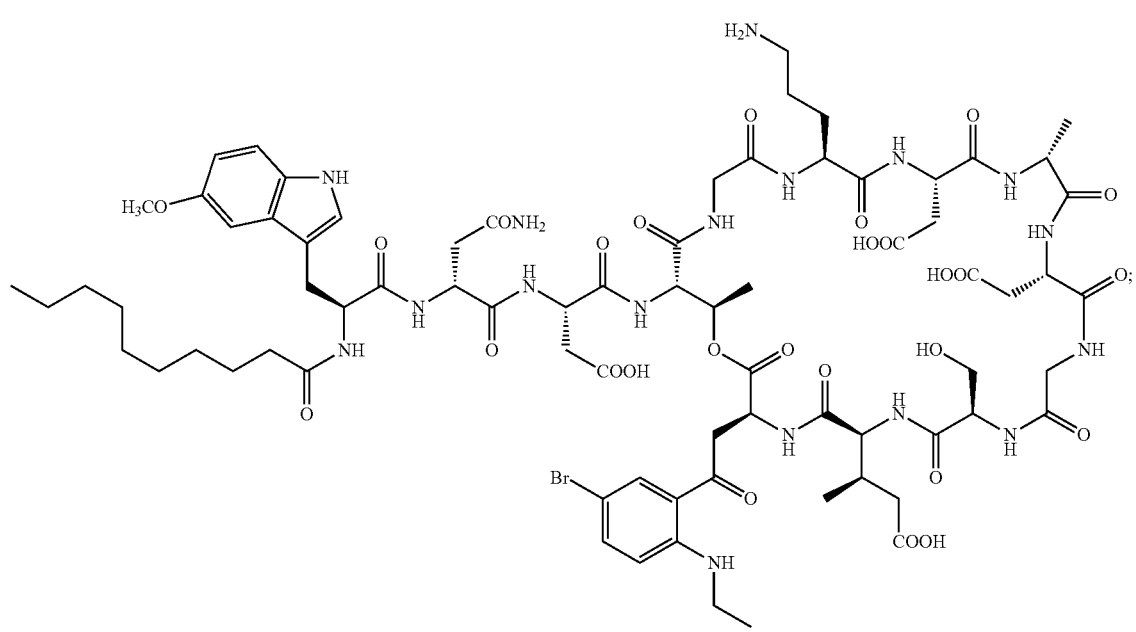

-continued
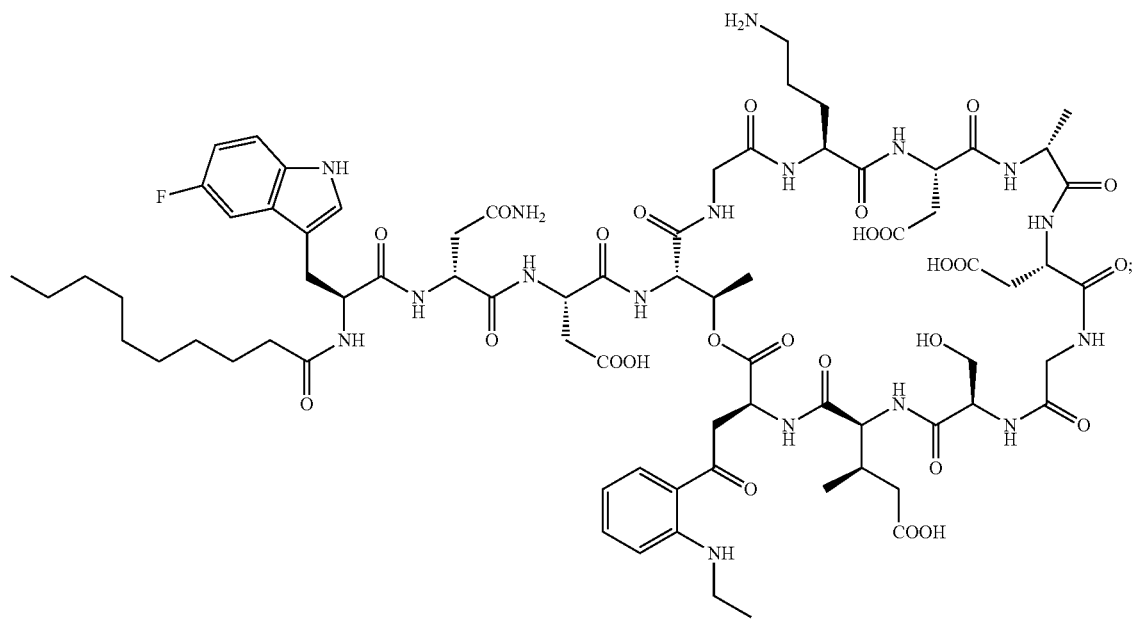
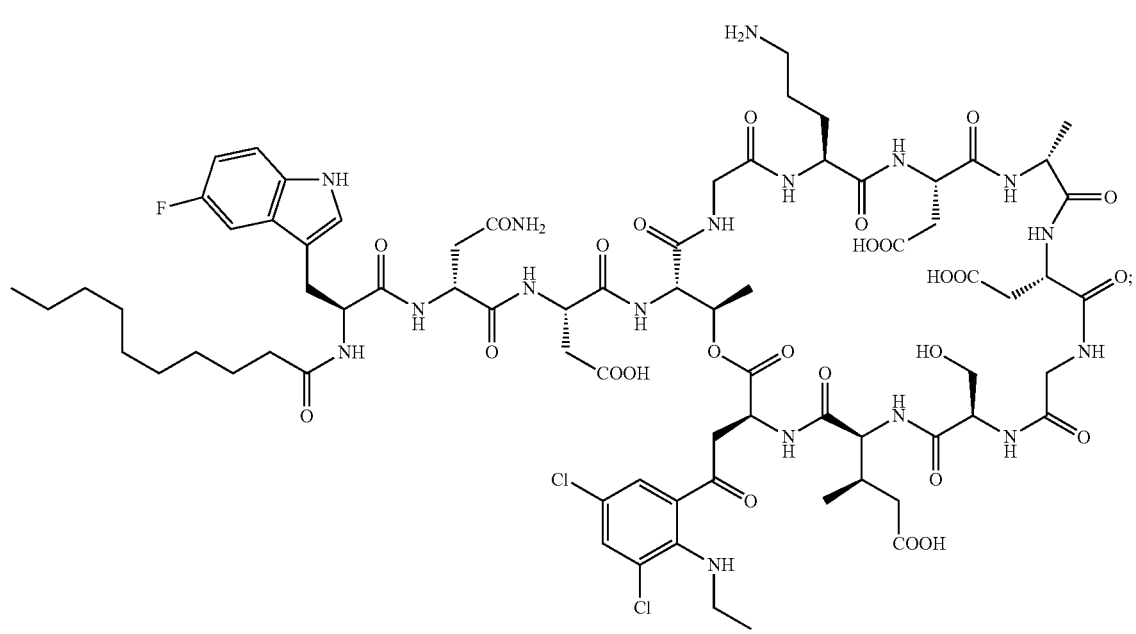

-continued
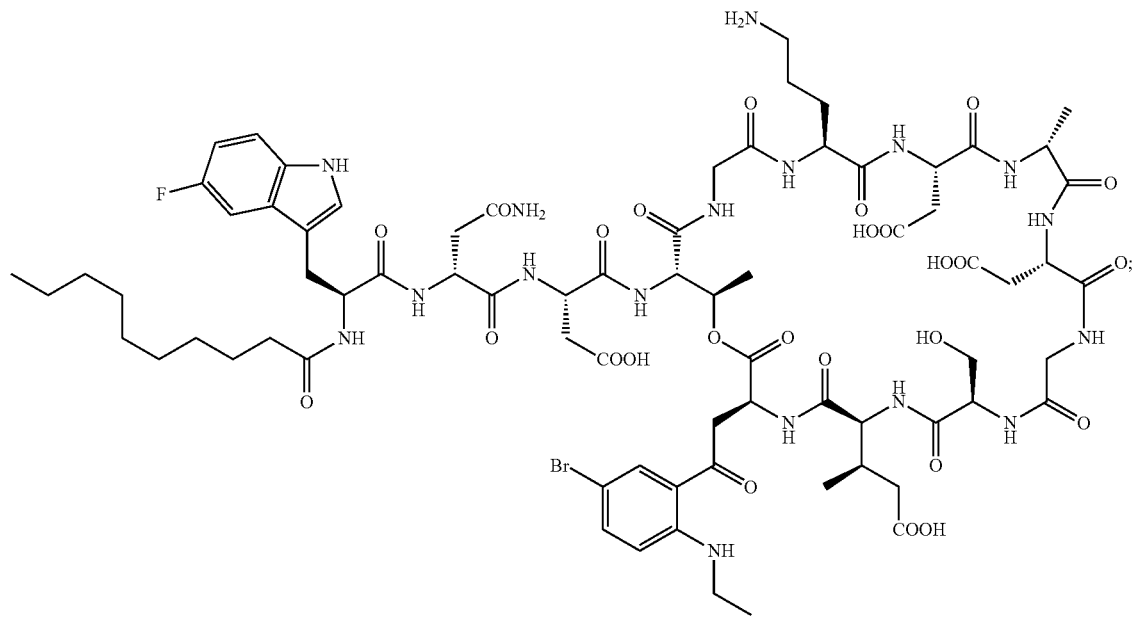
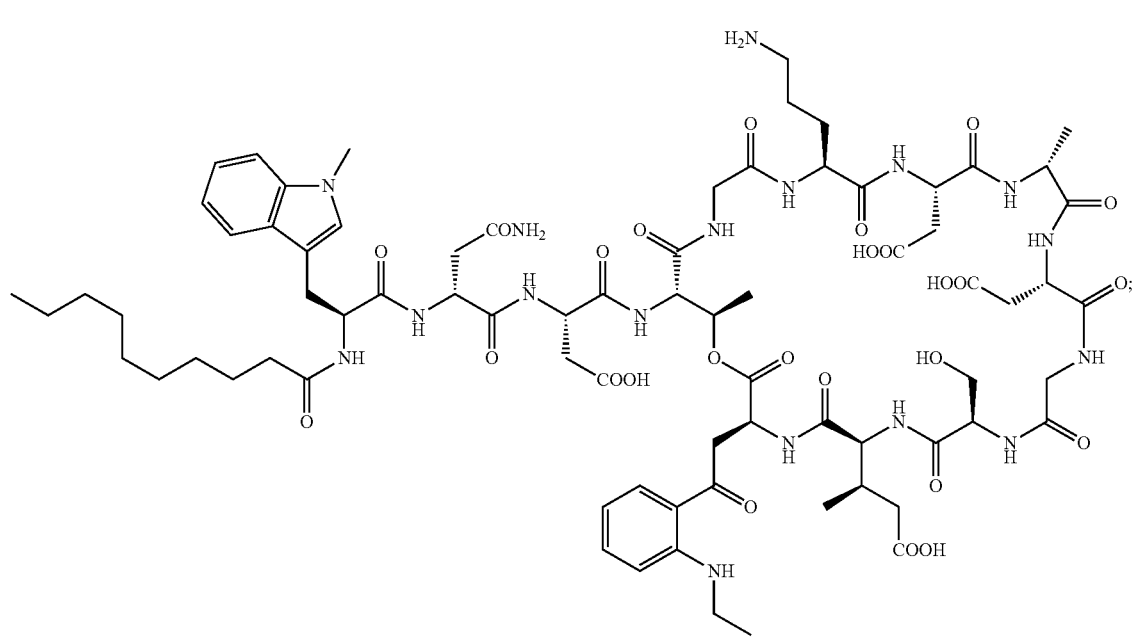

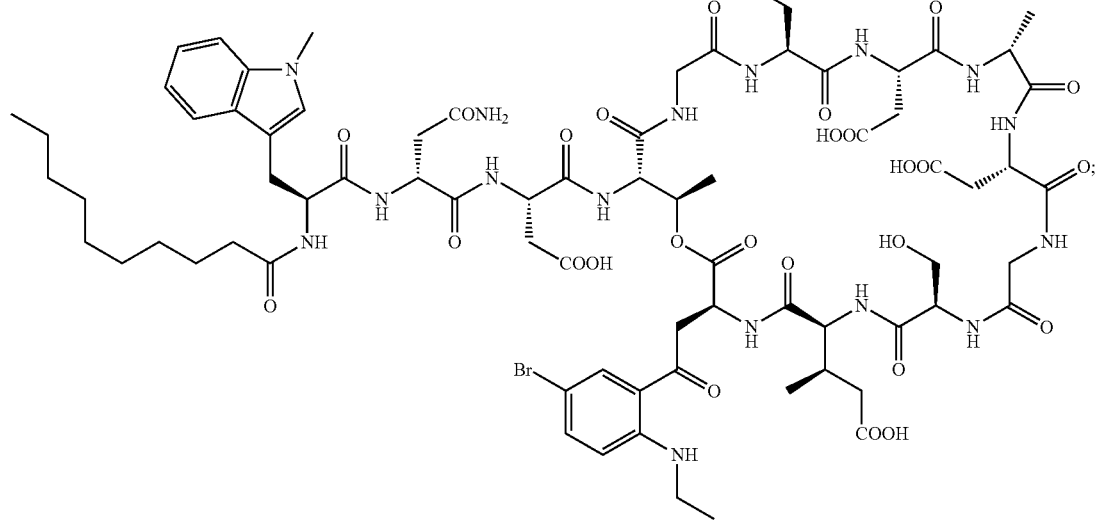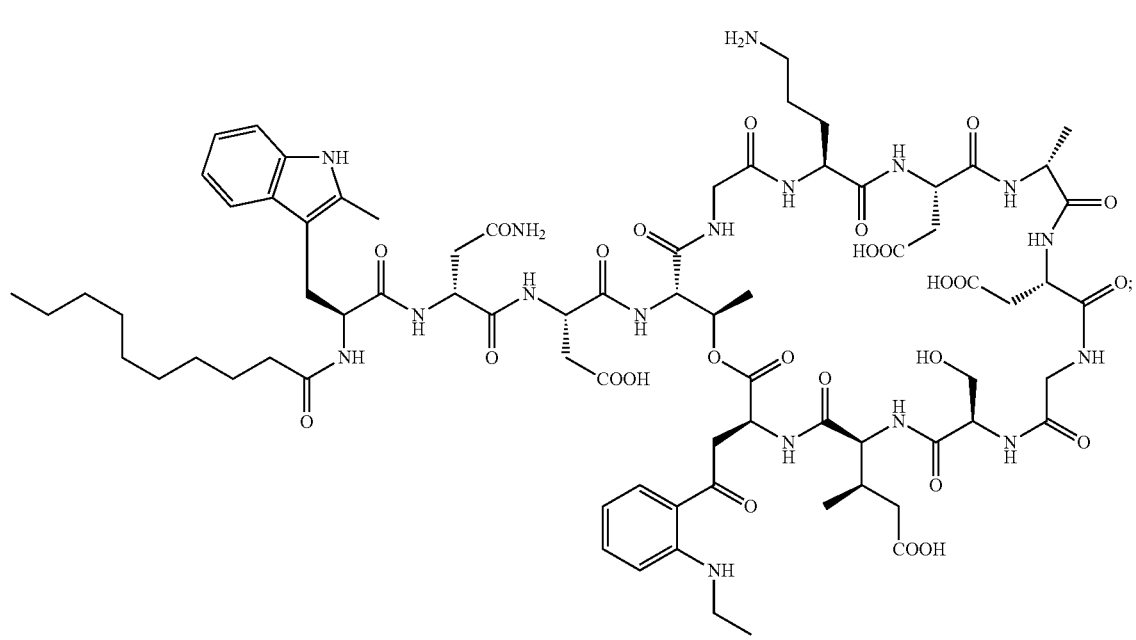

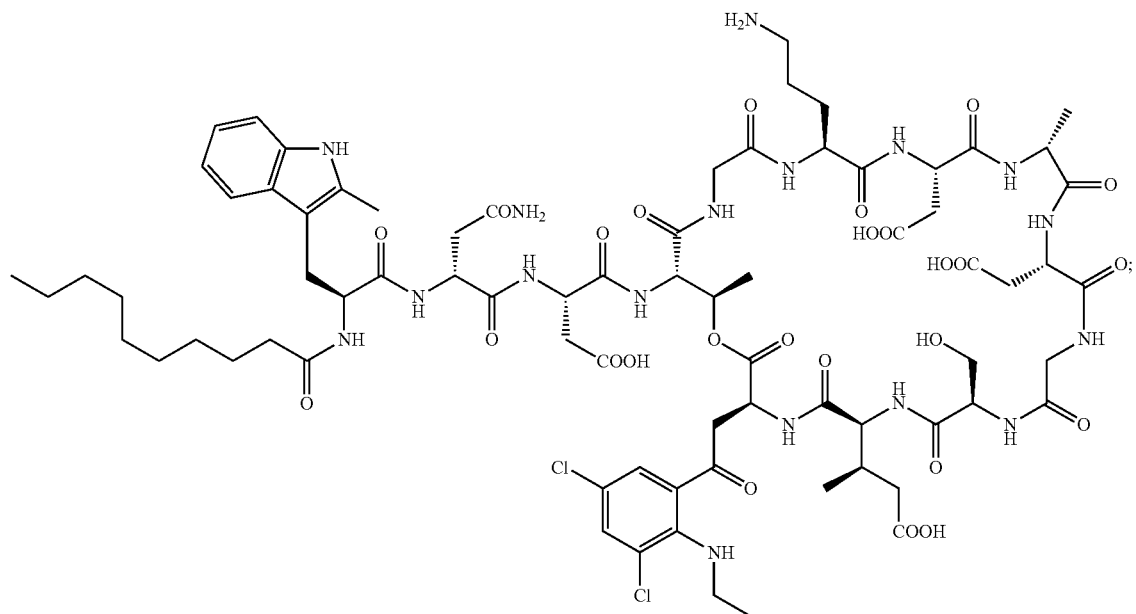
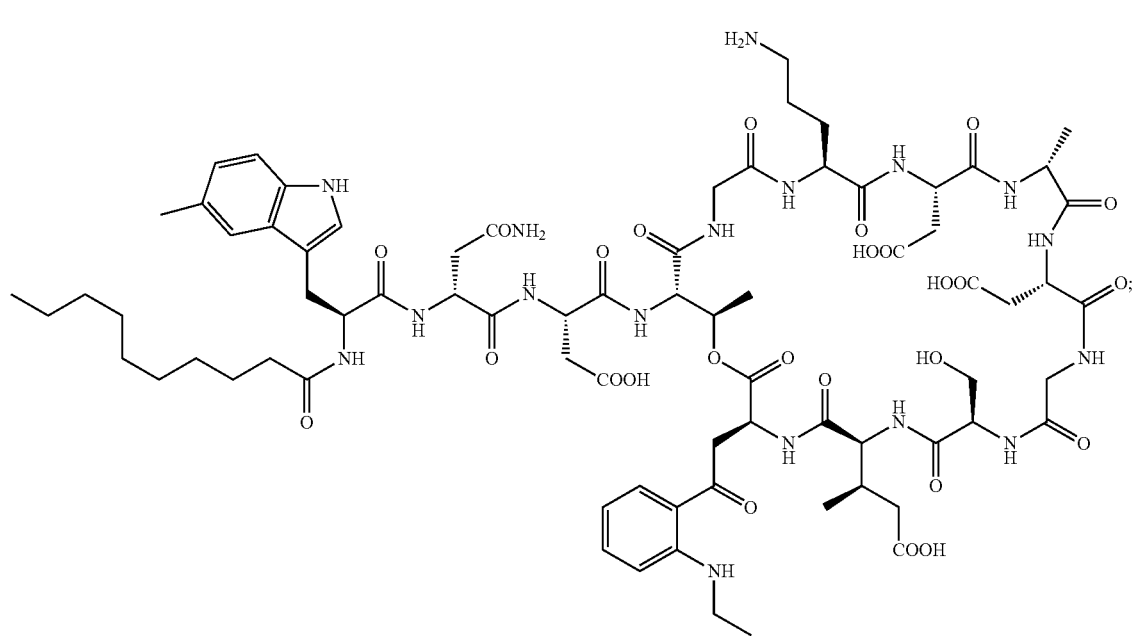

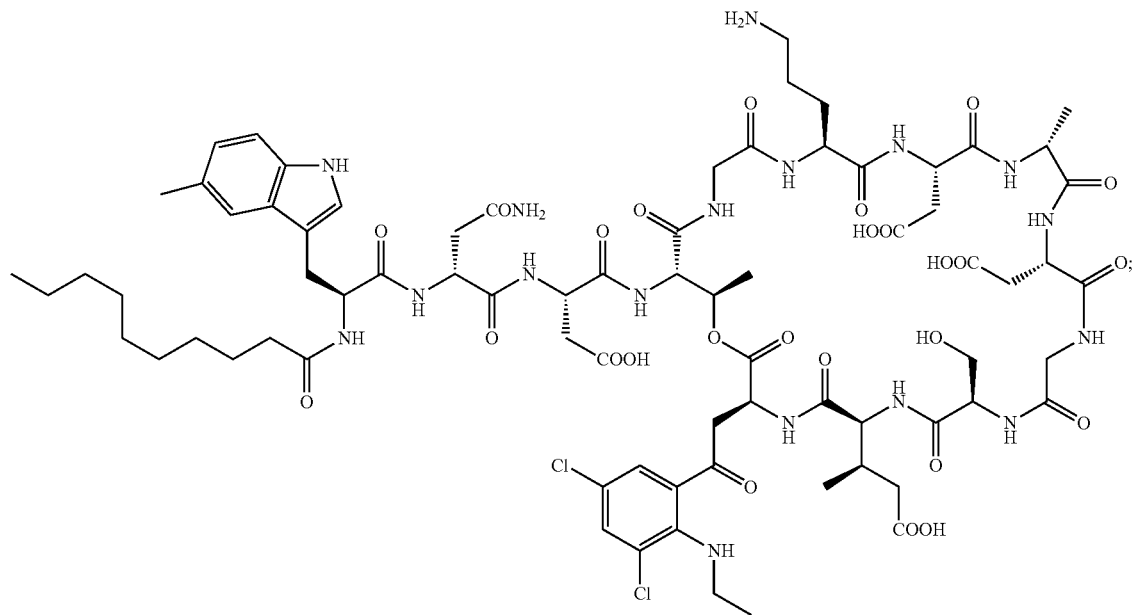
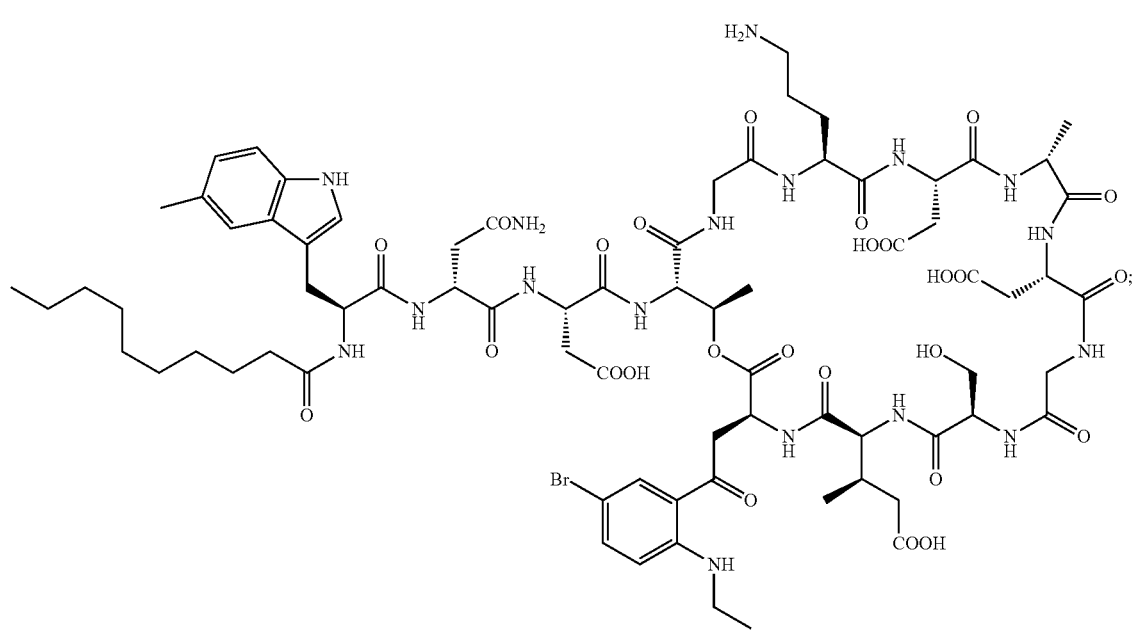

-continued
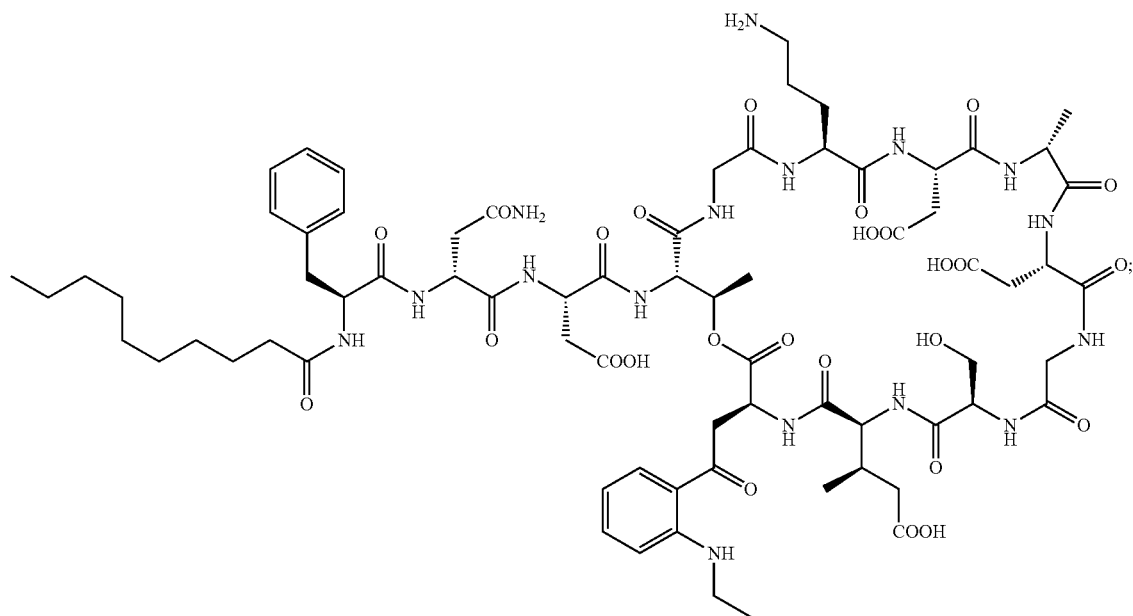
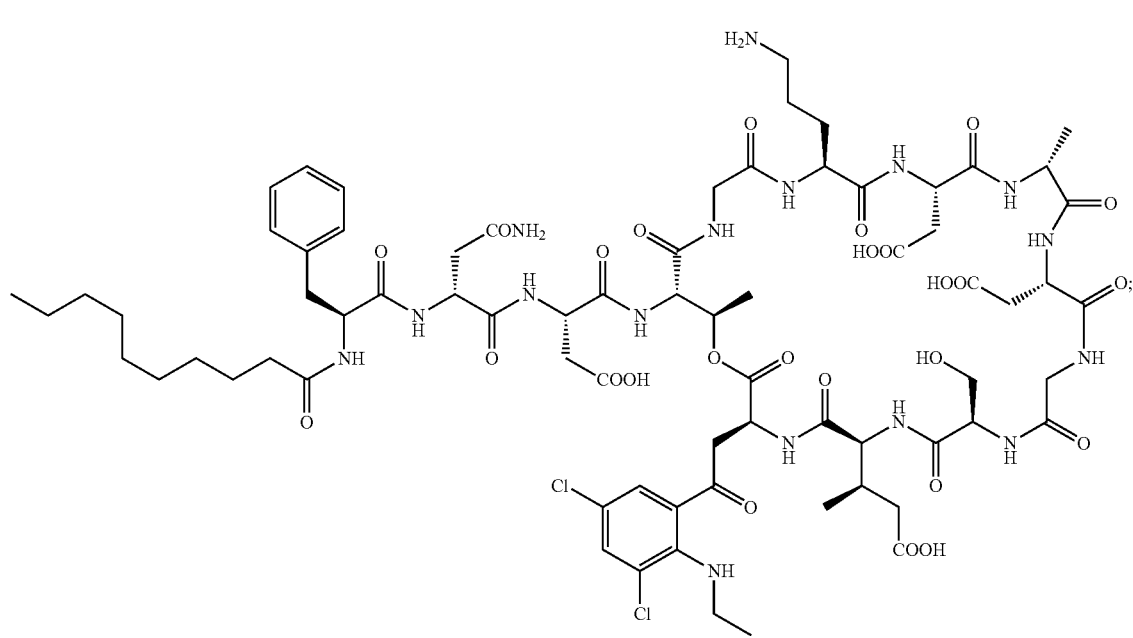

-continued
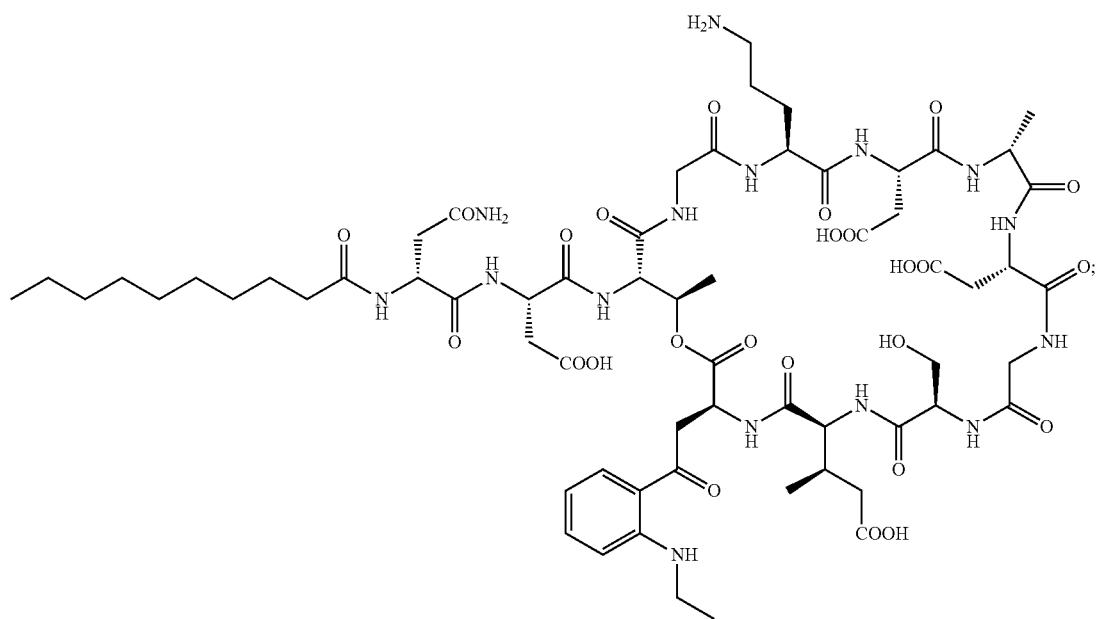
RP016
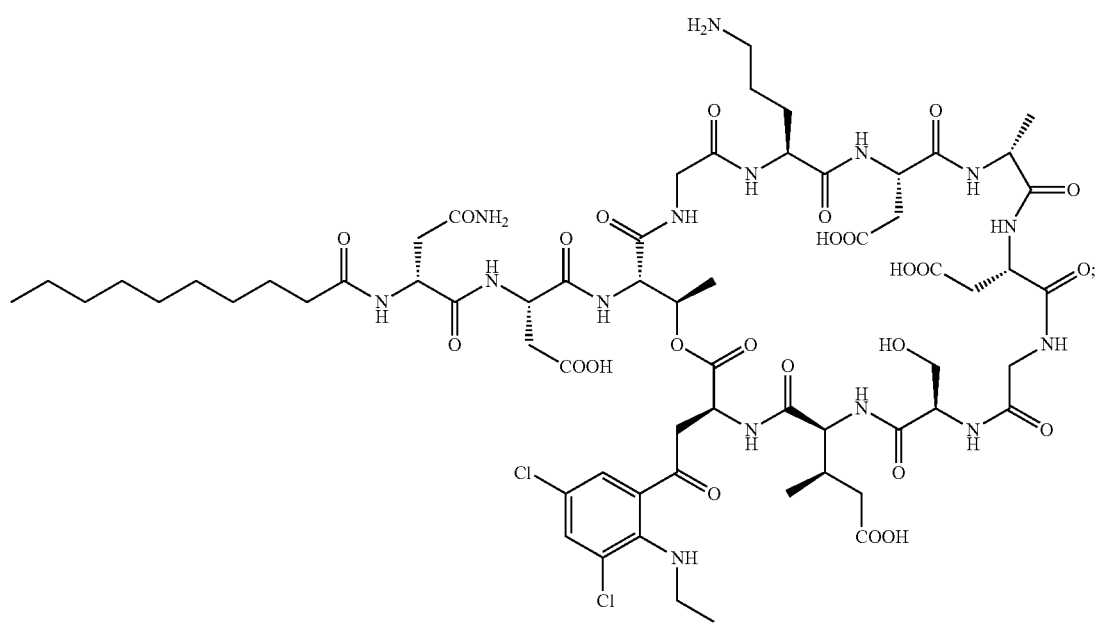
RP017

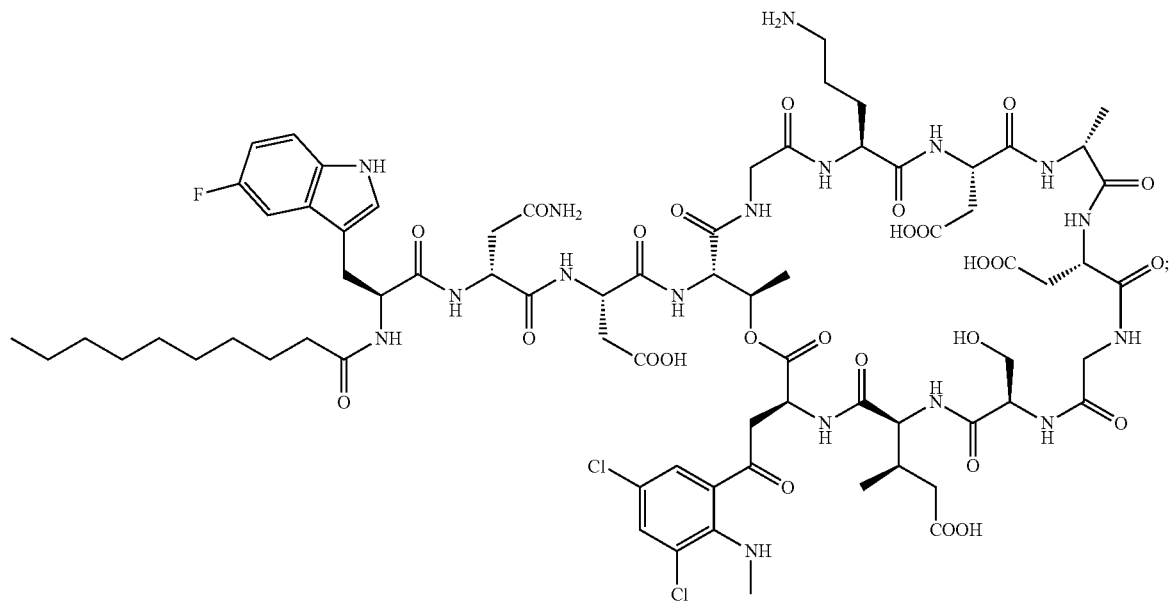
RP018
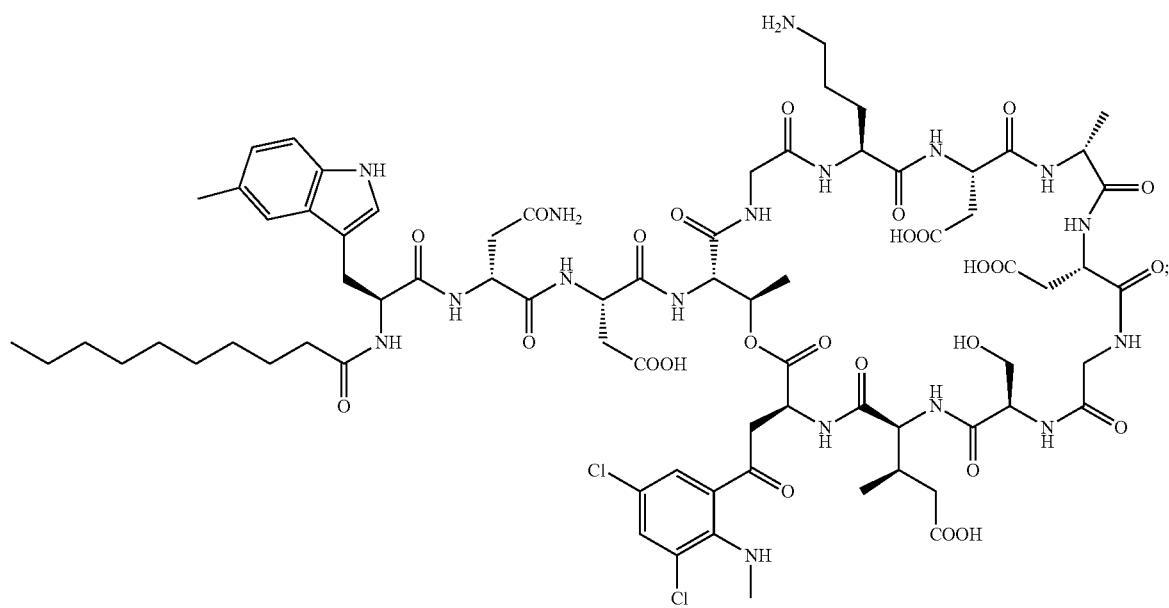
RP019

201 202
-continued
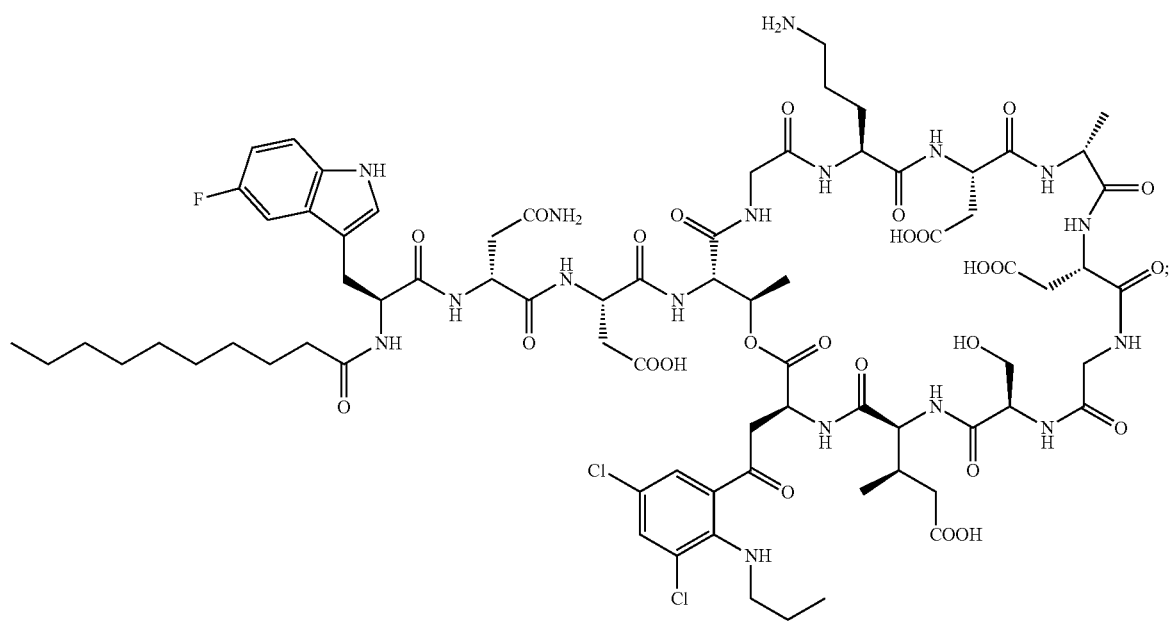
RP020
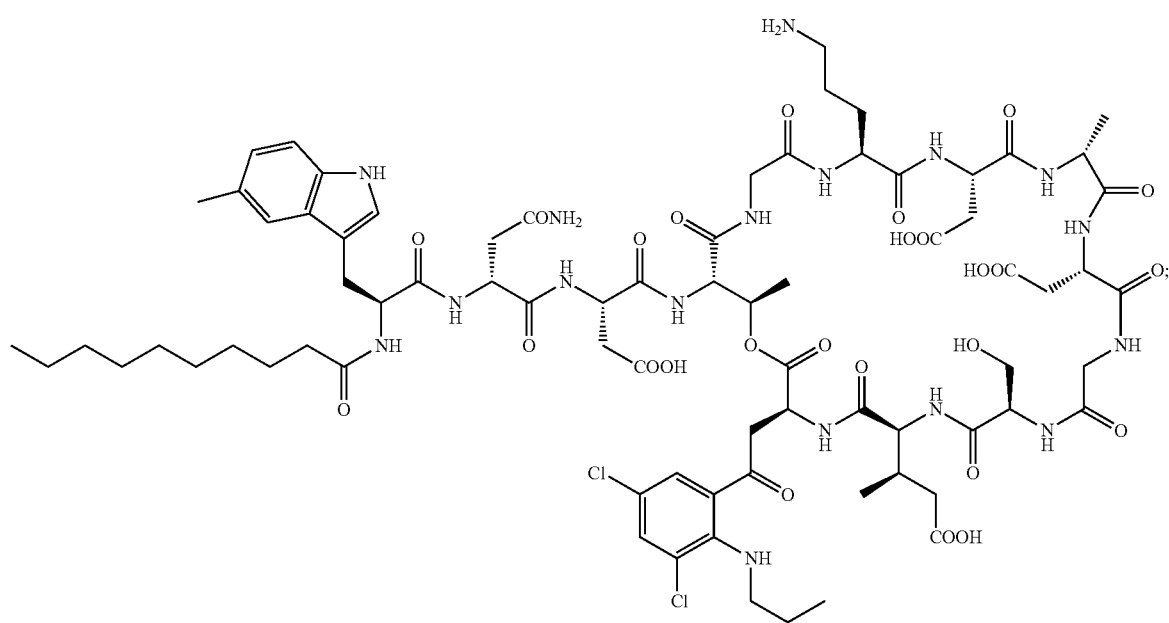
RP021

-continued

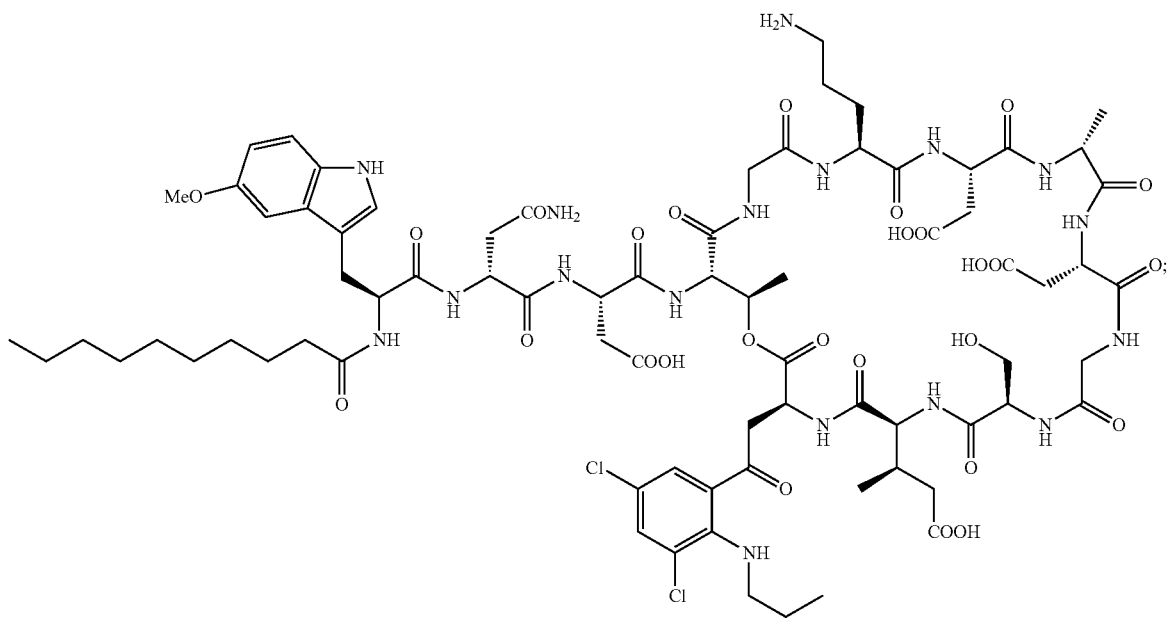

and pharmaceutically acceptable salts thereof.

6. A pharmaceutical composition comprising a compound or a pharmaceutically acceptable salt according to claim 1, and a pharmaceutically acceptable carrier.

7. A method of treating a mammal affected by bacterial infections, comprising administering to the mammal an effective amount of a compound of claim 1 or a pharmaceutically acceptable salt thereof, wherein the amount of the compound of claim 1 may be from 0.1 to 50 mg/kg per day, and wherein the compound of claim 1 may be administered in a single dose or multiple doses per day.

8. A compound of formula Inter-II for use in the synthesis of a lipopeptide having antibacterial activity, Formula Inter-II

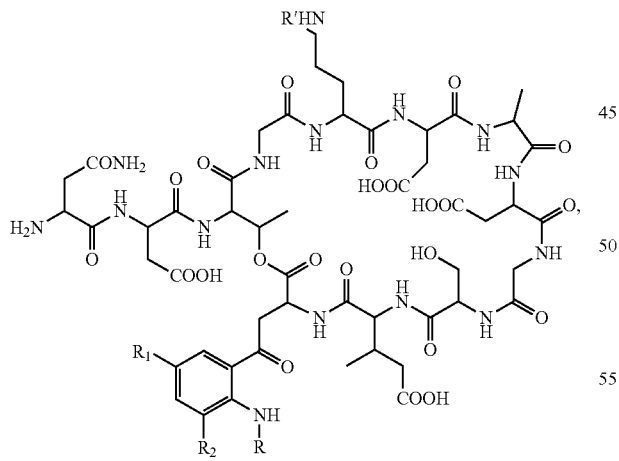

wherein:
R is selected from acyl, alkyl, alkenyl, alkynyl, cycloalkyl, cycloalkenyl, aryl, or heteroaryl; R' is an amino protective group, such as Boc; $R_1$ and $R_2$ are independently selected from hydrogen or halogen;
provided that at least one of R, $R_1$, and $R_2$ is not H; and their salts thereof.

* * * * *